United States Patent
Podolsky et al.

(10) Patent No.: US 9,237,949 B2
(45) Date of Patent: **\*Jan. 19, 2016**

(54) METHOD AND APPARATUS FOR HIP REPLACEMENT

(71) Applicant: iHip Surgical, LLC, Newport Beach, CA (US)

(72) Inventors: Anatol Podolsky, Corona Del Mar, CA (US); Yuri Garbuzov, Newport Coast, CA (US)

(73) Assignee: iHip Surgical, LLC, Newport Beach, CA (US)

( \* ) Notice: Subject to any disclaimer, the term of this patent is extended or adjusted under 35 U.S.C. 154(b) by 0 days.

This patent is subject to a terminal disclaimer.

(21) Appl. No.: 14/077,054

(22) Filed: Nov. 11, 2013

(65) Prior Publication Data

US 2014/0074250 A1    Mar. 13, 2014

Related U.S. Application Data

(60) Continuation of application No. 13/335,216, filed on Dec. 22, 2011, now Pat. No. 8,579,985, which is a (Continued)

(51) Int. Cl.
  *A61F 2/32*    (2006.01)
  *A61F 2/36*    (2006.01)

(52) U.S. Cl.
  CPC ............ *A61F 2/3609* (2013.01); *A61F 2/3662* (2013.01)

(58) Field of Classification Search
  CPC ....... A61F 2/3609; A61F 2/3601; A61F 2/30; A61F 2/36; A61F 2/3603; A61F 2/3607; A61F 2/3662; A61F 2/367; A61F 2/3672; A61F 2/3676; A61F 2002/30331; A61F 2002/30332; A61F 2002/30339; A61F 2002/3035; A61F 2002/30405; A61F 2002/30408; A61F 2002/30423; A61F 2002/36; A61F 2002/3609; A61F 2202/3625; A61F 2002/3859; A61F 2002/40; A61F 2/3859; A61F 2/40; A61F 2/4014; A61F 2/32; A61F 2002/32

USPC .............. 623/22.11, 22.36, 22.4–22.46, 623/23.11–23.15, 19.11–19.14; 606/62, 64, 606/65, 98

See application file for complete search history.

(56) References Cited

U.S. PATENT DOCUMENTS 2,612,159 A \* 9/1952 Collison ................. 606/67
2,679,245 A    5/1954 Timmermans
(Continued)

FOREIGN PATENT DOCUMENTS

CN    201150576 Y    11/2008
DE    2620907        11/1977
(Continued)

OTHER PUBLICATIONS

Cooper et al., "Corrosion at the Head-Neck Taper as a Cause for Adverse Local Tissue Reactions After Total Hip Arthroplasty," J Bone Joint Surg Am. 2012;94:1655-61 dated Sestember 12, 2012.
(Continued)

*Primary Examiner* — Alvin Stewart
(74) *Attorney, Agent, or Firm* — McDermott Will & Emery LLP

(57) ABSTRACT

Methods and apparatus for orthopedic replacement of the hip through three incisions with a modular prosthetic system assembled in vivo while substantially preserving muscles and soft tissues around the hip joint resulting in reduced healing time and decreased risk of dislocation. A prosthetic femoral stem is inserted into the femur. A prosthetic femoral neck is inserted from a point along the side of the patient's body and into the side of the femur and through a lateral bore in the prosthetic femoral stem to join the prosthetic femoral head. The methods and apparatus include structures and techniques for fixing or enhancing interconnection of implant components, such as by increasing the interconnection in an interference fit with one or more tapers, threads, and/or cooling of components prior to assembly.

21 Claims, 73 Drawing Sheets

Related U.S. Application Data continuation-in-part of application No. 13/049,619, filed on Mar. 16, 2011, now Pat. No. 8,211,183, which is a division of application No. 12/518,081, filed as application No. PCT/US2006/046795 on Dec. 7, 2006, now Pat. No. 8,029,573.

(56) References Cited

U.S. PATENT DOCUMENTS

| | | |
|---|---|---|
| 2,682,265 A | 6/1954 | Collison |
| 2,718,228 A | 9/1955 | Steenbrugghe |
| 2,719,522 A | 10/1955 | Hudack |
| 2,781,758 A | 2/1957 | Chevalier |
| 2,785,673 A | 3/1957 | Anderson |
| 2,947,308 A | 8/1960 | Gorman |
| 3,064,645 A | 11/1962 | Ficat |
| 3,067,740 A | 12/1962 | Haboush |
| 3,102,536 A | 9/1963 | Rose et al. |
| 3,466,670 A | 9/1969 | Christensen |
| 3,512,184 A | 5/1970 | Grove |
| 3,530,854 A | 9/1970 | Kearney |
| 3,605,123 A | 9/1971 | Hahn |
| 3,656,184 A | 4/1972 | Chambers |
| 3,658,056 A | 4/1972 | Huggler et al. |
| 3,683,421 A | 8/1972 | Martinie |
| 3,806,957 A | 4/1974 | Shersher |
| 3,829,904 A | 8/1974 | Ling et al. |
| 3,848,272 A | 11/1974 | Noiles |
| 3,859,669 A | 1/1975 | Shersher |
| 3,875,593 A | 4/1975 | Shersher |
| 3,896,505 A | 7/1975 | Timmermans |
| 3,903,549 A | 9/1975 | Deyerle |
| 3,906,550 A | 9/1975 | Rostoker et al. |
| 3,918,441 A | 11/1975 | Getscher |
| 3,939,497 A | 2/1976 | Heimke et al. |
| 3,943,576 A | 3/1976 | Sivash |
| 3,978,528 A | 9/1976 | Crep |
| 3,987,499 A | 10/1976 | Scharbach et al. |
| 4,012,795 A | 3/1977 | Dorre et al. |
| 4,016,651 A | 4/1977 | Kawahara et al. |
| 4,021,865 A | 5/1977 | Charnley |
| 4,051,559 A | 10/1977 | Pifferi |
| 4,060,472 A | 11/1977 | Alewitz |
| 4,080,666 A | 3/1978 | Fixel |
| 4,086,701 A | 5/1978 | Kawahara et al. |
| 4,089,071 A | 5/1978 | Kalnberz et al. |
| 4,101,985 A | 7/1978 | Baumann et al. |
| 4,115,875 A | 9/1978 | Rambert et al. |
| 4,129,903 A | 12/1978 | Huggler |
| 4,172,452 A | 10/1979 | Forte et al. |
| 4,198,711 A | 4/1980 | Zeibig |
| 4,225,981 A * | 10/1980 | Zeibig ............... 623/22.43 |
| 4,259,072 A | 3/1981 | Hirabayashi et al. |
| 4,282,618 A | 8/1981 | Wagner |
| 4,298,993 A | 11/1981 | Kovaleva et al. |
| 4,304,110 A | 12/1981 | Fain |
| 4,318,191 A | 3/1982 | Tepic |
| 4,385,405 A | 5/1983 | Teinturier |
| 4,404,691 A | 9/1983 | Buning et al. |
| 4,432,358 A | 2/1984 | Fixel |
| 4,488,319 A | 12/1984 | von Recum |
| 4,520,511 A | 6/1985 | Gianezio et al. |
| 4,530,114 A | 7/1985 | Tepic |
| 4,532,660 A | 8/1985 | Field |
| 4,532,661 A | 8/1985 | Halpern |
| 4,578,081 A | 3/1986 | Harder et al. |
| 4,608,055 A | 8/1986 | Morrey et al. |
| 4,619,659 A | 10/1986 | Witzel |
| 4,624,673 A | 11/1986 | Meyer |
| 4,629,280 A | 12/1986 | Semmler et al. |
| 4,630,601 A | 12/1986 | Harder et al. |
| 4,676,797 A | 6/1987 | Anapliotis et al. |
| 4,687,487 A | 8/1987 | Hintermann |
| 4,693,724 A | 9/1987 | Rhenter et al. |
| 4,709,854 A | 12/1987 | Biagini et al. |
| 4,712,541 A | 12/1987 | Harder et al. |
| 4,714,471 A | 12/1987 | Grundei |
| 4,714,478 A | 12/1987 | Fischer |
| 4,719,074 A | 1/1988 | Tsuno et al. |
| 4,728,330 A | 3/1988 | Comparetto |
| 4,728,334 A | 3/1988 | Spotorno |
| 4,733,654 A | 3/1988 | Marino |
| 4,752,295 A | 6/1988 | Frey et al. |
| 4,752,296 A | 6/1988 | Buechel et al. |
| 4,776,330 A | 10/1988 | Chapman et al. |
| 4,792,337 A | 12/1988 | Muller |
| 4,795,473 A | 1/1989 | Grimes |
| 4,822,368 A | 4/1989 | Collier |
| 4,822,370 A | 4/1989 | Schelhas |
| 4,823,366 A | 4/1989 | Williams |
| 4,827,917 A | 5/1989 | Brumfield |
| 4,834,756 A | 5/1989 | Kenna |
| 4,842,606 A | 6/1989 | Kranz et al. |
| 4,846,839 A | 7/1989 | Noiles |
| 4,851,007 A | 7/1989 | Gray |
| 4,871,369 A | 10/1989 | Muller |
| 4,878,917 A | 11/1989 | Kranz et al. |
| 4,895,571 A | 1/1990 | Grundei |
| 4,904,264 A | 2/1990 | Scheunemann |
| 4,908,032 A | 3/1990 | Keller |
| 4,917,530 A | 4/1990 | Engelhardt et al. |
| 4,919,673 A | 4/1990 | Willert et al. |
| 4,919,678 A | 4/1990 | Kranz |
| 4,919,679 A | 4/1990 | Averill et al. |
| 4,921,500 A | 5/1990 | Averill et al. |
| 4,936,853 A | 6/1990 | Fabian et al. |
| 4,938,773 A | 7/1990 | Strand |
| 4,944,764 A | 7/1990 | Stossel |
| 4,946,459 A | 8/1990 | Bradshaw et al. |
| 4,946,461 A | 8/1990 | Fischer |
| 4,957,510 A | 9/1990 | Cremascoli |
| 4,963,155 A | 10/1990 | Lazzeri et al. |
| 4,976,740 A | 12/1990 | Kleiner |
| 4,978,349 A | 12/1990 | Frigg |
| 4,978,357 A | 12/1990 | Goymann et al. |
| 4,985,037 A | 1/1991 | Petersen |
| 4,994,085 A | 2/1991 | Sawai et al. |
| 4,995,883 A | 2/1991 | Demane et al. |
| 4,998,937 A | 3/1991 | Grimes |
| 5,002,578 A | 3/1991 | Luman |
| 5,002,581 A | 3/1991 | Paxson et al. |
| 5,007,935 A | 4/1991 | Vincent et al. |
| 5,019,108 A | 5/1991 | Bertin et al. |
| 5,021,062 A | 6/1991 | Adrey et al. |
| 5,026,280 A | 6/1991 | Durr et al. |
| 5,032,125 A | 7/1991 | Durham et al. |
| 5,032,130 A | 7/1991 | Schelhas et al. |
| 5,035,712 A | 7/1991 | Hoffman |
| 5,037,438 A | 8/1991 | Davidson |
| 5,037,441 A | 8/1991 | Bouvet |
| 5,047,033 A | 9/1991 | Fallin |
| 5,047,060 A | 9/1991 | Henssge et al. |
| 5,058,936 A | 10/1991 | Kapgan et al. |
| 5,080,676 A | 1/1992 | May |
| 5,080,677 A | 1/1992 | Shelley |
| 5,080,685 A | 1/1992 | Bolesky et al. |
| 5,087,260 A | 2/1992 | Fixel |
| 5,100,407 A | 3/1992 | Conrad et al. |
| 5,108,437 A | 4/1992 | Kenna |
| 5,108,451 A | 4/1992 | Forte |
| 5,108,452 A | 4/1992 | DeMane et al. |
| 5,116,379 A | 5/1992 | McLardy-Smith |
| 5,123,926 A | 6/1992 | Pisharodi |
| 5,133,760 A | 7/1992 | Petersen et al. |
| 5,133,771 A | 7/1992 | Duncan et al. |
| 5,133,772 A | 7/1992 | Hack et al. |
| 5,135,529 A | 8/1992 | Paxson et al. |
| 5,139,424 A | 8/1992 | Yli-Urpo |
| 5,152,796 A | 10/1992 | Slamin |
| 5,152,798 A | 10/1992 | Kranz |
| 5,156,624 A | 10/1992 | Barnes |
| 5,156,626 A | 10/1992 | Broderick et al. |
| 5,163,961 A | 11/1992 | Harwin |
| 5,167,663 A | 12/1992 | Brumfield |

| | | | | | | |
|---|---|---|---|---|---|---|
| 5,181,928 A * | 1/1993 | Bolesky et al. ............ 623/22.42 | 5,800,557 A | 9/1998 | Elhami |
| 5,190,546 A | 3/1993 | Jervis | 5,817,098 A | 10/1998 | Albrektsson et al. |
| 5,193,679 A | 3/1993 | White | 5,865,850 A | 2/1999 | Matthews |
| 5,194,066 A | 3/1993 | Van Zile | 5,871,547 A | 2/1999 | Abouaf et al. |
| 5,197,720 A | 3/1993 | Renz et al. | 5,876,446 A | 3/1999 | Agrawal et al. |
| 5,197,988 A | 3/1993 | Spotorno et al. | 5,876,459 A | 3/1999 | Powell |
| 5,197,989 A | 3/1993 | Hinckfuss et al. | 5,879,407 A | 3/1999 | Waggener |
| 5,201,769 A | 4/1993 | Schutzer | 5,888,206 A | 3/1999 | Lob et al. |
| 5,201,882 A | 4/1993 | Paxson | 5,888,208 A | 3/1999 | Ro |
| 5,211,666 A | 5/1993 | Fetto | 5,902,303 A | 5/1999 | Eckhof et al. |
| 5,217,499 A | 6/1993 | Shelley | 5,902,340 A | 5/1999 | White et al. |
| 5,222,984 A | 6/1993 | Forte | 5,904,720 A | 5/1999 | Farrar et al. |
| 5,259,249 A | 11/1993 | Fetto | 5,906,644 A | 5/1999 | Powell |
| 5,286,260 A | 2/1994 | Bolesky et al. | 5,928,235 A | 7/1999 | Friedl |
| 5,312,406 A | 5/1994 | Brumfield | 5,931,871 A | 8/1999 | Baur et al. |
| 5,314,479 A | 5/1994 | Rockwood, Jr. et al. | 5,961,555 A | 10/1999 | Huebner |
| 5,330,536 A | 7/1994 | Tager et al. | 5,972,032 A | 10/1999 | Lopez et al. |
| 5,336,268 A | 8/1994 | Rispeter | 5,980,575 A | 11/1999 | Albrektsson et al. |
| 5,342,366 A | 8/1994 | Whiteside et al. | 5,997,582 A | 12/1999 | Weiss |
| 5,344,457 A | 9/1994 | Pilliar et al. | 6,010,535 A | 1/2000 | Shah |
| 5,360,238 A | 11/1994 | Godfrey et al. | 6,045,555 A | 4/2000 | Smith et al. |
| 5,362,311 A | 11/1994 | Amino et al. | 6,059,830 A | 5/2000 | Lippincott, III et al. |
| 5,365,661 A | 11/1994 | Mizuno et al. | 6,067,701 A * | 5/2000 | Vandewalle ................. 29/558 |
| 5,370,706 A | 12/1994 | Bolesky et al. | 6,074,424 A | 6/2000 | Perrone, Jr. et al. |
| 5,376,124 A | 12/1994 | Gustke et al. | 6,102,953 A | 8/2000 | Huebner |
| 5,376,125 A | 12/1994 | Winkler | 6,126,661 A | 10/2000 | Faccioli et al. |
| 5,376,126 A | 12/1994 | Lin | 6,126,691 A | 10/2000 | Kasra et al. |
| 5,389,107 A | 2/1995 | Nassar et al. | 6,136,036 A | 10/2000 | Scholz |
| 5,390,683 A | 2/1995 | Pisharodi | 6,139,552 A | 10/2000 | Horiuchi |
| 5,407,494 A | 4/1995 | Post | 6,142,998 A | 11/2000 | Smith et al. |
| 5,413,610 A | 5/1995 | Amino et al. | 6,156,069 A | 12/2000 | Amstutz |
| 5,454,813 A | 10/1995 | Lawes | 6,165,177 A | 12/2000 | Wilson et al. |
| 5,458,654 A | 10/1995 | Tepic | 6,165,223 A | 12/2000 | Metzger et al. |
| 5,480,451 A | 1/1996 | Grundei et al. | 6,168,627 B1 | 1/2001 | Huebner |
| 5,489,309 A | 2/1996 | Lackey et al. | 6,168,828 B1 | 1/2001 | Chernyshov et al. |
| 5,489,311 A | 2/1996 | Cipolletti | 6,187,049 B1 * | 2/2001 | Fujikawa et al. ............ 623/22.4 |
| 5,507,817 A | 4/1996 | Craig et al. | 6,190,416 B1 * | 2/2001 | Choteau et al. ............ 623/22.12 |
| 5,507,825 A | 4/1996 | Frei | 6,193,758 B1 | 2/2001 | Huebner |
| 5,507,826 A | 4/1996 | Besselink et al. | 6,197,062 B1 | 3/2001 | Fenlin |
| 5,507,830 A | 4/1996 | DeMane et al. | 6,197,063 B1 | 3/2001 | Dews |
| 5,514,182 A | 5/1996 | Shea | 6,197,065 B1 | 3/2001 | Martin et al. |
| 5,531,748 A | 7/1996 | de la Caffiniere | 6,214,052 B1 | 4/2001 | Burkinshaw |
| 5,549,703 A | 8/1996 | Daigle et al. | 6,221,074 B1 | 4/2001 | Cole et al. |
| 5,549,704 A | 8/1996 | Sutter | 6,224,601 B1 | 5/2001 | Friedl |
| 5,549,706 A | 8/1996 | McCarthy | 6,228,086 B1 | 5/2001 | Wahl et al. |
| 5,562,666 A | 10/1996 | Brumfield | 6,228,121 B1 | 5/2001 | Khalili |
| 5,569,263 A | 10/1996 | Hein | 6,231,611 B1 | 5/2001 | Mosseri |
| 5,571,203 A | 11/1996 | Masini | 6,235,031 B1 | 5/2001 | Hodgeman et al. |
| 5,578,035 A * | 11/1996 | Lin ................................. 606/68 | 6,238,435 B1 | 5/2001 | Meulink et al. |
| 5,580,247 A | 12/1996 | Gittleman | 6,248,095 B1 | 6/2001 | Giambattista et al. |
| 5,580,352 A | 12/1996 | Sekel | 6,248,112 B1 | 6/2001 | Gambale et al. |
| 5,584,695 A | 12/1996 | Lal Sachdeva et al. | 6,261,290 B1 | 7/2001 | Friedl |
| 5,591,233 A * | 1/1997 | Kelman et al. ............ 623/23.51 | 6,264,699 B1 | 7/2001 | Noiles et al. |
| 5,593,451 A | 1/1997 | Averill et al. | 6,277,082 B1 | 8/2001 | Gambale |
| 5,597,378 A | 1/1997 | Jervis | 6,284,002 B1 | 9/2001 | Sotereanos |
| 5,624,445 A | 4/1997 | Burke | 6,299,648 B1 | 10/2001 | Doubler et al. |
| 5,645,600 A | 7/1997 | Bimman | 6,309,395 B1 | 10/2001 | Smith et al. |
| 5,645,607 A | 7/1997 | Hickey | 6,319,286 B1 | 11/2001 | Fernandez et al. |
| 5,653,765 A | 8/1997 | McTighe et al. | 6,330,845 B1 | 12/2001 | Meulink |
| 5,672,284 A | 9/1997 | Devanathan et al. | 6,355,068 B1 | 3/2002 | Doubler et al. |
| 5,697,932 A | 12/1997 | Smith et al. | 6,371,991 B1 | 4/2002 | Manasas et al. |
| 5,702,480 A | 12/1997 | Kropf et al. | 6,379,360 B1 | 4/2002 | Ackeret et al. |
| 5,702,483 A | 12/1997 | Kwong | 6,379,388 B1 | 4/2002 | Ensign et al. |
| 5,713,902 A | 2/1998 | Friedl | 6,383,225 B2 | 5/2002 | Masini |
| 5,725,592 A | 3/1998 | White et al. | 6,383,227 B1 | 5/2002 | Baroud et al. |
| 5,725,595 A | 3/1998 | Gustilo | 6,409,730 B1 | 6/2002 | Green et al. |
| 5,725,597 A | 3/1998 | Hwang | 6,409,768 B1 | 6/2002 | Tepic et al. |
| 5,728,128 A | 3/1998 | Crickenberger et al. | 6,423,066 B1 | 7/2002 | Harder et al. |
| 5,735,905 A | 4/1998 | Parr | 6,428,578 B2 | 8/2002 | White |
| 5,741,262 A | 4/1998 | Albrektsson et al. | 6,432,110 B1 | 8/2002 | Richelsoph |
| 5,755,789 A * | 5/1998 | Deckner ................. 623/11.11 | 6,432,126 B1 | 8/2002 | Gambale et al. |
| 5,755,807 A | 5/1998 | Anstaett et al. | 6,432,141 B1 | 8/2002 | Stocks et al. |
| 5,755,810 A | 5/1998 | Cunningham | 6,440,171 B1 | 8/2002 | Doubler et al. |
| 5,766,262 A | 6/1998 | Mikhail | 6,443,954 B1 | 9/2002 | Bramlet et al. |
| 5,766,263 A | 6/1998 | Grundei et al. | 6,458,092 B1 | 10/2002 | Gambale et al. |
| 5,776,200 A | 7/1998 | Johnson et al. | 6,464,728 B1 | 10/2002 | Murray |
| 5,782,921 A | 7/1998 | Colleran et al. | 6,468,278 B1 | 10/2002 | Muckter |
| 5,800,553 A | 9/1998 | Albrektsson et al. | 6,479,565 B1 | 11/2002 | Stanley |
| 5,800,554 A | 9/1998 | Scholz | 6,482,237 B2 | 11/2002 | Mosseri |

| Patent No. | Date | Name |
|---|---|---|
| 6,494,913 B1 | 12/2002 | Huebner |
| 6,494,918 B1 | 12/2002 | Pope et al. |
| 6,503,252 B2 | 1/2003 | Hansson |
| 6,503,255 B1 | 1/2003 | Albrektsson et al. |
| 6,508,841 B2 | 1/2003 | Martin et al. |
| 6,517,541 B1 | 2/2003 | Sesic |
| 6,524,342 B1 | 2/2003 | Muhlhausler et al. |
| 6,607,561 B2 | 8/2003 | Brannon |
| 6,610,095 B1 | 8/2003 | Pope et al. |
| 6,610,099 B1 * | 8/2003 | Albrektsson et al. ...... 623/23.15 |
| 6,616,697 B2 | 9/2003 | Sotereanos |
| 6,620,170 B1 | 9/2003 | Ahern |
| 6,648,889 B2 | 11/2003 | Bramlet et al. |
| 6,656,187 B1 | 12/2003 | Camino |
| 6,682,568 B2 | 1/2004 | Despres, III et al. |
| 6,692,520 B1 | 2/2004 | Gambale et al. |
| 6,692,530 B2 | 2/2004 | Doubler et al. |
| 6,695,850 B2 | 2/2004 | Diaz |
| 6,695,883 B2 | 2/2004 | Crofford |
| 6,699,293 B2 | 3/2004 | White |
| 6,702,854 B1 | 3/2004 | Cheal et al. |
| 6,706,072 B2 | 3/2004 | Dwyer et al. |
| 6,706,073 B2 | 3/2004 | Draenert et al. |
| 6,709,425 B2 | 3/2004 | Gambale et al. |
| 6,712,855 B2 | 3/2004 | Martin et al. |
| 6,719,805 B1 | 4/2004 | Ahern |
| 6,723,129 B2 | 4/2004 | Dwyer et al. |
| 6,755,862 B2 | 6/2004 | Keynan |
| 6,755,865 B2 | 6/2004 | Tarabishy |
| 6,758,864 B2 | 7/2004 | Storer et al. |
| 6,764,108 B2 | 7/2004 | Ernst et al. |
| 6,786,929 B2 | 9/2004 | Gambale et al. |
| 6,800,095 B1 | 10/2004 | Pope et al. |
| 6,802,858 B2 | 10/2004 | Gambale et al. |
| 6,843,806 B2 | 1/2005 | Hayes, Jr. et al. |
| 6,851,160 B2 | 2/2005 | Carver |
| 6,866,683 B2 | 3/2005 | Gerbec et al. |
| 6,875,239 B2 | 4/2005 | Gerbec et al. |
| 6,887,276 B2 | 5/2005 | Gerbec et al. |
| 6,902,583 B2 | 6/2005 | Gerbec et al. |
| 6,905,502 B2 | 6/2005 | Penenberg |
| 6,913,623 B1 | 7/2005 | Zhu |
| 6,949,117 B2 | 9/2005 | Gambale et al. |
| 6,953,479 B2 | 10/2005 | Carson et al. |
| 6,969,406 B2 | 11/2005 | Tornier |
| 6,974,483 B2 | 12/2005 | Murray |
| 6,976,999 B2 | 12/2005 | Charlebois et al. |
| 6,986,790 B2 | 1/2006 | Ball et al. |
| 6,988,784 B2 | 1/2006 | Silverbrook |
| 6,991,656 B2 | 1/2006 | Mears |
| 7,004,972 B2 | 2/2006 | Yoon |
| 7,033,399 B2 | 4/2006 | Doubler et al. |
| 7,044,974 B2 | 5/2006 | Garber et al. |
| 7,044,975 B2 | 5/2006 | Cheal et al. |
| 7,097,664 B2 | 8/2006 | Despres, III et al. |
| 7,104,995 B2 | 9/2006 | Crofford |
| 7,135,044 B2 | 11/2006 | Bassik et al. |
| 7,141,073 B2 | 11/2006 | May et al. |
| 7,156,879 B1 | 1/2007 | Albrektsson et al. |
| 7,169,184 B2 | 1/2007 | Dalla Pria |
| 7,179,297 B2 | 2/2007 | McLean |
| 7,211,113 B2 | 5/2007 | Zelener et al. |
| 7,235,106 B2 | 6/2007 | Daniels et al. |
| 7,247,171 B2 | 7/2007 | Sotereanos |
| 7,255,716 B2 | 8/2007 | Pubols et al. |
| 7,273,499 B2 | 9/2007 | McCleary et al. |
| 7,297,166 B2 | 11/2007 | Dwyer et al. |
| 7,306,600 B2 | 12/2007 | Roth et al. |
| 7,338,286 B2 | 3/2008 | Porter et al. |
| 7,455,673 B2 | 11/2008 | Gotfried |
| 7,468,078 B2 | 12/2008 | Sederholm et al. |
| 7,494,509 B1 | 2/2009 | Hershberger et al. |
| 7,503,919 B2 * | 3/2009 | Shaw .................. 606/65 |
| 7,520,947 B2 | 4/2009 | Kennedy et al. |
| 7,527,627 B2 * | 5/2009 | Ferrante et al. .................. 606/64 |
| 7,569,075 B2 | 8/2009 | Johnson et al. |
| 7,572,294 B2 | 8/2009 | Meridew et al. |
| 7,582,092 B2 | 9/2009 | Jones et al. |
| D601,701 S | 10/2009 | Gotfried |
| 7,608,109 B2 | 10/2009 | Dalla Pria |
| 7,608,112 B1 * | 10/2009 | Kuczynski et al. ........ 623/22.11 |
| 7,648,078 B2 | 1/2010 | Kempf et al. |
| 7,655,162 B2 | 2/2010 | Kumar |
| 7,695,474 B2 | 4/2010 | Crofford |
| 7,695,521 B2 | 4/2010 | Ely et al. |
| 7,753,961 B2 * | 7/2010 | Chen et al. .................. 623/22.46 |
| 7,766,968 B2 | 8/2010 | Sweeney |
| 7,776,098 B2 | 8/2010 | Murphy |
| 7,794,503 B2 | 9/2010 | Daniels et al. |
| 7,799,029 B2 | 9/2010 | Jones |
| 7,828,851 B2 | 11/2010 | McCleary et al. |
| 7,833,275 B2 | 11/2010 | Mears et al. |
| 7,842,096 B2 | 11/2010 | Fridshtand et al. |
| 7,850,690 B2 * | 12/2010 | Frigg et al. ...................... 606/67 |
| 7,854,767 B2 | 12/2010 | May et al. |
| 7,901,411 B2 | 3/2011 | Frederick et al. |
| 7,909,881 B2 | 3/2011 | Boucher et al. |
| 7,914,584 B2 | 3/2011 | Bigsby et al. |
| 7,947,135 B2 | 5/2011 | Fonte |
| 7,955,396 B2 | 6/2011 | Terrill |
| 7,998,217 B1 | 8/2011 | Brown |
| 7,998,218 B1 | 8/2011 | Brown |
| 8,029,573 B2 * | 10/2011 | Podolsky ................... 623/22.42 |
| 8,052,755 B2 | 11/2011 | Naidu |
| 8,062,378 B2 | 11/2011 | Fonte |
| 8,066,779 B2 | 11/2011 | Gibbs et al. |
| 8,095,198 B2 | 1/2012 | Nycz et al. |
| 8,114,166 B2 | 2/2012 | Auxepaules et al. |
| 8,133,284 B2 | 3/2012 | Ely et al. |
| 8,137,486 B2 | 3/2012 | Fonte |
| 8,152,669 B2 | 4/2012 | Maguire et al. |
| 8,152,814 B2 | 4/2012 | Jones et al. |
| 8,182,484 B2 | 5/2012 | Grant et al. |
| RE43,482 E | 6/2012 | Mikol et al. |
| 8,211,183 B2 * | 7/2012 | Podolsky ................... 623/22.15 |
| 8,257,835 B2 | 9/2012 | Jani et al. |
| 8,262,709 B1 | 9/2012 | Powlan |
| 8,282,646 B2 | 10/2012 | Schoenefeld et al. |
| 8,303,590 B2 | 11/2012 | Elghazaly et al. |
| 8,303,668 B2 | 11/2012 | Despres, III et al. |
| 8,323,346 B2 | 12/2012 | Tepic |
| 8,323,349 B2 | 12/2012 | Schmid |
| 8,355,965 B2 | 1/2013 | Yamada |
| 8,357,205 B2 | 1/2013 | Rahaman et al. |
| 8,377,133 B2 | 2/2013 | Yuan et al. |
| 8,398,719 B2 | 3/2013 | Walter et al. |
| 8,398,790 B2 | 3/2013 | Fonte |
| 8,454,606 B2 * | 6/2013 | Frigg et al. ...................... 606/64 |
| 8,562,690 B1 | 10/2013 | Dickerson |
| 8,579,985 B2 * | 11/2013 | Podolsky et al. .......... 623/22.42 |
| 8,906,102 B2 | 12/2014 | Viscardi et al. |
| 2001/0008981 A1 | 7/2001 | Masini |
| 2001/0027345 A1 | 10/2001 | Merrill et al. |
| 2001/0049559 A1 | 12/2001 | Koo et al. |
| 2001/0049561 A1 | 12/2001 | Dews et al. |
| 2001/0051831 A1 | 12/2001 | Subba Rao et al. |
| 2002/0004685 A1 | 1/2002 | White |
| 2002/0007220 A1 | 1/2002 | Gie et al. |
| 2002/0038148 A1 | 3/2002 | Fernandez et al. |
| 2002/0040244 A1 | 4/2002 | Despres et al. |
| 2002/0045900 A1 | 4/2002 | Harder et al. |
| 2002/0049500 A1 | 4/2002 | Draenert |
| 2002/0058999 A1 | 5/2002 | Dwyer et al. |
| 2002/0072799 A1 | 6/2002 | Despres et al. |
| 2002/0072802 A1 | 6/2002 | O'Neil et al. |
| 2002/0103541 A1 | 8/2002 | Meyers et al. |
| 2002/0120340 A1 | 8/2002 | Metzger et al. |
| 2002/0120343 A1 | 8/2002 | Doubler et al. |
| 2002/0133234 A1 | 9/2002 | Sotereanos |
| 2002/0143333 A1 | 10/2002 | von Hoffmann et al. |
| 2002/0151984 A1 | 10/2002 | White |
| 2002/0156473 A1 * | 10/2002 | Bramlet et al. .................. 606/62 |
| 2002/0173792 A1 | 11/2002 | Severns et al. |
| 2003/0014119 A1 | 1/2003 | Capon et al. |
| 2003/0014123 A1 | 1/2003 | Copf et al. |
| 2003/0050704 A1 | 3/2003 | Keynan |
| 2003/0050706 A1 | 3/2003 | Draenert et al. |
| 2003/0071819 A1 | 4/2003 | Kondo et al. |

| | | |
|---|---|---|
| 2003/0074000 A1 | 4/2003 | Roth et al. |
| 2003/0074079 A1 | 4/2003 | McTighe et al. |
| 2003/0074083 A1 | 4/2003 | LeGros et al. |
| 2003/0088145 A1 | 5/2003 | Scott |
| 2003/0125808 A1 | 7/2003 | Hunter et al. |
| 2003/0130741 A1 | 7/2003 | McMinn |
| 2003/0171819 A1 | 9/2003 | Sotereanos |
| 2003/0181987 A1 | 9/2003 | Muirhead-Allwood |
| 2003/0204268 A1 | 10/2003 | Gerbec et al. |
| 2004/0054419 A1 | 3/2004 | Serra et al. |
| 2004/0064188 A1 | 4/2004 | Ball et al. |
| 2004/0068324 A1 | 4/2004 | Grundei |
| 2004/0107594 A1 | 6/2004 | Afriat |
| 2004/0122525 A1 | 6/2004 | Daniels et al. |
| 2004/0162621 A1 | 8/2004 | Crofford |
| 2004/0199259 A1 | 10/2004 | Pichon et al. |
| 2004/0210317 A1 | 10/2004 | Maroney et al. |
| 2004/0220673 A1 | 11/2004 | Pria |
| 2004/0260290 A1 | 12/2004 | Zander et al. |
| 2004/0267267 A1 | 12/2004 | Daniels et al. |
| 2004/0267372 A1 | 12/2004 | Vanasse et al. |
| 2004/0267373 A1 | 12/2004 | Dwyer et al. |
| 2005/0010223 A1 | 1/2005 | Gotfried |
| 2005/0010230 A1 | 1/2005 | Crofford |
| 2005/0015154 A1 | 1/2005 | Lindsey et al. |
| 2005/0049713 A1 | 3/2005 | Garber et al. |
| 2005/0125067 A1 | 6/2005 | Sweeney |
| 2005/0149047 A1 | 7/2005 | Parry et al. |
| 2005/0177159 A1 | 8/2005 | Guzman et al. |
| 2005/0203536 A1 | 9/2005 | Laffargue et al. |
| 2005/0283254 A1 | 12/2005 | Hayes et al. |
| 2006/0004465 A1 | 1/2006 | Bergin et al. |
| 2006/0030947 A1 | 2/2006 | Mears et al. |
| 2006/0052877 A9 | 3/2006 | Doubler et al. |
| 2006/0106463 A1 | 5/2006 | Bigsby et al. |
| 2006/0149247 A1 | 7/2006 | Frigg et al. |
| 2006/0155281 A1* | 7/2006 | Kaup et al. ............... 606/65 |
| 2006/0161262 A1 | 7/2006 | Chen et al. |
| 2006/0167557 A1 | 7/2006 | Terrill |
| 2006/0173548 A1 | 8/2006 | Auxepaules et al. |
| 2006/0173549 A1 | 8/2006 | Ragbir |
| 2006/0224245 A1* | 10/2006 | Siebel ................ 623/22.11 |
| 2006/0241606 A1 | 10/2006 | Vachtenberg et al. |
| 2007/0038306 A1* | 2/2007 | O—Gara ............... 623/22.42 |
| 2007/0043446 A1 | 2/2007 | Murray |
| 2007/0043448 A1 | 2/2007 | Murray |
| 2007/0050041 A1 | 3/2007 | Dietz et al. |
| 2007/0055381 A1 | 3/2007 | Berelsman et al. |
| 2007/0078464 A1 | 4/2007 | Jones et al. |
| 2007/0078519 A1* | 4/2007 | Klotz ................ 623/23.47 |
| 2007/0112430 A1 | 5/2007 | Simmen et al. |
| 2007/0142921 A1 | 6/2007 | Lewis et al. |
| 2007/0173838 A1 | 7/2007 | Li |
| 2007/0179568 A1 | 8/2007 | Nycz et al. |
| 2007/0179624 A1 | 8/2007 | Stone et al. |
| 2007/0198094 A1 | 8/2007 | Berelsman et al. |
| 2007/0219640 A1 | 9/2007 | Steinberg |
| 2007/0244566 A1 | 10/2007 | Daniels et al. |
| 2007/0244567 A1 | 10/2007 | Yang et al. |
| 2007/0255420 A1 | 11/2007 | Johnson et al. |
| 2007/0270846 A1 | 11/2007 | Metzinger |
| 2007/0270847 A1 | 11/2007 | Shaw |
| 2008/0051790 A1 | 2/2008 | Defossez |
| 2008/0133023 A1 | 6/2008 | Schlotterback et al. |
| 2008/0140077 A1* | 6/2008 | Kebaish ............... 606/64 |
| 2008/0140210 A1 | 6/2008 | Doubler et al. |
| 2008/0147066 A1 | 6/2008 | Longsworth et al. |
| 2008/0243264 A1 | 10/2008 | Fonte |
| 2008/0262498 A1 | 10/2008 | Fernandez Dell'Oca |
| 2008/0262629 A1 | 10/2008 | Fonte |
| 2009/0005876 A1 | 1/2009 | Dietz et al. |
| 2009/0076619 A1 | 3/2009 | Grappiolo et al. |
| 2009/0088862 A1 | 4/2009 | Thomas et al. |
| 2009/0088863 A1 | 4/2009 | Boucher et al. |
| 2009/0093887 A1 | 4/2009 | Walter et al. |
| 2009/0112330 A1 | 4/2009 | Grundei |
| 2009/0118837 A1 | 5/2009 | Winslow et al. |
| 2009/0125028 A1 | 5/2009 | Teisen et al. |
| 2009/0149963 A1 | 6/2009 | Sekel |
| 2009/0171466 A1 | 7/2009 | Frazee et al. |
| 2009/0187255 A1 | 7/2009 | Jani et al. |
| 2009/0204226 A1 | 8/2009 | Fonte |
| 2009/0264885 A1 | 10/2009 | Grant et al. |
| 2009/0270996 A1 | 10/2009 | Meulink et al. |
| 2009/0281630 A1 | 11/2009 | Delince et al. |
| 2009/0287214 A1 | 11/2009 | Yu |
| 2009/0306787 A1 | 12/2009 | Crabtree et al. |
| 2009/0326534 A1 | 12/2009 | Yamazaki et al. |
| 2010/0063504 A1 | 3/2010 | Munro et al. |
| 2010/0094293 A1 | 4/2010 | McClellan et al. |
| 2010/0100193 A1 | 4/2010 | White |
| 2010/0114324 A1 | 5/2010 | Gibbs et al. |
| 2010/0137863 A1 | 6/2010 | Munro |
| 2010/0161069 A1 | 6/2010 | Ragbir |
| 2010/0174284 A1* | 7/2010 | Schwammberger et al. ... 606/62 |
| 2010/0174377 A1 | 7/2010 | Heuer |
| 2010/0174380 A1 | 7/2010 | Lewis |
| 2010/0179551 A1 | 7/2010 | Keller et al. |
| 2010/0179662 A1 | 7/2010 | Verne et al. |
| 2010/0191344 A1 | 7/2010 | Grundei et al. |
| 2010/0217265 A1 | 8/2010 | Chen et al. |
| 2010/0222891 A1 | 9/2010 | Goodfried et al. |
| 2010/0228354 A1 | 9/2010 | Ely et al. |
| 2010/0241239 A1 | 9/2010 | Smith |
| 2010/0249781 A1 | 9/2010 | Haidukewych et al. |
| 2010/0249852 A1* | 9/2010 | Brumfield et al. ........... 606/282 |
| 2010/0249943 A1 | 9/2010 | Bergin et al. |
| 2010/0256638 A1 | 10/2010 | Tyber et al. |
| 2010/0256758 A1 | 10/2010 | Gordon et al. |
| 2010/0268229 A1 | 10/2010 | Siravo et al. |
| 2011/0009965 A1 | 1/2011 | Ankem |
| 2011/0009976 A1* | 1/2011 | Cruchet .................. 623/22.46 |
| 2011/0015752 A1 | 1/2011 | Meridew |
| 2011/0035021 A1 | 2/2011 | Bergin et al. |
| 2011/0046745 A1 | 2/2011 | Daniels et al. |
| 2011/0054474 A1 | 3/2011 | Metzinger et al. |
| 2011/0054626 A1 | 3/2011 | Thomas et al. |
| 2011/0060337 A1 | 3/2011 | Ferrante et al. |
| 2011/0066253 A1 | 3/2011 | Langhorn et al. |
| 2011/0087228 A1 | 4/2011 | Ferrante et al. |
| 2011/0106270 A1 | 5/2011 | Huff et al. |
| 2011/0166665 A1 | 7/2011 | Podolsky |
| 2011/0192563 A1 | 8/2011 | Fonte |
| 2011/0196369 A1 | 8/2011 | Osman |
| 2011/0196372 A1 | 8/2011 | Murase |
| 2011/0218641 A1 | 9/2011 | Smith et al. |
| 2011/0257758 A1 | 10/2011 | Smith et al. |
| 2011/0264233 A1* | 10/2011 | Song .................... 623/22.42 |
| 2011/0282395 A1* | 11/2011 | Beyar et al. .............. 606/301 |
| 2012/0010720 A1 | 1/2012 | Dickerson |
| 2012/0022661 A1 | 1/2012 | McLean |
| 2012/0065737 A1 | 3/2012 | Chow |
| 2012/0116529 A1* | 5/2012 | Forsell .................. 623/23.11 |
| 2012/0123554 A1 | 5/2012 | Fonte |
| 2012/0130502 A1 | 5/2012 | Podolsky et al. |
| 2012/0157997 A1* | 6/2012 | Sohngen .................. 606/64 |
| 2012/0172992 A1 | 7/2012 | Fockens |
| 2012/0191092 A1* | 7/2012 | Buettler et al. .............. 606/64 |
| 2012/0226283 A1 | 9/2012 | Meridew et al. |
| 2012/0226361 A1 | 9/2012 | Podolsky |
| 2012/0265202 A1 | 10/2012 | Schwammberger et al. |
| 2013/0030543 A1 | 1/2013 | Morrey et al. |
| 2013/0060347 A1 | 3/2013 | McMinn |
| 2013/0073050 A1 | 3/2013 | McEntire et al. |
| 2013/0079888 A1 | 3/2013 | Meulink |
| 2013/0204392 A1 | 8/2013 | Podolsky .................. 623/22.42 |
| 2013/0261762 A1 | 10/2013 | Kennedy |
| 2013/0310947 A1* | 11/2013 | Cremascoli et al. ........ 623/23.35 |
| 2013/0338780 A1 | 12/2013 | Berchoux et al. |
| 2014/0114425 A1 | 4/2014 | Ekelund et al. |
| 2014/0128986 A1 | 5/2014 | Podolsky |
| 2014/0180289 A1* | 6/2014 | Lee et al. ................ 606/64 |

FOREIGN PATENT DOCUMENTS

| | | |
|---|---|---|
| DE | 2854334 | 6/1980 |
| DE | 3205577 | 10/1982 |
| DE | 3340767 | 5/1985 |

| | | | | | | |
|---|---|---|---|---|---|---|
| DE | 8701164 U1 | 6/1987 | EP | 1004283 A2 | 5/2000 |
| DE | 4031520 | 4/1992 | EP | 1132064 A2 | 9/2001 |
| DE | 19505609 | 8/1996 | EP | 1240879 A2 | 9/2002 |
| DE | 19610741 C1 | 11/1997 | EP | 1344505 A2 | 9/2003 |
| DE | 19723339 | 12/1998 | FR | 1099519 A | 9/1955 |
| DE | 19852945 | 5/2000 | FR | 1122634 A | 9/1956 |
| DE | 20007950 U1 | 7/2000 | FR | 2183230 | 12/1973 |
| DE | 10120331 | 11/2002 | FR | 2225141 | 11/1974 |
| DE | 10223474 | 12/2003 | FR | 2575383 | 7/1986 |
| DE | 102005005657 | 8/2006 | FR | 2629707 | 10/1989 |
| EP | 000549 | 2/1979 | FR | 2639820 | 6/1990 |
| EP | 010527 | 4/1980 | FR | 2646078 | 12/1990 |
| EP | 023608 | 2/1981 | FR | 2647669 A1 | 12/1990 |
| EP | 024008 | 2/1981 | FR | 2651118 | 3/1991 |
| EP | 071242 A2 | 2/1983 | FR | 2674119 | 9/1992 |
| EP | 099167 | 1/1984 | FR | 2705558 | 12/1994 |
| EP | 251583 A2 | 1/1988 | GB | 2209947 A | 6/1989 |
| EP | 257118 | 3/1988 | IE | 201407 | 11/1986 |
| EP | 257359 | 3/1988 | IE | 832620 A2 | 4/1998 |
| EP | 283706 | 9/1988 | RU | 2108071 C1 | 4/1998 |
| EP | 321170 | 6/1989 | RU | 2108766 C1 | 4/1998 |
| EP | 338774 A2 | 10/1989 | WO | WO-85/05027 | 11/1985 |
| EP | 359457 | 3/1990 | WO | WO-93/08770 | 5/1993 |
| EP | 376658 A2 | 7/1990 | WO | WO-94/17757 | 8/1994 |
| EP | 382395 | 8/1990 | WO | WO-96/13233 | 5/1996 |
| EP | 399920 | 11/1990 | WO | WO-00/72785 A2 | 12/2000 |
| EP | 433121 | 6/1991 | WO | WO-01/49218 A2 | 7/2001 |
| EP | 441577 A2 | 8/1991 | WO | WO-03/094763 | 11/2003 |
| EP | 464961 A2 | 1/1992 | | | |
| EP | 495340 | 7/1992 | | | |
| EP | 556997 | 8/1993 | | | |
| EP | 567349 | 10/1993 | | | |
| EP | 586824 | 3/1994 | | | |
| EP | 714645 | 6/1996 | | | |
| EP | 878177 A2 | 11/1998 | | | |
| EP | 913132 | 5/1999 | | | |

OTHER PUBLICATIONS

Prokhorov, "Sovetskaya entisklopediya," Bolshaya sovetskaya entsiklopediya, Moscow, 1972, tom 8, p. 455-456, col. 1354, paragraph 1.

* cited by examiner

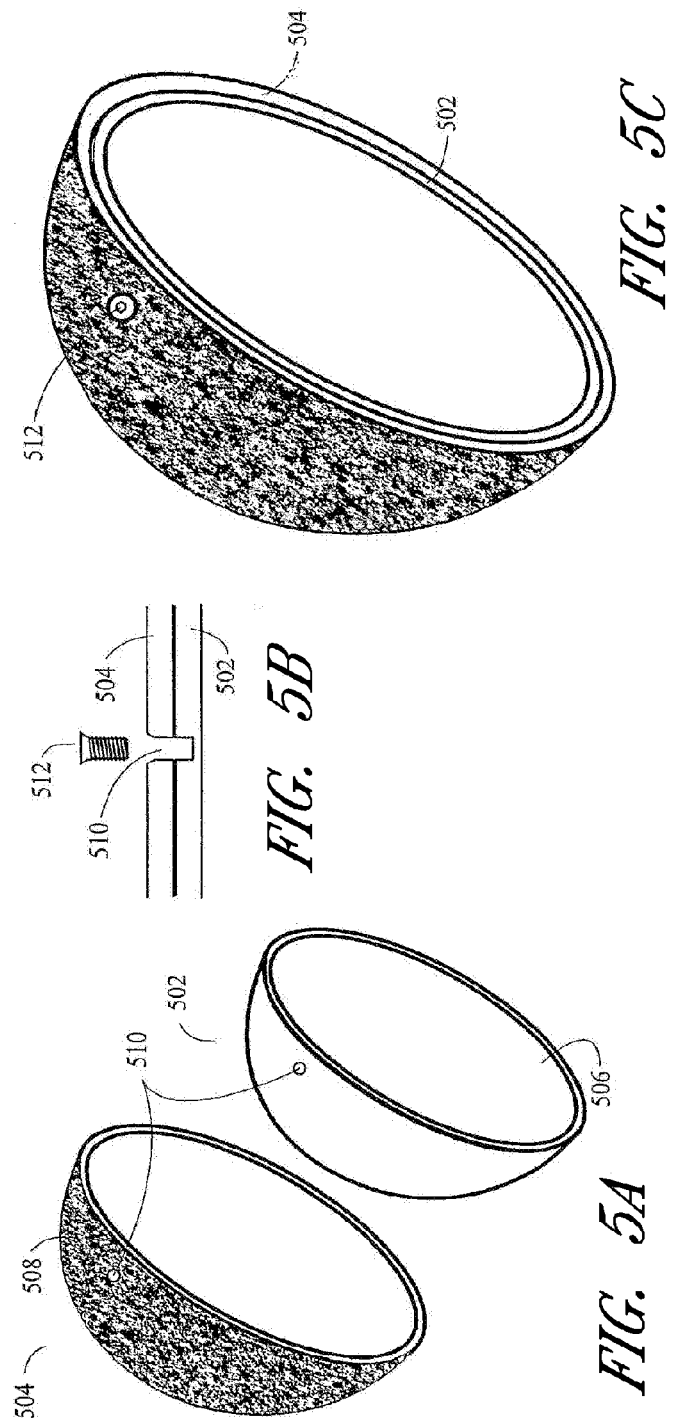

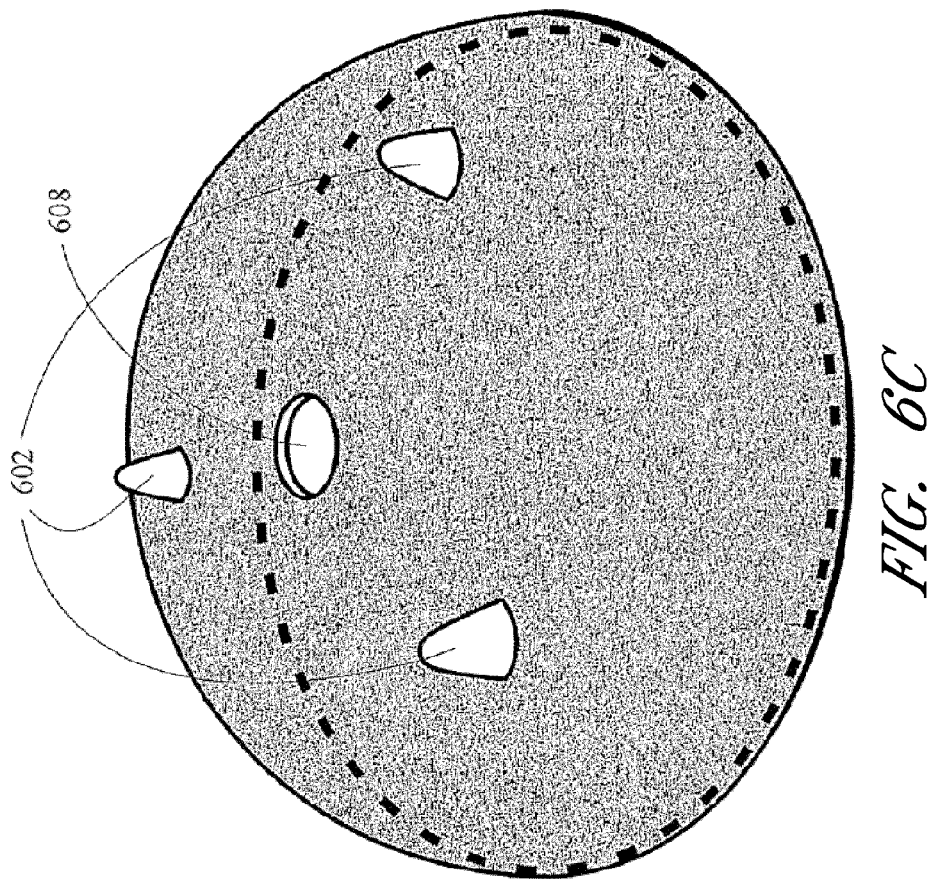
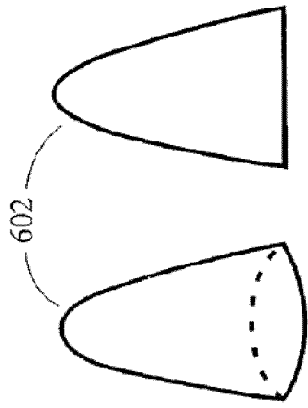
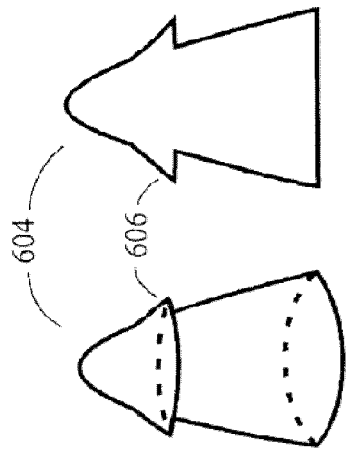
FIG. 6C
FIG. 6A
FIG. 6B

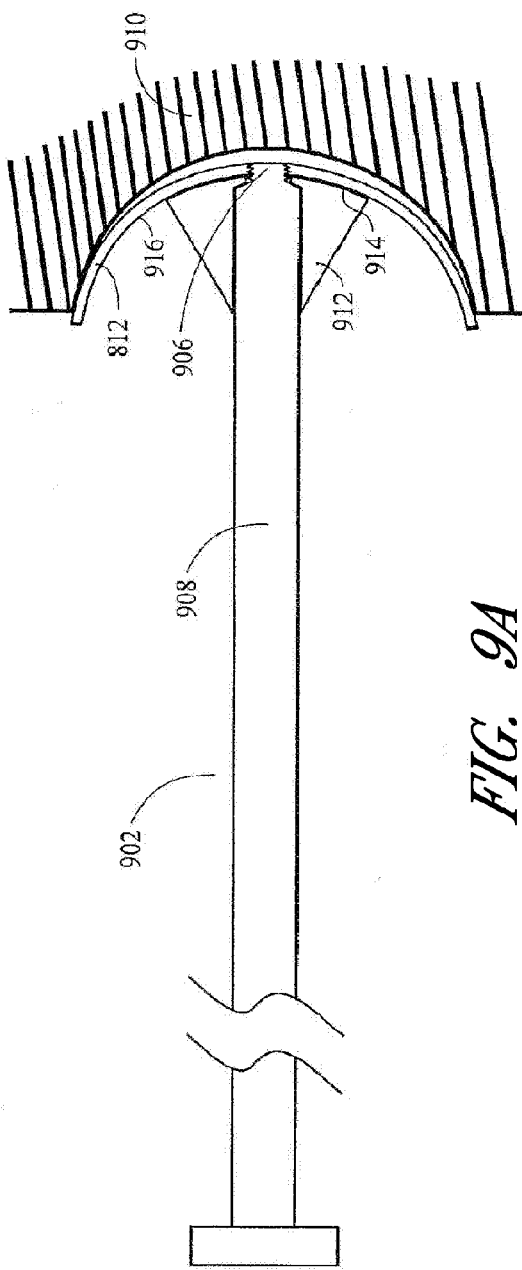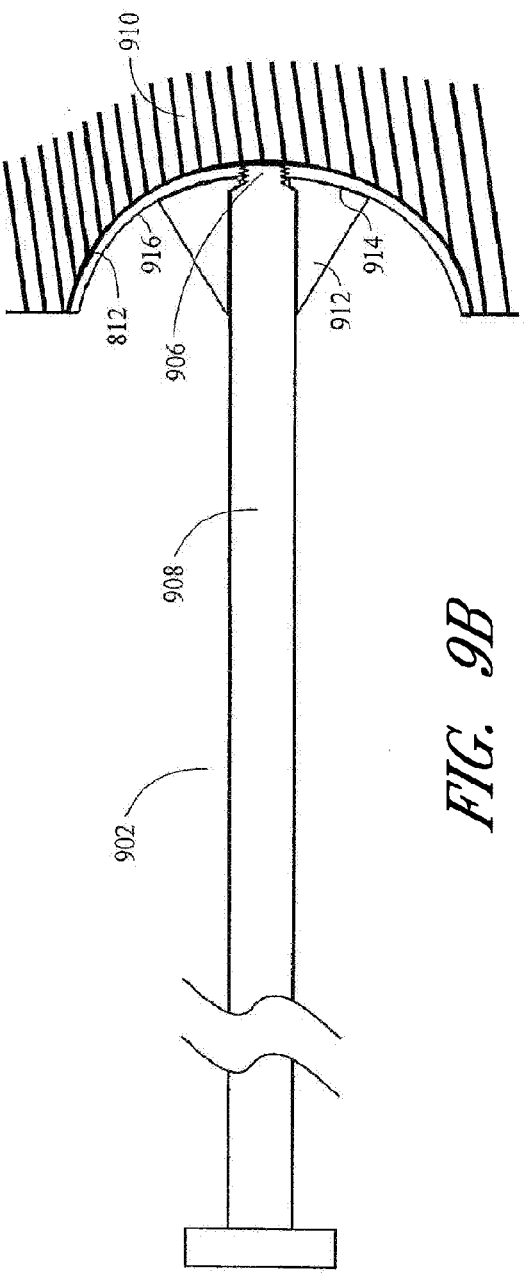

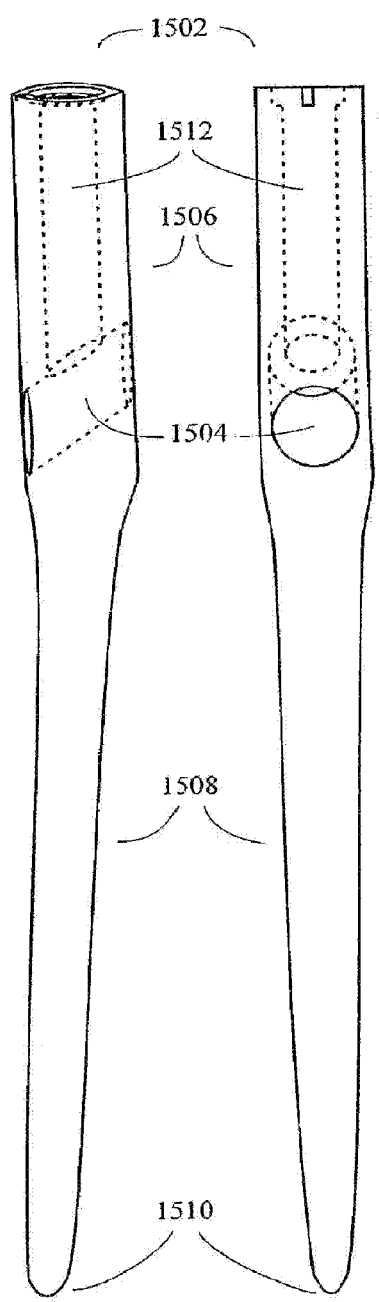
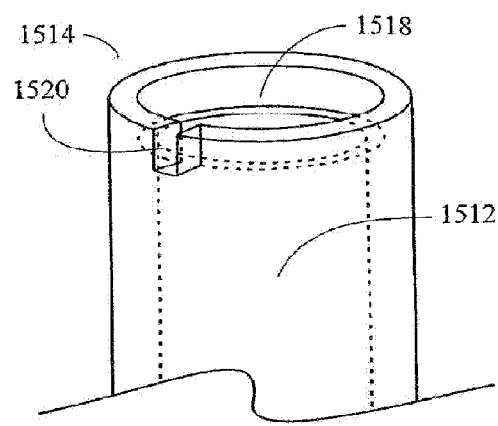
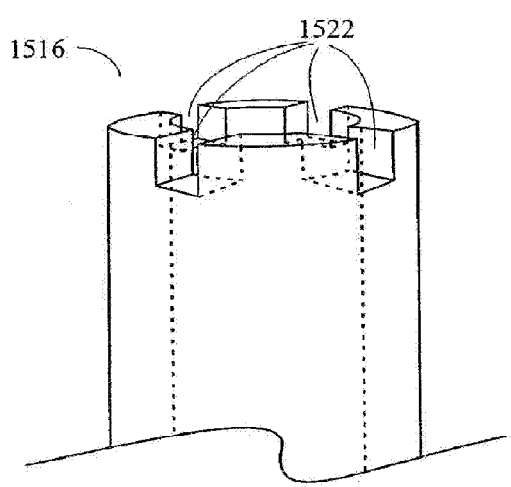
FIG. 15A  FIG. 15B  FIG. 15C  FIG. 15D

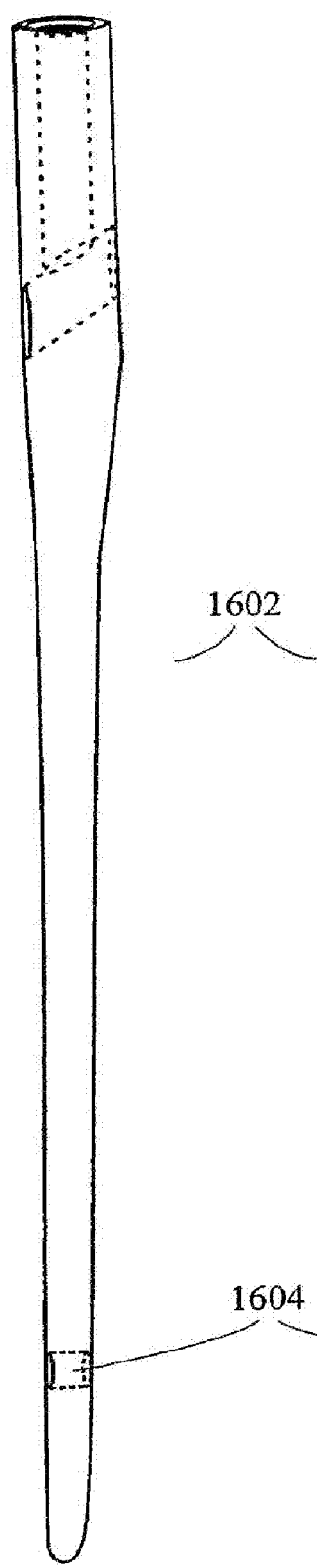
*FIG. 16A*     *FIG. 16B*

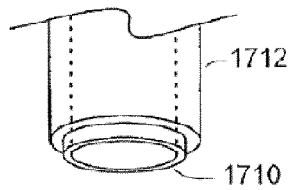
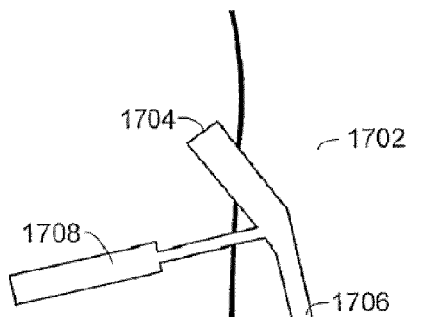
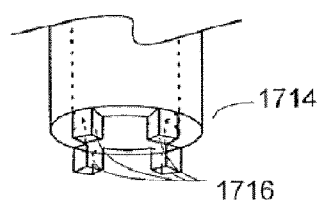
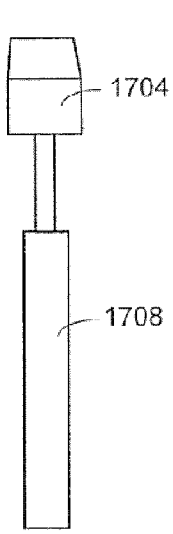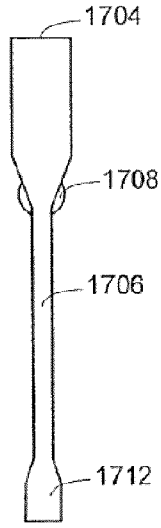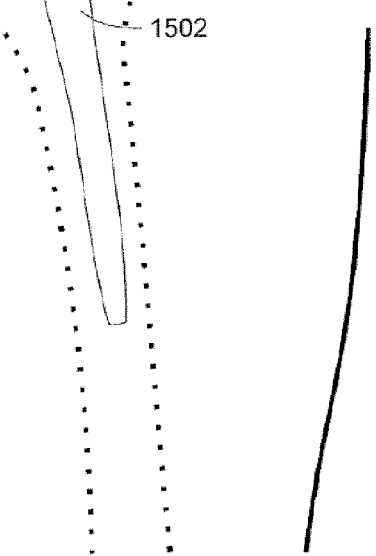
FIG. 17D
FIG. 17E
FIG. 17B  FIG. 17C  FIG. 17A

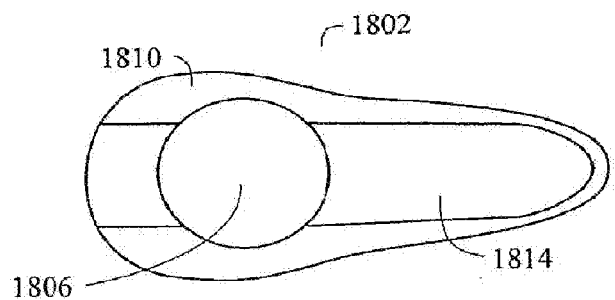
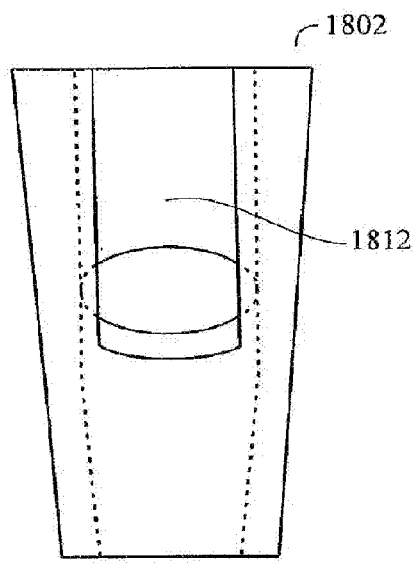
FIG. 18A
FIG. 18B
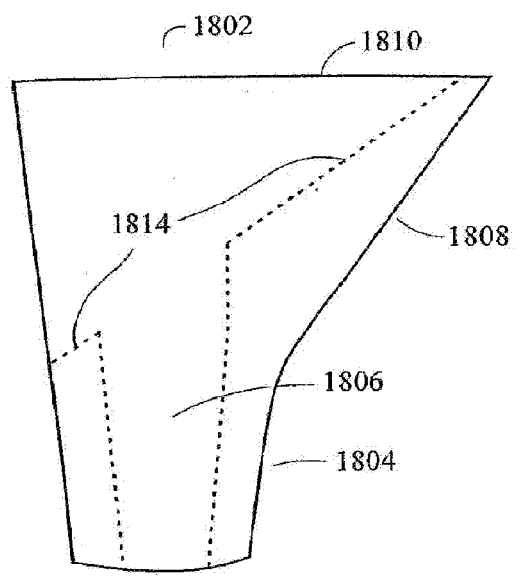
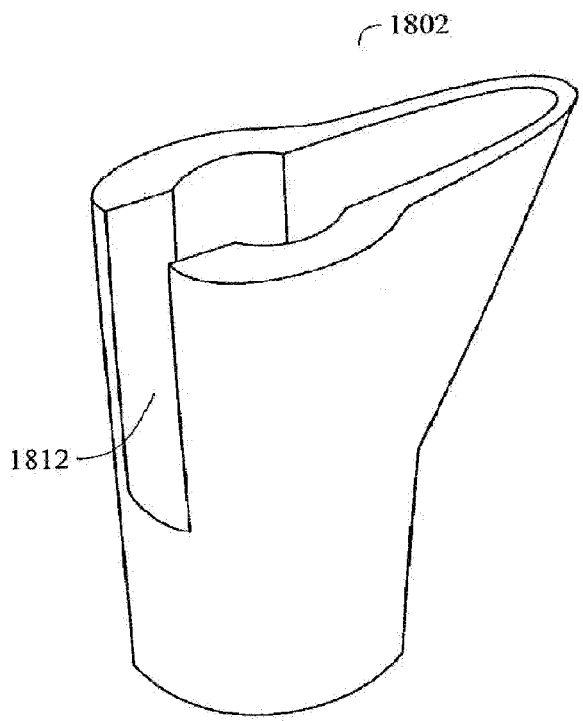
FIG. 18C
FIG. 18D

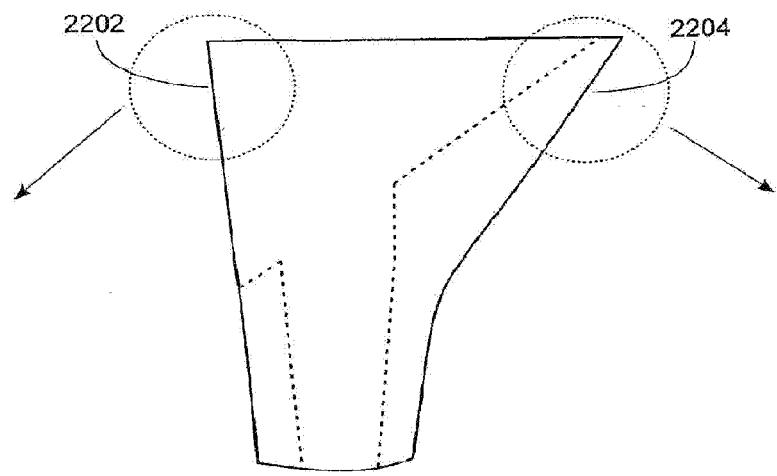
FIG. 22A
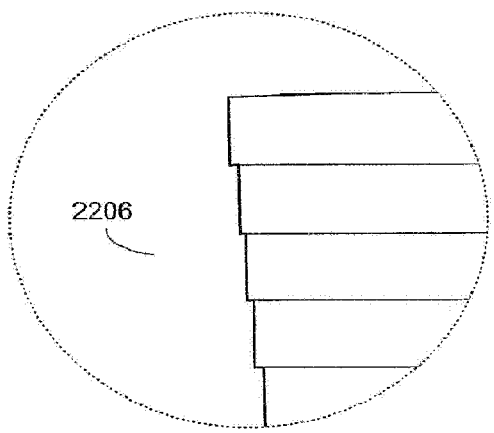 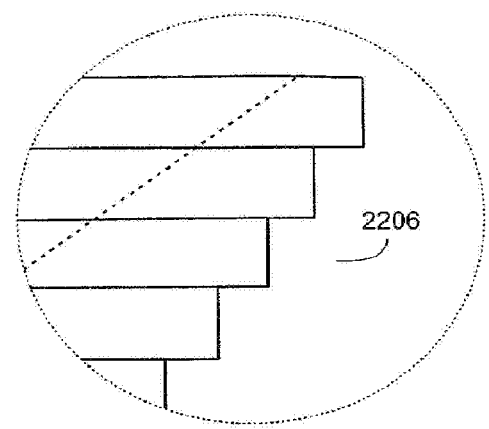
FIG. 22B　　　FIG. 22C

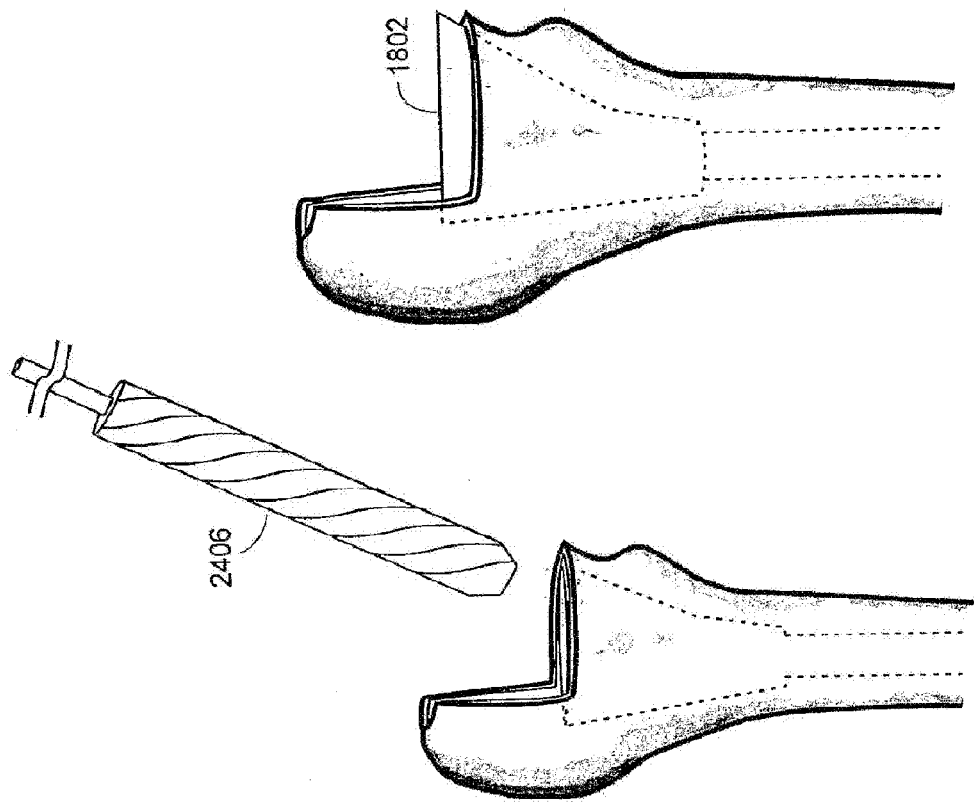
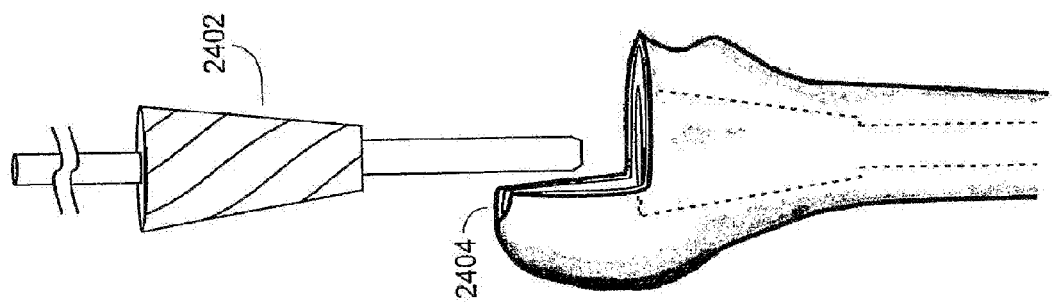
FIG. 24A  FIG. 24B  FIG. 24C

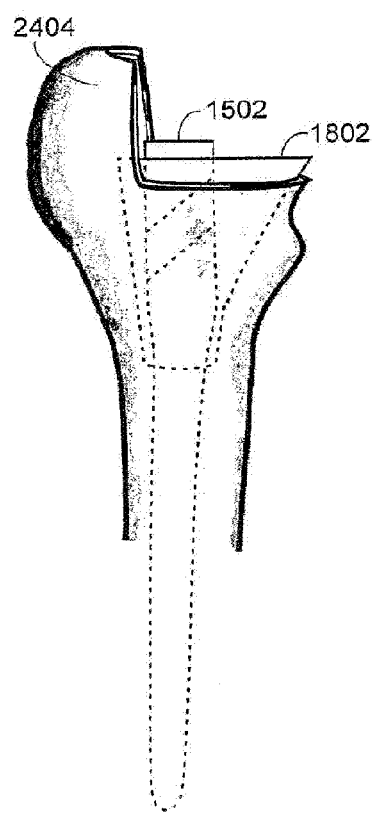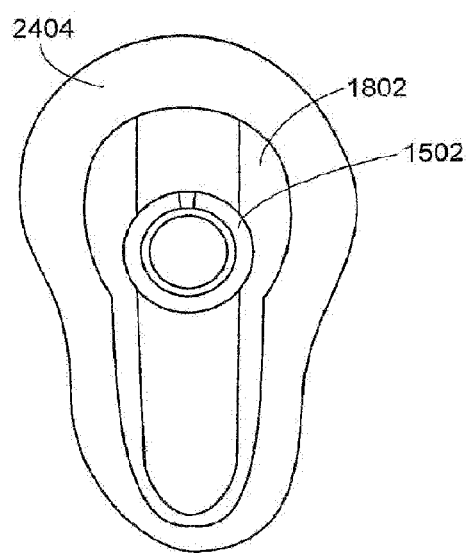
FIG. 25A
FIG. 25B

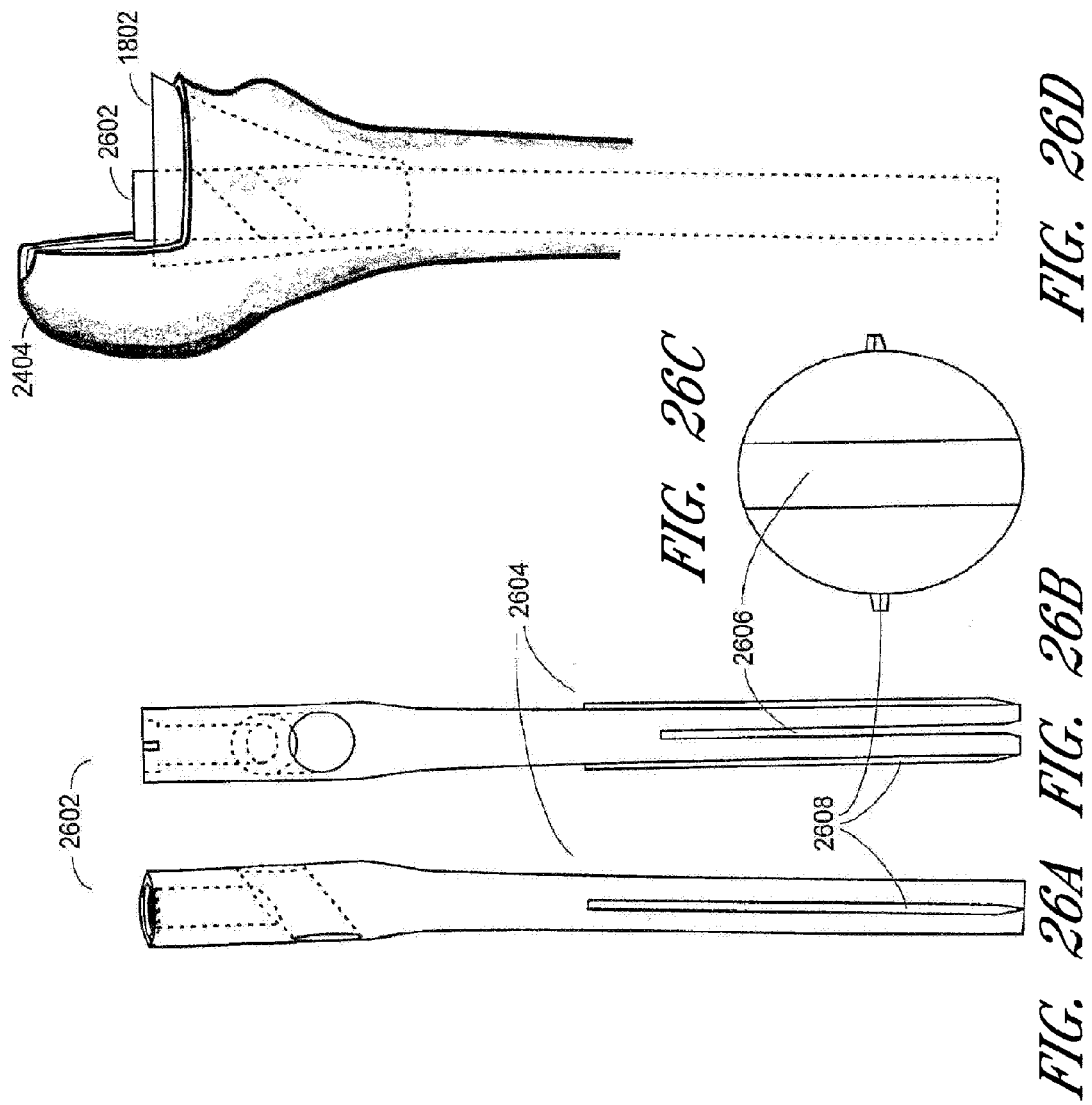

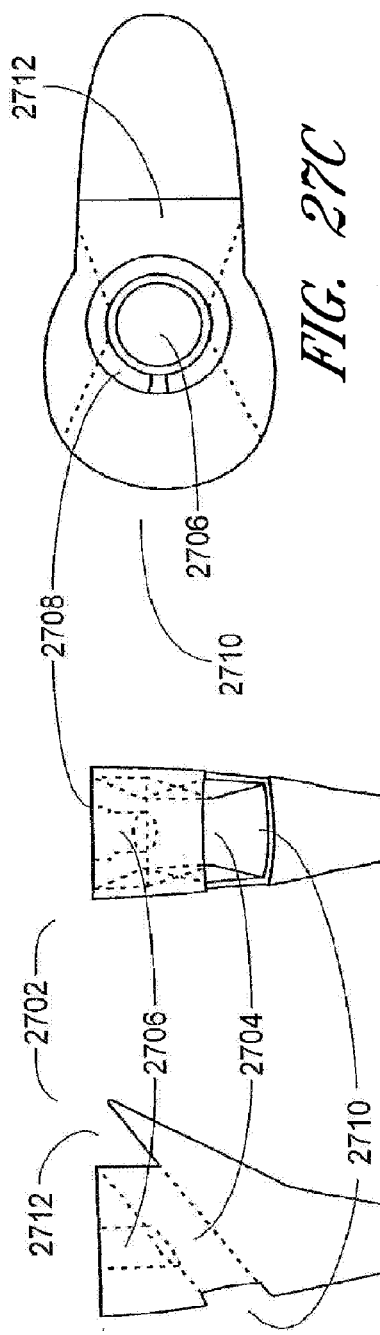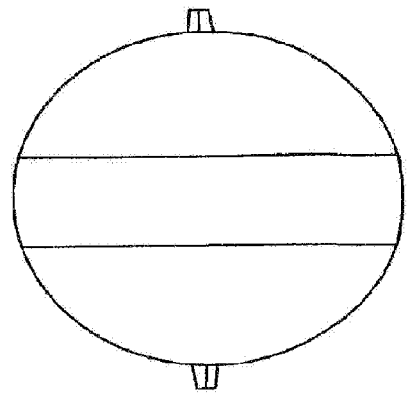

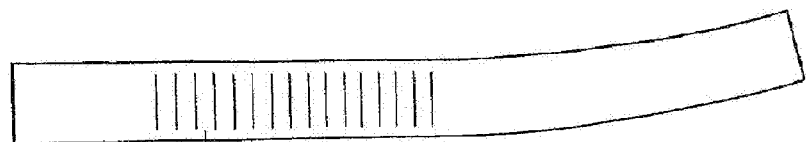
FIG. 27F
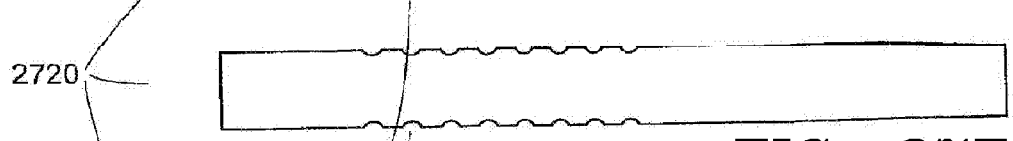
FIG. 27E
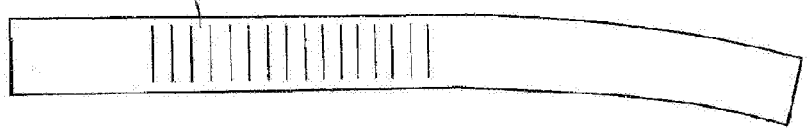
FIG. 27G
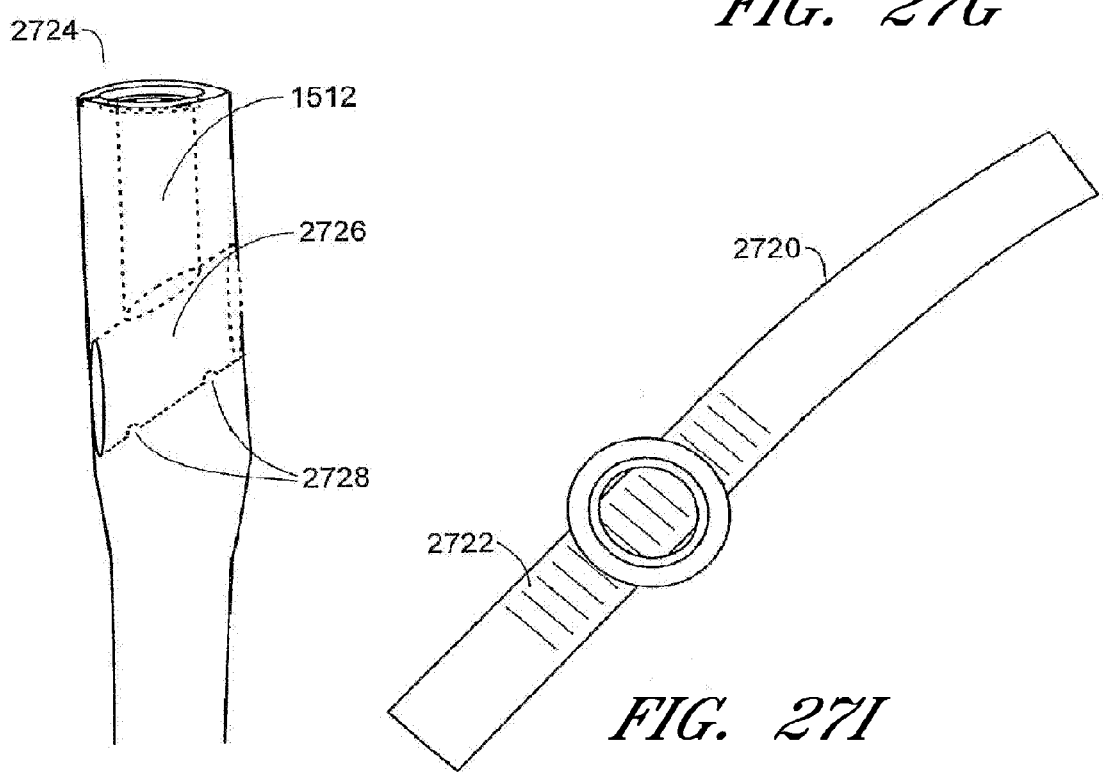
FIG. 27H
FIG. 27I

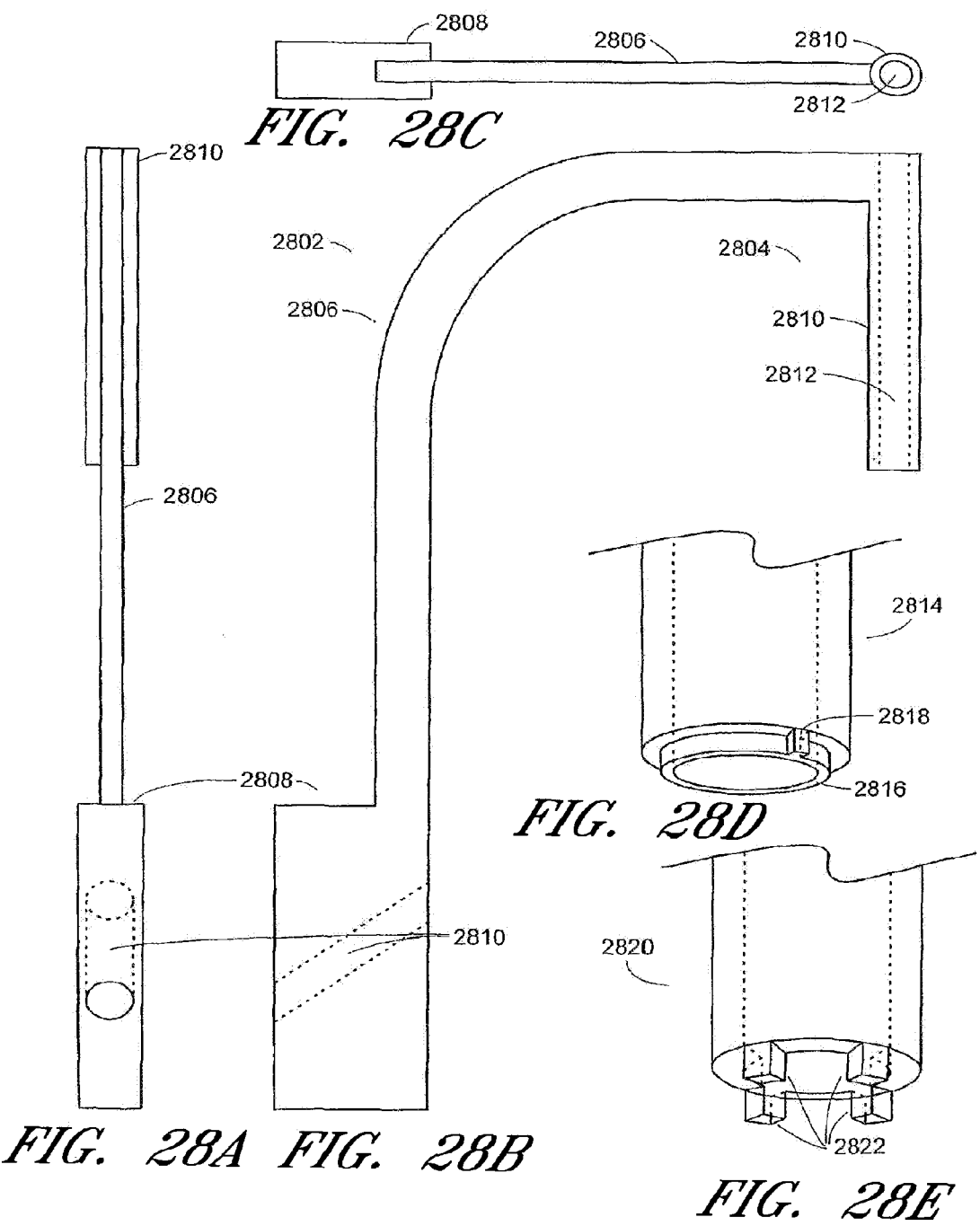

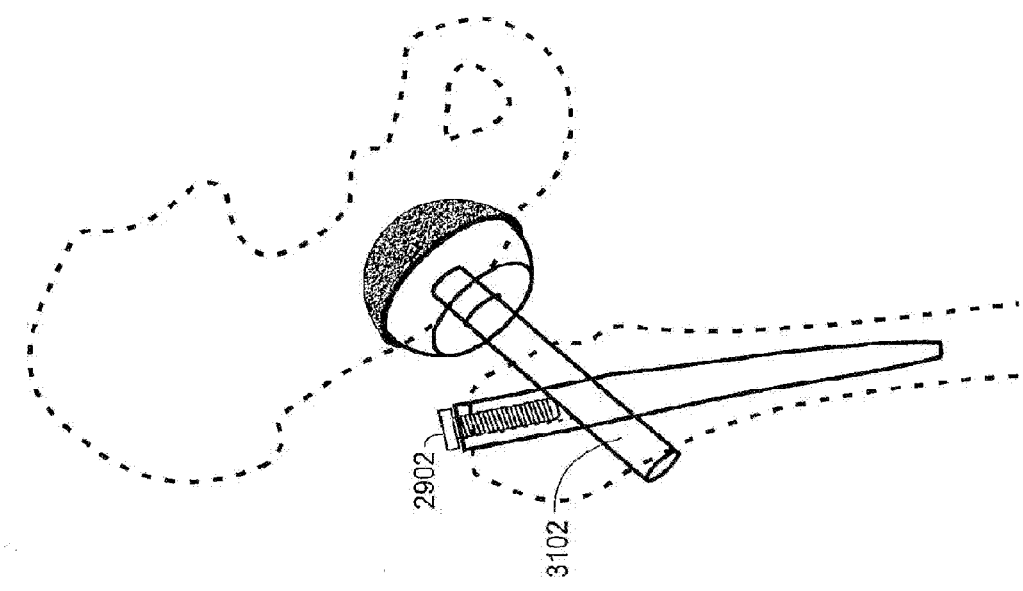
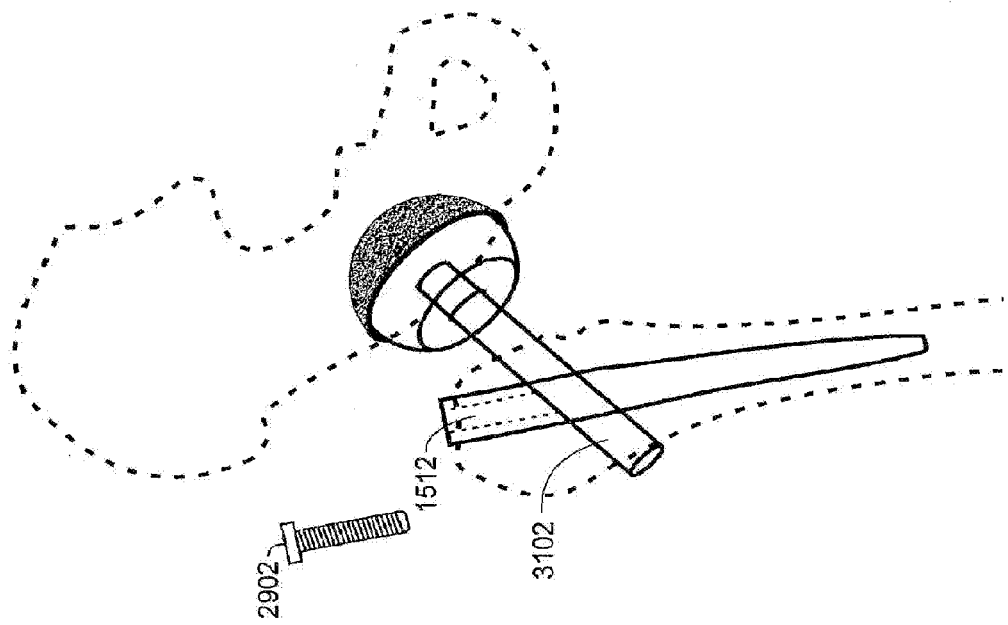

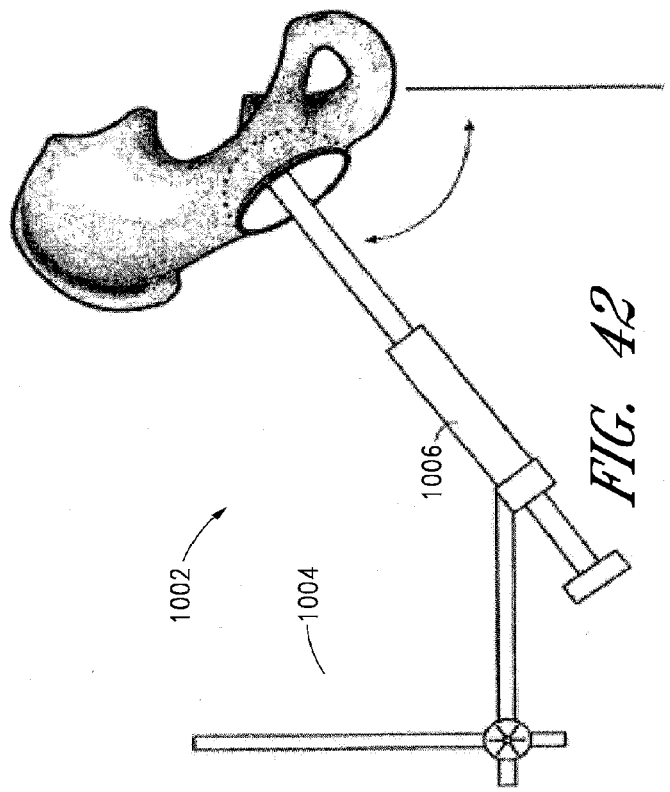
FIG. 41
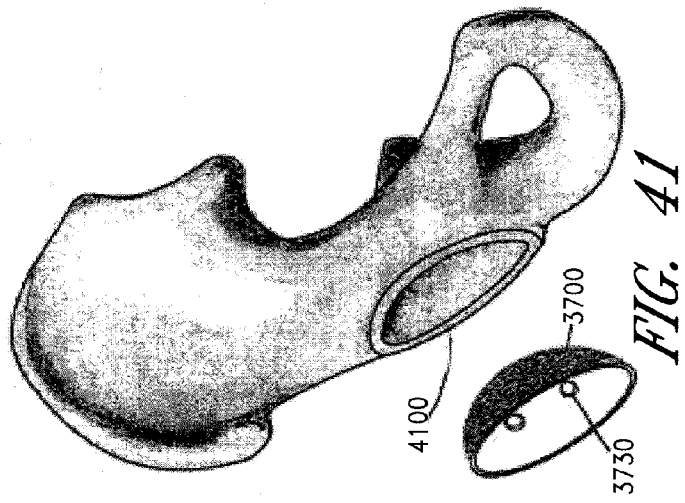
FIG. 42
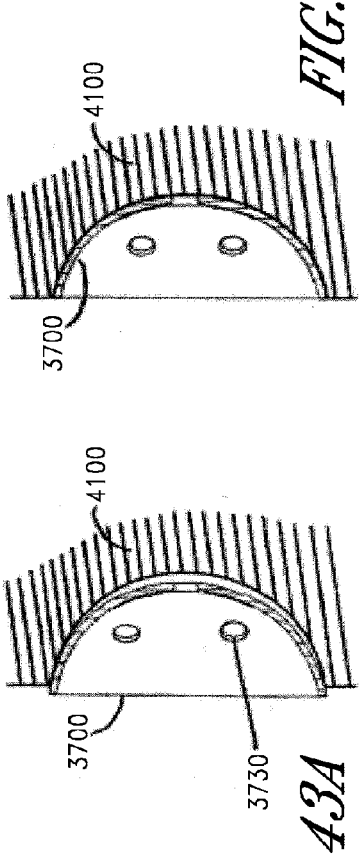
FIG. 43A
FIG. 43B

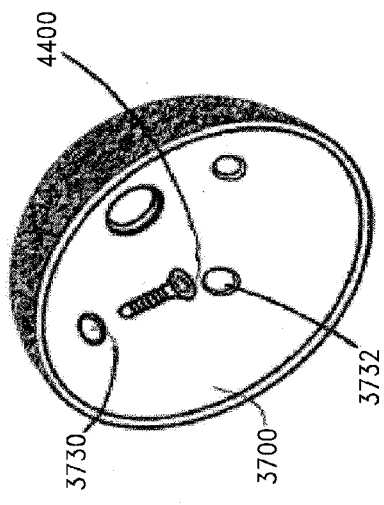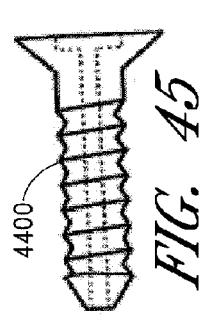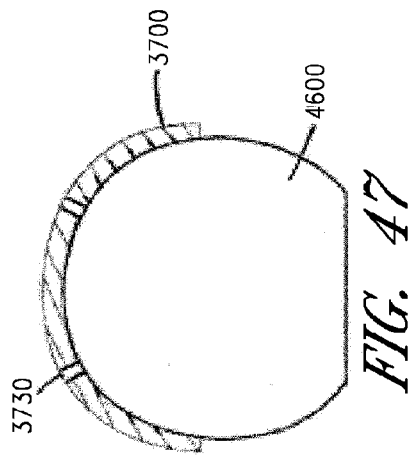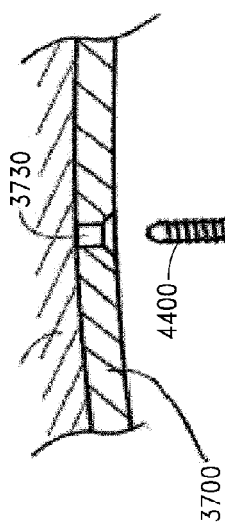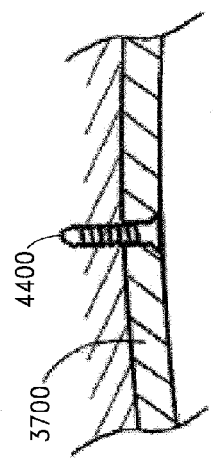
FIG. 44A  FIG. 44B  FIG. 44C  FIG. 45  FIG. 46  FIG. 47

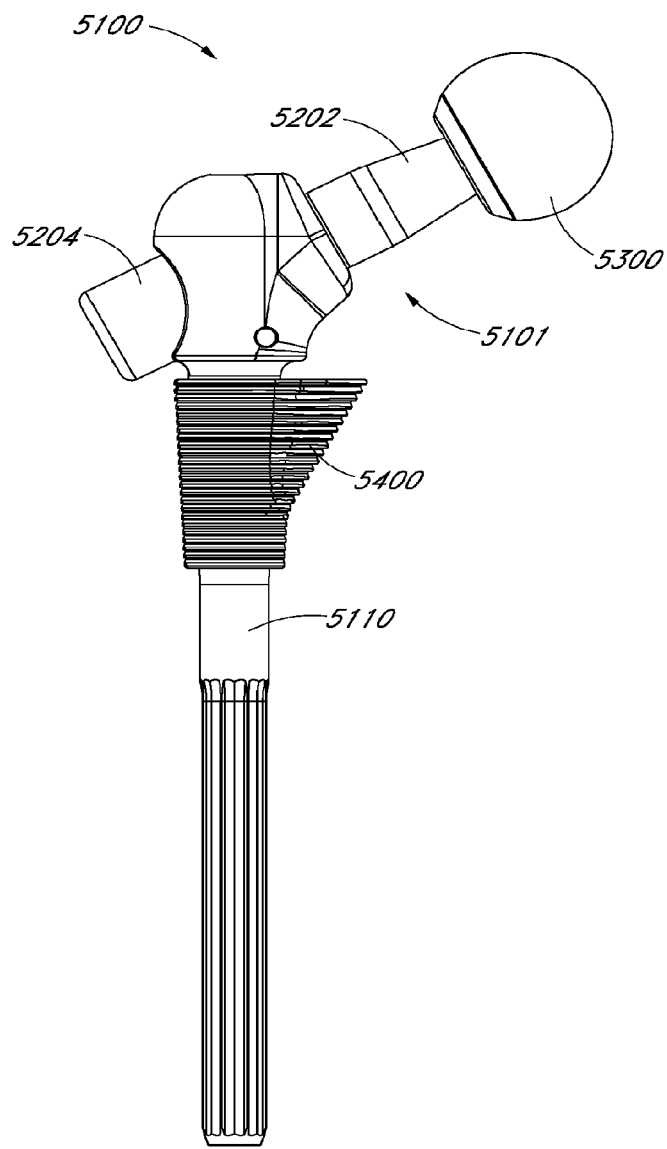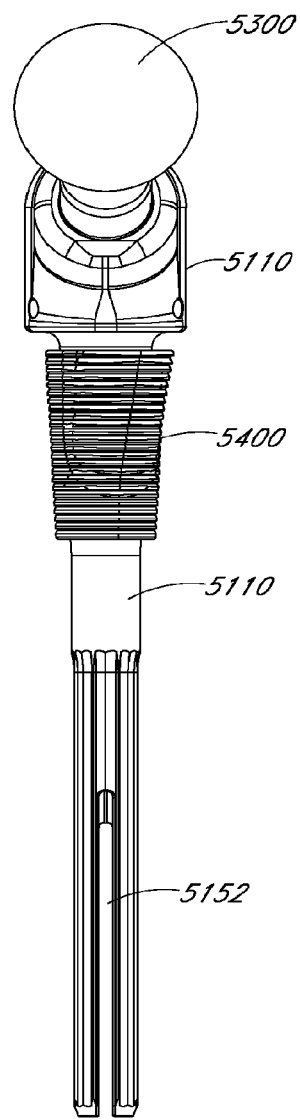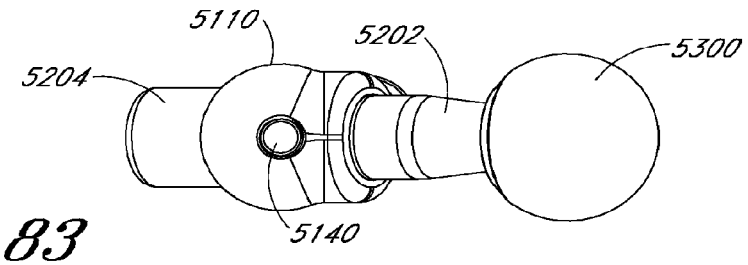
FIG. 81
FIG. 82
FIG. 83

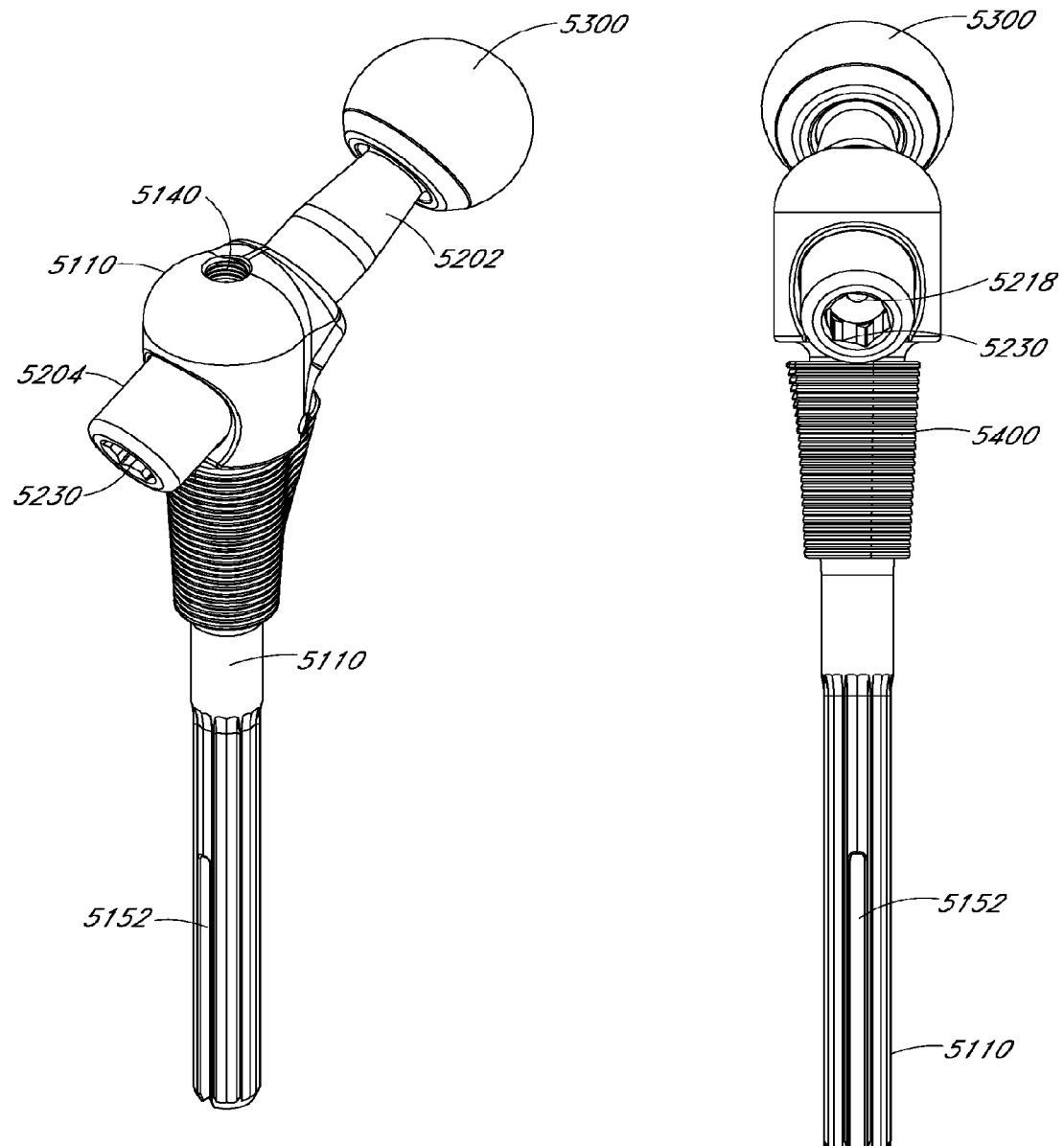
FIG. 84
FIG. 85
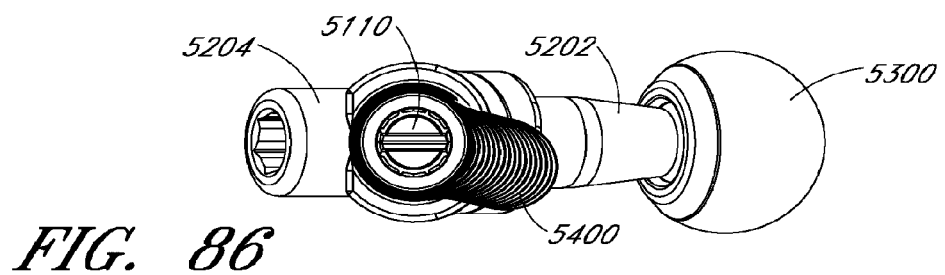
FIG. 86

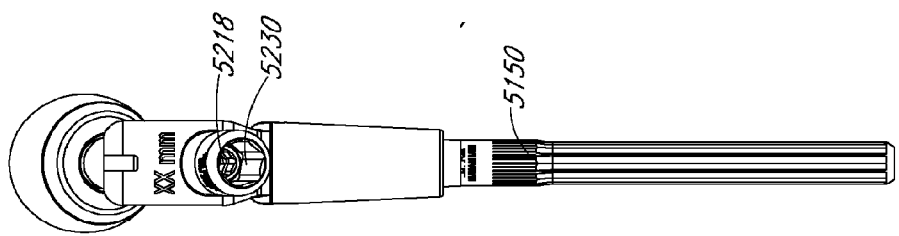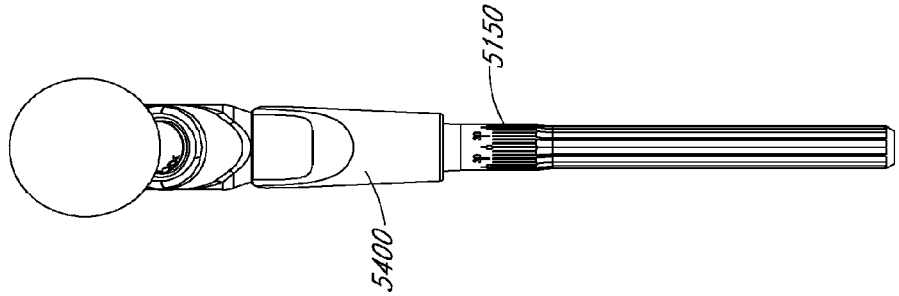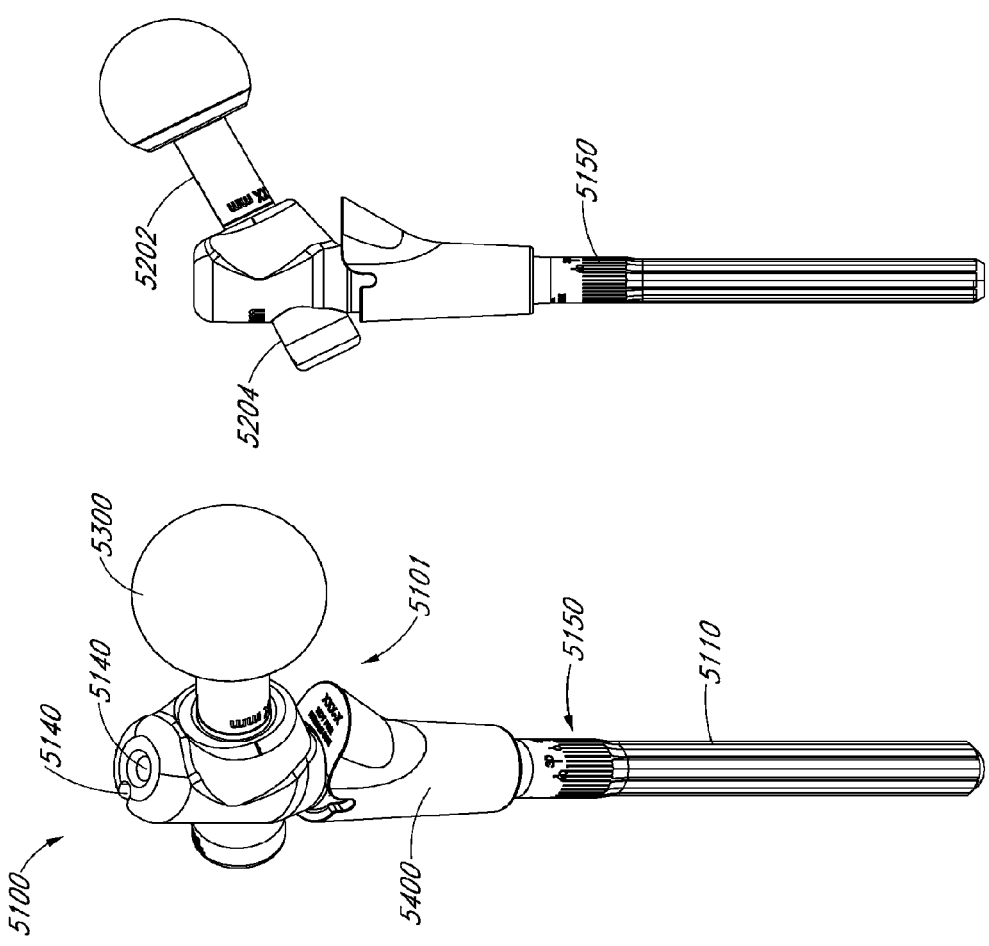

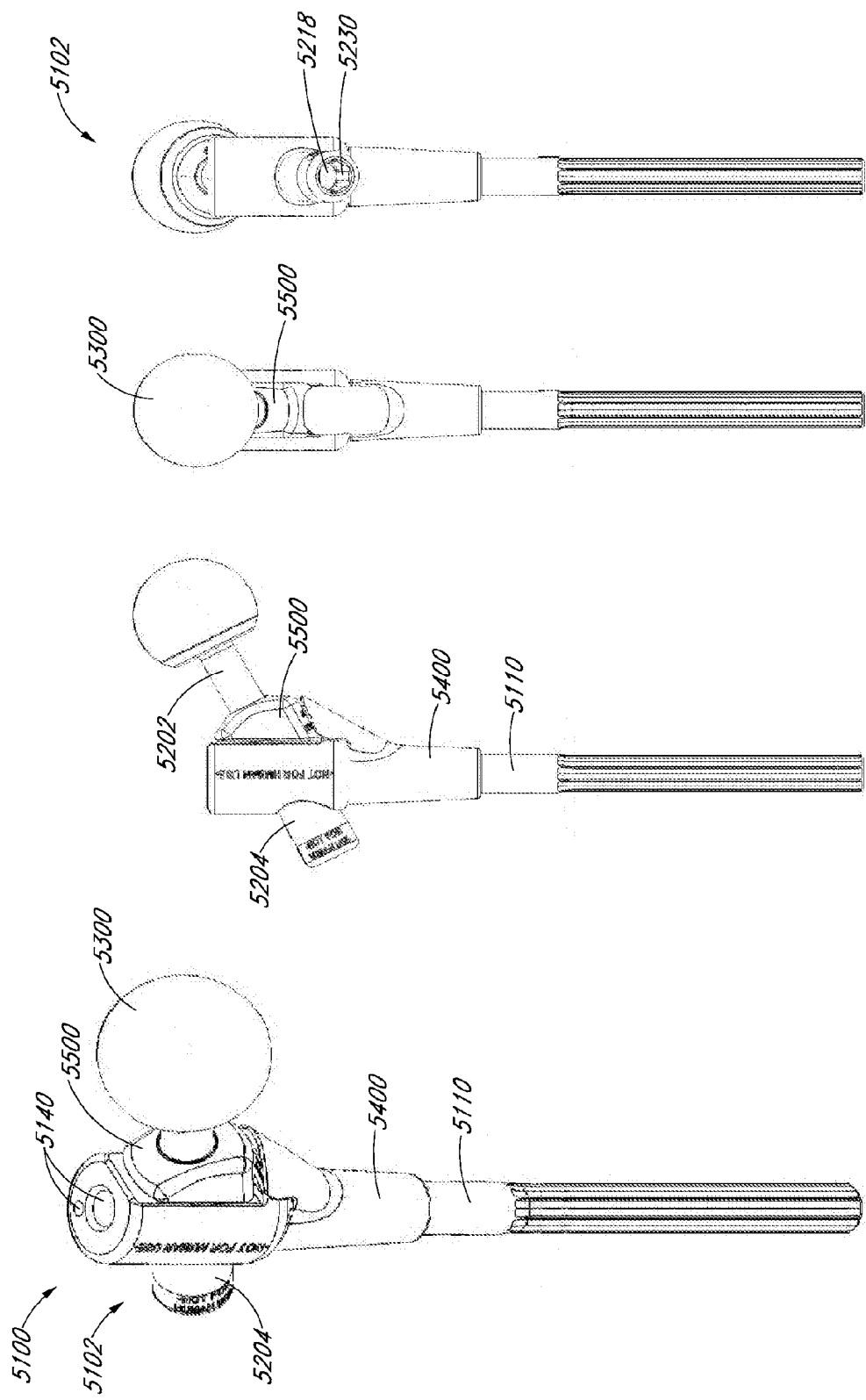

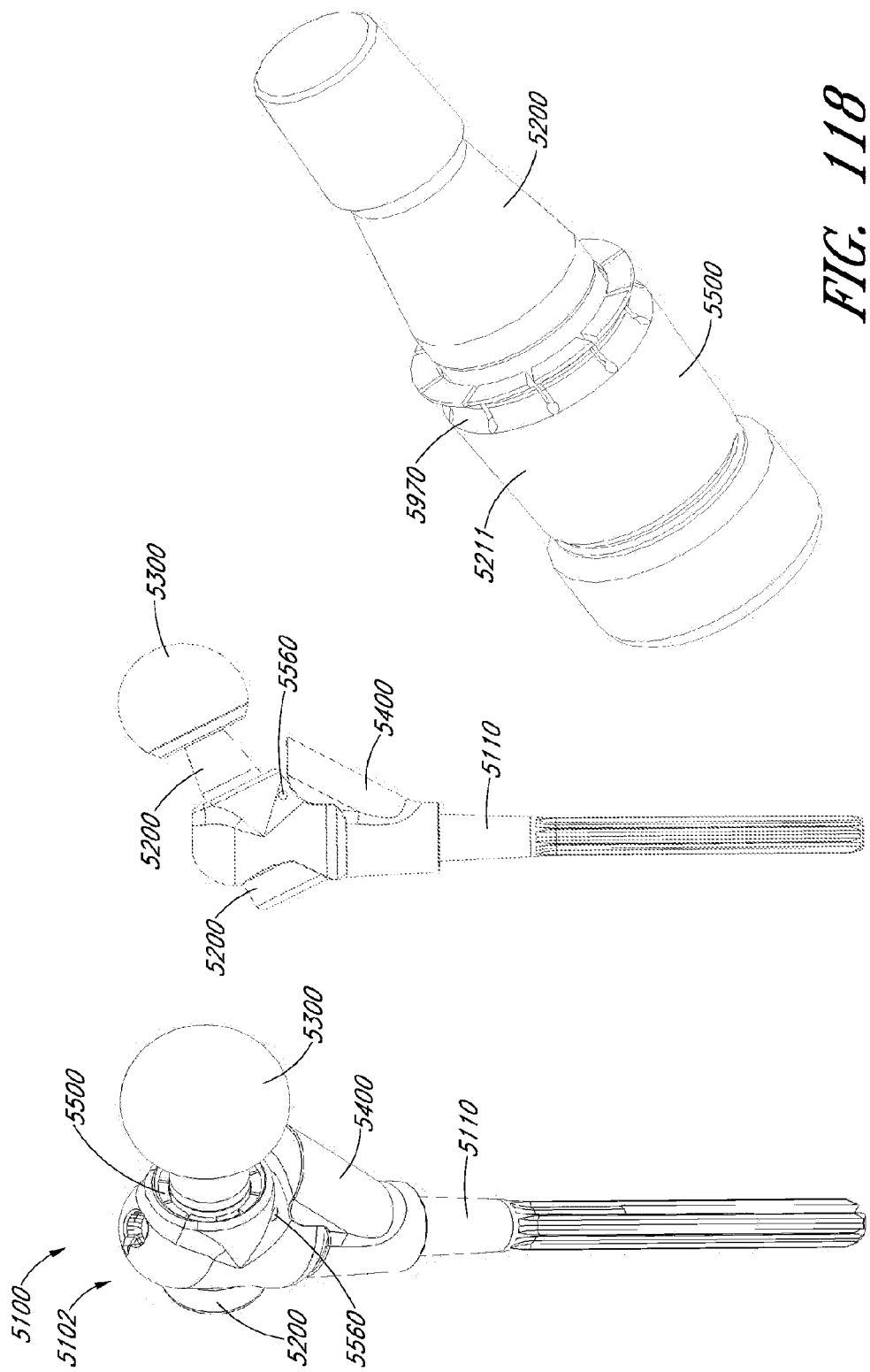

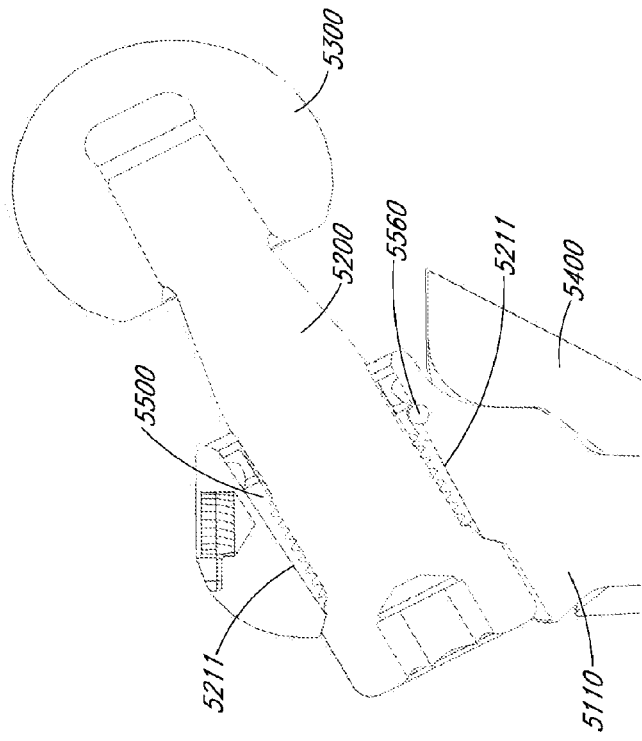
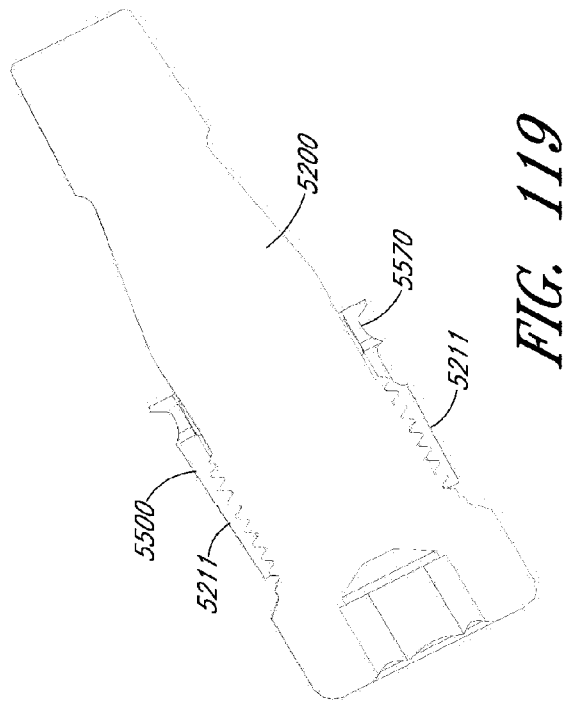
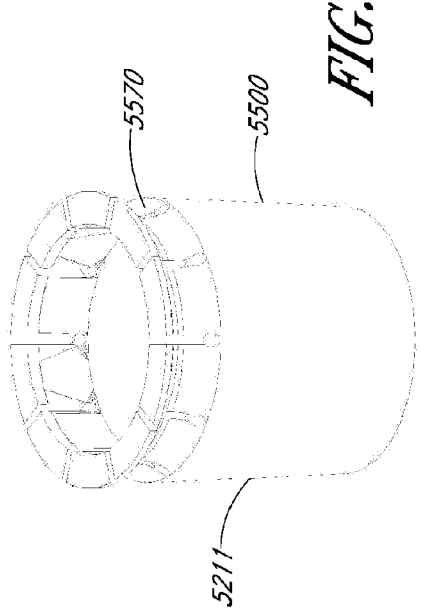

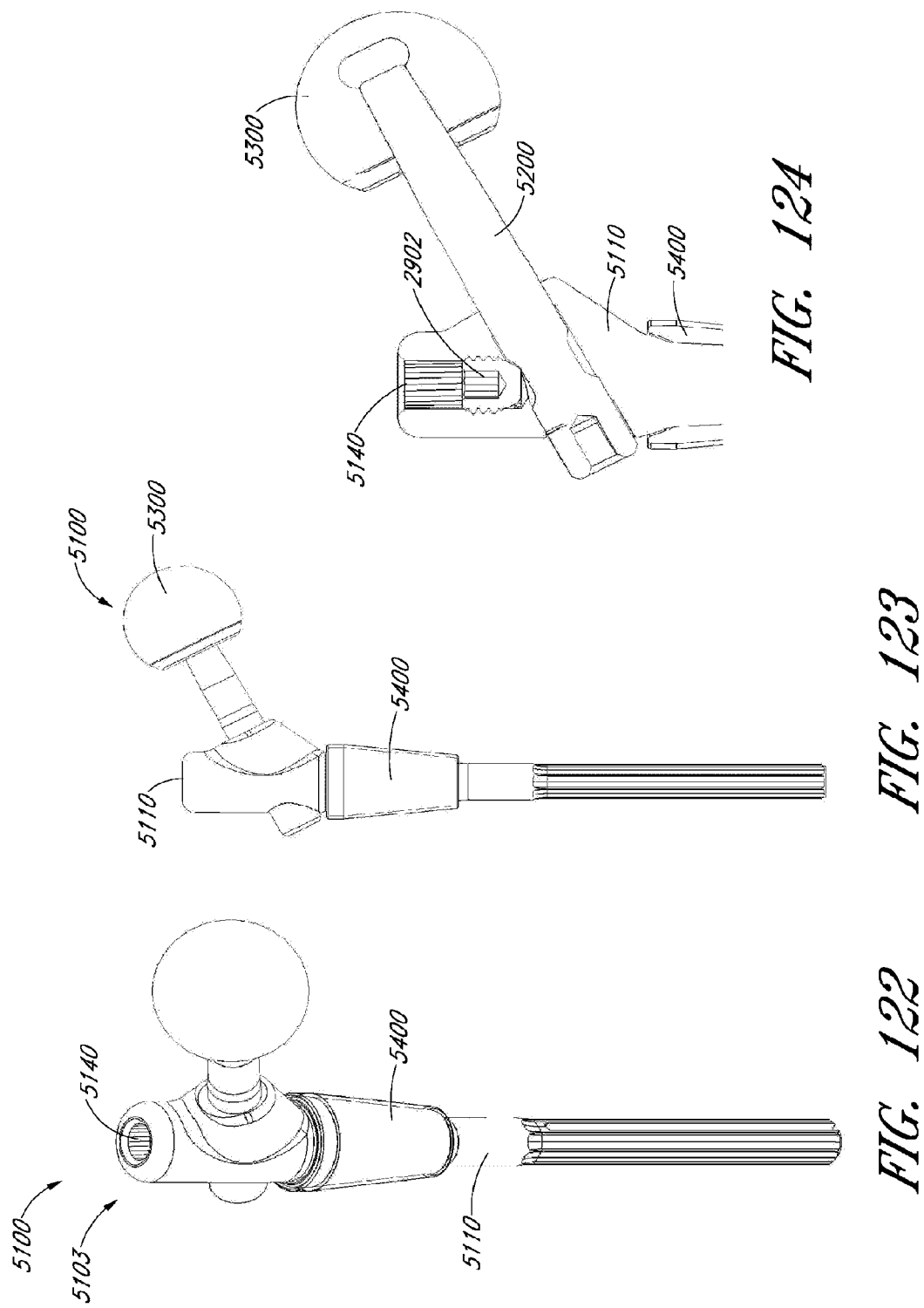

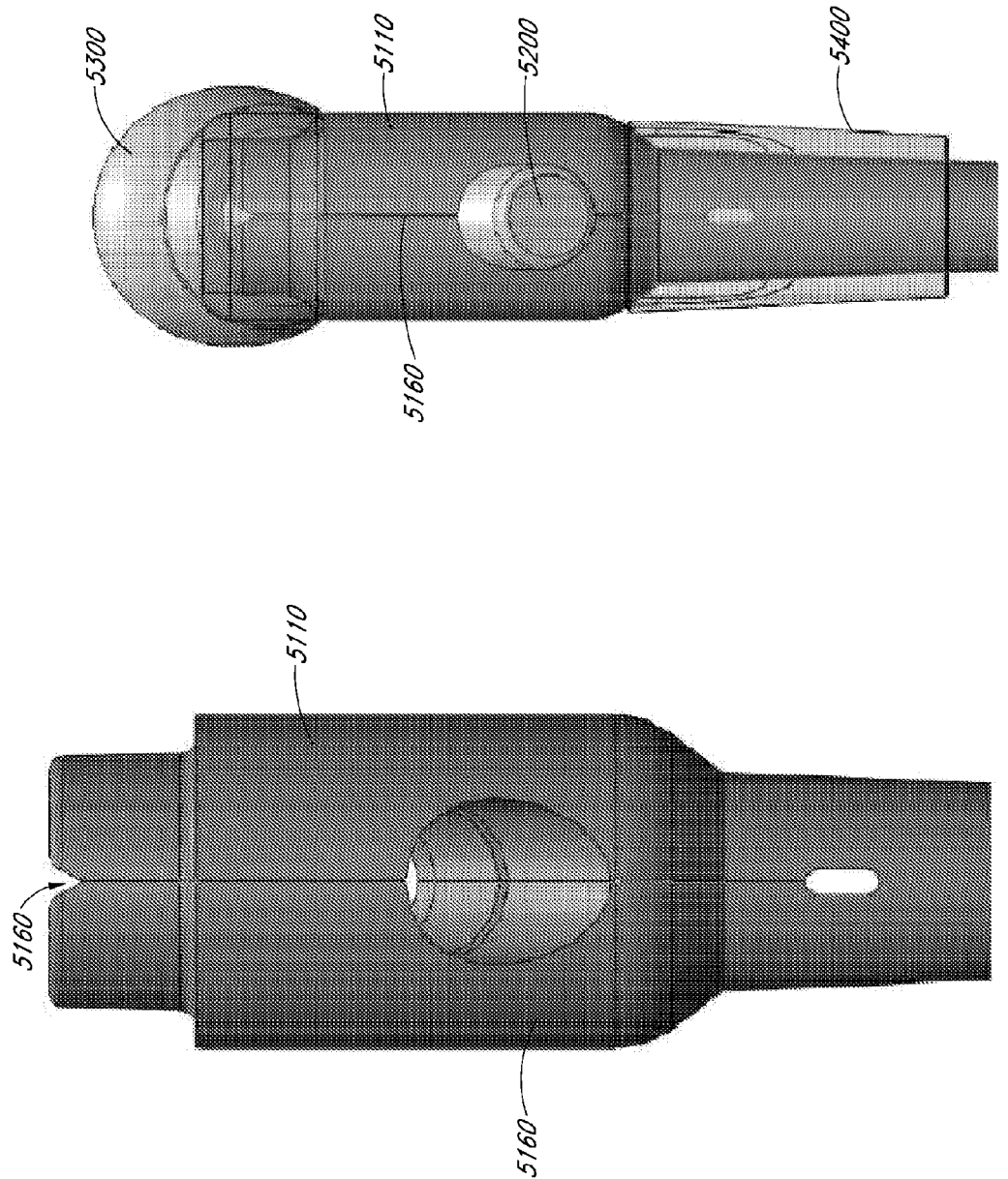

METHOD AND APPARATUS FOR HIP REPLACEMENT

CROSS-REFERENCE TO RELATED APPLICATIONS

This is application is a continuation application of U.S. application Ser. No. 13/335,216, filed Dec. 22, 2011, which is a continuation-in-part of U.S. application Ser. No. 13/049,619, filed Mar. 16, 2011, and issued as U.S. Pat. No. 8,211,183, which is a divisional application of U.S. application Ser. No. 12/518,081, filed Jun. 5, 2009 and issued as U.S. Pat. No. 8,029,573, which is a U.S. National Phase application of PCT/US2006/046795, filed in English on Dec. 7, 2006 and published as WO 2008/069800 A1 on Jun. 12, 2008, each of which are incorporated by reference in their entireties herein.

BACKGROUND

1. Field

Embodiments of the present invention relate to medical methods and apparatus, and more particularly to a method and apparatus for minimally invasive total- or hemi-hip arthroplasty.

2. Description of the Related Art

Early methods and apparatus for performing total hip replacement generally involve a long incision and with open visualization of the trochanteric region of the femur, the femoral head and the acetabulum. However, such techniques result in substantial dissection and disruption of muscles and tissues around the hip joint. The substantial disruption of the tissues creates risk of dislocation and can require months for rehabilitation and healing.

Some less invasive or minimally invasive techniques for total hip replacement have also been described. See, e.g., U.S. Pat. Nos. 7,004,972, 6,991,656 or 6,695,850, the entireties of the contents of which are incorporated herein by reference. As one example, information published by the American Academy of Orthopaedic Surgeons generally describes minimally invasive techniques that use a 3-6 centimeter incision and, as compared to traditional techniques, involve less splitting or detaching of muscles and tendons and less soft tissue dissection. However, many existing minimally invasive techniques still involve substantial disruption of the soft tissue envelope around the hip joint, including the tissue disruption required to create space in which to place and fit a prosthetic femoral neck and head between the femur and the acetabulum. Moreover, many existing techniques have failed to adequately address the problem of numerous trial reductions and dislocations often required to achieve proper fit of the prosthetics which not only causes additional disruption to the tissues, but also consumes valuable time. For example, some hip arthroplasty procedures involve two relatively large incisions in tissue in order to access the anatomy for insertion of the hip replacement components. Many of these techniques involve significant rotation, dislocation and damage to the bone and surrounding tissue, including muscles, ligaments, blood vessels, and nerves. Sometimes, the leg must be bent up to 60 degrees, with twisting and pinning of the leg, which in roughly 6% of procedures, results in a new bone break during the implantation procedure. In some instances, insertion of hip implant components through two incisions involve significant contortion and damage to tissue, resulting in increased recovery and healing time, and component sizes that are limited in length or dimension for access through the one or two incisions. For example, a stem or intramedullary rod length is often limited or shortened in order to fit in a two incision technique. There is a present need for methods and apparatus that provide for efficient hip replacement while maintaining the integrity of the tissues proximate to the hip joint.

SUMMARY

In accordance with some embodiments disclosed herein, various systems, components, and methods of use and surgery are provided to enhance the quality, reliability, and compatibility of implantation systems. These apparatuses and methods can be utilized for various types of implantation systems and methods of surgery, site and system preparation, and implantation. For example, embodiments of apparatuses disclosed herein for joint replacement may be used in joints of the human body. Embodiments of the methods disclosed herein can also be used for implanting medical devices in the body, such as prosthetic joints. These joints can include, but are not limited to the shoulder, the hip, the knee, etc. However, some embodiments can be provided in which the apparatuses and methods are used in other areas and with other structures. In some embodiments, implants are described in relation to a total hip arthroplasty. In some embodiments, implants are described in relation to a hemiarthroplasty, which includes a head replacement but no acetabular cup replacement.

Various embodiments of devices and methods for hip arthroplasty have advantages over other techniques and technology. For example, certain anterior incision techniques using one or two large incisions can have intraoperative fractures reported in up to 6% of techniques that use an anterior total hip replacement approach. Various embodiments of devices and methods for hip arthroplasty involve modular parts inserted through three smaller incisions, allowing for shorter operative times. In some embodiments, the modular device and methods result in less damage or trauma to tissue, including but not limited to blood vessels, muscles, fat, ligaments, tendons, bone, and other tissue. For example, in some embodiments, the present invention has an operative time of 30-40 minutes, which is significantly shorter than the one to two hour average time to perform an anterior only approach. In some embodiments, the procedure allows both an easy access to the acetabulum through an anterior approach, and easy insertion of a long femoral stem through a superior incision to assure distal fit. In some embodiments, a sleeve is inserted through anterior incision and is adaptable to the patient's anatomy with its proximal fill. In some embodiments, a stem component implant is inserted more in line with femoral canal to avoid intraoperative fractures. In some embodiments, a stem implant can be configured for longer lengths for improved intramedullary canal bone engagement. In some embodiments, the procedure does not require repeated trial reductions. In some embodiments, a modular neck component implant is inserted through a small (e.g. half inch or less) third incision through lateral femoral cortex small drill hole. In some embodiments, the present invention has advantages over two-incision techniques. In some embodiments, the present technique allows for smaller posterosuperior incision due to smaller modular femoral component circumference, and the smooth shape of that component causes less damage to hip abductors and is safer for the superior gluteal nerve. In some embodiments, a larger sleeve insertion through an anterior incision protects abductors. In some embodiments, the present invention has advantages over posterior minimally invasive surgery (MIS) techniques, which can involve cutting of posterior hip short external rotator muscles and the posterior capsule. In some embodiments, the present technique avoids disruption of posterior hip short external rotator muscles and posterior capsule, which is beneficial for the prevention of dislocations. In some embodiments, the present invention has advantages over other modular neck devices that involve insertion through a large incision that may require multiple trial reductions. In some embodiments, the present invention does not use repeat trial reductions, instead involving insertion of a modular neck implant component through a small incision in the lateral femoral cortex.

In some embodiments, the present invention offers a total or partial hip replacement system and a hip fracture treatment device in combination with truly minimally invasive surgical (MIS) technique. In some embodiments, both femoral neck and intertrochanteric hip fractures can be treated. In some embodiments, hemiarthroplasty can be performed with a femoral neck and intramedullary rod for intertrochanteric fracture fixation.

In some embodiments, the present invention offers an additional advantage with a fixed prosthetic femoral neck that extends from a first point external to the femur and through the femur to a second point where it joins the prosthetic femoral head. In some embodiments, a modular neck component that is inserted laterally through a bore in the stem provides advantages in reducing the amount of rotation, dislocation, and tissue damage that occurs in other techniques.

In one embodiment, a prosthetic femoral neck having a head engagement end is configured to fixedly join the neck engagement portion of the prosthetic femoral head, the prosthetic femoral neck configured to be advanced from a position along a side of a patient's body, through a side of the femur opposite the acetabulum, and through the lateral bore of the intramedullary rod such that the head engagement end of the prosthetic femoral neck fixedly joins the neck engagement portion of the prosthetic femoral head while a portion of the prosthetic femoral neck occupies the lateral bore.

In some embodiments, the device is configured for bone replacement, with parts that will last 20-30 years or more, which are configured to bear the loads associated with the bone replaced. In some embodiments, the device is configured for bone fixation, with parts that may last a year or long enough to share the load while bone heals.

In some embodiments, modularity of components in conjunction with the technique for in vivo insertion and implantation through three incisions provides for a device that can be configured with a relatively longer stem, a longer neck, and/or a larger head for better positioning, better distal fit, and sounder implantation in the intramedullary canal of a bone.

In one embodiment, a modular prosthetic hip system for hip arthroplasty includes a prosthetic femoral stem implant component, a prosthetic femoral neck implant component and a prosthetic femoral head implant component. In one embodiment, the prosthetic femoral stem implant component includes a neck implant bore. In one embodiment, the prosthetic femoral stem implant component is configured to be inserted in a femur such that at least a portion of a proximal end of the prosthetic femoral stem implant component is positioned within a trochanteric region of the femur and a distal end of the prosthetic femoral stem implant component is positioned in an intramedullary canal of the femur. In one embodiment, the prosthetic femoral neck implant component includes a bore engaging portion configured for lateral advancement through the neck implant bore and for fixed attachment to the neck implant bore of the prosthetic femoral stem implant component. In one embodiment, the bore engaging portion includes at least one tapered surface for fixedly attaching the prosthetic femoral neck implant to the prosthetic femoral stem implant component with at least one interference fit. In one embodiment, the prosthetic femoral neck implant component includes a head engaging end. In one embodiment, the prosthetic femoral head implant component attachable to the head engaging end of the prosthetic femoral neck implant component. In one embodiment, the prosthetic femoral head implant configured to fit rotatably within an acetabulum.

In one embodiment, the bore engaging portion further comprises a thread for engagement of the neck implant bore to the prosthetic femoral neck implant. In one embodiment, the thread is configured to lock the femoral neck implant component in the femoral stem implant component with an interference fit between the thread and the at least one tapered surface. In one embodiment, the femoral neck implant component includes a distal neck portion and a proximal cap portion. In one embodiment, the distal neck portion includes the head engaging end, a bore engaging portion, and a cap securing end. In one embodiment, the bore engaging portion includes a Morse taper and a thread. In one embodiment, the cap securing end includes an external cap thread. In one embodiment, the proximal cap portion includes an internal cap thread for adjustable engagement with the external cap thread. In one embodiment, the cap securing end includes an a distal neck engaging portion configured for releasable connection to a distal neck portion driving tool, and the proximal cap portion includes a proximal cap end engagement structure configured for releasable connection to a proximal cap portion driving tool. In one embodiment, the proximal cap portion further includes a cap bore engaging portion configured for engagement with the neck implant bore of the femoral stem implant component, at least a portion of the cap bore engaging portion having a tapered surface. In one embodiment, the prosthetic femoral head implant is configured to fit rotatably within a prosthetic acetabular cup in the acetabulum. In one embodiment, the modular prosthetic hip system further includes a sleeve implant component configured for anchoring the stem implant component to a bone.

In one embodiment, a minimally-invasive method of assembling a modular prosthetic hip system, includes inserting the femoral head implant component through an anterior Smith-Peterson incision, inserting the sleeve implant component through an anterior Smith-Peterson incision, inserting the femoral stem implant component through a superior-lateral incision, inserting the femoral neck implant component through an inferior lateral incision, and assembling the prosthetic hip system in vivo in a patient. In one embodiment, the assembling the prosthetic hip system includes attaching the femoral stem implant component to the sleeve implant component, locking the femoral neck implant component in a neck implant bore in the femoral neck implant component, and attaching a head engaging end of the femoral neck implant component to the femoral head implant component.

In one embodiment, the method includes lowering the temperature of at least a portion of the femoral neck component, interconnecting the femoral neck component with the femoral stem component, and permitting the temperature of the portion of the femoral neck component to rise such that an interference fit between the femoral neck component and the femoral stem component is increased. In one embodiment, the method includes lowering the temperature of at least a portion of a third component, interconnecting the portion of the third component with a portion of at least one of the femoral neck component and the femoral stem component in a second interference fit; and permitting the temperature of the portion of the third component to rise such that the interference fit between the third component and one of the femoral neck component and the femoral stem component is increased.

In one embodiment, a modular prosthetic hip system for hip arthroplasty includes a prosthetic femoral stem implant component, a prosthetic femoral neck implant component and a prosthetic femoral head implant component. In one embodiment, the prosthetic femoral stem implant component has a neck implant bore that includes a bore thread and at least one tapered surface. In one embodiment, the prosthetic femoral stem implant component is configured to be inserted in a femur such that at least a portion of a proximal end of the prosthetic femoral stem implant component is positioned within a trochanteric region of the femur and a distal end of the prosthetic femoral stem implant component is positioned in an intramedullary canal of the femur. In one embodiment, the prosthetic femoral neck implant component includes a bore engaging portion configured to fixedly join the neck implant bore of the prosthetic femoral stem implant component, the bore engaging portion includes a bore thread and at least one tapered surface for fixedly attaching the prosthetic femoral neck implant to the prosthetic femoral stem implant component with at least one interference fit. In one embodiment, the prosthetic femoral neck implant component includes a head engaging end. In one embodiment, the prosthetic femoral head implant component is attachable to the head engaging end of the prosthetic femoral neck implant component, the prosthetic femoral head implant configured to fit rotatably within an acetabulum.

In one embodiment, the femoral neck implant component includes a distal neck portion and a proximal cap portion. In one embodiment, the distal neck portion includes the head engaging end, a bore engaging portion, and a cap securing end. In one embodiment, the bore engaging portion includes the at least one taper and the bore thread, the cap securing end includes an external cap thread, and the proximal cap portion includes an internal cap thread for adjustable engagement with the external cap thread. In one embodiment, the cap securing end includes a distal neck engaging portion configured for releasable connection to a distal neck portion driving tool. In one embodiment, the proximal cap portion includes a proximal cap end engagement structure configured for releasable connection to a proximal cap portion driving tool. In one embodiment, the proximal cap portion further includes a cap bore engaging portion configured for engagement with the neck implant bore of the femoral stem implant component. In one embodiment, at least a portion of the cap bore engaging portion has a tapered surface.

In one embodiment, a method of interconnecting components of a prosthetic joint system includes lowering the temperature of at least a portion of a first component, interconnecting the first portion of the first component with a second component in an interference fit, and permitting the temperature of the portion of the first component to rise such that the interference fit between the first and second components is increased.

In one embodiment, the method further includes lowering the temperature of at least a portion of a third component, interconnecting the portion of the third component with a portion of at least one of the first and second components in an interference fit, and permitting the temperature of the portion of the third component to rise such that the interference fit between the third component and one of the first and second components is increased. In one embodiment, the first component is a femoral neck component of a prosthetic hip system and the second component is a femoral stem component. In one embodiment, the first component and the second component are interconnected with at least one Morse taper. In one embodiment, the first component and the second component are interconnected with at least two Morse tapers.

Some embodiments of the present invention concern methods of performing a hip arthroplasty that can comprise some, or all of (1) surgically accessing an acetabulum, (2) preparing the acetabulum to receive a prosthetic acetabular cup (in embodiments with total hip arthroplasty), (3) seating the prosthetic acetabular cup in the prepared acetabulum, (4) fitting a prosthetic femoral head within the prosthetic acetabular cup, the prosthetic femoral head rotatable with respect to the prosthetic acetabular cup, (5) surgically accessing a femur, (6) preparing the femur to receive an intramedullary rod, the intramedullary rod having a neck bore, (7) inserting into the femur at least a portion of the intramedullary rod including the neck bore, (8) creating a femoral bore into the femur, the femoral bore defining a passage through the femur from a side of the femur opposite the acetabulum and through the neck bore in the inserted intramedullary rod, (9) inserting a head-engaging end of a prosthetic femoral neck into the femoral bore, through the neck bore in the inserted intramedullary rod to engage the prosthetic femoral head, and (10) joining the head-engaging end of the prosthetic femoral neck to the prosthetic femoral head. One embodiment further includes fixing the prosthetic femoral neck with respect to the inserted intramedullary rod. Additional advantage may be achieved in an embodiment wherein the fixed prosthetic femoral neck extends from a first point external to the femur and through the femur to a second point where it joins the prosthetic femoral head. In one embodiment, the femoral bore is created before a natural femoral head is removed. In one embodiment, at least one anterior incision provides surgical access to the acetabulum and to the femur. In one embodiment, a posterior incision provides surgical access to the femur. In one embodiment, the present invention includes removably fixing an alignment tool to the intramedullary rod, the alignment tool having a guide bore which, when the alignment tool is removably fixed to the intramedullary rod, is in alignment with the neck bore of the intramedullary rod, and advancing a drilling bit through the guide bore, through the side of the femur opposite the acetabulum, through the neck bore in the intramedullary rod in a direction toward the acetabulum.

Some methods may also derive advantages from an embodiment wherein the alignment tool further comprises a first fixation keyway and the intramedullary rod further comprises a second fixation keyway which removably interlocks with the first fixation keyway to facilitate removable fixation of the alignment tool to the intramedullary rod. The method may derive additional advantage from an embodiment wherein the diameters of the prosthetic acetabular cup and the prosthetic femoral head both exceed 50 millimeters. A further advantageous aspect of this method is one wherein the prosthetic acetabular cup includes at least one fixation bore and wherein seating the acetabular cup includes rotationally driving a fixation screw through the fixation bore to fix the prosthetic acetabular cup in a seated position within the prepared acetabulum. In one embodiment, the method is one wherein a hollow channel in the fixation screw is positioned to direct bodily fluid into a space between the prosthetic femoral head and the prosthetic acetabular cup. The method may derive additional benefit from an embodiment wherein at least part of the prosthetic acetabular cup is cobalt chromium. Still further advantage may be derived from an embodiment wherein the inner surface of the acetabular cup and the outer surface of the acetabular cup are made from different materials. In one embodiment, the insertion of at least a portion of the intramedullary rod comprises inserting a guide wire into the intramedullary canal of the femur. In one embodiment, a reamer is used in preparation of the acetabulum, the reamer having a reaming head and reaming shaft, the reaming head removable from the reaming shaft, the reaming head without the reaming shaft positioned at the acetabulum through the acetabular surgical access, the reaming shaft positioned through a second surgical access to engage the positioned reaming head. Additional benefit may be derived from this aspect in an embodiment of the method wherein the reaming shaft is positioned through the femoral bore to engage the positioned reaming head. Still further benefit may be derived from an embodiment of the method wherein an impactor is used in seating prosthetic acetabular cup in the acetabulum, the impactor having an impactor head and an impactor shaft, the impactor head removable from the impactor shaft, the impactor head without the impactor shaft positioned through the acetabular surgical access to engage the prosthetic acetabular cup, the impactor shaft positioned through a second surgical access to engage the positioned impactor head. Additional benefit from the method may be derived from an embodiment wherein the impactor shaft is positioned through the femoral bore to engage the positioned impactor head.

In one embodiment, a method of performing a hip arthroplasty comprises any of the following steps, in any order: surgically accessing a femur and preparing it to receive a support sleeve, the support sleeve comprising a rod bore and a neck passage; seating the support sleeve into a trochanteric region of the femur; inserting an intramedullary rod into the femur and through the rod bore of the support sleeve, the diameter of the rod bore configured to receive and hold a proximal region of the intramedullary rod while a distal stem of the intramedullary rod extends deeper into the femoral canal, the intramedullary rod comprising a neck bore aligned with the neck slot of the support sleeve; inserting a prosthetic femoral neck from a position along a side of a patient's body, through a first side (such as, in one non-limiting example, the lateral cortex) of the femur, through the neck passage and the neck bore to fixedly engage the prosthetic femoral head; and fixing the prosthetic femoral neck with respect to the intramedullary rod to thereby position the femur to usefully approximate normal rotational capacity with respect to the acetabulum.

In one embodiment, a method of performing a total hip arthroplasty comprises any of the following steps, in any order: (1) surgically accessing an acetabulum and preparing it to receive a prosthetic acetabular cup and prosthetic femoral head, (2) seating the prosthetic acetabular cup and prosthetic femoral head, the prosthetic femoral head rotatable within the prosthetic acetabular cup, (3) surgically accessing a femur and preparing it to receive a support sleeve, the support sleeve comprising a rod bore and a neck passage, (4) seating the support sleeve into a trochanteric region of the femur, (5) inserting an intramedullary rod into the femur and through the rod bore of the support sleeve, the diameter of the rod bore configured to receive and hold a proximal region of the intramedullary rod while a distal stem of the intramedullary rod extends deeper into the femoral canal, the intramedullary rod comprising a neck bore aligned with the neck slot of the support sleeve, (6) inserting a prosthetic femoral neck from a position along a side of a patient's body (e.g. such as through the lateral cortex in one embodiment), through a first side of the femur, through the neck passage and the neck bore to fixedly engage the prosthetic femoral head, and (7) fixing the prosthetic femoral neck with respect to the intramedullary rod to thereby position the femur to usefully approximate normal rotational capacity with respect to the acetabulum. In one embodiment, the prosthetic femoral head is rotatably fixed within the prosthetic acetabular cup prior to surgically accessing the acetabulum. In one embodiment, bone-engaging walls of the support sleeve comprise a plurality of planar surfaces substantially perpendicular to the femoral canal. In one embodiment, the diameters of the prosthetic acetabular cup and the prosthetic femoral head both exceed 50 millimeters. Additional advantage may be derived from an aspect of the embodiment wherein the outer surface of the prosthetic acetabular cup includes irregularities penetrable by new acetabular bone growth. In one embodiment, the outer surface of the prosthetic acetabular cup includes protrusions facilitating seating within the prepared acetabulum. In one embodiment, fixing the prosthetic femoral neck with respect to the intramedullary rod comprises rotationally driving a threaded fixation bolt into a threaded fixation bore in the intramedullary rod to exert a fixation force upon the prosthetic femoral neck, the threaded fixation bore perpendicular to and connecting with the neck bore. In one embodiment, the fixation force upon the prosthetic femoral neck forces one or more ridges in the neck bore to engage one or more grooves formed in the prosthetic femoral neck.

One embodiment of an apparatus for total hip replacement comprises (1) a prosthetic femoral head comprising a partially spherical head portion configured to fit rotatably within a prosthetic acetabular cup seated in an acetabulum, the prosthetic femoral head also comprising a neck engagement portion configured to fixedly join a prosthetic femoral neck, (2) an intramedullary rod configured to be inserted within a femur such that at least a portion of a proximal end of the intramedullary rod is positioned within a trochanteric region of the femur and a distal end of the intramedullary rod is positioned deeper in the femur, the intramedullary rod including a lateral bore, and (3) a prosthetic femoral neck having a head engagement end configured to fixedly join the neck engagement portion of the prosthetic femoral head, the prosthetic femoral neck configured to be advanced from a position along a side of a patient's body, through a side of the femur opposite the acetabulum, and through the lateral bore of the intramedullary rod such that the head engagement end of the prosthetic femoral neck fixedly joins the neck engagement portion of the prosthetic femoral head while a portion of the prosthetic femoral neck occupies the lateral bore. In one embodiment, the intramedullary rod includes a threaded neck fixation bore extending from the proximal end of the intramedullary rod into the lateral bore, and wherein a threaded fixation screw removably tightened into the neck fixation bore fixes the prosthetic femoral neck relative to the intramedullary rod in a position in which the head engagement end of the prosthetic femoral neck fixedly joins the neck engagement portion of the prosthetic femoral head. In one embodiment, at least a shaft portion of the prosthetic femoral neck has a non-circular cross-section. In one embodiment, a shaft portion of the prosthetic femoral neck is curved. In one embodiment, the diameter of the partially spherical head portion of the prosthetic femoral head is at least 50 millimeters. Additional advantage may be derived from an embodiment of this apparatus wherein the distal end of the intramedullary rod comprises at least two prongs. In one embodiment, an outer bone-engaging surface of the distal end of the intramedullary rod is configured to include at least one flute. One embodiment further comprises a support sleeve adapted to be seated in the trochanteric region of the femur, the support sleeve including a rod bore and a neck passage, the rod bore configured to hold a portion of the proximal end of the intramedullary rod while the distal end of the intramedullary rod is positioned deeper in the femur such that the neck passage is aligned with the lateral bore of the intramedullary rod to accommodate advancement of the prosthetic femoral neck through both the neck passage and the lateral bore. In one embodiment, fixation ridges formed on a surface defining, at least in part, the neck passage engage the prosthetic femoral neck to resist movement of the prosthetic femoral neck within the neck passage. In one embodiment, a shaft portion of the prosthetic femoral neck is curved and wherein at least one fixation groove is formed in both top and bottom sides of the prosthetic femoral neck. Additional advantage may be derived from an embodiment of the apparatus further comprising a neck cover configured to connect to the support sleeve to maintain separation between bodily tissues and a portion of the prosthetic femoral neck. In one embodiment, respective surfaces of the lateral bore and the prosthetic femoral neck are configured to resist movement of the prosthetic femoral neck within the lateral bore. Still further advantage may be derived from an embodiment of the apparatus further comprising a prosthetic acetabular cup configured for seating in an acetabulum. In one embodiment, the prosthetic acetabular cup is seated using an impactor comprising an impaction head with a convex impaction surface configured to nondestructively engage a portion of a concave surface of the prosthetic acetabular cup. In one embodiment, one or more protrusions on the outer surface of the prosthetic acetabular cup penetrate into acetabular bone when the prosthetic acetabular cup is seated in the acetabulum.

In one embodiment, a method for total hip arthroplasty comprises one or more of the following steps, in any order: (1) fixing a prosthetic femoral head in a position rotatable with respect to an acetabulum, (2) creating a bore in a femur from a side of the femur opposite the acetabulum and extending in a direction toward the acetabulum, (3) joining an end of a prosthetic femoral neck to the prosthetic femoral head after advancing the end of the prosthetic femoral neck into the bore to engage the prosthetic femoral head, and (4) fixing the position of the prosthetic femoral neck with respect to the femur.

In one embodiment of a system for total hip arthroplasty comprises (1) means for fixing a prosthetic femoral head in a position rotatable with respect to an acetabulum, (2) means for creating a bore in a femur from a side of the femur opposite the acetabulum and extending in a direction toward the acetabulum, (3) means for joining an end of a prosthetic femoral neck to the prosthetic femoral head after advancing the end of the prosthetic femoral neck into the bore to engage the prosthetic femoral head, and (4) means for fixing the position of the prosthetic femoral neck with respect to the femur.

Some embodiments can provide a prosthetic hip system comprising a prosthetic femoral head and a prosthetic acetabular cup. The acetabular cup can define a generally rounded body having an inner surface and an outer surface. The acetabular cup can be formed as a monolithic body being configured to be anchored to an acetabulum of a patient. The acetabular cup can comprise a plurality of apertures extending through the cup for providing at least a visual indication of whether the acetabular cup is spaced from or seated against the acetabulum during placement of the acetabular cup. The inner surface can define a contact area against which the prosthetic femoral head can articulate, the inner surface of the acetabular cup being configured to engage with the prosthetic femoral head. Further, the acetabular cup can comprise a rigid material for minimizing deflection of the acetabular cup. The monolithic construction of the acetabular cup can further define a minimized thickness such that an interior volume of the acetabular cup is maximized in order to accommodate larger prosthetic head sizes for minimizing dislocation of the head from the cup. In some embodiments, the apertures can be configured to receive fastening mechanisms for anchoring the acetabular cup to the acetabulum. Further, the apertures can define a bevel. For example, the apertures can define a bevel that comprises a tapered surface extending between a side surface of the aperture and the inner surface of the acetabular cup.

Some embodiments can also provide a method of interconnecting components of a prosthetic joint system. The method can comprise: lowering the temperature of a portion of a first component; interconnecting the first portion of the first component with a second component in an interference fit; permitting the temperature of the portion of the first component to rise such that the interference fit between the first and second components is increased. In various embodiments, an interference fit can be a press fit, a friction fit, and/or a compression fit. In one embodiment, an interference fit is increased when the fit is strengthened, or a fixed fit is improved.

Additionally, the method can comprise: lowering the temperature of a portion of a third component; interconnecting the portion of the third component with a portion of one of the first and second components in an interference fit; and permitting the temperature of the portion of the third component to rise such that the interference fit between the third component and one of the first and second components is increased. Further, the first component can be a femoral neck of a prosthetic hip system and the second component is a support sleeve supportable by an intramedullary rod. In one embodiment, components can be interconnected with one or more tapers. In one embodiment, components can be interconnected with a one or more Morse tapers. In one embodiment, the first component and the second component can be interconnected using a Morse taper. In some embodiments, the first component can be a femoral neck of a prosthetic hip system, the second component can be a support sleeve supportable by an intramedullary rod, and the third component can be a fastening component that can coupled to both the femoral neck and the support sleeve. Further, the first, second, and third components can be interconnected using Morse tapers.

Some embodiments can provide a prosthetic hip system comprising an acetabular cup that can be configured as a monoblock cup. The cup can be configured to maximize rigidity while also maximizing interior volume of the cup in order to minimize dislocations. Further, the cup can be configured to be anchored to the acetabulum using fastening mechanisms, such as screws, while providing excellent frictional characteristics and minimizing negative effects of typical prosthetic joint use and wear. Some of the embodiments disclosed herein reflect the realization that despite the possible advantages that monoblock acetabular cups may provide, monoblock acetabular cups have had an unacceptable failure rate. For example, the Durom Acetabular Cup from Zimmer Holdings is a monoblock acetabular cup that was approved by the FDA in 2006. The Durom Acetabular Cup was designed for use in young, active patients who are likely to outlive a conventional hip prosthesis. The Durom Cup would be implanted by knocking the cup into the reamed and prepared acetabulum of the patient without the use of screws. The omission of screws provided a smooth joint surface on which the prosthetic femoral head could be seated. Although some surgeons had success implanting the Durom Cup since it was launched in the U.S. in 2006, a subset have reported cup loosenings and revisions of the acetabular component used in total hip replacement procedures. In 2008, problems with the Durom Acetabular Cup surfaced. Some doctors publicly warned other orthopedists that patients were experiencing high Durom Acetabular Cup failure rates. Zimmer's own research data estimates that some doctors experienced hip failure rates as high as 5.7% with the Durom Cup, as high as 8% by other sources. The main complaint was that patients receiving the Durom Acetabular Cup experienced overwhelming pain following their hip replacement surgery, requiring them to undergo additional revision or corrective surgery. It is now believed that the high implant failure rates of the Durom Acetabular Cup were due to inability to bond with the host bone, which caused the implanted hip replacement part to migrate. Doctors noticed that although first year x-rays looked acceptable, radiolucent lines or migration often occurred within two years for some patients. Because the cups would not bond well with the host bone, the cup could often pop free if slight contact was made against the edge of the cup. Additionally, the cups would begin developing radiolucent lines, migrate, and tilt into varus. Some doctors believed that the fixation surface was not good on the Durom cups. Also, some doctors believed that a circular cutting surface on the periphery of the cup prevented the cup from fully seating.

However, the failure of monoblock acetabular cups might be attributable to factors that are not fully addressed by the prior art or knowledge in the medical profession. Accordingly, some of the embodiments disclosed herein incorporate various structural features that address and overcome such deficiencies. Thus, some of the embodiments disclosed herein provide an acetabular cup in a monoblock configuration that can provide these superior advantages of a monoblock acetabular cup while avoiding the deficiencies and problems associated with the prior art, such as the Durom Cup. Some embodiments disclosed herein provide a monoblock acetabular cup having a plurality of mounting apertures. The mounting apertures can be configured to receive a mechanical fastener (e.g., a screw, a wood screw, etc.) in order to fixate the cup relative to the acetabulum. The mounting apertures can be configured to define a bevel that allows a head of a screw to be disposed below an interior contact surface of the cup. As discussed further below, the total surface area of the interior contact surface of the cup can be decreased by a minimal amount such that friction and fretting between the surface of a prosthetic femoral head and the interior contact surface of the cup are minimized. Thus, embodiments of the monoblock acetabular cup disclosed herein can experience reduced wear, such as fretting wear, vibrational wear, chafing, fatigue, wear oxidation, friction oxidation, false brinelling, molecular attrition, fretting fatigue, and corrosion.

In some embodiments, the mounting apertures can be configured to allow the surgeon to inspect (e.g., visually) and confirm that the cup has been properly seated in the acetabulum of the patient. Some embodiments can provide a plurality of mounting apertures that allows the seating of the cup to be inspected from several points along the interface of the cup and the acetabulum. For example, once the cup has been placed into a socket of the acetabulum, the surgeon can inspect the placement of the cup relative to the acetabulum by identifying whether a gap or space of unacceptable dimension is present between the cup and the acetabulum. If a gap or space is present at more than an acceptable number of locations along the interface of the cup and the acetabulum, the surgeon may reposition the cup as desired until a proper position is achieved. Methods of implanting an acetabular cup can be provided that comprise these and other aspects.

Some embodiments can also provide a monoblock acetabular cup having a desired rigidity so as to allow only an acceptable amount of deformation when installed into the socket of the pelvis. The cup can exhibit an allowable degree of deformation such that when installed, the inner contact surface of the acetabular cup maintains a desired shape. For example, some embodiments may exhibit little or no deformation from a spherical inner contact surface. Accordingly, the cup can be installed without losing a desired geometry that allows a prosthetic femoral head to properly mate with the cup without creating undesired friction or pressure points along the inner contact surface.

In some embodiments, a prosthetic joint system and methods of use can be provided that utilizes a unique interconnection between joint components to provide a stable coupling with superior strength and permanence. For example, in an embodiment of a hip prosthesis system, a support sleeve of the system can be coupled to a prosthetic femoral neck using one or more Morse tapers. In some embodiments, the neck can comprise first and second portions that fit into the support sleeve. In one embodiment, the first and second portions can be threadably coupled to the support sleeve and/or to each other. Further, in some embodiments, the components of the system can be cooled and thereby shrunk prior to being interconnected such that the components are able to warm and expand upon implantation and interconnection. In some embodiments, the components of the system, such as the prosthetic femoral neck, can be frozen in liquid nitrogen prior to interconnection with the support sleeve. Accordingly, in some embodiments, the Morse tapers of the components can achieve a high degree of interference without requiring forcible insertion and trauma.

These and other embodiments of the present invention are disclosed and described below. It will be appreciated that other embodiments and all substantial equivalents are within the scope of the inventions.

BRIEF DESCRIPTION OF THE DRAWINGS

Various features of embodiments of the inventions are described below with reference to the drawings. The illustrated embodiments are intended to illustrate, but not to limit, the inventions. The drawings described herein are for illustration purposes only and are not intended to limit the scope of the present disclosure in any way. Embodiments of the present invention will become more fully understood from the detailed description and the accompanying drawings. The drawings contain the following figures:

FIG. 5A illustrates a representation of an inner and an outer portion of a two-piece prosthetic cup with aligned holes used to join the two pieces in accordance with one embodiment of the present invention;

FIG. 5B illustrates a representation of aligned holes formed in walls of inner and outer cup portions of a two-piece prosthetic cup and a screw to be inserted through the holes to fix the cup portions relative to each other in accordance with one embodiment of the present invention;

FIG. 5C illustrates a two-piece prosthetic cup in accordance with one embodiment of the present invention;

FIG. 5D illustrates a cross-sectional view of an embodiment of a two-piece prosthetic cup in accordance with one embodiment of the present invention wherein the two pieces are joined by a lip formed into the rim of the inner cup;

FIG. 5E illustrates a two-piece prosthetic cup in accordance with an embodiment of the present invention wherein the two pieces are joined by a lip formed into the rim of an inner cup portion;

FIG. 6A illustrates a representation of a three-dimensional perspective and cross-sectional view of an anchoring protrusion for an outer surface of a prosthetic acetabular cup in accordance with one embodiment of the present invention;

FIG. 6B illustrates a representation of a three-dimensional perspective and cross-sectional view of an anchoring protrusion for an outer surface of a prosthetic acetabular cup in accordance with another embodiment of the present invention;

FIG. 6C illustrates a representation of a prosthetic acetabular cup having a plurality of anchoring protrusions in accordance with an embodiment of the present invention;

FIG. 9A illustrates a representation of an impactor tool joined to a prosthetic acetabular cup in position for impacting in accordance with an embodiment of the present invention;

FIG. 9B illustrates a representation of an impactor tool joined to a prosthetic acetabular cup impacted into an acetabulum in accordance with an embodiment of the present invention;

FIG. 15A illustrates a representation of a three-dimensional side view of an intramedullary rod with a femoral neck bore in accordance with an embodiment of the present invention;

FIG. 15B illustrates a representation of a three-dimensional front view of an intramedullary rod with a femoral neck bore in accordance with an embodiment of the present invention;

FIG. 15C illustrates a representation of a fixation keyway formed in an end of an intramedullary rod in accordance with an embodiment of the present invention;

FIG. 15D illustrates a representation of a fixation keyway formed in an end of an intramedullary rod in accordance with another embodiment of the present invention;

FIG. 16A illustrates a representation of a three-dimensional side view of an intramedullary rod with a femoral neck bore and a distal fixation bore in accordance with an embodiment of the present invention;

FIG. 16B illustrates a representation of a three-dimensional front view of an intramedullary rod with a femoral neck bore and a distal fixation bore in accordance with an embodiment of the present invention;

FIG. 17A illustrates a representation of a side view of a driving tool engaged with an intramedullary rod to be driven into a femoral canal in accordance with an embodiment of the present invention;

FIG. 17B illustrates a representation of a rear view of a driving tool in accordance with an embodiment of the present invention;

FIG. 17C illustrates a representation of a top down view of a driving tool in accordance with an embodiment of the present invention;

FIG. 17D illustrates a representation of a fixation keyway in an end of a driving tool in accordance with an embodiment of the present invention;

FIG. 17E illustrates a representation of a fixation keyway in an end of a driving tool in accordance with another embodiment of the present invention;

FIG. 18A illustrates a representation of a top down view of a support sleeve for an intramedullary rod in accordance with an embodiment of the present invention;

FIG. 18B illustrates a representation of a rear view of a support sleeve for an intramedullary rod in accordance with an embodiment of the present invention;

FIG. 18C illustrates a representation of a side view of a support sleeve for an intramedullary rod in accordance with an embodiment of the present invention;

FIG. 18D illustrates a representation of a perspective view of a support sleeve for an intramedullary rod in accordance with an embodiment of the present invention;

FIG. 22A illustrates a representation of a cutaway side view of a support sleeve having stepped bone-engaging outer surfaces in accordance with another embodiment of the present invention;

FIG. 22B illustrates a representation of a close-up view of a support sleeve having a stepped bone-engaging outer surface in accordance with an embodiment of the present invention as illustrated in FIG. 22A;

FIG. 22C illustrates a representation of a close-up view of a support sleeve having a stepped bone-engaging outer surface in accordance with an embodiment of the present invention as illustrated in FIG. 22A;

FIG. 24A illustrates a representation of a conical drill bit positioned above a proximal portion of a femur, the conical drill bit to remove material from the femur to facilitate positioning a support sleeve in the proximal portion of the femur in accordance with an embodiment of the present invention;

FIG. 24B illustrates a representation of a drill bit positioned above and at an angle to a proximal portion of a femur, the drill bit to remove material from the femur to facilitate positioning a support sleeve in the proximal portion of the femur in accordance with an embodiment of the present invention;

FIG. 24C illustrates a representation of a support sleeve positioned in a proximal portion of a femur in accordance with an embodiment of the present invention;

FIG. 25A illustrates a representation of a proximal portion of a femur with cutaway side view illustrating positioning of a support sleeve and intramedullary rod in accordance with an embodiment of the present invention;

FIG. 25B illustrates a representation of a top down view of a proximal portion of a femur with a support sleeve and intramedullary rod positioned in accordance with an embodiment of the present invention;

FIG. 26A illustrates a representation of a side view of an intramedullary rod having a split and fluted distal end in accordance with an embodiment of the present invention;

FIG. 26B illustrates a representation of a front view of an intramedullary rod having a split and fluted distal end in accordance with an embodiment of the present invention;

FIG. 26C illustrates a representation of a bottom up view of a split and fluted distal end of an intramedullary rod in accordance with an embodiment of the present invention;

FIG. 26D illustrates a representation of a proximal portion of a femur with cutaway side view illustrating positioning of a support sleeve and intramedullary rod having a split and fluted distal end in accordance with an embodiment of the present invention;

FIG. 27A illustrates a representation of a side view of an intramedullary rod with proximal femoral support structure in accordance with an embodiment of the present invention;

FIG. 27B illustrates a representation of a front view of an intramedullary rod with proximal femoral support structure in accordance with an embodiment of the present invention;

FIG. 27C illustrates a representation of a top down view of an intramedullary rod with proximal femoral support structure in accordance with an embodiment of the present invention;

FIG. 27D illustrates a representation of a bottom up view of a split and fluted distal end of an intramedullary rod with proximal femoral support structure in accordance with an embodiment of the present invention;

FIG. 27E illustrates a representation of a side view of a prosthetic femoral neck having preconfigured ridges for fixation within a neck bore of an intramedullary rod in accordance with an embodiment of the present invention;

FIG. 27F illustrates a representation of a top down view of a prosthetic femoral neck having preconfigured ridges for fixation within a neck bore of an intramedullary rod and a curved prosthetic femoral neck shaft in accordance with an embodiment of the present invention;

FIG. 27G illustrates a representation of a bottom up view of a prosthetic femoral neck having preconfigured ridges for fixation within a neck bore of an intramedullary rod and a curved prosthetic femoral neck shaft in accordance with an embodiment of the present invention;

FIG. 27H illustrates a representation of an upper portion of an intramedullary rod showing a neck bore with gripping ridges formed therein for fixedly engaging ridges of a prosthetic femoral neck inserted therethrough in accordance with an embodiment of the present invention;

FIG. 27I illustrates a representation of a top down view of an intramedullary rod having a neck bore and illustrating a representation of a prosthetic femoral neck inserted through the neck bore in accordance with an embodiment of the present invention;

FIG. 28A illustrates a representation of a side cutaway view of a neck bore guide tool in accordance with an embodiment of the present invention;

FIG. 28B illustrates a representation of a rear cutaway view of a neck bore guide tool in accordance with an embodiment of the present invention;

FIG. 28C illustrates a representation of a top down view of a neck bore guide tool in accordance with an embodiment of the present invention;

FIG. 28D illustrates a representation of a perspective cutaway view of a fixation keyway of a neck bore guide tool for engaging a proximal end of an intramedullary rod in accordance with an embodiment of the present invention;

FIG. 28E illustrates a representation of a perspective cutaway view of a fixation keyway of a neck bore guide tool for engaging a proximal end of an intramedullary rod in accordance with another embodiment of the present invention;

FIG. 32A illustrates a representation of a prosthetic acetabular cup, a prosthetic femoral head and neck, and an intramedullary rod installed in a femur, and also illustrates a representation of a fixation screw to fix the position of the prosthetic femoral neck within the neck bore of the intramedullary rod in accordance with an embodiment of the present invention;

FIG. 32B illustrates a representation of a prosthetic acetabular cup, a prosthetic femoral head and neck, and an intramedullary rod installed in a femur, and also illustrates a representation of a fixation screw fixing the position of the prosthetic femoral neck within the neck bore of the intramedullary rod in accordance with an embodiment of the present invention;

FIG. 41 is a representation of a prosthetic acetabular cup in relation to an acetabulum in preparation for impacting, in accordance with an embodiment.

FIG. 42 is a representation of an impactor tool having apparatus indicative of an abduction angle in accordance with an embodiment.

FIG. 43A is a representation of a prosthetic acetabular cup in a preliminary impacted position, wherein the cup is not fully seated against the acetabulum, in accordance with an embodiment.

FIG. 43B is a representation of a prosthetic acetabular cup in a fully impacted position, wherein the cup is fully seated against the acetabulum, in accordance with an embodiment.

FIG. 44A is a representation of a cross-sectional view of a wall of a prosthetic acetabular cup in relationship to an acetabulum, with a fixation screw positioned to be fitted into a hole in the wall to fix the prosthetic acetabular cup to the acetabulum in accordance with an embodiment.

FIG. 44B is a representation of an inner surface of a prosthetic acetabular cup with a fixation screw positioned to be fitted into a hole in the inner surface to fix the prosthetic acetabular cup to an acetabulum in accordance with an embodiment.

FIG. 44C is a representation of a cross-sectional view of a wall of a prosthetic acetabular cup in relationship to an acetabulum, with a fixation screw fitted through a hole in the wall and fixing the prosthetic acetabular cup to the acetabulum in accordance with an embodiment.

FIG. 45 is a representation of a fixation screw having a shaft bore in accordance with an embodiment.

FIG. 46 is a representation of a prosthetic femoral head in position for placement in relation to an impacted prosthetic acetabular cup in accordance with an embodiment.

FIG. 47 is a representation of a prosthetic femoral head positioned in a prosthetic acetabular cup in accordance with an embodiment.

FIG. 61 is a schematic side view of a hip arthroplasty procedure using a prosthetic hip system with a femoral neck orientation guide according to an embodiment of the present invention.

FIG. 62 is a schematic side view of a hip arthroplasty procedure using a prosthetic hip system with an implant insertion and drill guide according to an embodiment of the present invention.

FIG. 63 is a schematic side view of a hip arthroplasty procedure using a prosthetic hip system with a femoral neck length gauge according to an embodiment of the present invention.

FIG. 64 is a schematic front view of a hip arthroplasty procedure using a prosthetic hip system with an implant insertion and drill guide according to an embodiment of the present invention.

FIG. 65 is a schematic front view of a hip arthroplasty procedure using a prosthetic hip system with an implant insertion and drill guide according to an embodiment of the present invention.

FIG. 66 is a schematic exploded isometric view of a prosthetic hip system according to an embodiment of the present invention.

FIG. 67 is a schematic isometric front view of the prosthetic hip system according to FIG. 66.

FIG. 68 is a schematic isometric side view of the prosthetic hip system according to FIG. 66.

FIG. 69 is a schematic partial cross-sectional side view of the prosthetic hip system according to FIG. 66.

FIG. 70 is a schematic isometric view of an interface for a stem according to an embodiment of the present invention.

FIG. 71 is a schematic isometric view of an interface for a stem according to an embodiment of the present invention.

FIG. 72 is a schematic isometric view of an interface for a stem according to an embodiment of the present invention.

Figures 73, 74:
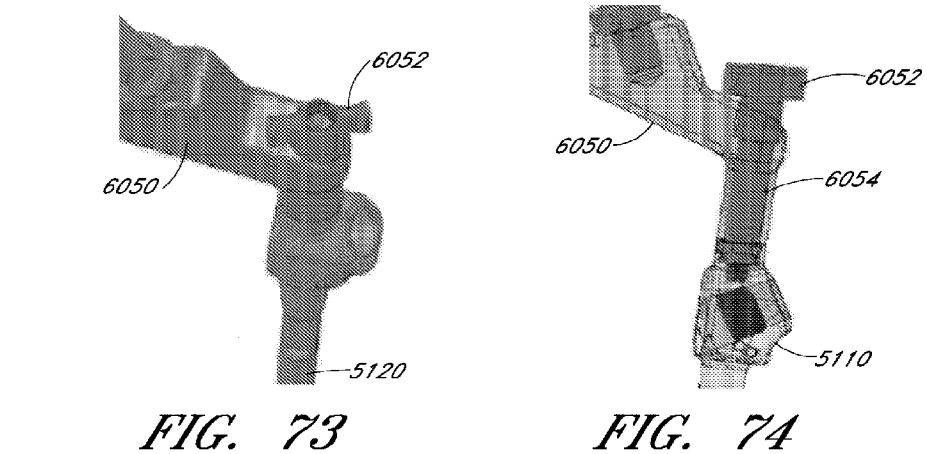

FIG. 73 is a schematic isometric view of a stem interface control according to an embodiment of the present invention.

FIG. 74 is a schematic front view of a stem interface control according to an embodiment of the present invention.

Figure 75:
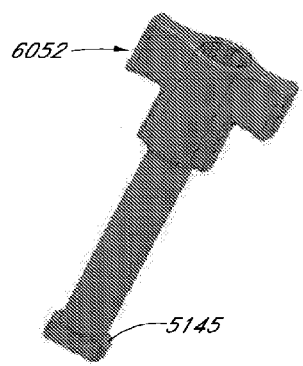

FIG. 75 is a schematic isometric view of a stem interface control according to an embodiment of the present invention.

Figures 76, 77:
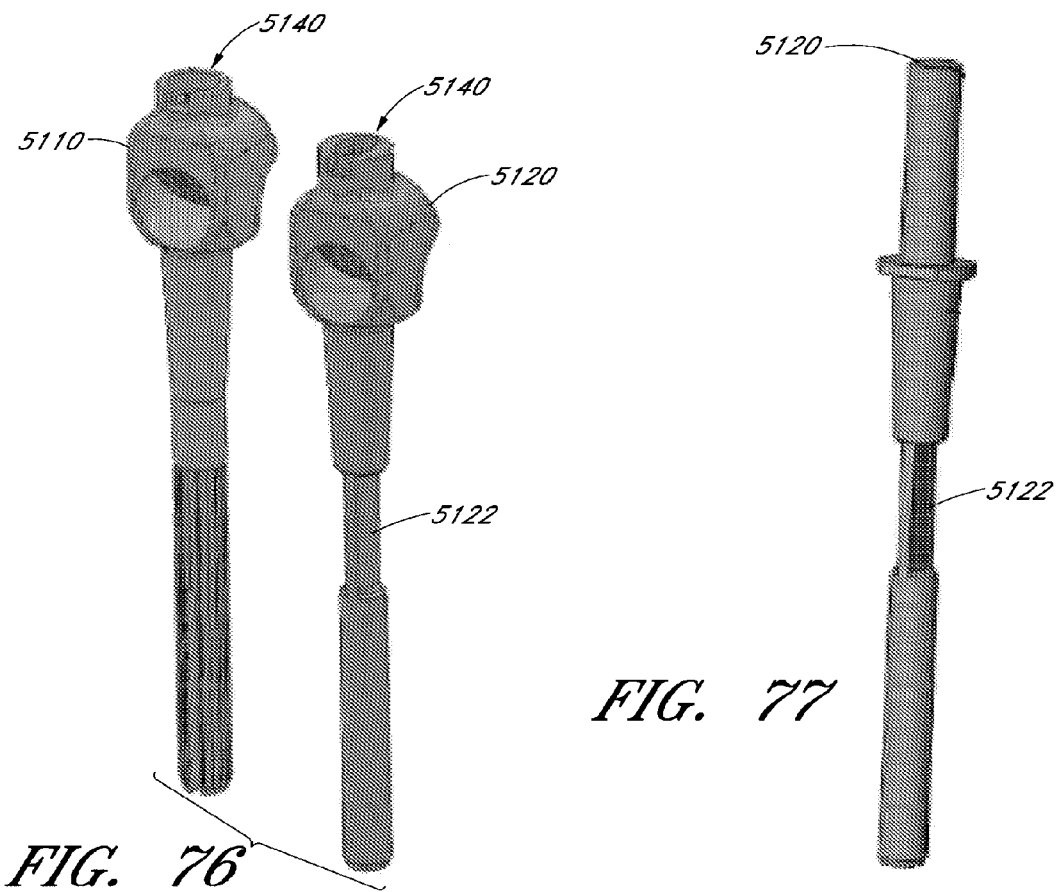

FIG. 76 is a schematic isometric views of stems and trial stems according to embodiments of the present invention.

FIG. 77 is a schematic isometric view of a trial stem according to an embodiment of the present invention.

Figures 78, 79, 80:
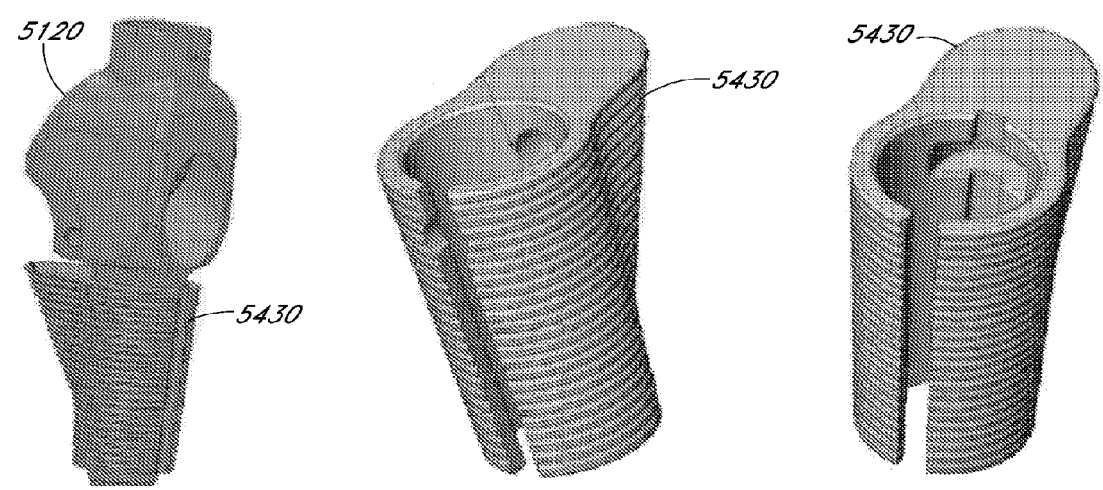

FIG. 78 is a schematic isometric view of a stem and sleeve according to an embodiment of the present invention.

FIG. 79 is a schematic isometric view of a slotted sleeve according to an embodiment of the present invention.

FIG. 80 is a schematic isometric view of a slotted sleeve according to an embodiment of the present invention.

FIG. 81 is a schematic front view of a prosthetic hip system according to an embodiment of the present invention.

FIG. 82 is a schematic side view of the prosthetic hip system according to FIG. 81.

FIG. 83 is a schematic top view of the prosthetic hip system according to FIG. 81.

FIG. 84 is a schematic isometric view of the prosthetic hip system according to FIG. 81.

FIG. 85 is a schematic side view of the prosthetic hip system according to FIG. 81.

FIG. 86 is a schematic bottom view of the prosthetic hip system according to FIG. 81.

Figure 87:
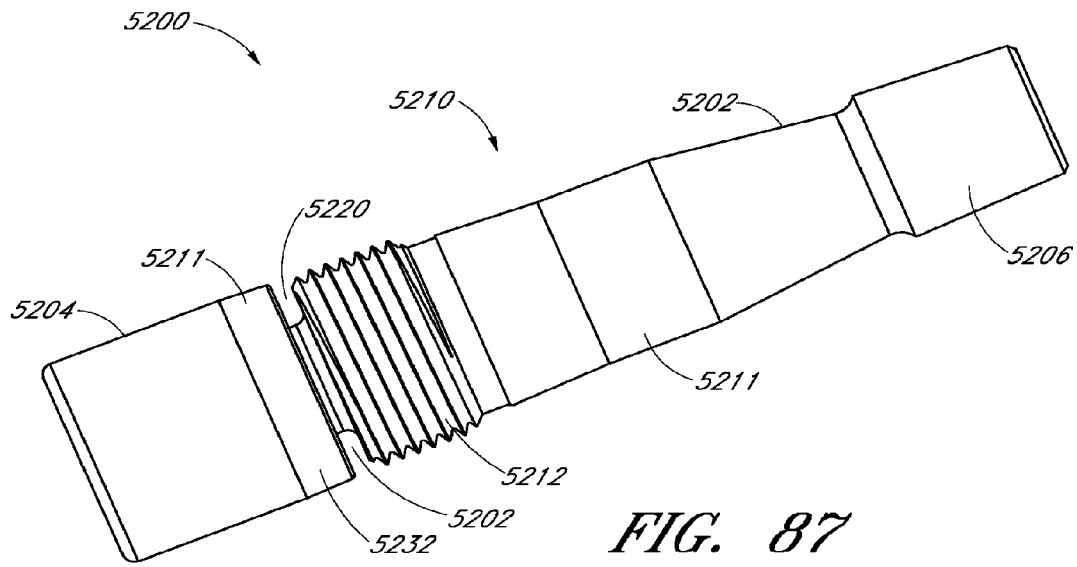

FIG. 87 is a schematic side view of a neck implant according to an embodiment of the present invention.

Figure 88:
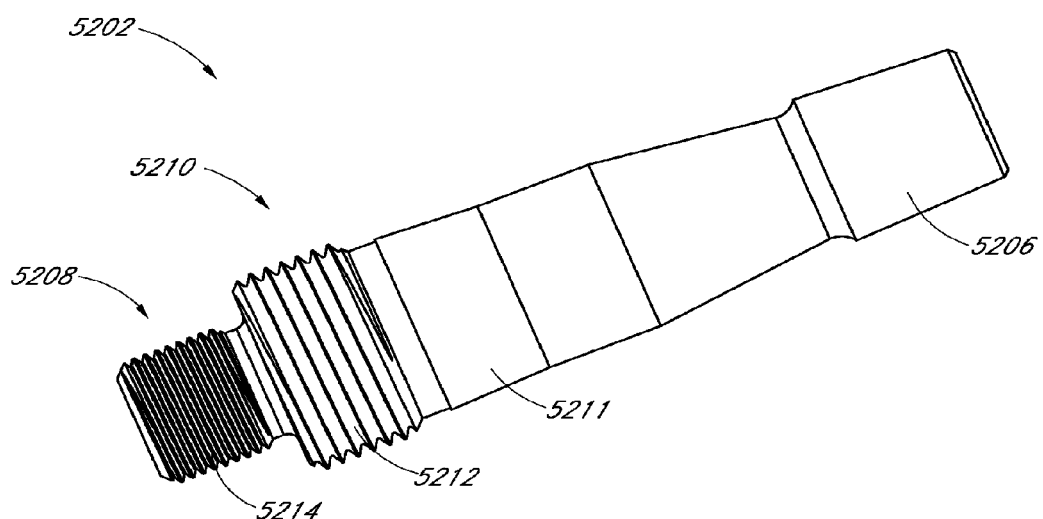

FIG. 88 is a schematic side view of a distal neck portion of a neck implant according to an embodiment of the present invention.

Figure 89:
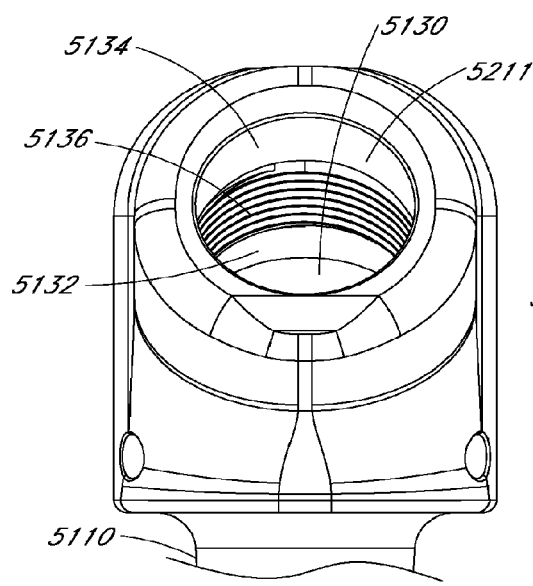

FIG. 89 is a schematic distal side view of a stem with a neck implant bore according to an embodiment of the present invention.

Figure 90:
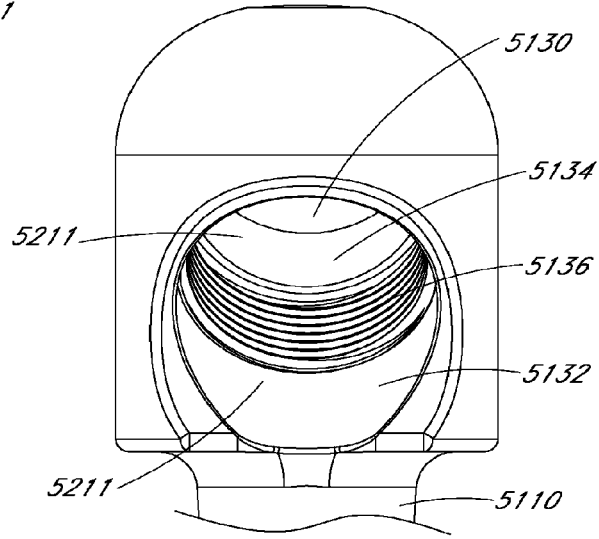

FIG. 90 is a schematic proximal side view of the stem with a neck implant bore according to FIG. 89.

Figure 91:
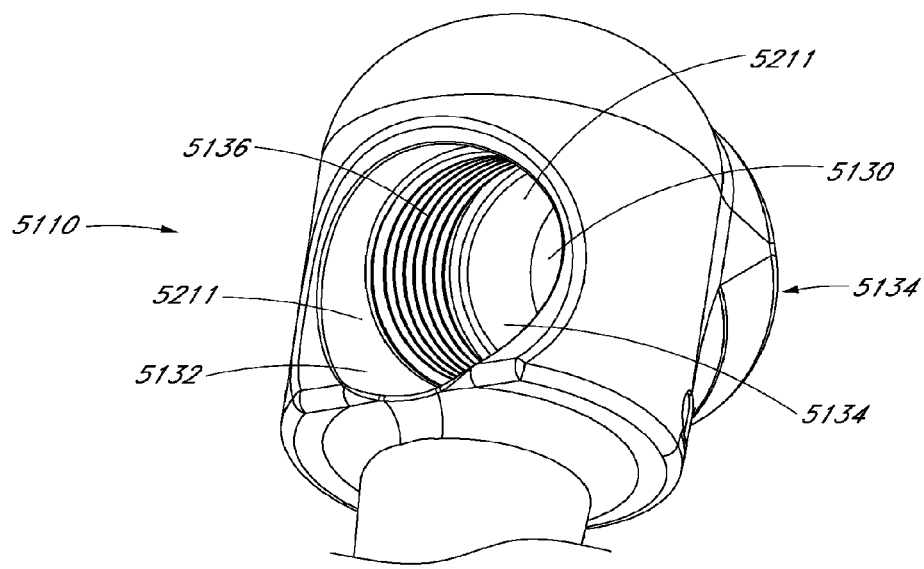

FIG. 91 is a schematic isometric view of the stem with a neck implant bore according to FIG. 89.

Figure 92:
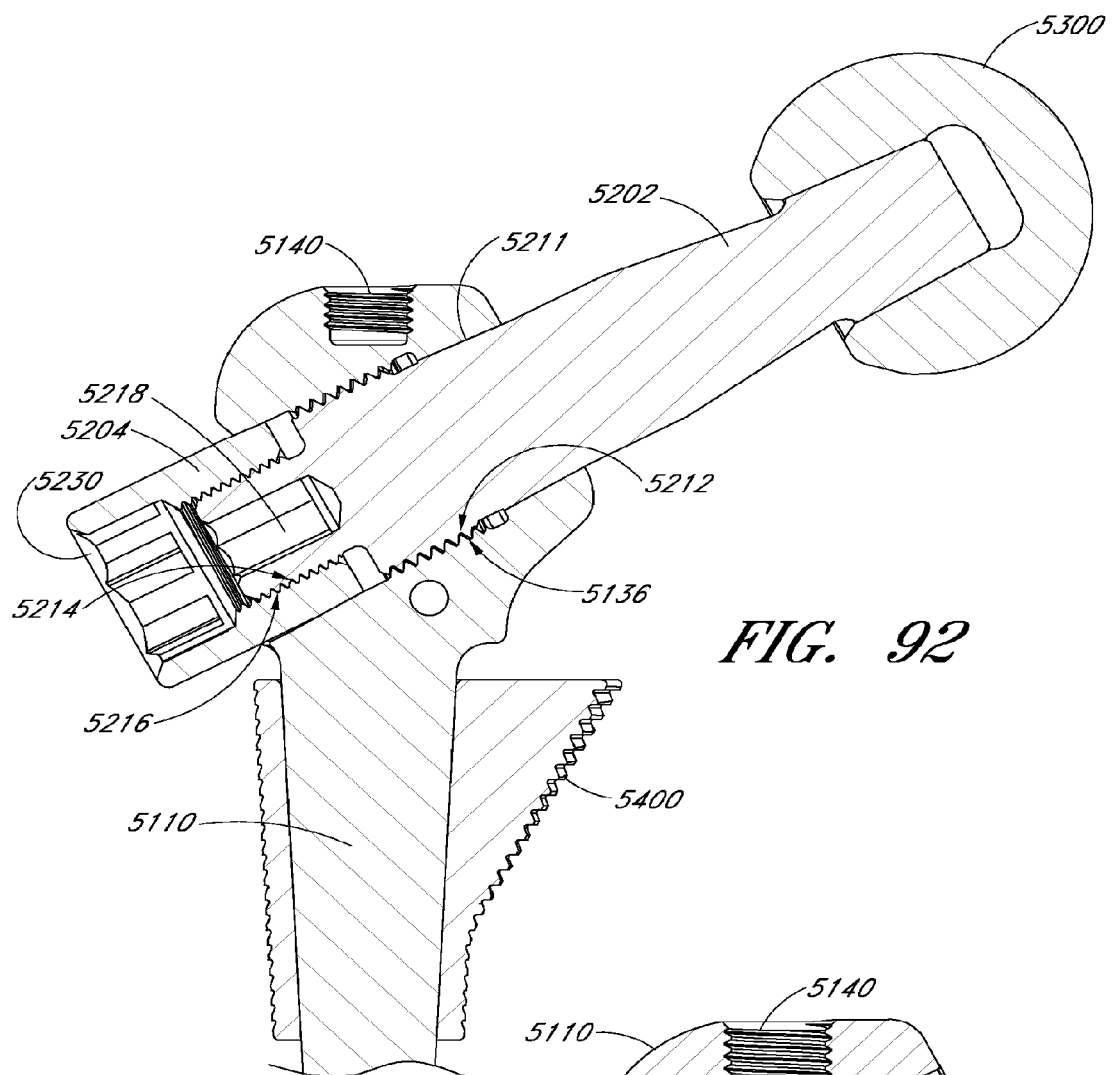

FIG. 92 is a schematic partial cross-sectional front view of the prosthetic hip system according to FIG. 81.

Figure 93:
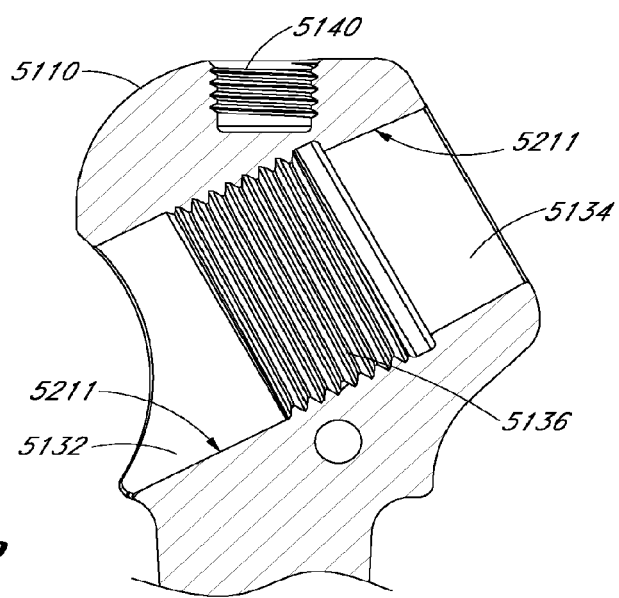

FIG. 93 is a schematic partial cross-sectional front view of the prosthetic hip system according to FIG. 81.

Figure 94:
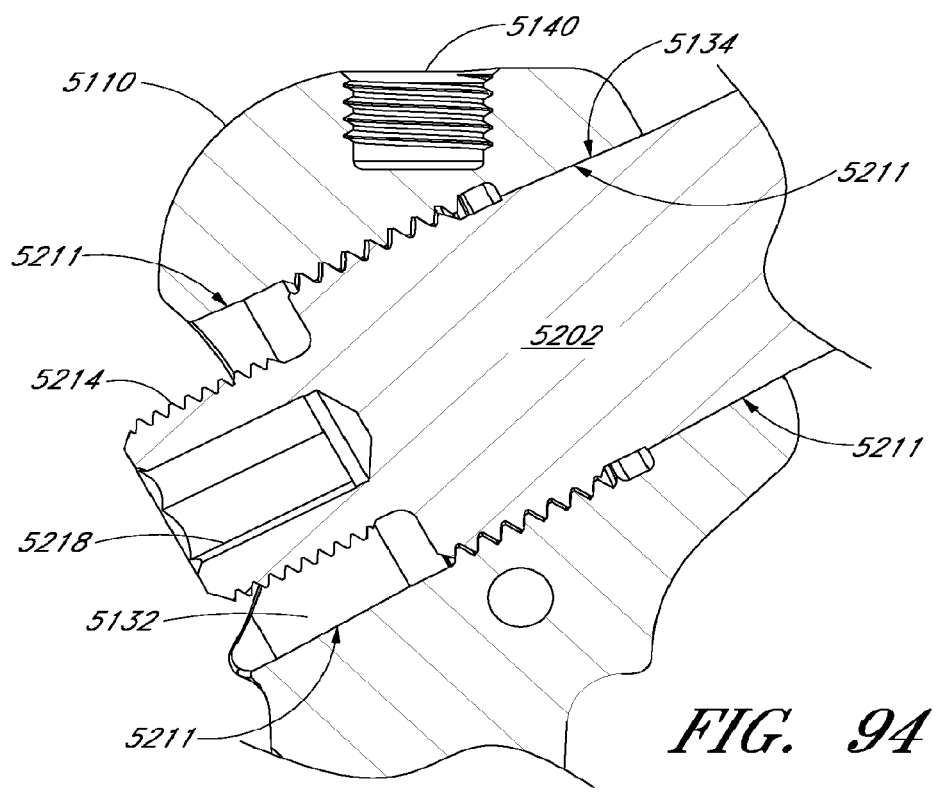

FIG. 94 is a schematic partial cross-sectional front view of the prosthetic hip system according to FIG. 81.

Figure 95:
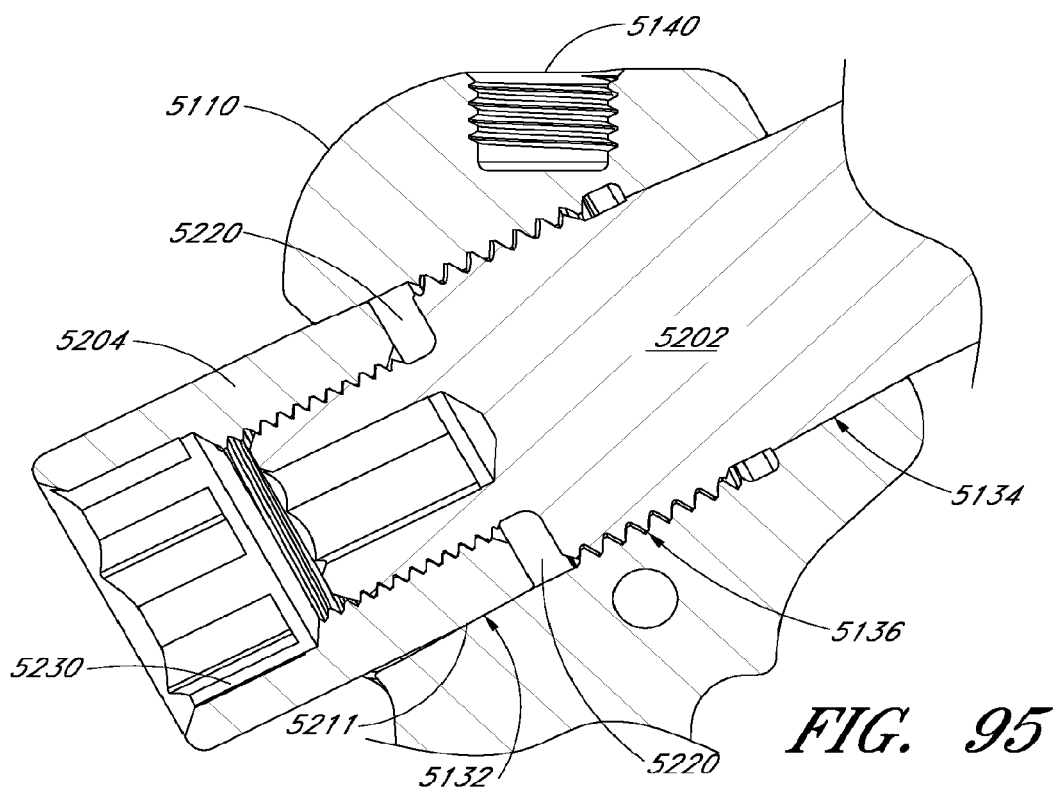

FIG. 95 is a schematic partial cross-sectional front view of the prosthetic hip system according to FIG. 81.

FIG. 96 is a schematic isometric view of a prosthetic hip system according to an embodiment of the present invention.

FIG. 97 is a schematic front view of the prosthetic hip system according to FIG. 96.

FIG. 98 is a schematic distal side view of the prosthetic hip system according to FIG. 96.

FIG. 99 is a schematic proximal side view of the prosthetic hip system according to FIG. 96.

Figure 100:
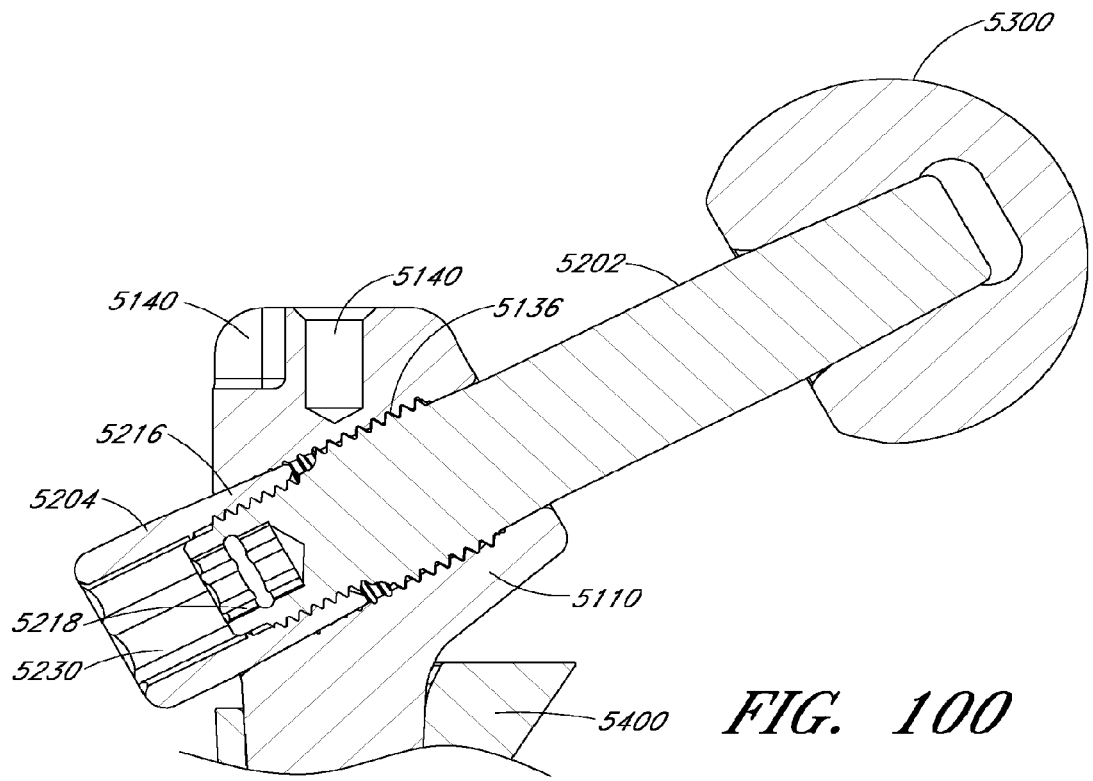

FIG. 100 is a schematic partial cross-sectional front view of the prosthetic hip system according to FIG. 96.

Figure 101:
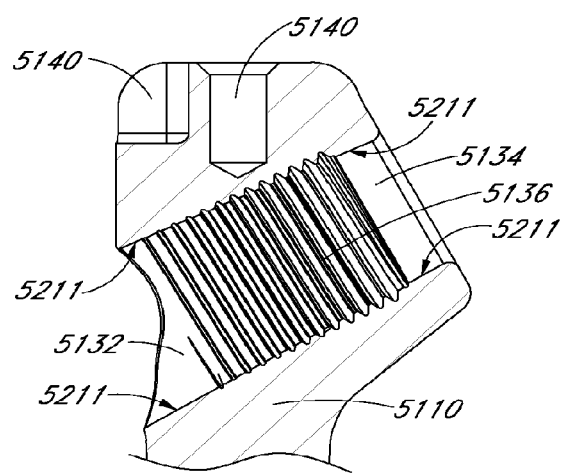

FIG. 101 is a schematic partial cross-sectional front view of the prosthetic hip system according to FIG. 96.

Figure 102:
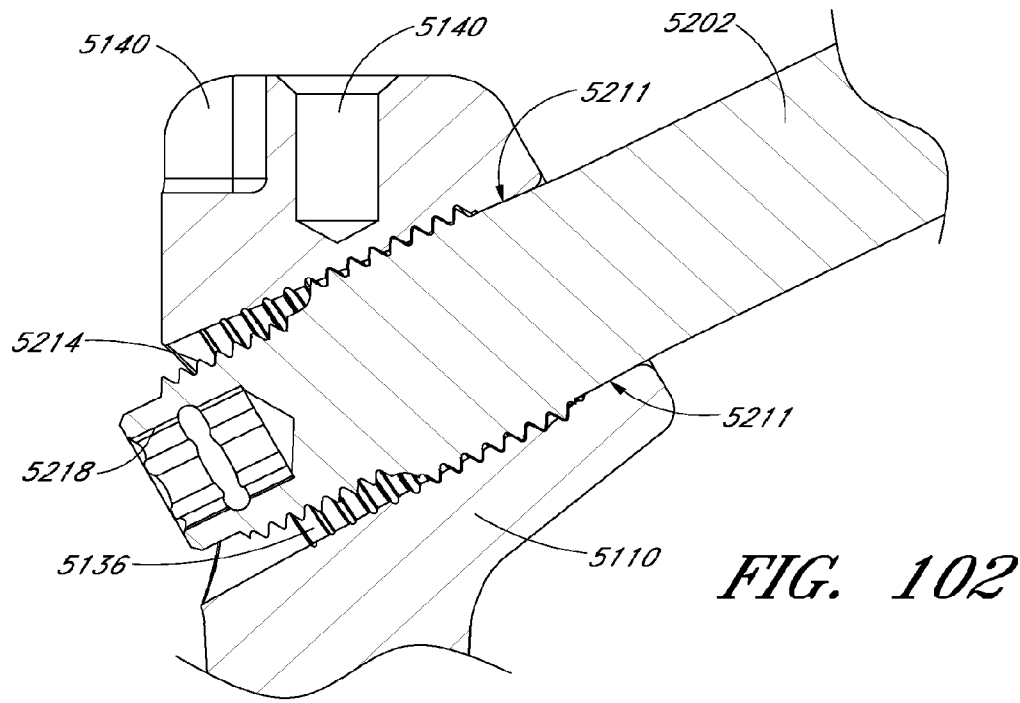

FIG. 102 is a schematic partial cross-sectional front view of the prosthetic hip system according to FIG. 96.

Figure 103:
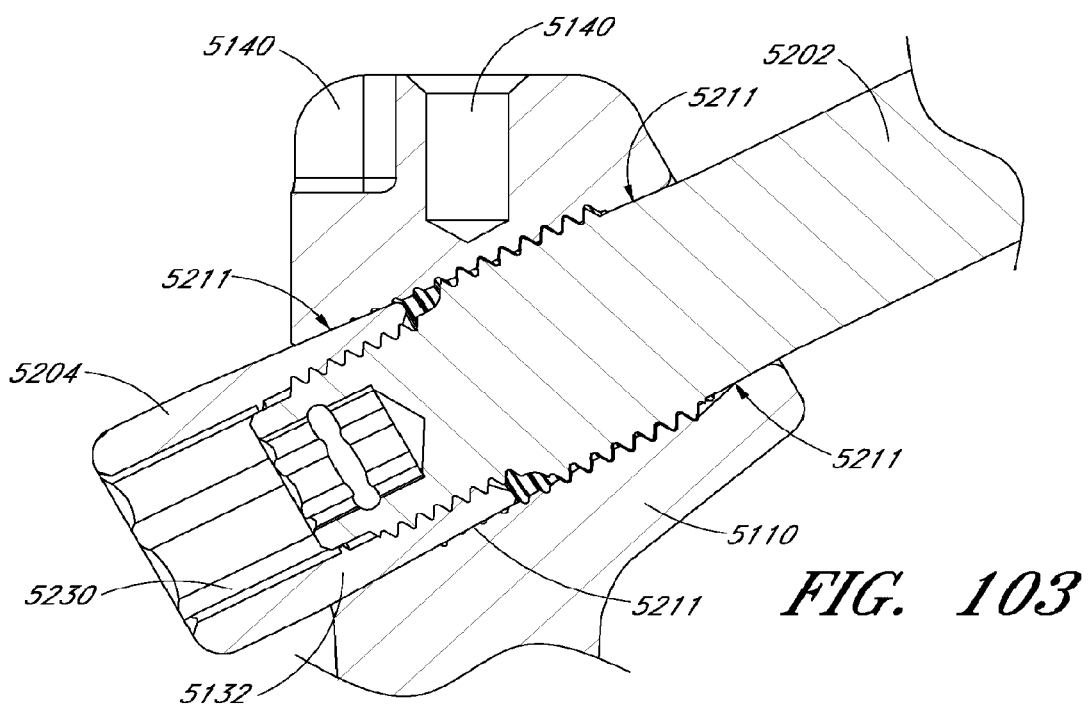

FIG. 103 is a schematic partial cross-sectional front view of the prosthetic hip system according to FIG. 96.

FIG. 104 is a schematic isometric view of a collet lock prosthetic hip system according to an embodiment of the present invention.

FIG. 105 is a schematic front view of the prosthetic hip system according to FIG. 104.

FIG. 106 is a schematic distal side view of the prosthetic hip system according to FIG. 104.

FIG. 107 is a schematic proximal side view of the prosthetic hip system according to FIG. 104.

Figure 108:
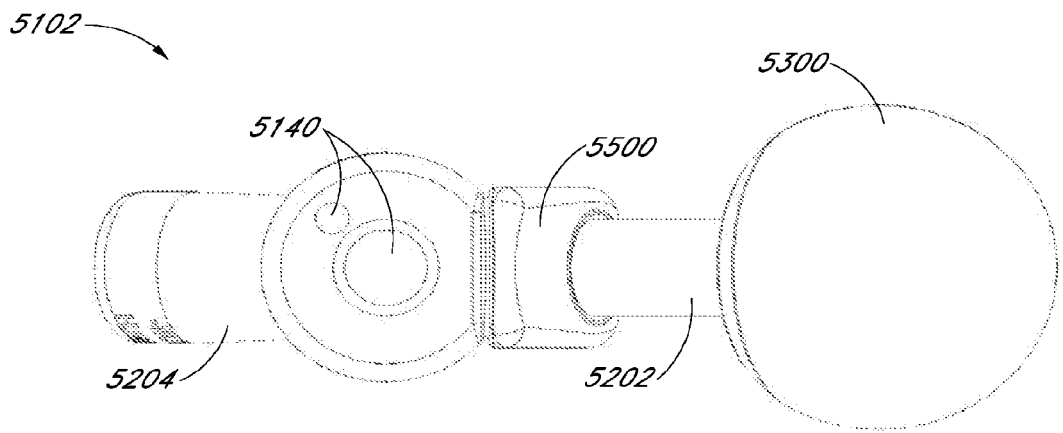

FIG. 108 is a schematic top view of the prosthetic hip system according to FIG. 104.

Figure 109:
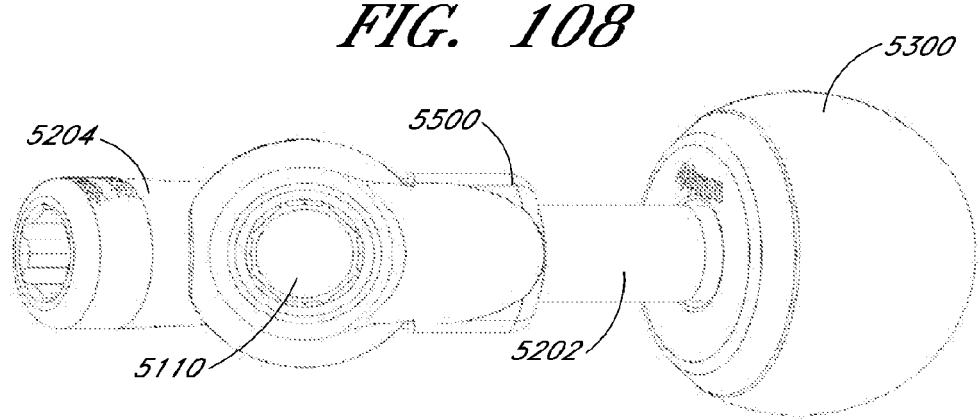

FIG. 109 is a schematic bottom view of the prosthetic hip system according to FIG. 104.

Figure 110:
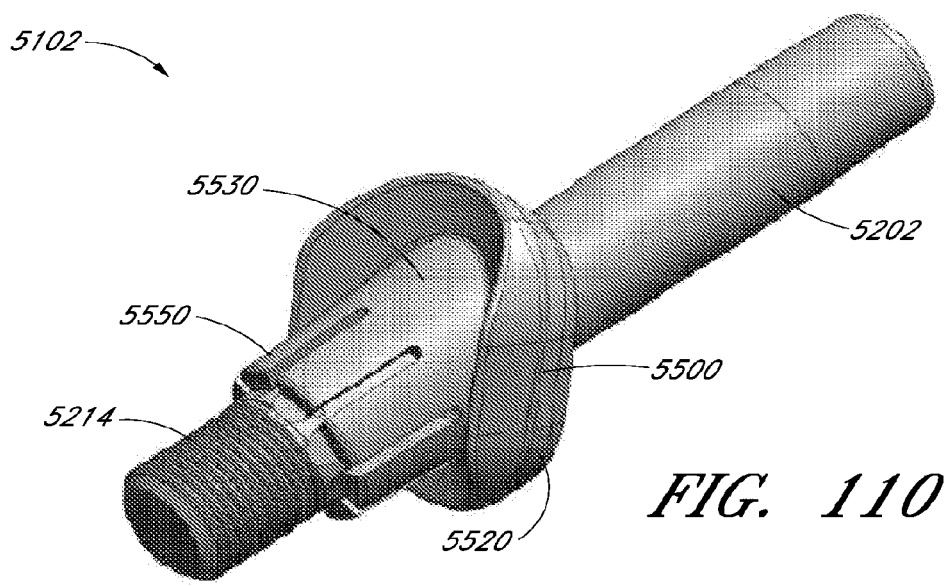

FIG. 110 is a schematic isometric view of a neck implant with a collet according to an embodiment of the present invention.

Figure 111:
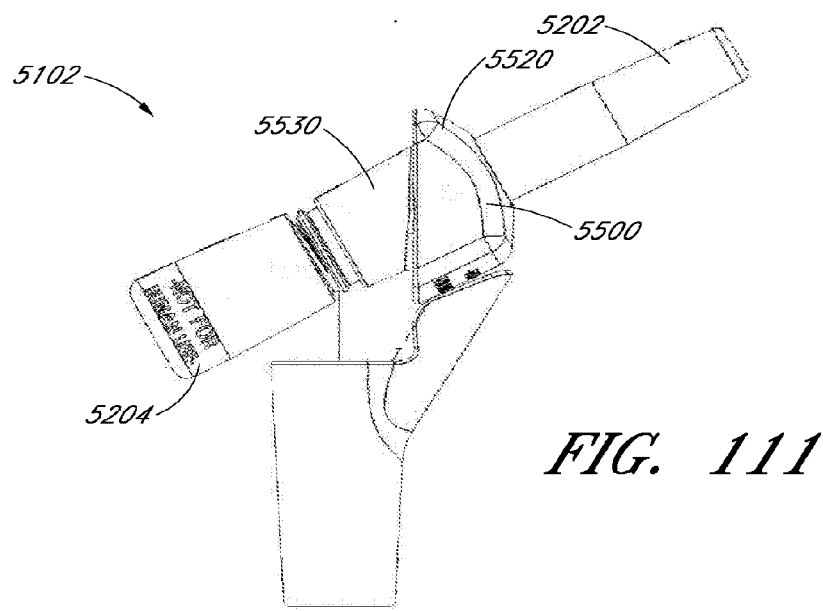

FIG. 111 is a schematic front view of the prosthetic hip system according to FIG. 104.

Figure 112:
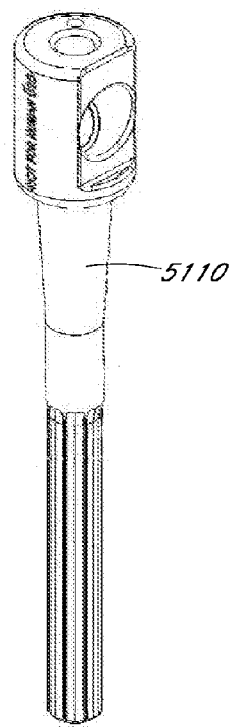

FIG. 112 is a schematic isometric view of the prosthetic hip system according to FIG. 104.

Figure 113:
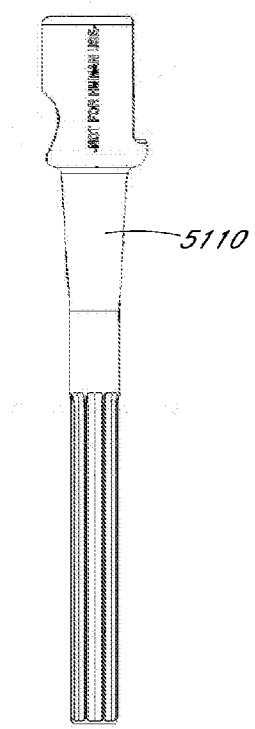

FIG. 113 is a schematic front view of the prosthetic hip system according to FIG. 104.

Figure 114:
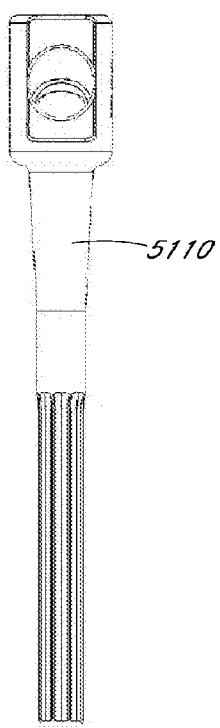

FIG. 114 is a schematic side view of the prosthetic hip system according to FIG. 104.

Figure 115:
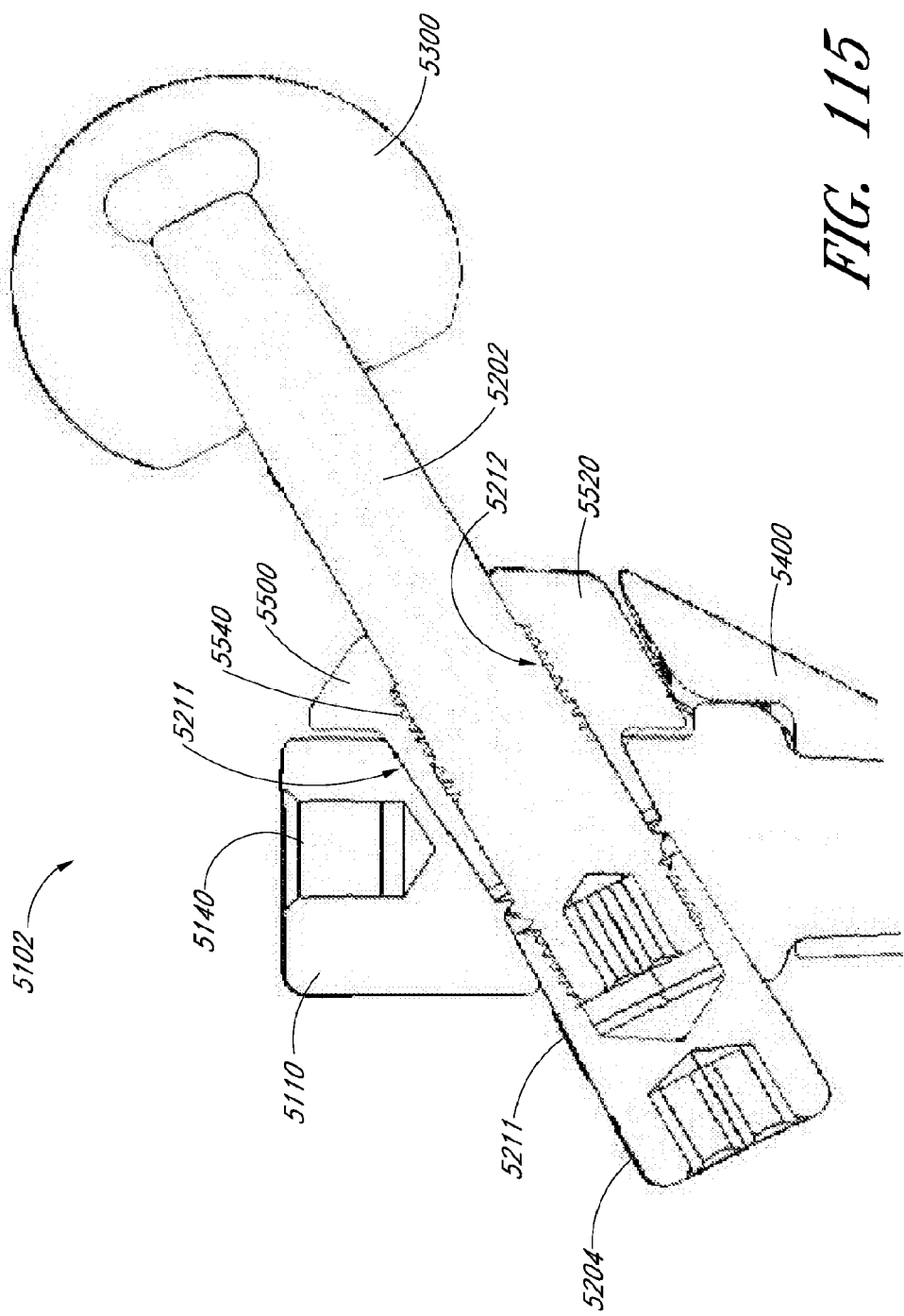

FIG. 115 is a schematic partial cross-sectional front view of the prosthetic hip system according to FIG. 104.

FIG. 116 is a schematic isometric view of a collet lock prosthetic hip system according to an embodiment of the present invention.

FIG. 117 is a schematic front view of the prosthetic hip system according to FIG. 116.

FIG. 118 is a schematic isometric view of a neck implant with a collet according to an embodiment of the present invention.

FIG. 119 is a schematic partial cross-sectional front view of a neck implant with a collet according to FIG. 116.

FIG. 120 is a schematic partial cross-sectional front view of the prosthetic hip system according to FIG. 116.

FIG. 121 is a schematic isometric view of a collet according to an embodiment of the present invention.

FIG. 122 is a schematic isometric view of a screw-lock prosthetic hip system according to an embodiment of the present invention.

FIG. 123 is a schematic front view of the prosthetic hip system according to FIG. 122.

FIG. 124 is a schematic partial cross-sectional front view of the prosthetic hip system according to FIG. 122.

Figures 125, 126:
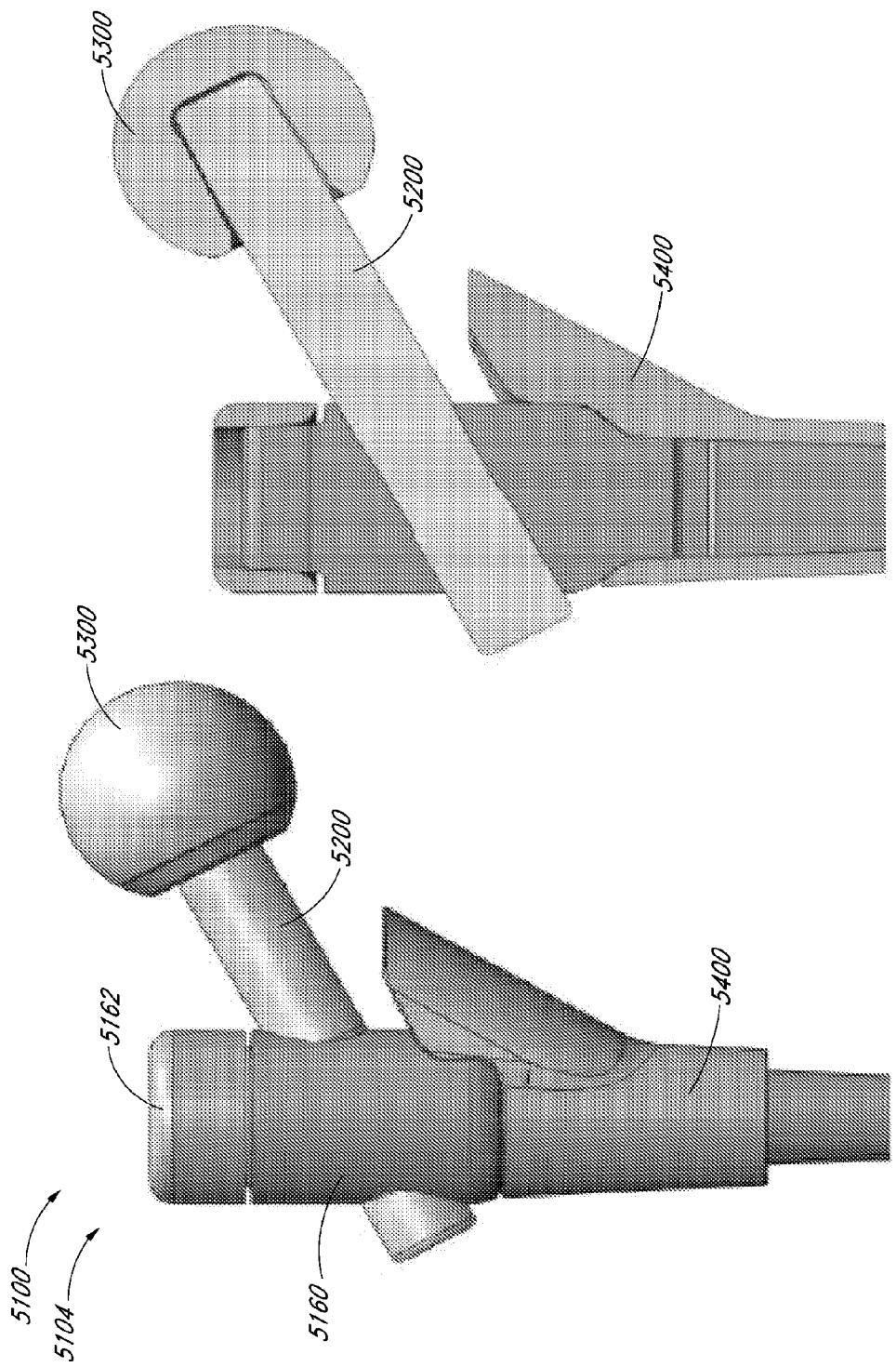

FIG. 125 is a schematic front view of a split-stem prosthetic hip system according to an embodiment of the present invention.

FIG. 126 is a schematic partial cross-sectional front view of the prosthetic hip system according to FIG. 125.

FIG. 127 is a schematic proximal side view of the prosthetic hip system according to FIG. 125.

FIG. 128 is a schematic proximal side view of the prosthetic hip system according to FIG. 125.

Throughout the figures, the same reference numerals and characters, unless otherwise stated, are used to denote like features, elements, components or portions of the illustrated embodiments. In certain instances, similar names may be used to describe similar components with different reference numerals which have certain common or similar features. Moreover, while the subject invention will now be described in detail with reference to the figures, it is done so in connection with the illustrative embodiments. It is intended that changes and modifications can be made to the described embodiments without departing from the true scope and spirit of the subject invention as defined by the appended claims.

DETAILED DESCRIPTION OF THE PREFERRED EMBODIMENT

While the present description sets forth specific details of various embodiments, it will be appreciated that the description is illustrative only and should not be construed in any way as limiting. Additionally, it is contemplated that although particular embodiments of the present inventions may be disclosed or shown in the context of hip surgeries, such as total hip arthroplasty or hemiarthroplasty, such embodiments can be used in other surgical techniques and devices. Furthermore, various applications of such embodiments and modifications thereto, which may occur to those who are skilled in the art, are also encompassed by the general concepts described herein.

Embodiments of the methods, systems, components, and devices disclosed herein can be used for various joints of the body, such as the shoulder, hip, and the like. As discussed in the above-noted publications, joint replacements for the hip are common and have several factors that can be considered when designing a hip prosthetic system and methods of implantation. In the present disclosure, reference is made to a prosthetic hip joint and system. However, the systems and methods disclosed herein can be used for various joints in the body. Thus, the present disclosure should be construed as applicable to methods, systems, components, and devices for any of the various joints of the body, such as the shoulder, hip, and the like.

In accordance with one embodiment of a method in accordance with the present invention, a patient is placed in the supine position on a standard operating table. As is known, specialized viewing tables and/or viewing systems may be used as desired, and the present invention is not limited by a particular type of table or viewing system.

Figure 1:
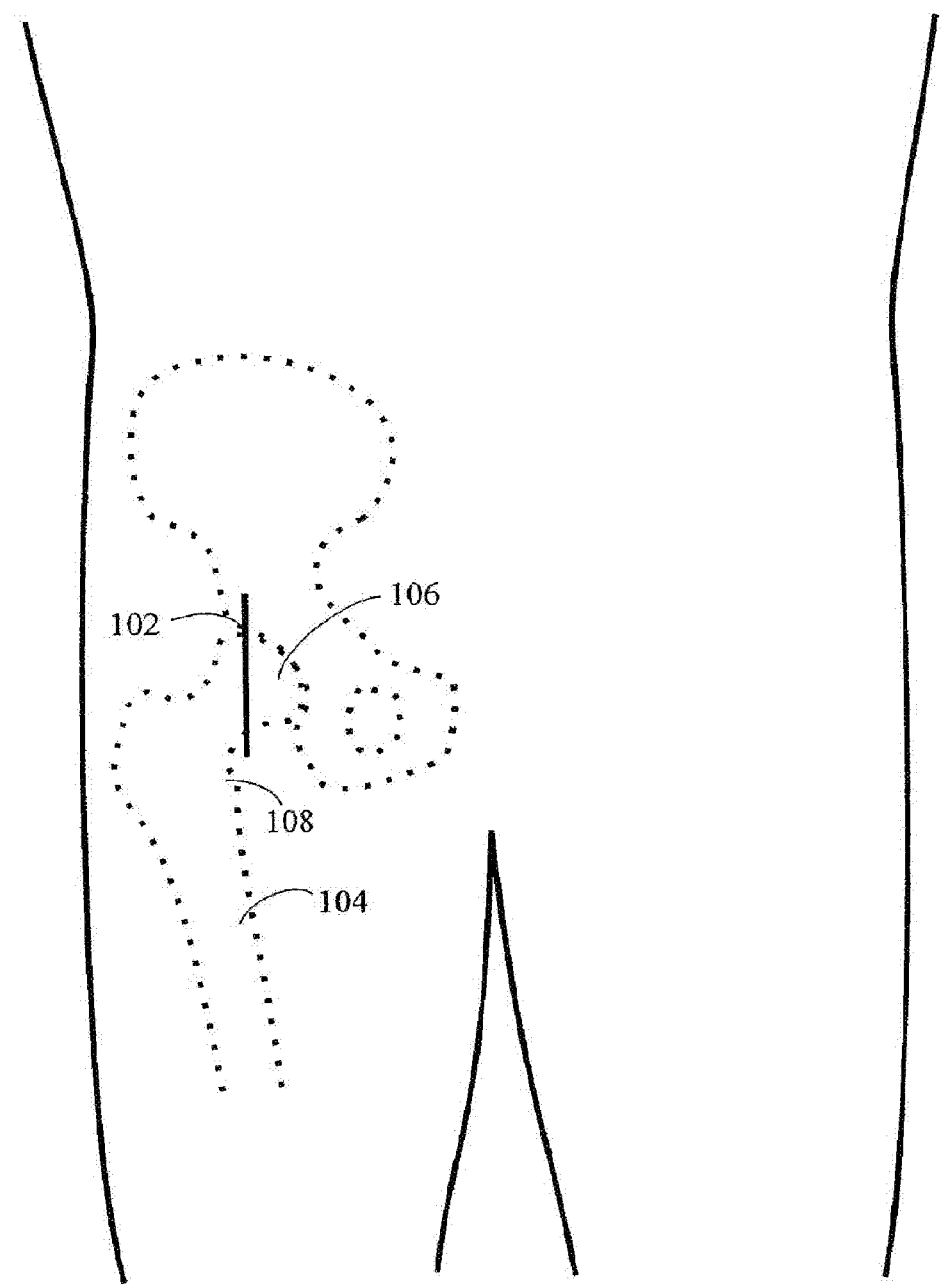
FIG. 1 illustrates a representation of an initial incision in accordance with one embodiment of the present invention.

FIG. 1 illustrates a representation of an initial incision 102 in accordance with one embodiment of the present invention. An anterior approach that may be used in this embodiment is to perform, with the patient in supine position, a portion of a Smith-Peterson approach (Hoppenfeld and deBoer, Surgical Exposures in Orthopaedics—The Anatomic Approach, 1984) making approximately a 2-3 cm incision 102 located preferably along a line that is approximately parallel to the length of the femur 104 and positioned approximately over the femoral head 106, with the distal (toward the patient's foot) extent of the line extending approximately to a point lateral to the lesser trochanter 108. This approach provides safe access to the hip joint by exploiting the internervous plane between the sartorius and the tensor fasciae latae and avoiding the femoral and superior gluteal nerves. This internervous plane is developed by known methods. The incision may advantageously be extended in either direction as needed.

Figure 2:
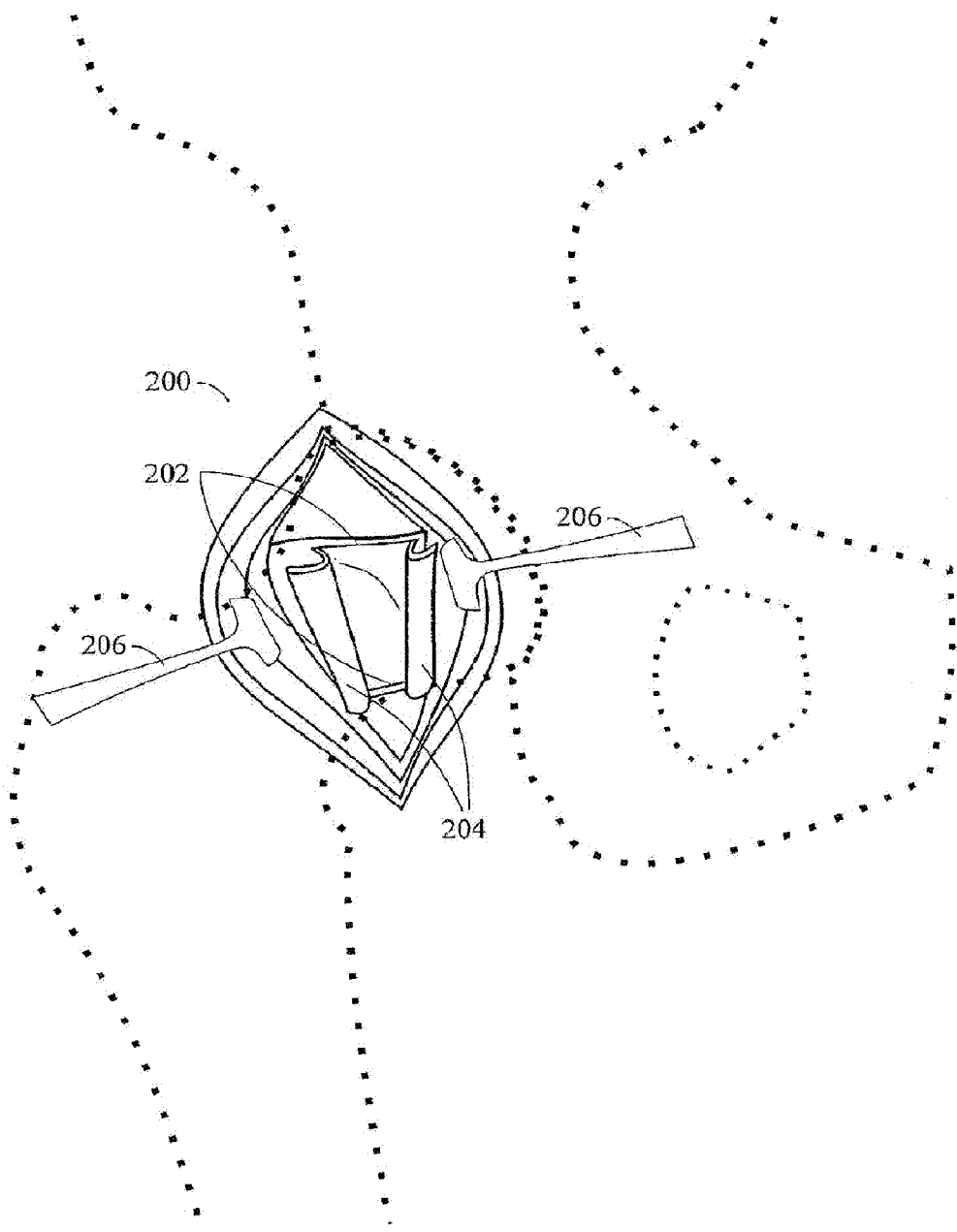
FIG. 2 illustrates a representation of a surgical access to a hip joint capsule in accordance with one embodiment of the present invention.

Also, in accordance with known technique, the deeper internervous plane between the rectus femoris and the gluteus medius is developed. With the internervous planes developed, and with retraction of muscles and tissue, the hip joint capsule may be accessed and visualized. FIG. 2 illustrates a representation of a surgical access 200 to a hip joint capsule in accordance with one embodiment of the present invention.

The hip joint capsule itself may then be incised, in one embodiment of the present invention, from approximately the mid-point of the femoral head and extending along the axis of the femoral neck to approximately a point on a line between the greater and lesser trochanters.

Secondary incisions 202 may then be made to form flaps in the hip joint capsule walls that may be retracted to access the femoral neck, the femoral head and the acetabulum. In accordance with known technique, an "H" type incision may be used to create the capsular flaps 204, which may then be held open by suture or retractors 206 to expose the femoral neck.

It will be appreciated that other surgical approaches may be used to access the femoral neck and acetabulum regions, and the present invention is not limited by any particular surgical approach.

Figure 3C:
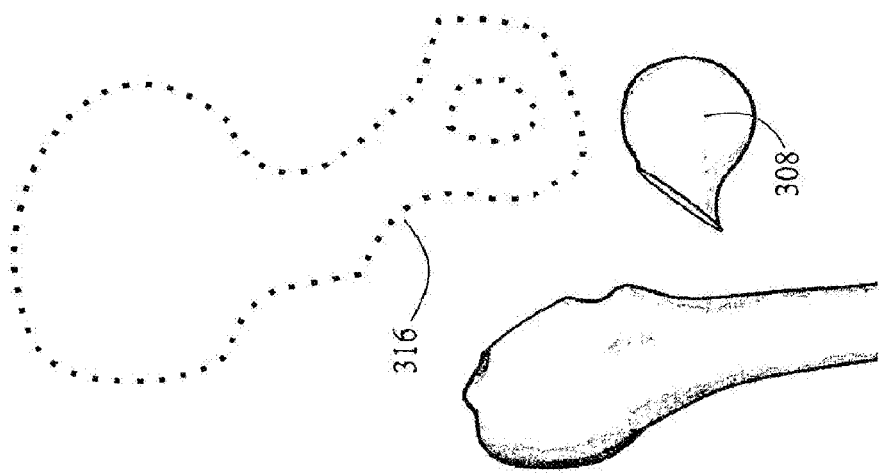
FIG. 3C illustrates a representation of removal of a femoral head in accordance with one embodiment of the present invention.

With the femoral neck accessed, both it and the femoral head may then be excised. A cutting tool, such as, for example, an oscillating saw, may be used to make cuts in the femoral neck. FIG. 3A illustrates a representation of cut lines 302, 304 in a femoral neck 306 in accordance with one embodiment of the present invention.

Preferably, two cut lines are defined: the first cut line 302 begins approximately at the point where the femoral neck 306 joins the greater trochanter and extends across the femoral neck 306 to end approximately at a point about 1.5 cm posterior to the lesser trochanter 310; and the second cut line 304 begins approximately at the point where the femoral neck 306 joins the femoral head 308 and extends across the femoral neck 306 to end at the same end point as the first cut line 302, namely, at the point approximately 1.5 cm posterior to the lesser trochanter 310.

Figure 3B:
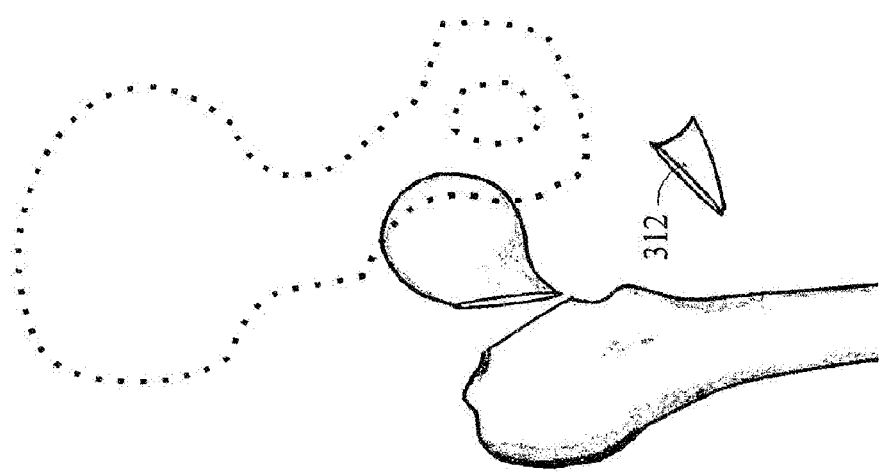
FIG. 3B illustrates a representation of removal of a portion of a femoral neck in accordance with one embodiment of the present invention.
Figure 3A:
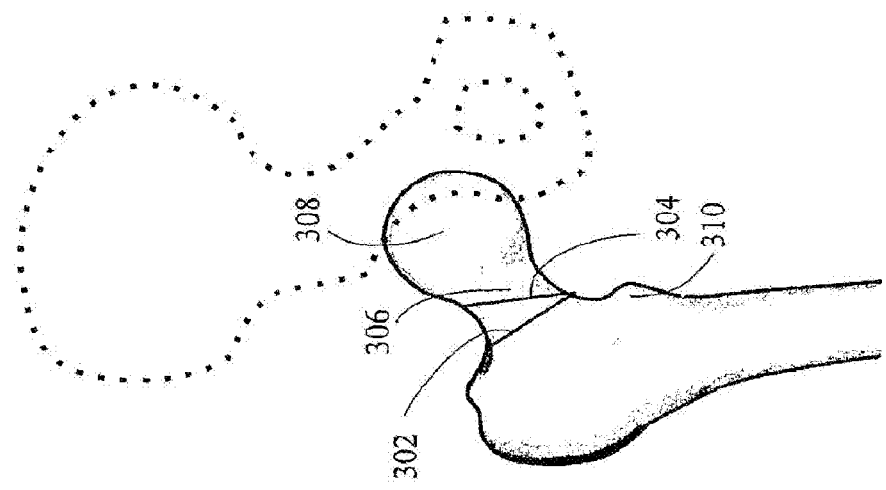
FIG. 3A illustrates a representation of cut lines in a femoral neck in accordance with one embodiment of the present invention.

FIG. 3B illustrates a representation of removal of a portion of a femoral neck in accordance with one embodiment of the present invention. It will be appreciated that two cuts in the femoral neck made along the first and second cut lines 302, 304, define and loosen a wedge-shaped piece 312 of the femoral neck 306, which piece may then be removed. It will be further appreciated that different cut lines may be used to loosen and remove different portions of the femoral neck 306 without departing from the present invention.

With the wedge-shaped piece 312 of the femoral neck 306 removed, the femoral head 308 may be accessed for removal. FIG. 3C illustrates a representation of removal of a femoral head 308 in accordance with one embodiment of the present invention.

After adjusting retractors to better access and visualize the femoral head 308 and acetabulum 316, and in accordance with known technique, a circular cutting tool may be inserted behind the femoral head 308 and may be used to sever the ligamentum teres, substantially freeing the femoral head 308 for removal using a corkscrew or an appropriately-sized forceps. Any difficulty in removing the femoral head 308 through the surgical access may easily be overcome by morselizing the femoral head 308 and removing the morsels and debris.

After confirming complete removal of the femoral head 308 and related debris, attention is then turned to preparing the acetabulum to receive a prosthetic acetabular cup. The present invention is not limited by the size of a prosthetic femoral head or the size of a prosthetic acetabular cup.

Figure 4A:
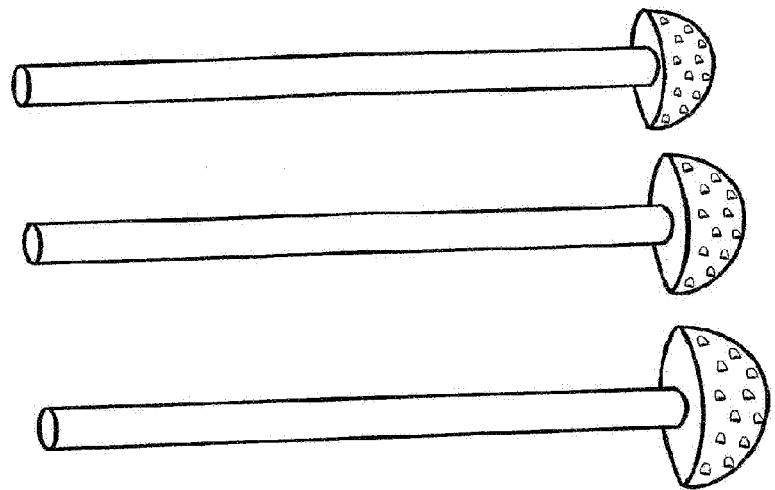
FIG. 4A illustrates a representation of a series of reamer tools stepped in size.

The acetabulum is prepared using known techniques, including removal of tissue from the cotyloid fossa and trimming of the labrum as needed. Osteophytes, cysts and the like may be removed from the area. The acetabulum may be progressively reamed using a series of standard reamers having progressively larger cutting heads designed to remove bone and to create a hemispherical concavity in the healthy subchondral bleeding bone that remains. FIG. 4A illustrates a representation of a series of reamer tools stepped in size. It will be appreciated that numerous reaming tools exist for reaming an acetabulum to receive a prosthetic acetabular cup, and the present invention is not limited by any particular reaming tool or any particular form of cutting head on a reaming tool.

Figure 4B:
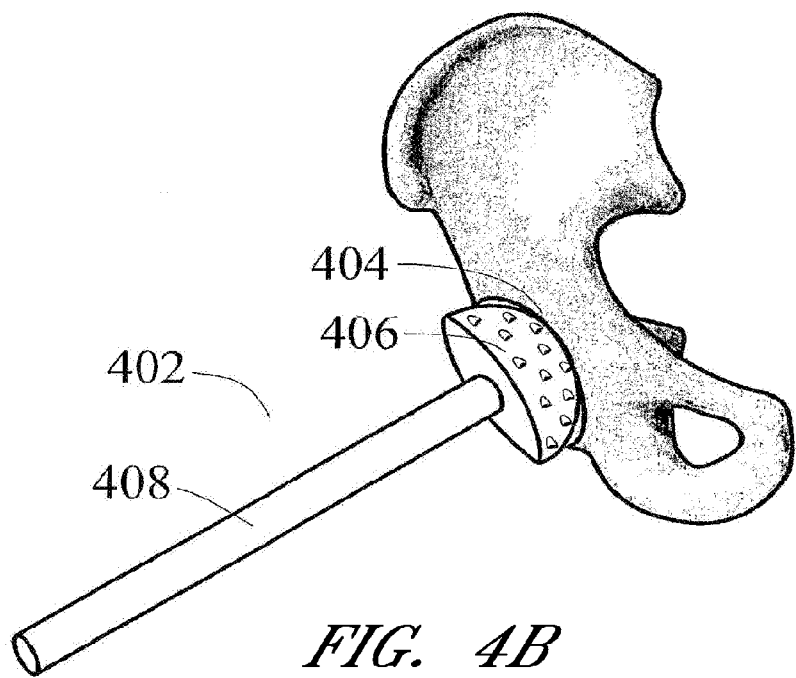
FIG. 4B illustrates a representation of reaming of an acetabulum in accordance with one embodiment of the present invention.

FIG. 4B illustrates a representation of reaming of an acetabulum 404 in accordance with one embodiment of the present invention. A reamer 402 comprises a reamer head 406 and a reamer shaft 408. The reamer head 406 may be removable from the reamer shaft 408, such as, for example, by spiral threads formed in the non-engaging side of the reamer head 406 which engage spiral threads formed into the end of the reamer shaft 408 when the reamer head 406 is rotated in the direction opposite from that in which it is configured to remove material from an acetabulum. The reamer head 406, as will be readily appreciated, may be configured to remove material from an acetabulum to create a roughly hemispherical void. The reamer 402 may be oriented at approximately 30 degrees of anteversion to achieve a desired degree of acetabular cup anteversion. The reamer 402 may also preferably be oriented to achieve a desirable abduction angle of approximately 45 degrees. Angles of anteversion and abduction may be adjusted in view of patient-specific anatomy. Templates and radiographs may be used to assist in orienting and sizing, and endoscopic or fluoroscopic imaging may assist the use of progressively larger reamers to achieve the properly-sized receiving area in the acetabulum 404. As will be readily appreciated, the acetabulum 404 is carefully under-reamed about 1-2 mm to achieve the best fit during impacting of the prosthetic acetabular cup. In an embodiment including the use of a prosthetic acetabular cup of 58 mm diameter, the acetabulum 404 may be reamed to form a hemispherical concavity of approximately 56-57 mm.

In a preferred embodiment of the present invention an acetabular cup of relatively large outside diameter, such as, for example, 58 mm is used along with an appropriately matched prosthetic femoral head having a relatively large outside diameter, such as, for example, 52 mm. It will be appreciated that smaller or larger respective diameters, such as, for example, 30-75 mm, or even larger or smaller depending upon various factors such as patient anatomy, may be used without departing from the present invention. Nor is the present invention limited by any particular material for the prosthetic femoral head or the acetabular cup, which may preferably be made from cobalt chromium, but could also be made from titanium, tantalum, surgical grade stainless steel, ceramic, alumina ceramic or other materials of suitable strength and acceptance properties.

The prosthetic acetabular cup may also be made from more than one of these materials. FIG. 5A illustrates a representation of an inner 502 and an outer 504 portion of a two-piece prosthetic cup with aligned holes 510 used to join the two pieces in accordance with one embodiment of the present invention. For example, an outer cup 504 may be formed from titanium and may also be machined or grit-blasted to have a mesh-like, porous or roughened outer surface 508. A cobalt chromium inner cup 502 machined to have a smooth inner surface 506 may be fit into the titanium outer cup, such that the combination forms a unitary prosthetic acetabular cup. The outer and inner cups may be fixedly joined (1) by press-fitting the inner cup into the outer cup, or (2) by using one or more screws inserted through the outer cup and into the inner cup, or (3) by machining an outward facing circumferential flange or lip around the perimeter of the inner cup and fitting the lip around the perimeter of the outer cup and then pressing or pinching the lip to grip the perimeter of the outer cup, or (4) by other means such as welding or soldering or medical grade adhesives.

FIG. 5B illustrates a representation of a cutaway view of aligned holes 510 formed in walls of inner and outer cup portions of a two-piece prosthetic cup and a screw 512 to be inserted through the holes 510 to fix the cup portions relative to each other in accordance with one embodiment of the present invention. FIG. 5C illustrates a two-piece prosthetic cup in joined by a screw 512 accordance with one embodiment of the present invention. It will be appreciated that such embodiments may use more than one set of such aligned holes.

FIG. 5D illustrates a cross-sectional view of an embodiment of a two-piece prosthetic cup in accordance with one embodiment of the present invention wherein outer 514 and inner 516 cup pieces are joined by a lip 518 formed into the rim of the inner cup. FIG. 5E illustrates a two-piece prosthetic cup in accordance with an embodiment of the present invention wherein the outer 514 and inner 516 cup pieces are joined by the lip 518 formed into the rim of the inner cup piece. Other embodiments of the two-piece acetabular cup are contemplated in which different materials are used such as, for example, tantalum for the outer cup and alumina ceramic for the inner cup. As will be appreciated, numerous combinations of materials having sufficient strength and acceptance properties are possible.

The partially spherical inner surface of the acetabular cup and the engaging partially spherical outer surface of the prosthetic femoral head may be highly polished for reduced friction. Press-fit and other prosthetic acetabular cups known in the art may be used without departing from aspects of the present invention. Such press-fit cups include designs offered by numerous manufacturers, including Depuy, Zimmer and Wright Medical.

In a preferred embodiment, the acetabular cup of approximately 40 to 70 mm near-hemispherical diameter may be made from cobalt chromium, and may be hemispherically shaped and polished in the interior of the cup to minimize friction in a metal-on-metal engagement of the outer hemispherical surface of the prosthetic femoral head, which may be made from the same material, and also precisely shaped for fit and polished to minimize friction. In a further preferred embodiment, the inner surface of the prosthetic acetabular cup comprises less than a full hemisphere, and may extend through an angle ranging from approximately 150 degrees to approximately 179.9 degrees about a radial center. It is contemplated that, following the surgical procedure, bodily fluid may collect between the outer surface of the prosthetic femoral head and the inner surface of the prosthetic acetabular cup and may further reduce friction between the surfaces and also reduce wear upon the surfaces. The present invention is not limited by the material of the inner surface of the prosthetic acetabular cup, which, in addition to the foregoing examples, may also be polyethylene, PEAK or other like material provided in the form of a liner that is press fit or otherwise fixed in place to form an inner surface of the prosthetic acetabular cup.

The outer surface of the acetabular cup is machined to engage the surgically prepared bone of the acetabulum. In a preferred embodiment, the outer surface of the prosthetic acetabular cup is machined to have a mesh-like and/or porous surface or grit-blasted or Titanium plasma sprayed to have a roughened surface (e.g., for press-fit anchoring) to grip the surgically prepared bone surface of the acetabulum to prevent displacement and slippage during the cup insertion process and, as time passes after the procedure, to permit and receive bone growth into recesses in the outer surface of the prosthetic acetabular cup to prevent slippage and displacement as the patient makes use of the prosthetic hip joint.

In another embodiment of the invention, the prosthetic acetabular cup may include one or more protrusions or fins formed on its outer surface to further engage the acetabular bone and prevent slippage and/or rotation of the cup relative to the acetabulum. FIG. 6A illustrates a representation of a three-dimensional perspective and cross-sectional view of an anchoring protrusion 602 for an outer surface of a prosthetic acetabular cup in accordance with one embodiment of the present invention. FIG. 6B illustrates a representation of a three-dimensional perspective and cross-sectional view of an anchoring protrusion 604 for an outer surface of a prosthetic acetabular cup in accordance with another embodiment of the present invention. In this embodiment, each rounded conical protrusion 604 may include a circumferential indentation 606 to form a lateral lip approximately mid-way up the side of the conical structure. The indentation and lip advantageously engage new bone growth to resist displacement and assist fixation of the prosthetic acetabular cup over time. The protrusions may take the form of one or more spikes, small posts and/or ridges with or without barb-like or lip structures suitably shaped for penetrating and/or engaging the acetabular bone. FIG. 6C illustrates a representation of an outer surface of a prosthetic acetabular cup having a plurality of anchoring protrusions 602 in accordance with an embodiment of the present invention.

The prosthetic acetabular cup may also include a threaded impaction bore 608 located at or near its near-hemispherical center. During impacting of the acetabular cup, the threaded impaction bore 608 engages a threaded head of an impactor tool to hold the acetabular cup in place during impacting to help ensure secure seating. This example of a prosthetic acetabular cup includes three approximately rounded conical protrusions 602 located on the outer surface of the acetabular cup approximately equidistant from each other and each approximately equidistant from the rim of the cup and the impaction bore 608. It will be appreciated that alternative placements of the protrusions or fins 602 may be used. Each protrusion may have a slightly rounded and/or dulled tip.

Figure 7:
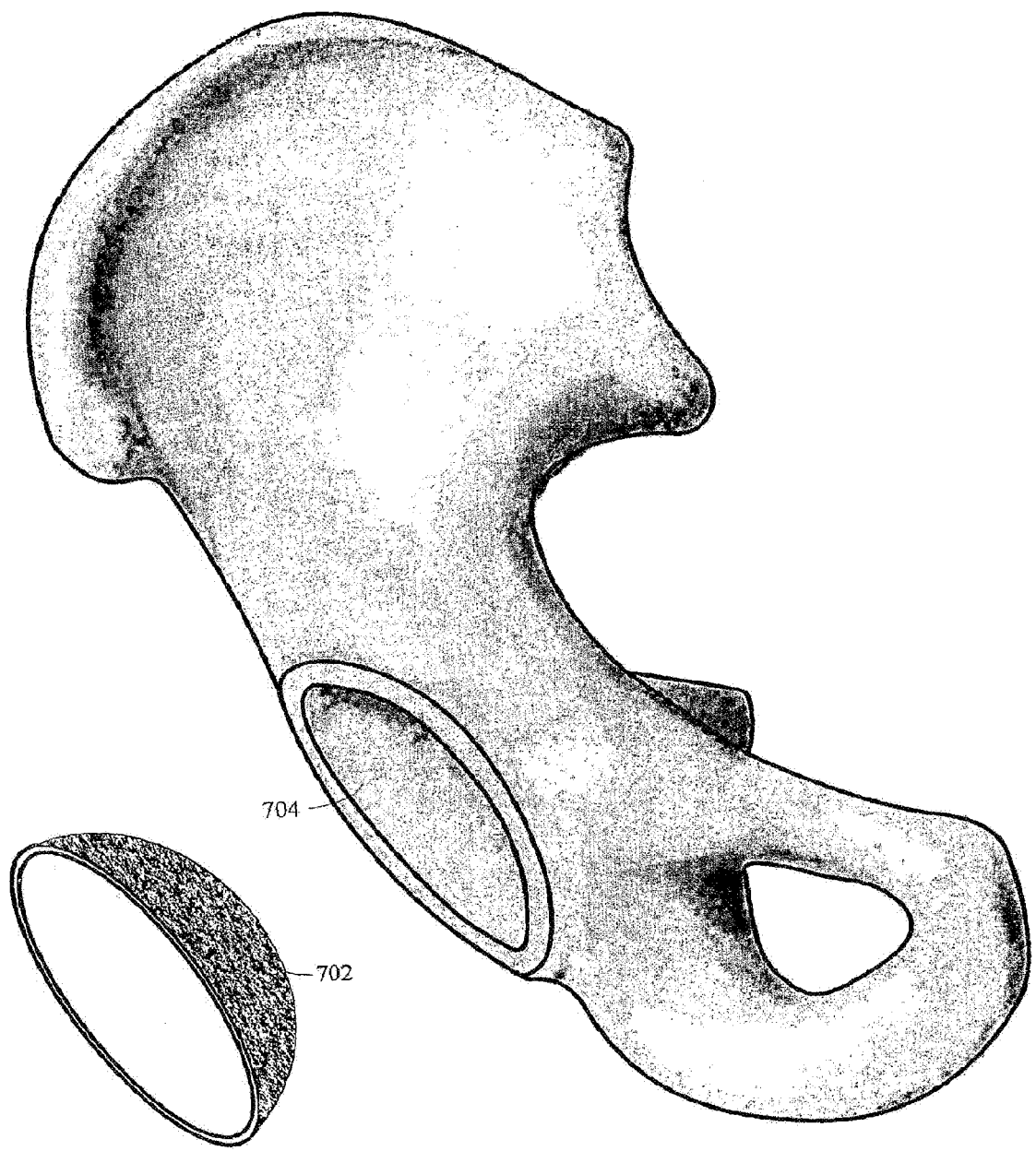
FIG. 7 illustrates a representation of a prosthetic acetabular cup in relationship to an acetabulum in preparation for impacting in accordance with an embodiment of the present invention.

FIG. 7 illustrates a representation of a prosthetic acetabular cup 702 in preparation for impacting in a reamed acetabulum 704 in accordance with an embodiment of the present invention. An outer surface of the prosthetic acetabular cup 702 may have a porous surface to engage bone growth from the reamed surface of the acetabulum 704. Additional fixation may be derived from protrusions along the outer surface of the prosthetic acetabular cup 702 and/or from fixation screws inserted through fixation bores.

Figure 8B:
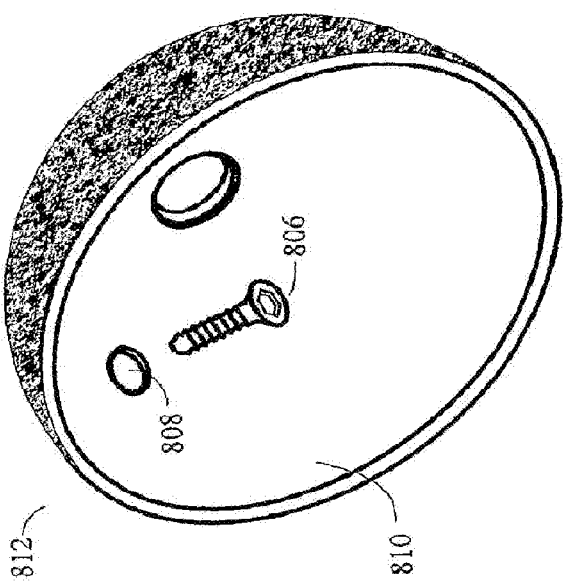
FIG. 8B illustrates a representation of an inner surface of a prosthetic acetabular cup with a fixation screw positioned to be fitted into a hole in the inner surface to fix the prosthetic acetabular cup to an acetabulum in accordance with an embodiment of the present invention.
Figure 8D:
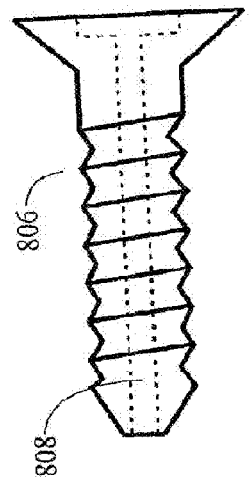
FIG. 8D illustrates a representation of a fixation screw having a shaft bore in accordance with an embodiment of the present invention.
Figure 8A:
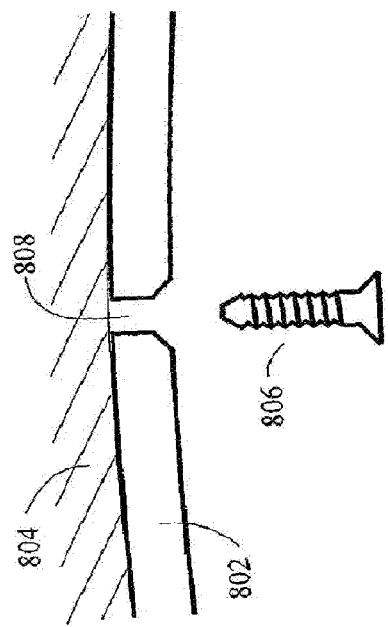
FIG. 8A illustrates a representation of a cross-sectional view of a wall of a prosthetic acetabular cup in relationship to an acetabulum, with a fixation screw positioned to be fitted into a hole in the wall to fix the prosthetic acetabular cup to the acetabulum in accordance with an embodiment of the present invention.

In a preferred embodiment, the prosthetic acetabular cup includes one or more placement fixation bores, which may have beveled edges. FIG. 8A illustrates a representation of a cross-sectional view of a wall 802 of a prosthetic acetabular cup in relationship to an acetabulum 804, with a fixation screw 806 positioned to be fitted into a placement fixation bore 808 in the wall 802 to fix the prosthetic acetabular cup to the acetabulum 804 in accordance with an embodiment of the present invention. FIG. 8B illustrates a representation of an inner surface 810 of a prosthetic acetabular cup 812 with a fixation screw 806 positioned to be fitted into a placement fixation bore 808 extending through the wall of the prosthetic acetabular cup 812 to receive the fixation screw 806 and thereby fix the prosthetic acetabular cup 812 to an acetabulum. In a preferred embodiment, the prosthetic acetabular cup 812 includes a placement fixation bore 808 at a point approximately midway between the rim of the prosthetic acetabular cup 812 and the hemispherical center.

Figure 8C:
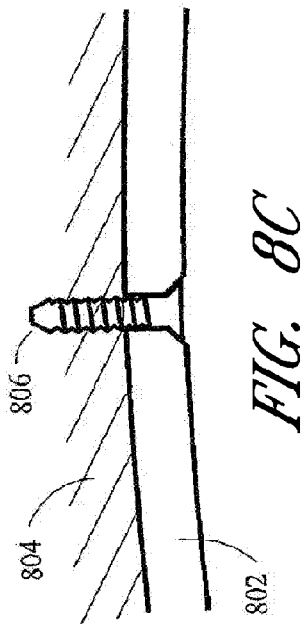
FIG. 8C illustrates a representation of a cross-sectional view of a wall of a prosthetic acetabular cup in relationship to an acetabulum, with a fixation screw fitted through a hole in the wall and fixing the prosthetic acetabular cup to the acetabulum in accordance with an embodiment of the present invention.

FIG. 8C illustrates a representation of a cross-sectional view of the wall 802 of a prosthetic acetabular cup 812 in relationship to the acetabulum 804 with the fixation screw 806 fitted through the placement fixation bore in the wall and fixing the prosthetic acetabular cup to the acetabulum 804. In one embodiment, the diameter of the placement fixation bore 808 is slightly larger at the inner surface and slightly smaller further along the bore toward the outer surface of the prosthetic acetabular cup so that the bore is slightly tapered for at least a portion of its length, and a head of the fixation screw 806 may be likewise tapered so that, when threaded into bone through the placement fixation bore 808 and tightened, the head of the fixation screw 806 is fully recessed into the tapered region of the placement fixation bore 808 and thus advantageously creates no friction or wear by any engagement of the outer surface of the prosthetic femoral head.

Accordingly, to further assure seating fixation of the prosthetic acetabular cup 812 in the acetabulum, a fixation screw 806 or similarly suitable anchoring device is fit through the placement fixation bore 808 to affix the prosthetic acetabular cup 812 into the reamed acetabulum 804. Such use of the placement fixation bore 808 advantageously supports the impacting step by further avoiding slippage of the prosthetic acetabular cup 812 and reducing any consequent need for repeated trials of acetabular cup placement or further surgical procedures to properly fit, secure and seat the prosthetic acetabular cup 812.

In a further preferred embodiment of the present invention, the fixation screw 806 includes a central bore creating an open path approximately along its longitudinal center from head to tip. FIG. 8D illustrates a representation of a fixation screw 806 having a central bore 814 in accordance with an embodiment of the present invention. It is contemplated that the central bore 814 in the fixation screw 806 advantageously permits fluid to enter from the bone and through the central bore 814 into the space between the outer surface of the prosthetic femoral head and the inner surface of the prosthetic acetabular cup 812 and thereby further minimizes friction and wear resulting from the movement of those two surfaces relative to each other.

With the acetabulum prepared, the prosthetic acetabular cup may be seated into place, for example, by impaction. FIG. 9A illustrates a representation of a cutaway view of an impactor tool 902 joined to a prosthetic acetabular cup 812 in position for impacting in accordance with an embodiment of the present invention.

A threaded portion 906 of a shaft 908 of the impactor tool 902 may be threaded into the impaction bore of the prosthetic acetabular cup 812 to hold the cup in relation to the impactor tool 902 while it is impacted into the prepared acetabulum 910. As shown, a conical sleeve 912 having a convex engaging surface 914 formed to engage the inner surface 916 of the prosthetic acetabular cup 812 may be fitted around the threaded end of the shaft 908 of the impactor tool 902 to advantageously spread the force of the impaction across additional area of the inner surface of the prosthetic acetabular cup 812. Advantageously, the conical sleeve 912 may be made from any surgically acceptable material that will not scratch, score or damage the inner surface of the prosthetic acetabular cup 812 during impaction. A few taps on the end of the impactor tool 902 opposite the threaded portion 906 may impact the prosthetic acetabular cup 812 firmly into the acetabulum 910. FIG. 9B illustrates a representation of a cutaway view of the impactor tool 902 in relation to a prosthetic acetabular cup 904 impacted into an acetabulum 910 in accordance with an embodiment of the present invention.

Figure 10:
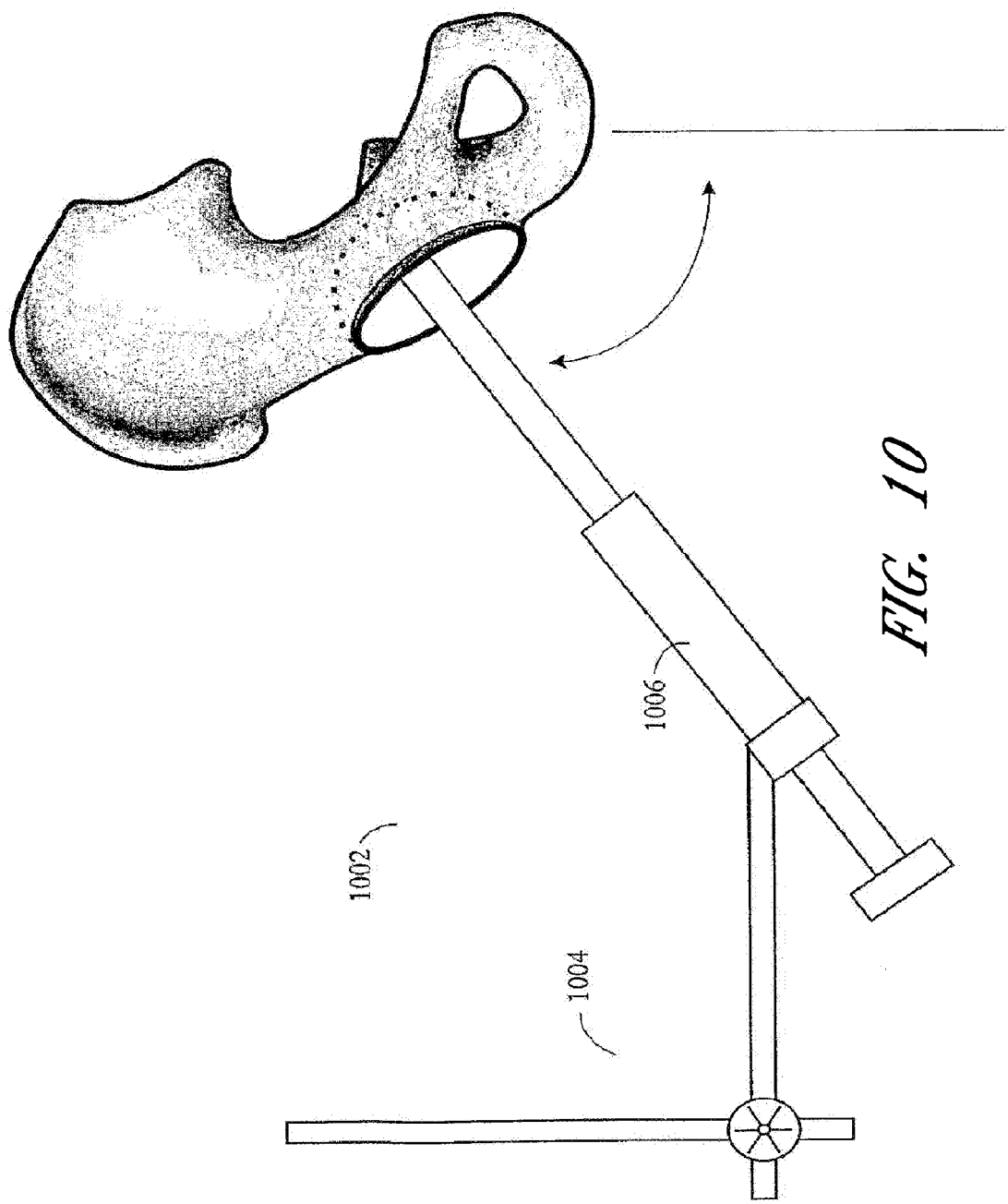
FIG. 10 illustrates a representation of an impactor tool having apparatus indicative of an abduction angle in accordance with an embodiment of the present invention.

As is generally known, the impactor tool may include apparatus indicative of an abduction angle. FIG. 10 illustrates a representation of an impactor tool having apparatus 1002 indicative of an abduction angle in accordance with an embodiment of the present invention. A guide bar assembly 1004 rotatably fixed to a cylindrical sleeve 1006 fit over the shaft of the impactor tool advantageously assists in measuring and/or confirming the angle of abduction, which may desirably be approximately 45 degrees.

Once the prosthetic acetabular cup is impacted into and properly seated in the acetabulum, and preferably after proper orientation of the prosthetic acetabular cup has been confirmed, the impactor tool 902 may be removed by unscrewing it from the threaded impaction bore in the prosthetic acetabular cup 812.

With the prosthetic acetabular cup 812 impacted into place, the fixation screw 806 may be threaded through the fixation bore 808 and into the bone of the acetabulum. Preferably the fixation bore 808 is oriented approximately toward the iliac crest where acetabular bone is sufficiently thick to receive the fixation screw 806, which may be approximately 7-14 mm long. It will be appreciated that the prosthetic acetabular cup 812 may have additional fixation bores oriented toward thick bony areas of the acetabulum, and that additional fixation screws tightened through these bores may provide for additional fixation of the prosthetic acetabular cup 812.

Figure 11:
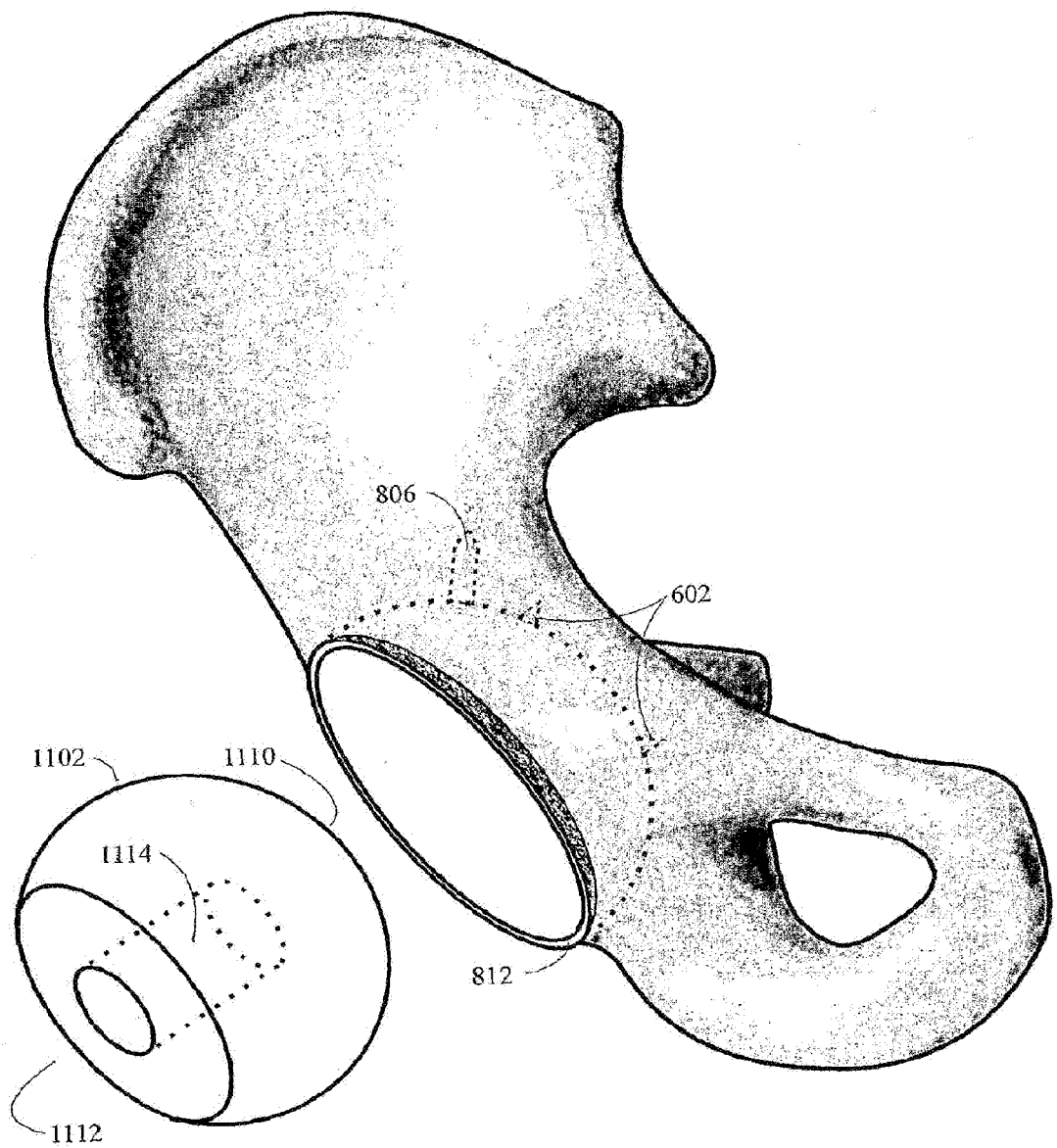
FIG. 11 illustrates a representation of a prosthetic femoral head in position for placement in relation to an impacted prosthetic acetabular cup in accordance with an embodiment of the present invention.

Attention is then turned to fitting the prosthetic femoral head into the prosthetic acetabular cup 812. FIG. 11 illustrates a representation of a prosthetic femoral head 1102 in position for placement in relation to a seated prosthetic acetabular cup 812 fixed by a fixation screw 806 or by protrusions 602 in accordance with an embodiment of the present invention. In a preferred embodiment, the prosthetic femoral head 1102 at a cup-engaging end 1110 comprises a partial sphere having a curvature machined to precisely fit the inner surface of the prosthetic acetabular cup 812. The partial sphere of the prosthetic femoral head 1102 may extend, in various embodiments from approximately 160 degrees to approximately 340 degrees, and thus may comprise any range from somewhat less than a hemisphere to nearly a full sphere.

In accordance with the present invention, the prosthetic femoral head at a neck engaging end 1112 includes structural means to receive and engage a prosthetic femoral neck. In a preferred embodiment, neck engagement may be achieved by a very slightly and narrowingly tapered cylindrical neck bore 1114 machined approximately 2 cm into the prosthetic femoral head from the neck engaging end 1112 inward toward the center of the prosthetic femoral head, such that a head-engaging end of a prosthetic femoral neck comprising roughly 2 cm of cylindrical shaft having a Morse taper matched to that of the neck bore 1114 may be driven by impact into the neck bore 1114, resulting in a fit sufficiently permanent to operatively support load-bearing movement about the prosthetic hip without slippage. It will be appreciated that such Morse taper modular joining techniques have been known for many years to successfully achieve such fit. It will also be appreciated that a neck bore 1114 may extend more than or less than 2 cm into the prosthetic femoral head, and that in such cases, the head-engaging end of the prosthetic femoral neck will be of a roughly corresponding length of more than or less than 2 cm. Also, the diameter of the neck bore 1114 will be approximately 11-13 mm (and will very gradually decrease as the bore extends into the prosthetic femoral head to accommodate the taper), although it will be appreciated that smaller or larger diameters may be used, and it will also be appreciated that the shaft diameter of the head-engaging end of the prosthetic femoral neck will be of a diameter matching that of the neck bore 1114.

Figure 12:
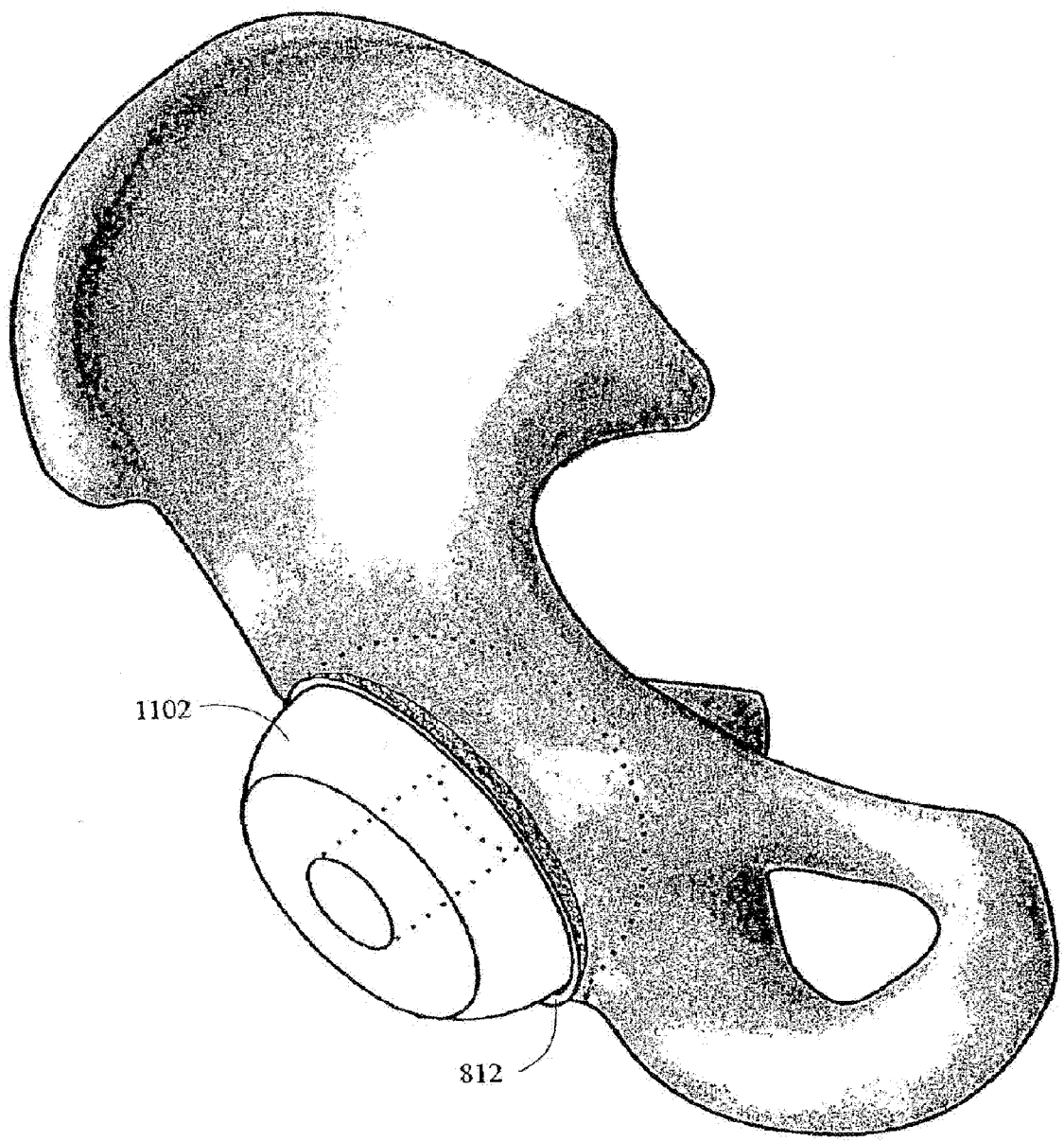
FIG. 12 illustrates a representation of a prosthetic femoral head positioned in a prosthetic acetabular cup in accordance with an embodiment of the present invention.

In one embodiment, the partial sphere of the prosthetic femoral head is placed against the exposed rim of the hemispherical inner surface of the prosthetic acetabular cup 812. As will be appreciated, one or more light taps using a firm rubber-headed impacting tool may then seat the prosthetic femoral head properly into the prosthetic acetabular cup 812. FIG. 12 illustrates a representation of a prosthetic femoral head 1102 positioned in a prosthetic acetabular cup 812 in accordance with an embodiment of the present invention.

In still another embodiment of the present invention, the acetabular cup, as described above but optionally without the placement fixation hole and optionally with anchoring protrusions or fins, is pre-operatively fitted (for example, previously machined to optimal tolerance gap, e.g. 100 micron) with the prosthetic femoral head. Advantageously, the pre-operatively assembled prosthetic acetabular cup and prosthetic femoral head—which may advantageously be sterilely packaged together—may be impacted into the prepared acetabulum as a single unit. As will be appreciated, an impacting insertion device may fit into the Morse taper of the prosthetic femoral head and also connect to or engage the rim of the prosthetic acetabular cup for rotation control.

In another embodiment (not shown), a different attachment technique may be used to join the prosthetic femoral head to a prosthetic femoral neck. For example, the prosthetic femoral head, rather than include a neck bore, may include a neck shaft. The neck shaft may extend approximately 2 cm outward from the neck-engaging end of the prosthetic femoral head. The neck shaft may be approximately 11-13 mm in diameter (though smaller or larger diameters could be used), with the diameter slightly decreasing along the neck shaft in the direction away from the center of the prosthetic femoral head, to form a Morse taper. It will be appreciated that a prosthetic femoral neck in approximately the form of a cylindrical shaft, may be machined to include a bore in one end having a receiving Morse taper of proper dimension to engage the neck shaft. It will be appreciated that still further methods and structures exist that could be adapted to the prosthetic femoral head and prosthetic femoral neck to facilitate the joining of these two prostheses.

Attention is then turned to preparation of the proximal femur for introduction of an intramedullary rod. In accordance with the present invention, the intramedullary rod, as described in various forms herein, may have characteristics of a femoral stem. The intramedullary rod may advantageously be inserted into the patient's femur 104 using surgical technique which requires only minimal exposure of the femur.

Figure 13:
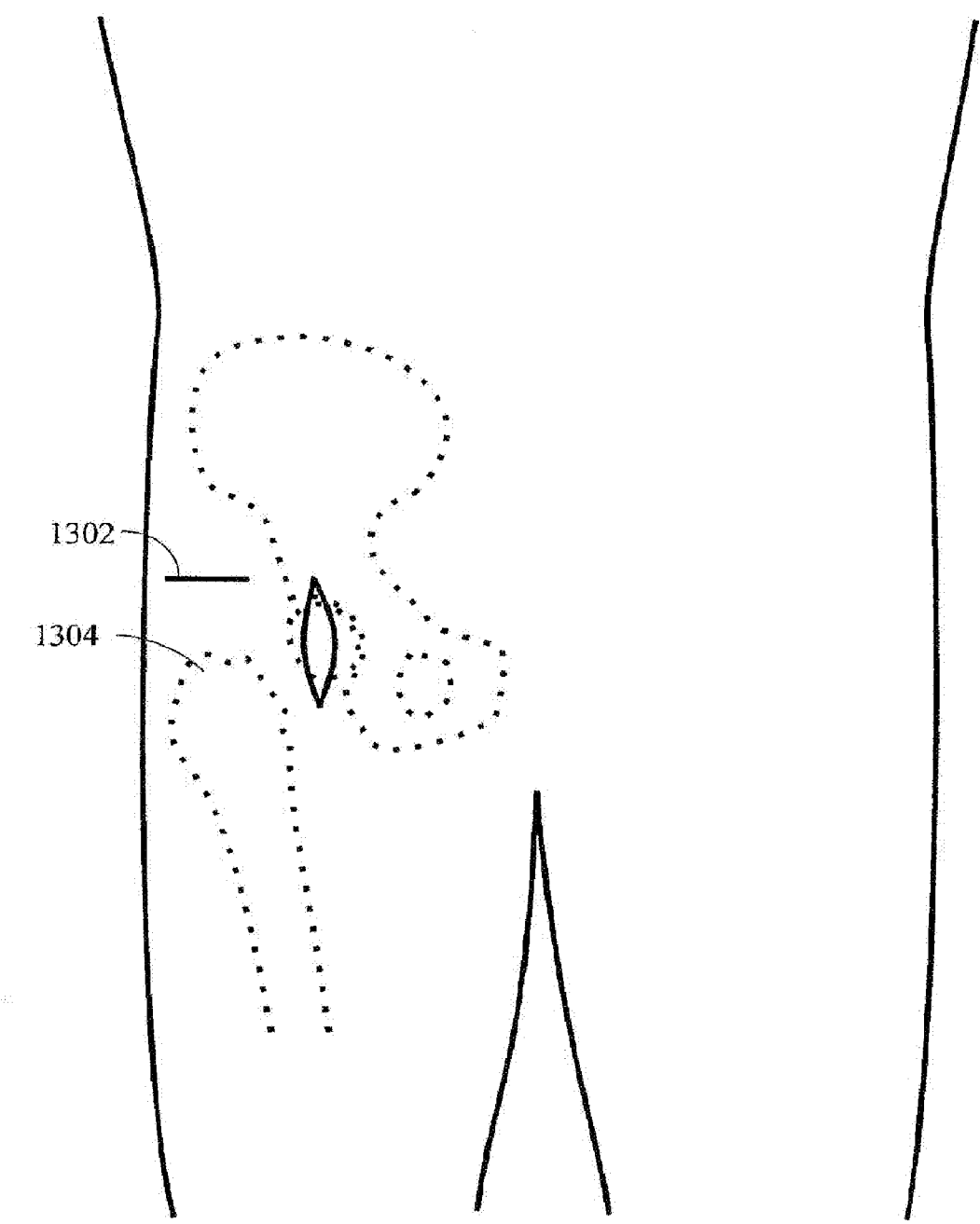
FIG. 13 illustrates a representation of a second incision in accordance with an embodiment of the present invention.

An incision of approximately 3-4 cm is made at approximately a mid-portion of Smith-Peterson anterior approach. FIG. 13 illustrates a representation of an incision 1302 in accordance with an embodiment of the present invention. Access to the proximal femur may be attained by a lateral longitudinal incision proximal to the greater trochanter, dissecting down to the gluteus maximus fascia longitudinally in the direction of the wound, separating the underlying muscle fibers and palpating the medial tip of the greater trochanter; the entry point may be penetrated by a cannulated awl and a guide wire may be inserted into the intramedullary canal. The guide wire may be centered in the canal in the lateral view on C-arm image.

Reaming and/or broaching may be done over the guide wire. In this manner, safe access may be gained to the upper surface of the femur 1304 around and about the greater trochanter.

In another embodiment, surgical access to the acetabulum and to the proximal femur may be obtained by a somewhat longer portion of a Smith-Peterson anterior approach.

Figure 14:
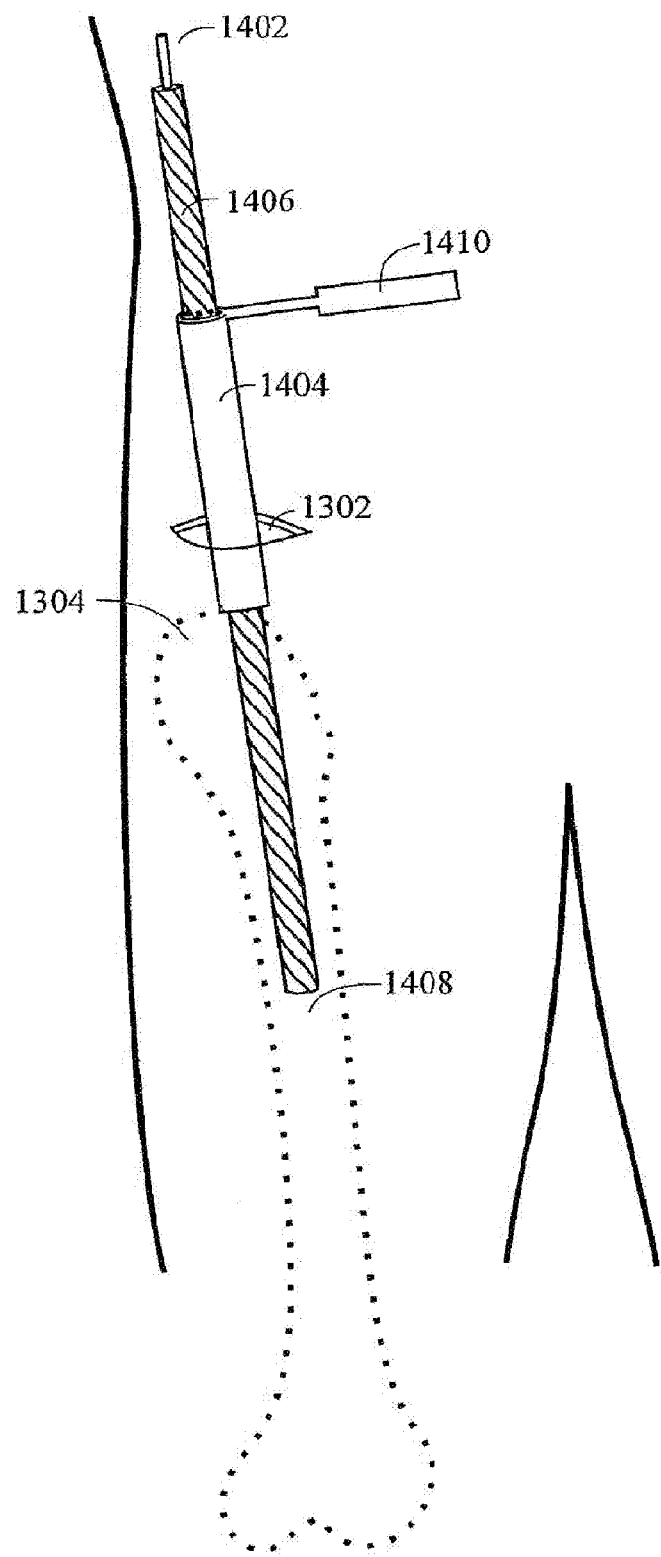
FIG. 14 illustrates a representation of a femoral reaming tool with a tissue protecting guide in accordance with an embodiment of the present invention.

With access to the upper portion of the proximal femur 1304 attained, and using known surgical technique, tissues along the upper surface of the femur 1304 are reflected by a tissue protector. FIG. 14 illustrates a representation of a femoral reaming tool 1402 with a tissue protecting guide 1404 in accordance with an embodiment of the present invention.

The reamer 1402 comprises a drilling bit 1406 rotated by a drill motor (not shown) while being directed into the intramedullary canal 1408 of the femur 1304 by a guide wire to a depth sufficient to accommodate most if not all of the length of the distal end of the intramedullary rod. Reamers of increasing diameter may be used to progressively achieve a bore in the proximal femur of sufficient diameter to accommodate that of the proximal region of the intramedullary rod. Tissues along the surgical access may be protected from the rotating reamer bit and the bit itself may be guided by the use of a tubular tissue protector 1404 to which is affixed a handle 1410 for ease of use. As is known, over-reaming by approximately one millimeter may facilitate advantageous blood flow after the intramedullary rod has been inserted. Advantageously, the use of a guide wire or guide pin may assist in accurate reaming and/or broaching and/or introduction of an intramedullary rod.

The intramedullary rod may be made from any biocompatible material of sufficient strength, however titanium alloy is preferred. FIG. 15A illustrates a representation of a three-dimensional side view of an intramedullary rod 1502 with a femoral neck bore 1504 in accordance with an embodiment of the present invention, and FIG. 15B illustrates a representation of a three-dimensional front view of the intramedullary rod 1502 in accordance with the embodiment of the present invention. The present invention is not limited to a particular length of the intramedullary rod 1502, which may be from 15-40 cm long, or possibly shorter or longer depending for example upon patient anatomy.

The intramedullary rod 1502 includes a proximal region 1506 that may be approximately 6-8 cm long and may have a diameter of around 15-18 mm, and the rod also includes a stem 1508 distal to the proximal region having a diameter of around 10 mm, and the stem 1508 may taper distally with a gradually narrowing diameter terminating in a rounded point 1510. It will be appreciated that the intramedullary rod 1502 may curve slightly along its length to advantageously align with the longitudinal center of the femur 104.

In another embodiment, the proximal region may be somewhat shorter, for example, from 4-6 cm. This embodiment may be preferred in procedures involving additional removal of bone from the proximal region of the femur and/or in combination with a support sleeve as is described in more detail below.

The intramedullary rod includes a lateral neck bore 1504 through the proximal region 1506 at an angle that advantageously permits a shaft-like prosthetic femoral neck to be inserted at an insertion side of the neck bore 1504 and therethrough to engage the prosthetic femoral head 1102, which may preferably and advantageously already be in place in the prosthetic acetabular cup 812. The diameter of the neck bore 1504 may preferably be approximately 10-12 mm, but it will be appreciated that the diameter could be somewhat smaller or larger. The angle of the neck bore may be around 130 degrees, or may be more or less depending upon patient anatomy and condition of the proximate bones and tissues.

The intramedullary rod also includes a fixation bore 1512 that runs longitudinally from the center of the proximal region

1506 through the longitudinal center of the intramedullary rod 1502 until it meets the neck bore 1504 approximately 4 cm from the proximal end. The fixation bore 1512 may preferably have a diameter of approximately 8 mm, but may be more or less. The fixation bore 1512 is preferably spiral threaded to receive locking or fixation screws as described herein.

The proximal end of the intramedullary rod 1502 includes a keyway providing for fixation of other structures relative to the intramedullary rod. FIG. 15C illustrates a representation of a fixation keyway 1514 formed in the proximal end of an intramedullary rod 1502 in accordance with an embodiment of the present invention, and FIG. 15D illustrates a representation of another fixation keyway 1516 formed in the proximal end of an intramedullary rod 1502 in accordance with another embodiment of the present invention.

In one embodiment, a circular keyway 1514 comprises a key bore 1518 of approximately 12 mm in diameter and of about 2 mm depth centered on the longitudinal axis of the intramedullary rod and machined into the proximal end of the intramedullary rod 1502. The key bore 1518 defines a circular step within the proximal end of the intramedullary rod 1502. In one embodiment, the keyway further includes a notch 1520 in the rim of the proximal end of the intramedullary rod 1502 defined by the key bore 1518. In one embodiment, the notch 1520 is about 2 mm wide and 2 mm deep. The notch 1520 is aligned circumferentially about the longitudinal axis of the intramedullary rod to coincide with the center of the circular hole at the insertion side of the neck bore 1504. It will be appreciated that another structure having a recessed circular rim may engage the keyway, and that a 2 mm protrusion projecting outward from the recessed circular rim of the other structure may fit in the notch 1520 of the keyway to prevent the other structure from rotating with respect to the intramedullary rod 1502 along the longitudinal axis.

An alternative embodiment of a keyway 1516 (see FIG. 15D) includes four roughly rectangular recesses 1522 formed in the rim of the proximal end of the intramedullary rod 1502. The rectangular recesses may be approximately 2 mm deep and 2 mm wide. It will be appreciated that another structure having projections matched to the recesses 1522 may engage the keyway 1516 and may prevent the intramedullary rod 1502 from rotating about its longitudinal axis relative to the other structure.

It will be appreciated that any and all of the dimensions of the intramedullary rod 1502, including the lengths and diameters and tapers of the proximal region, the stem and the bores, may be smaller or larger as indicated by patient anatomy, condition of any of the bones and tissues or other circumstances.

FIG. 16A illustrates a representation of a three-dimensional side view of an intramedullary rod 1602 with a distal fixation bore 1604 in accordance with an embodiment of the present invention, and FIG. 16B illustrates a representation of a three-dimensional front view of such an intramedullary rod 1602. It will be appreciated that a pin or screw may be inserted through a side of the distal femur to engage the distal fixation bore 1604. Accordingly, this intramedullary rod 1602 may be advantageous in providing additional fixation, particularly in an anti-rotational manner, in relation to the femur 104. Moreover, this intramedullary rod 1602 provides the additional advantage of readily treating peri-prosthetic fractures following a hip procedure, wherein the intramedullary rod used in the initial procedure may be replaced by the intramedullary rod 1602 having a longer distal stem, which, in combination with a pin or screw in the fixation bore 1604 to secure the distal femur, provides adequate support structure to treat such fracture. This versatility in facilitating and simplifying treatment of peri-prosthetic fractures is another advantage of the present invention.

Turning to the insertion of the intramedullary rod 1502 in the femur 104, a driving tool may advantageously be securely attached to the keyway 1514 located at the proximal end of the intramedullary rod. FIG. 17A illustrates a representation of a side view of a driving tool 1702 engaging an intramedullary rod 1502 to be driven into a femoral canal in accordance with an embodiment of the present invention. FIG. 17B illustrates a representation of a rear side view of the driving tool 1702 in accordance with the embodiment, and FIG. 17C illustrates a representation of a top down view of the driving tool 1702.

A driving surface 1704 of the driving tool 1702 transfers force from light hammer blows along an elongated head shaft 1706 through the keyway 1514 to the intramedullary rod 1502 so that the rod is driven by the blows into the marrow canal. The driving tool 1702 may preferably made from stainless steel, or another material sufficiently hard and heavy that it withstands hammer blows and effectively transfers force, and may also be repeatedly sterilized. The driving tool 1702 may be held by a handle 1708 during insertion of the intramedullary rod 1502. Imaging may be used to facilitate and confirm proper orientation and location of the intramedullary rod 1502 within the marrow canal.

In one embodiment, a keyway formed in a rod-engaging end of the driving tool 1702 holds the driving tool 1702 securely in relation to the intramedullary rod 1502 while it is being driven into the femur 104.

FIG. 17D illustrates a representation of a keyway 1710 formed in an engaging end 1712 of the driving tool 1702 in accordance with an embodiment of the present invention. As shown, the circular keyway 1710 formed on the engaging end 1712 of the driving tool 1702 engages the circular keyway 1514 on the proximal end of the intramedullary rod 1502. The circular keyway 1710 permits the driving tool to rotate with respect to the longitudinal axis of the intramedullary rod 1502 while remaining laterally centered over the top of the intramedullary rod 1502 for effective driving of the intramedullary rod 1502. It will be appreciated that, in this embodiment, the circular keyway 1710 on the engaging end 1712 of the driving tool 1712 includes no protrusion along the circular rim and thus nothing engages the notch 1520 in the circular keyway on the proximal end of the intramedullary rod 1502.

FIG. 17E illustrates a representation of another embodiment of a keyway 1714 in an engaging end of the driving tool 1702 in accordance with an embodiment of the present invention. The keyway 1714 includes four protrusions 1716 extending circumferentially around the perimeter of the engaging end 1712 of the driving tool. As such, it will be appreciated that the protrusions 1716 may fit into and engage recessions around the perimeter of a receiving keyway 1516, as described above, to hold the driving tool 1702 steady in relation to the intramedullary rod 1502 while the driving tool 1702 is being used to drive the intramedullary rod 1502 into the femur 104.

In another embodiment, a support sleeve may be fixed within the proximal region of the femur to use the bone mass in that region to further support the intramedullary rod 1502. FIG. 18A illustrates a representation of a top down view of a support sleeve 1802 for an intramedullary rod 1502 in accordance with an embodiment of the present invention. FIG. 18B illustrates a representation of a rear view of the support sleeve 1802, and FIG. 18C illustrates a representation of a side view of the support sleeve 1802. FIG. 18D illustrates a representation of a perspective view of the support sleeve 1802.

The support sleeve 1802 may advantageously be generally shaped to fit within the proximal region of the femur. The support sleeve 1802 may be made from titanium in one embodiment with a grit-blasted roughened outer surface. It will be appreciated that the support sleeve 1802 may be made from other materials, such as cobalt chromium, ceramic, stainless steel or other materials of sufficient strength and acceptance qualities. It will also be appreciated that the bone engaging surfaces of the support sleeve 1802 may have one or more of a variety of textures as described above to facilitate gripping of and fixation within bone.

With reference to FIG. 18C, the support sleeve 1802 includes a narrow-angled conical portion 1804 with a central rod bore 1806 which, when the support sleeve 1802 is in place within the femur 104, is approximately aligned with the longitudinal center of the femur 104. The diameter of the conical portion 1804 may be around 2-3 cm at the distal end and around 2.5-4 cm at the proximal end, however the diameters may be somewhat larger or smaller depending on patient anatomy and/or tightness of fit desired. The central rod bore 1806 may have a diameter only very slightly larger than that of the proximal region of the intramedullary rod 1502. The central rod bore 1806 may also be slightly tapered—larger at the proximal end and smaller at the distal end—to ensure a tight fit around the proximal region of the intramedullary rod 1502.

The support sleeve 1802 also includes a roughly triangular shaped portion 1808 projecting from the conical portion 1806 starting approximately midway along the longitudinal length of the support sleeve 1802. When the support sleeve 1802 is in place in the femur 104, the triangular portion 1808 may extend outward laterally from the cylindrical portion in a direction toward the acetabulum and may rise over the lower trochanter to occupy the space within the proximal femur above the lower trochanter. When the support sleeve 1802 is fit into place, an upper and laterally extending flat surface 1810 of the support sleeve 1802 may extend from a point below the greater trochanter and in the direction of and a small distance past the lower trochanter. The flat surface 1810 may occupy a plane that is roughly perpendicular to the length of the femur 104 and situated around 1-1.5 cm above the lower trochanter. In one embodiment, the upper flat surface 1810 extends laterally approximately 3-5 millimeters beyond the lower trochanter toward the acetabulum.

Advantageously, with respect to FIG. 18D, the support sleeve 1802 includes a neck slot 1812 to accommodate a prosthetic femoral neck. The neck slot 1812 may be cut in a wall of the conical portion 1804 of the support sleeve 1802 that is opposite the triangular portion 1808 and may extend longitudinally from the proximal extent of the wall to a point approximately halfway toward the distal extent of the wall. The neck slot 1812 may be sufficiently wide to accommodate the diameter of the prosthetic femoral neck, allowing it to pass through the neck slot 1812. The neck slot 1812 may extend laterally from the wall into the support sleeve 1802 to a point above the lower trochanter. From a point at the distal extent of the neck slot 1812 along the wall, a floor 1814 of the neck slot 1812 may rise into the support sleeve 1802 toward the proximal end of the support sleeve 1802 at an angle of preferably 30-40 degrees, but the angle could be more or less. The neck slot 1812 may also divide the upper flat surface 1810 of the support sleeve 1802 from the end nearest the greater trochanter to a point approximately 1 or 2 mm from the end of the flat surface 1810 nearest the lower trochanter. The neck slot 1812 in the support sleeve 1802 advantageously permits the prosthetic femoral neck to occupy a substantially straight path through the support sleeve 1802 at an appropriate angle to engage the prosthetic femoral head.

Figure 19C:
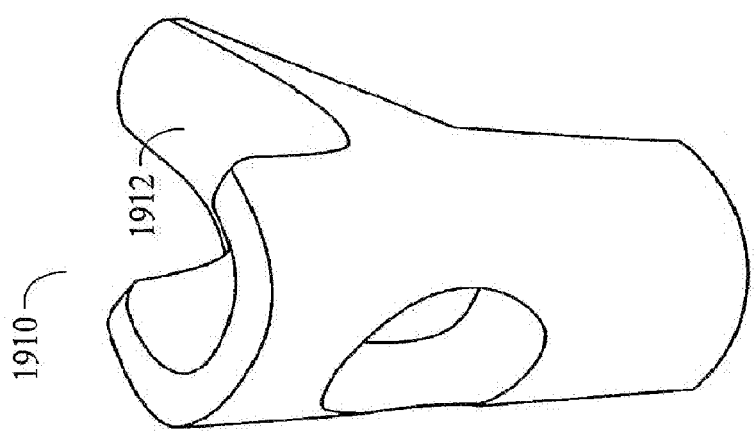
FIG. 19C illustrates a representation of a perspective view of a support sleeve for an intramedullary rod in accordance with yet another embodiment of the present invention.
Figure 19B:
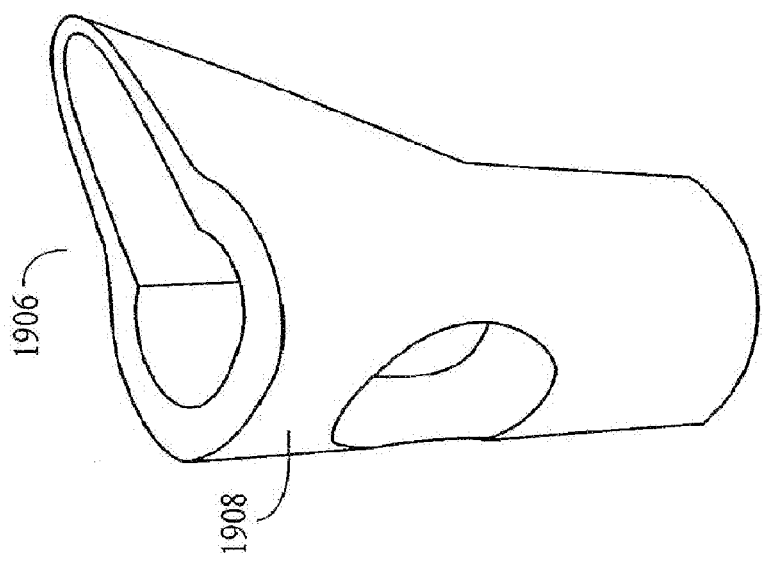
FIG. 19B illustrates a representation of a perspective view of a support sleeve for an intramedullary rod in accordance with still another embodiment of the present invention.
Figure 19A:
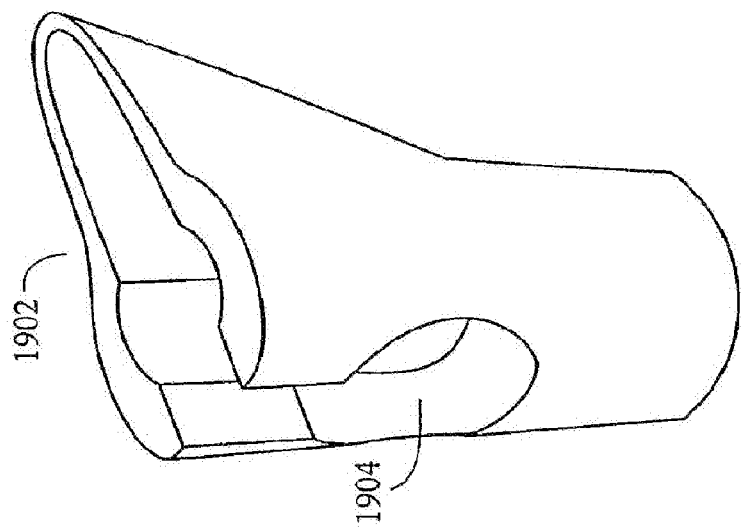
FIG. 19A illustrates a representation of a perspective view of a support sleeve for an intramedullary rod in accordance with another embodiment of the present invention.

Other embodiments of the support sleeve may also provide advantages. For example, it will be appreciated that embodiments of support sleeves with neck passages that differ from the neck slot 1812 may advantageously be used. FIG. 19A illustrates a representation of a perspective view of a support sleeve 1902 for an intramedullary rod 1502 in accordance with another embodiment of the present invention, wherein the support sleeve 1902 includes a widened area 1904 in the neck slot permitting greater lateral freedom of movement for a prosthetic femoral neck. FIG. 19B illustrates a representation of a perspective view of another embodiment of a support sleeve 1906 wherein the support sleeve 1906 includes a widened area as in the embodiment shown in FIG. 19A, but also a portion 1908 of the neck slot above the widened area is closed off. FIG. 19C illustrates a representation of a perspective view of another embodiment of a support sleeve 1910 wherein the support sleeve 1910 includes a widened area as in the embodiment shown in FIG. 19A, and includes the closed-off portion of the neck slot as in the embodiment shown in FIG. 19B, and also omits lateral walls of the neck slot in the triangular portion of the support sleeve while including a flat surface 1912 to support the prosthetic femoral neck.

Figure 20A:
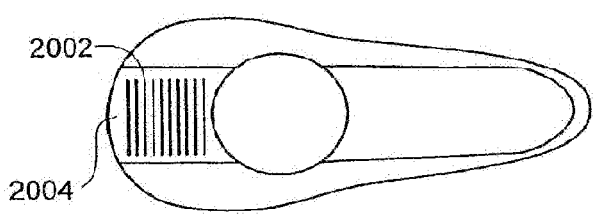
FIG. 20A illustrates a representation of a top down view of a support sleeve having ridges to engage a prosthetic femoral neck in accordance with an embodiment of the present invention.
Figure 20B:
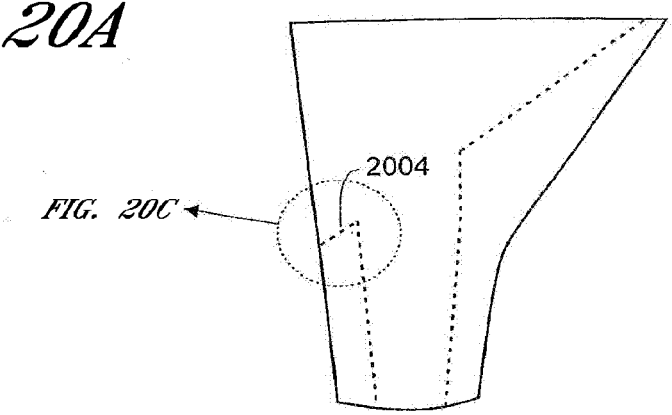
FIG. 20B illustrates a representation of a cutaway side view of a support sleeve having ridges to engage a prosthetic femoral neck in accordance with an embodiment of the present invention.
Figure 20C:
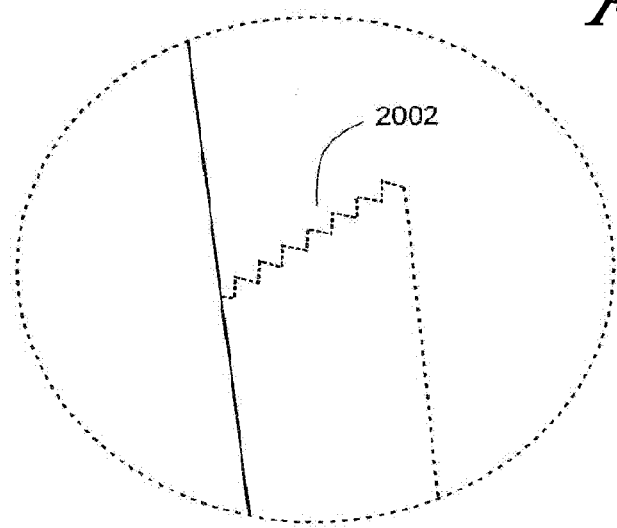
FIG. 20C illustrates a representation of a close-up view of the support sleeve having ridges to engage a prosthetic femoral neck in accordance with an embodiment of the present invention as illustrated in FIG. 20B.

Additional provisions may be made in the support sleeve to provide for fixation of a prosthetic femoral neck. FIG. 20A illustrates a representation of a top down view of a support sleeve having ridges to engage a prosthetic femoral neck in accordance with an embodiment of the present invention. FIG. 20B illustrates a representation of a cutaway side view of the support sleeve having engaging ridges, and FIG. 20C illustrates a representation of a close-up view of the engaging ridges provided in the cutaway side view of FIG. 20B. As shown in FIGS. 20A, 20B and 20C, gripping ridges 2002 may be formed along the surface of at least a portion of the slot floor 2004, preferably the portion of the slot floor 2004 extending from the wall of the sleeve opposite the triangular portion of the sleeve to the central bore. Each ridge may be perpendicular to the length of the floor of the slot and may be around 10-12 mm long and extend outward from the floor of the slot approximately 0.5 mm, and the ridges may be spaced approximately 0.5-1 mm apart. It will be appreciated that ridges of other dimensions, smaller or larger, may be formed. Advantageously, in one embodiment, the ridges grip opposing ridges that may be formed into the shaft of the prosthetic femoral neck to assist in preventing the prosthetic femoral neck from slipping or moving relative to the support sleeve.

Figure 21B:
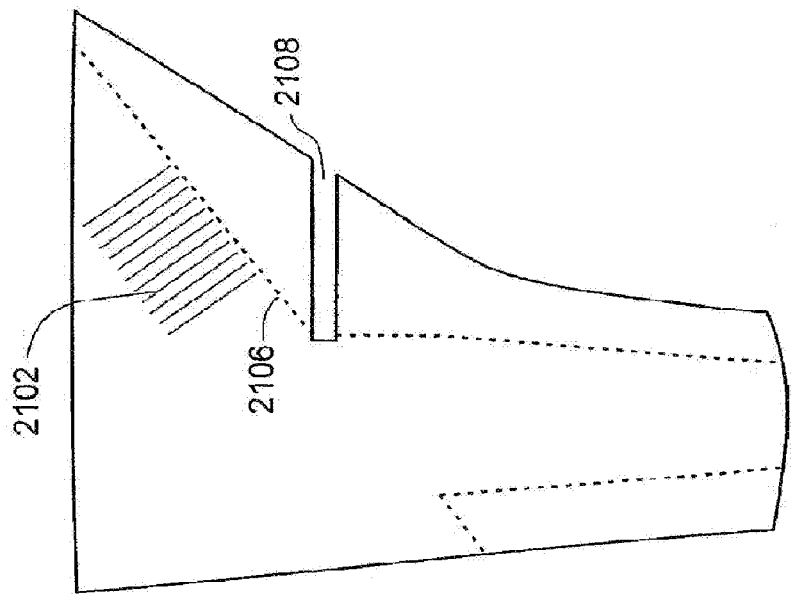
FIG. 21B illustrates a representation of a cutaway side view of a support sleeve having ridges to engage a prosthetic femoral neck in accordance with another embodiment of the present invention.
Figure 21A:
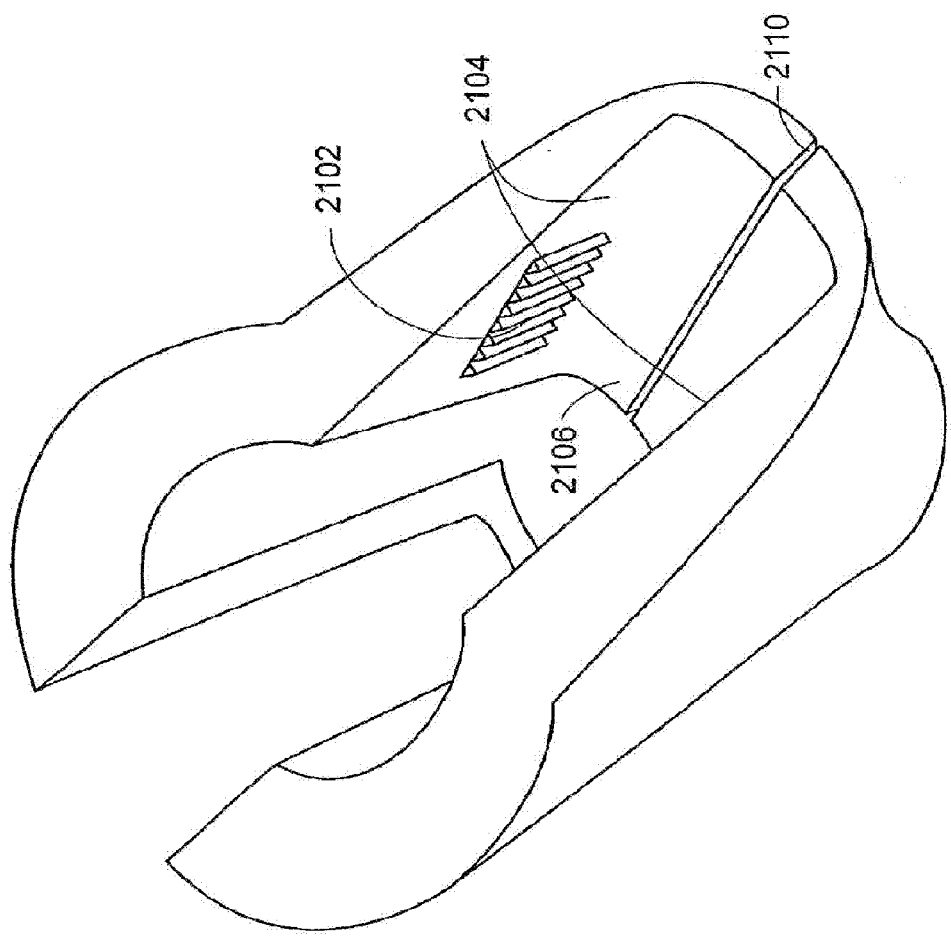
FIG. 21A illustrates a representation of a perspective view of a support sleeve having ridges to engage a prosthetic femoral neck in accordance with another embodiment of the present invention.

In another embodiment the gripping ridges may advantageously engage threads of a fixation screw fit between the shaft of the prosthetic femoral neck and the floor of the neck slot, in which position the fixation screw exerts a pressure force on both the prosthetic femoral neck and the floor of the support sleeve that may assist in preventing the prosthetic femoral neck from slipping or moving relative to the support sleeve. In another embodiment neck fixation ridges may be formed along opposing inner walls of the neck slot 1812. FIG. 21A illustrates a representation of a perspective view of a support sleeve having neck fixation ridges 2102 along the walls 2104 of a neck slot to engage a prosthetic femoral neck in accordance with another embodiment of the present invention. FIG. 21B illustrates a representation of a cutaway side view of the support sleeve having such ridges 2102 to engage a prosthetic femoral neck. The neck fixation ridges 2102 may be approximately perpendicular to the plane formed by the floor 2106 of the slot 1812, and each neck fixation ridge may be approximately 10-12 mm long and extend outward from the slot wall about 0.5 mm. The neck fixation ridges may be spaced about 0.5-1 mm apart and may be located along the surface of the inner walls 2104 of the neck slot 1812 between the central bore 1806 and the end of the slot approximately above the lower trochanter. Each neck fixation ridge may have angled flat surfaces that facilitate movement in one direction and restrict movement in the opposite direction. Accordingly, each ridge may include a restricting surface occupying a plane substantially perpendicular to a straight line running along the length of the slot floor 2004, and each ridge may also include a lower friction surface occupying a plane angled at approximately 30 degrees from the plane occupied by the inner wall of the slot, with the distance between the planes widening in the direction of the acetabulum. It will be appreciated that the neck fixation ridges 2102 may use such surfaces to permit a prosthetic femoral neck with similar, but opposing ridges formed along its shaft to travel through the neck slot 1812 in the direction of the acetabulum, and to restrict travel in the opposite direction.

In still another embodiment, one or more additional slots may be formed into the support sleeve to permit spreading of the walls 2104 of the neck slot 1812 while a ridged prosthetic femoral neck passes between them. Preferably, a first lateral slot 2108 in the support sleeve may be made from a point approximately lateral to the lower trochanter and extending laterally through the triangular portion of the neck sleeve to the central bore 1806. Also preferably, a second slot 2110 may be formed along a line bisecting the floor 2106 of the neck slot from the central rod bore outward and may extend distally through triangular portion of the neck sleeve until it meets the first lateral slot 2108. It will be appreciated that these two additional slots remove substantial matter from the support sleeve that acts to prevent the walls 2104 of the neck slot from moving relative to each other. It will also be appreciated that the force required to separate the walls 2104 of the neck slot away from each other may be regulated by their thickness, the hardness and rigidity of the material from which they are made and also by removal of matter that joins them, and that these factors may be adjusted in many ways to permit the walls 2104 of the neck slot to move an appropriate degree to allow a prosthetic femoral neck with fixation ridges to pass through the neck slot when the prosthetic femoral neck is urged with moderate force in a direction toward the acetabulum, and to substantially restrict movement of the prosthetic femoral neck in the direction away from the acetabulum.

In one embodiment the surfaces of the support sleeve that rest upon the inner bone of the proximal region of the femur may be stepped. FIG. 22A illustrates a representation of a cutaway side view of a support sleeve having stepped, bone-engaging outer surfaces in accordance with another embodiment of the present invention. FIG. 22B illustrates a representation of a close-up view of a stepped, bone-engaging outer surface of a support sleeve shown in FIG. 22A, and FIG. 22C illustrates a representation of a close-up view of another stepped, bone-engaging outer surface of the support sleeve shown in FIG. 22A. As shown, the slope of the outer walls 2202, 2204 of the support sleeve, may be accommodated by a series of vertical and horizontal steps 2206, with each vertical (longitudinal) step extending approximately 2-4 mm, and each horizontal (lateral) step extending approximately 0.5-1 mm. These steps 2206 formed in the supporting surfaces may advantageously reduce shear force and convert it to downward and better-supporting compressive force. Grooved, pronged, porous and/or other surface treatments may be used independently of or to support stepped surfaces to reduce sliding and shear forces.

Figure 23A:
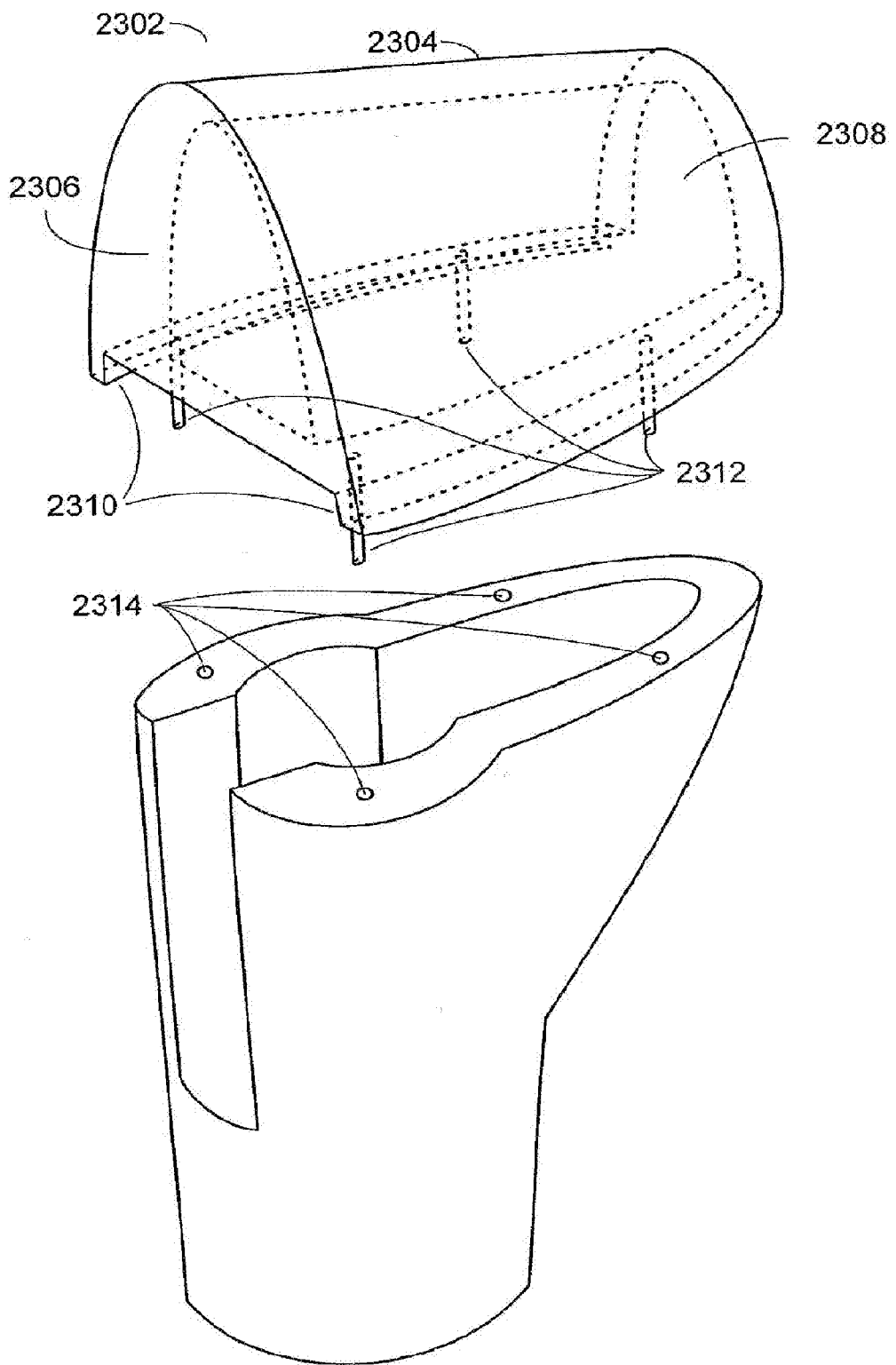
FIG. 23A illustrates a representation of a three-dimensional perspective view of a support sleeve and support sleeve cover configured to be removably joined in accordance with an embodiment of the present invention.
Figure 23B:
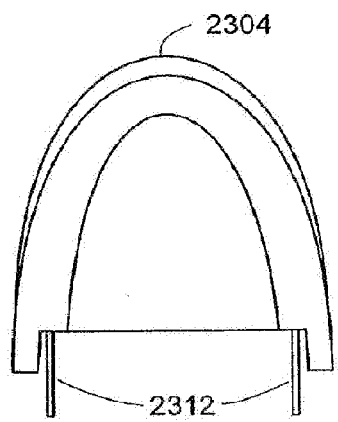
FIG. 23B illustrates a representation of a rear view of a support sleeve cover in accordance with an embodiment of the present invention.
Figure 23C:
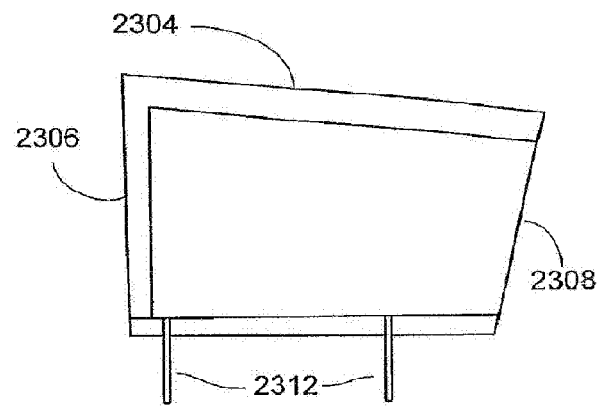
FIG. 23C illustrates a representation of a cutaway side view of a support sleeve cover in accordance with an embodiment of the present invention.
Figure 23D:
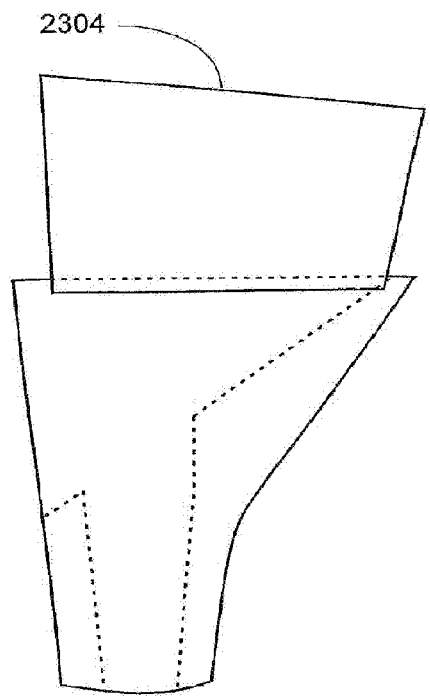
FIG. 23D illustrates a representation of a cutaway side view of a support sleeve cover removably attached to a support sleeve in accordance with an embodiment of the present invention.

In another embodiment, a support sleeve cover fits to the lateral flat surface at the proximal end of the support sleeve. FIG. 23A illustrates a representation of a perspective view of a support sleeve 1802 and support sleeve cover 2302 configured to be removably joined to the support sleeve 1802 in accordance with an embodiment of the present invention. FIG. 23B illustrates a representation of a rear view of the support sleeve cover 2302, FIG. 23C illustrates a representation of a cutaway side view of the support sleeve cover 2302, and FIG. 23D illustrates a representation of a cutaway side view of the support sleeve 2302 cover fitted to a support sleeve 1802.

The support sleeve cover 2302, when in place, advantageously supports the muscles and tissues at the proximal end of the femur, and holds them close to their original position despite removal of matter from the proximal femur. The support sleeve cover 2302, in one embodiment, includes a roughly parabolic hood 2304 which, when in place, extends laterally from the greater trochanter to the lesser trochanter. The support sleeve cover 2302 includes a wall 2306 at the end of the hood 2304 nearest the greater trochanter. At the opposite end of the hood over the lower trochanter, the support sleeve cover includes an opening 2308—in one embodiment an arched opening—which may be advantageously occupied by the prosthetic femoral neck when it is engaged with the prosthetic femoral head 1102. The support sleeve cover 2302 also includes a lip 2310 formed around its distal perimeter to engage and fit over the lateral flat surface of the support sleeve 1802. In one embodiment, cylindrical engagement pins 2312 extend distally from a flat surface inside the lip 2310. Each cylindrical engagement pin may be approximately 7-10 mm long. The cylindrical engagement pins 2312 may have a diameter of 0.5-2 mm that may be the same as the diameter of engagement bores 2314 formed into the lateral flat surface of the support sleeve. In one embodiment, four cylindrical engagement pins 2312 and four respective engagement bores 2314 are arranged in roughly a rectangular pattern about the central rod bore of the support sleeve. The engagement bores 2314 receive the cylindrical engagement pins 2312 to advantageously hold the support sleeve cover 2302 in place relative to the support sleeve 1802.

To prepare the femur 104 to receive a support sleeve 1802 in accordance with an embodiment of the present invention, the proximal end of the femur may be prepared with an osteotome, oscillating saw or other appropriate tool to remove roughly one quarter of the proximal tip of the femur. More specifically, in one embodiment, the portion to be removed is preferably that which extends laterally from the proximal tip of the greater trochanter toward the lesser trochanter and which extends distally from the tip of the greater trochanter to a point approximately 1-1.5 cm proximal to the lower trochanter. It will be appreciated that, in one embodiment, removal of this approximate quarter of the proximal tip of the femur may provide substantial access to the inner region of the proximal end of the femur, particularly to the triangular region above the lower trochanter. It will also be appreciated that differing portions of the proximal end of the femur may be removed to provide substantial access to its space without departing substantially from the methods and apparatus of the present invention.

In one embodiment, the inner region of the proximal end of the femur may be reamed with a drilling bit having at least a distal diameter substantially the same as the diameter of the distal end of the conical portion of the support sleeve. FIG. 24A illustrates a representation of a conical drill bit 2402 positioned above a proximal portion of a femur 2404 to remove material from the femur to facilitate positioning a support sleeve in the proximal portion of the femur 2404 in accordance with an embodiment of the present invention.

The conical bit 2402 may be directed into the proximal end of the femur 2404 substantially aligned with the central canal of the femur. It will be appreciated that guiding and/or imaging tools may be used to control the angle and depth of the reaming to remove only as much material as needed to position the support sleeve.

Additional reaming may be performed with the bit directed from a point above the lower trochanter and angled approximately 30 degrees and into the center of the proximal end of the femur 2404 to remove material in roughly a triangular region to accommodate placement of the support sleeve. FIG. 24B illustrates a representation of a drill bit 2406 positioned above and at an angle to the proximal portion of the femur 2404 to optionally remove additional material from the femur to facilitate positioning the triangular portion of a support sleeve in the proximal portion of the femur 2404. In another embodiment, compaction broaching, as is known, may be used to place the support sleeve and may advantageously result in removal of less cancellous bone. FIG. 24C illustrates a representation of a support sleeve 1802 positioned in a proximal portion of a femur 2404 in accordance with an embodiment of the present invention.

It will be appreciated that, with marrow canal reaming performed such as, for example, in the manner described above in connection with FIG. 14, and with a support sleeve 1802 positioned in the proximal portion of the femur 2404, such as, for example, in the manner illustrated in FIG. 24C, that steps described above in connection with insertion of an intramedullary rod 1502 (see, for example, FIG. 17) may be performed to insert the intramedullary rod 1502 through the central rod bore 1806 of the support sleeve 1802 and into the marrow canal.

FIG. 25A illustrates a representation of a proximal portion of a femur 2404 with a cutaway side view illustrating positioning of a support sleeve 1802 and an intramedullary rod 1502 inserted therethrough in accordance with an embodiment of the present invention. FIG. 25D illustrates a representation of a top down view of the proximal portion of the femur 2404 with the support sleeve 1802 in place and the intramedullary rod 1502 positioned therethrough.

The present invention contemplates additional embodiments of an intramedullary rod consistent with supporting a prosthetic femoral neck introduced through the side of the femur opposite the hip joint. For example, FIG. 26 illustrates a representation of a side view of an intramedullary rod 2602 having a split and fluted distal end 2604 in accordance with an embodiment of the present invention. FIG. 26B illustrates a representation of a front view of the intramedullary rod 2602 having a split and fluted distal end 2604, and FIG. 26C illustrates a representation of a bottom up view of the split and fluted distal end 2604. In such embodiment, at least one slot 2606 is formed in the distal end 2604 of the intramedullary rod 2602, and extends from the tip of the distal end 2604 longitudinally along the shaft of the intramedullary rod 2602 for approximately 15% to 75% of the length of the intramedullary rod 2602. The slot 2606 may be approximately 2-10 mm wide, but could be wider or narrower. It will be appreciated that a slotted distal end forms one or more prongs, depending on the number of slots, such as, for example, four prongs created by two intersecting slots, or three prongs created by two parallel slots.

The distal end 2604 of the intramedullary rod 2602 may also include one or more flutes 2608 formed along the outside of the shaft of the distal end 2604. The flute 2608 extends approximately 1-3 mm from the surface of the shaft in the direction perpendicular to the length of the shaft. The flute 2608 may be approximately 1-5 mm wide, but could be wider or narrower. Lengthwise, the flute 2608 may extend approximately the length of the slot 2606, but may be shorter or longer. In one embodiment, the flute may be a projection (as shown in FIGS. 26A-C) extending away from the center of the shaft, and in another embodiment, the flute may be a recess or groove formed into the shaft toward the center of the shaft. FIG. 26D illustrates a representation of a proximal portion of a femur 2404 with cutaway side view illustrating positioning of a support sleeve 1802 and intramedullary rod 2602 having a split and fluted distal end 2604 inserted therethrough.

In one such embodiment, the intramedullary rod 2602 may have a stem portion with a larger diameter, preferably in the range of 10-13 mm, and may be cylindrical in shape with little or no narrowing distally. The slot 2606 may bisect the stem from its distal end 2604 and may preferably extend proximally approximately 6-10 cm. The slot may also preferably be approximately 1-5 mm wide. The slotted stem may advantageously reduce stress along the length of the femur 104 and also provide superior fill within the femoral canal. The one or more flutes may also advantageously cut into the interior bony walls of the femoral canal to provide additional fill and also to provide rotational resistance between the intramedullary rod 2602 and the femur 104. It will be appreciated that these variations in the stem of the intramedullary rod may be used with either a longer or shorter proximal region.

It will be understood that the use of the support sleeve in combination with an intramedullary rod achieves high levels of fit and fill within the femur 104 both proximally and distally. It is further contemplated that a hip replacement kit in accordance with the present invention may include a number of support sleeves of gradually increasing dimensions and may also include a number of intramedullary rods of gradually increasing dimensions. The dimensions of the central bore of each of the support sleeves may, however, remain fixed to firmly engage the proximal region of any of the intramedullary rods, the diameter and shape of which may also remain constant among all of the intramedullary rods. As contemplated, the variety of combinations of support sleeve and intramedullary rod provided by the kit further advantageously permits even greater, patient-specific fit and fill of the prosthetics to the femur both proximally and distally.

In another embodiment, an intramedullary rod includes a proximal region having dimensions substantially similar to those described above in connection with various support sleeves. This embodiment may also include a stem in any of the variations described above. FIG. 27A illustrates a representation of a side view of an intramedullary rod 2702 with proximal femoral support structure in accordance with an embodiment of the present invention, and FIG. 27B illustrates a representation of a front view of the intramedullary rod 2702. FIG. 27C illustrates a representation of a top down view of the intramedullary rod 2702 with proximal femoral support structure, and FIG. 27D illustrates a representation of a bottom up view of a split and fluted distal end of an intramedullary rod 2702 with proximal femoral support structure. In accordance with this embodiment, the proximal region of the intramedullary rod 2702 includes a neck bore 2704 and a fixation bore 2706, and also includes a circular keyway 2708, which may be formed as described above in connection with FIG. 15C. As will be readily appreciated, the femur preparation and reaming steps described above in connection with intramedullary rod and support sleeve may be used to prepare the femur 104 to receive such embodiment of the intramedullary rod 2702. This embodiment provides advantages of the support sleeves and intramedullary rods described above without using a separate sleeve. In addition, the neck bore 2704 may advantageously be formed to be wider at the insertion 2710 and exit 2712 points of the neck bore 2704, permitting adjustment of the angle of the prosthetic femoral neck in relation to the intramedullary rod 2702.

A prosthetic femoral neck in accordance with the present invention may be essentially a straight shaft, which may be slightly tapered on one end to fixedly join a prosthetic femoral head by insertion into a neck bore (see FIG. 11 and related description). In one embodiment, a prosthetic femoral neck may have a circular cross section. It will be appreciated that the cross-sectional shape may differ, and other embodiments are specifically contemplated such as, for example, oval, square, rectangular, triangular, irregular or other cross-sectional shapes may be used, where the shape of the neck bore in the intramedullary rod is configured to correspondingly receive a prosthetic femoral neck having such cross-sectional shape. While a circular cross-section of a head-engaging end of a prosthetic femoral neck may be used with the remainder of the prosthetic femoral neck having a different cross-sectional shape, in another embodiment the neck-receiving bore in the prosthetic femoral head may be configured to receive a head-engaging end of a prosthetic femoral neck having a cross-sectional shape other than circular. In addition, a prosthetic femoral neck may include fixation ridges formed therein to fix its position relative to an intramedullary rod. In one embodiment, the fixation ridges may be formed roughly perpendicular to the lengthwise direction of the shaft of the prosthetic femoral neck to engage the fixation ridges described above in connection with FIGS. 20A, B, C and 21A, B. In another embodiment, a prosthetic femoral neck may be curved and/or may include fixation grooves. FIG. 27E illustrates a representation of a side view of a curved prosthetic femoral neck 2720 having preconfigured fixation grooves 2722 to fix the position of the prosthetic femoral neck 2720 relative to an intramedullary rod in accordance with an embodiment of the present invention. FIG. 27F illustrates a representation of a top down view of a curved prosthetic femoral neck 2720 having preconfigured fixation grooves 2722, and FIG. 27G illustrates a representation of a bottom up view of a curved prosthetic femoral neck 2720 having preconfigured fixation grooves 2722. It will be appreciated that the prosthetic femoral neck 2720 may be used to facilitate advantageous angling of the femoral head in relation to the intramedullary rod and also may be used for right or left hip joint repair simply by flipping it upside down.

FIG. 27H illustrates a representation of an upper portion of an example of an intramedullary rod 2724 having a neck bore 2726 with at least one groove-engaging ridge 2728 configured to be used with a prosthetic femoral neck, such as prosthetic femoral neck 2720, having fixation grooves 2722. FIG. 27I illustrates a representation of a top down view of the intramedullary rod 2724 having a neck bore and a prosthetic femoral neck 2720 having fixation grooves 2722 inserted through the neck bore. It will be readily appreciated that a fixation bolt threaded into the fixation bore 1512 may provide force that causes the fixation grooves 2722 to engage the ridges 2728 to fix the position of the prosthetic femoral neck relative to the intramedullary rod 2724.

With the intramedullary rod in place, and with support sleeve if one is used, attention is then turned to insertion of the prosthetic femoral neck. An alignment tool may advantageously be fixed to the intramedullary rod to provide an accurate guide for drilling a straight bore to meet the path defined by the neck bore in the intramedullary rod, thereby facilitating straightforward insertion of the prosthetic femoral neck. FIG. 28A illustrates a representation of a side cutaway view of a neck bore alignment tool 2802 in accordance with an embodiment of the present invention. FIG. 28B illustrates a representation of a rear view of the neck bore alignment tool 2802, and FIG. 28C illustrates a representation of a top down view of the neck bore alignment tool 2802. FIG. 28D illustrates a representation of a perspective cutaway view of a keyway of the neck bore alignment tool 2802 for engaging a proximal end of an intramedullary rod 1502. FIG. 28E illustrates a representation of a perspective cutaway view of an alternative keyway 2820 for engaging a proximal end of an intramedullary rod 1502.

The alignment tool 2802 has a rod-engaging end 2804, a curving handle section 2806, and a guide block 2808 that includes a guide bore 2810. The rod-engaging end 2804 comprises a cylindrical shaft 2812 approximately 4-8 cm in length and approximately 1.5 to 2 cm in diameter. The cylindrical shaft 2812 includes a fixation bore 2814 extending the full length of the shaft, and the fixation bore 2814 may have a diameter of approximately 8 mm, but that diameter could be more or less.

The rod-engaging end 2804 of the alignment tool 2802 includes a keyway 2814 located at its end. The keyway 2814 includes a recessed circular rim 2816 and a protrusion 2818 projecting outward from the rim 2816. The circular rim 2816 is recessed about 2 mm inward from the outer surface of the cylindrical shaft 2810. The protrusion 2818 is approximately 2 mm wide and projects approximately 2 mm outward from the rim 2816. It will be appreciated that the approximately 2 mm protrusion along the circular rim 2816 of the keyway 2814 may advantageously engage the 2 mm notch in the circular keyway 1514 at the proximal end of the intramedullary rod 1502 to prevent rotation of the alignment tool 2802 with respect to the intramedullary rod 1502.

As illustrated in FIG. 28E, an alternative keyway 2820 includes four protrusions extending from the end of the cylindrical shaft 2812. The four protrusions may be approximately 2 mm long and 2 mm wide. It will be appreciated that the keyway 2820 may advantageously engage the intramedullary rod keyway 1516 (see FIG. 15D) to prevent the alignment tool 2802 and intramedullary rod 1502 from rotating relative to each other about an axis running through the longitudinal center of their respective fixation bores 2812, 1512. It will be appreciated that other, differentially structured keyways could be used to prevent such rotation.

Figure 29A:
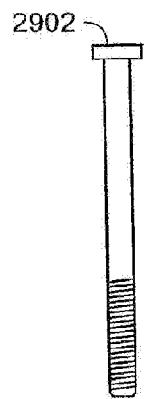
FIG. 29A illustrates a representation of a fixation bolt for joining an end of a neck bore guide tool to an end of an intramedullary rod in accordance with an embodiment of the present invention.
Figure 29B:
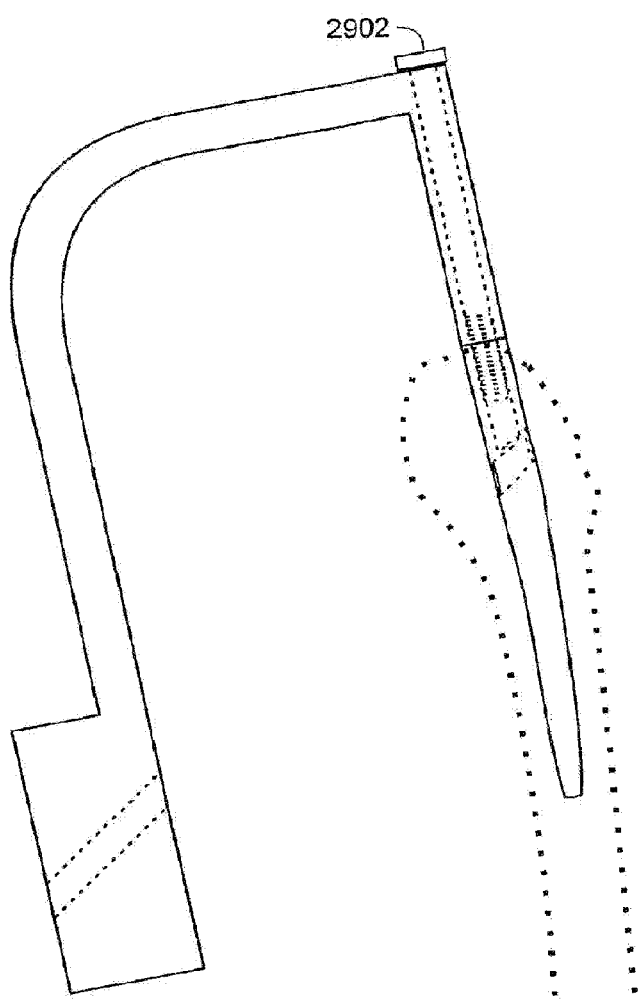
FIG. 29B illustrates a representation of a cutaway side view of a neck bore guide tool removably joined with a fixation bolt and interlocking keyway to a proximal end of an intramedullary rod in accordance with an embodiment of the present invention.

When the circular keyway of the alignment tool is properly engaged with the circular keyway of the intramedullary rod, a fixation bore of the alignment tool is aligned to the fixation bore of the intramedullary rod, and a fixation screw may be introduced through the alignment bore of the alignment tool and rotationally threaded into the fixation bore of the intramedullary rod. FIG. 29A illustrates a representation of a fixation screw 2902 for joining the rod-engaging end 2804 of the alignment tool 2802 to an end of an intramedullary rod 1502 that has been inserted into a femur 104 in accordance with an embodiment of the present invention. FIG. 29B illustrates a representation of a cutaway side view of the alignment tool 2802 removably joined with the fixation bolt 2902 and interlocking keyways (e.g., 2814, 1514) to a proximal end of the intramedullary rod 1502. As will be readily appreciated, the head of the fixation screw 2902 may be machined to be engaged by a straight edge, Phillips-type, hexagonal or other shaped rotational driver. Using an appropriate rotational driver, the fixation screw 2902 may be tightened to securely fix the position of the alignment tool 2802 with respect to the intramedullary rod 1502.

When the alignment tool 2802 is properly fixed relative to the intramedullary rod 1502, a guide bore 2810 of the alignment tool 2802 provides a path such that a straight shaft inserted through the guide bore 2810 and toward the patient's leg will pass through the neck bore 1504 in the proximal end of the intramedullary rod 1502 that has been positioned within the femur. The guide bore 2810 advantageously facilitates introduction of a straight guide wire from a point on the side of the patient's leg below the proximal femur through skin and subcutaneous tissue, into the femur, through the neck bore 1504 of the intramedullary rod 1502, out of the femur and toward the neck-engaging bore 1114 of the prosthetic femoral head 1102. It will be appreciated that imaging may be used to confirm proper location of the guide wire.

Figure 30:
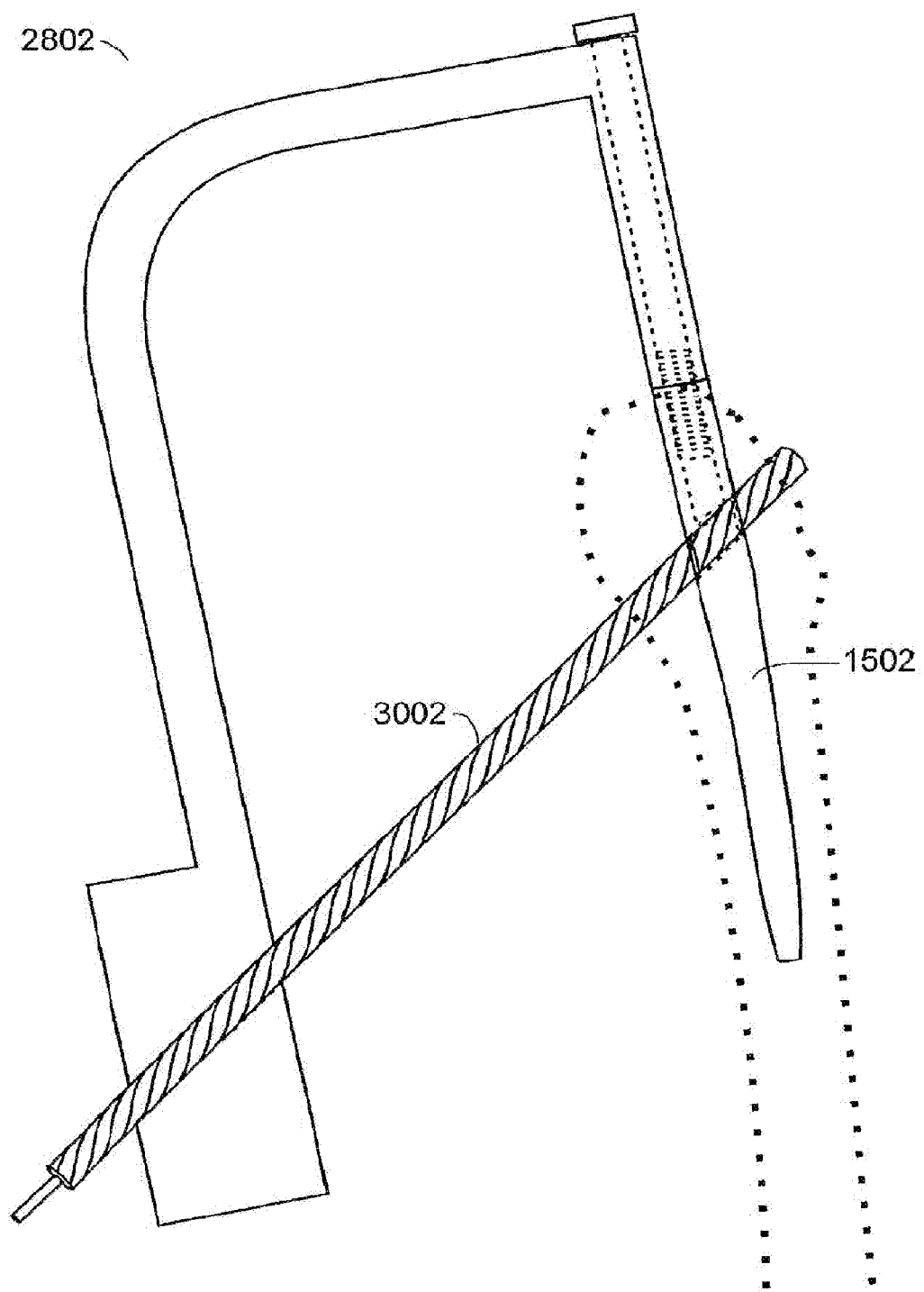
FIG. 30 illustrates a representation of a cutaway side view of a neck bore guide tool removably joined with a fixation bolt and interlocking keyway to a proximal end of an intramedullary rod and with a neck bore drill bit guided through the neck bore guide tool and through the proximal femur and through the neck bore of the intramedullary rod in accordance with an embodiment of the present invention.

After any adjustment or alignment suggested by the guide wire, a drill bit having a diameter sufficient to accommodate the largest diameter of the prosthetic femoral neck may be introduced into the guide bore of the alignment tool. In one embodiment, the guide bore has a diameter approximately the same as the neck bore in the intramedullary rod. Alternatively, a series of drill bits stepped in size may be used to gradually increase the diameter of the bore to a size sufficient for the prosthetic femoral neck. FIG. 30 illustrates a representation of a cutaway side view of the alignment tool 2802 removably joined with the fixation screw 2902 and interlocking keyway (e.g., 2814, 1514) to the proximal end of the intramedullary rod 1502 and with a neck bore drill bit 3002 guided through the guide bore 2810 of the alignment tool 2802 and through the proximal femur and through the neck bore 1504 of the intramedullary rod 1502 in accordance with an embodiment of the present invention. It will be understood that a drill motor may rotate the neck bore drill bit 3002 as it is introduced into the guide bore 2810 to create a neck insertion bore. In creating the neck insertion bore, the rotating neck bore drill bit 3002 is introduced through the guide bore 2810, into the leg of the patient, into the femur, through the neck bore 1504 of the intramedullary rod 1502 and through the other side of the femur. Accordingly, the neck-insertion bore creates a path through the femur, through which the prosthetic femoral neck may be advantageously introduced from one side of the femur and through the neck bore 1504 in the intramedullary rod 1502 such that the head-engaging end of the prosthetic femoral neck may engage the prosthetic femoral head 1102 on the opposite side of the femur. With the neck-insertion bore created, the alignment tool 2802 may be detached by loosening the fixation screw 2902 and removing the alignment tool 2802.

In one embodiment, a neck-sizing shaft may advantageously be introduced through the neck insertion bore to determine the optimal length of the prosthetic femoral neck. The neck-sizing shaft may be of similar diameter to the prosthetic femoral neck. However, a head-engaging end of the neck-sizing shaft may be of slightly smaller diameter than that of the actual prosthetic femoral neck to avoid fixedly engaging the prosthetic femoral head 1102 and to thereby facilitate removal of the neck-sizing shaft after trial fitting. The neck-sizing shaft may be introduced through the neck insertion bore such that the head-engaging end of the neck-sizing shaft enters the neck bore 1114 of the prosthetic femoral head 1102 and thereby engages the prosthetic femoral head 1102. Holding the femur steady and with moderate force applied to the neck-sizing shaft in the direction of the hip joint, a fixation screw 2902 may be threaded into the fixation bore 1512 of the intramedullary rod 1502 and tightened to fix the neck-sizing shaft relative to the intramedullary rod 1502. The fit and positioning of the prosthetic femoral neck and femur relative to the hip may then be tested, and by loosening the fixation screw 2902 and adjusting the neck-sizing shaft and retightening the fixation screw 2902, additional fit testing may determine an optimal length of the prosthetic femoral neck. When fit is deemed optimal, predetermined length markings along the neck-sizing shaft may be consulted to determine the proper length for the prosthetic femoral neck. The proper length of the prosthetic femoral neck preferably provides proper distance and angle between the femur 104 and acetabulum and provides a length of approximately 1-2 mm of the prosthetic femoral neck protruding outside the femur on the side of the femur away from the patient's hip.

Figure 31:
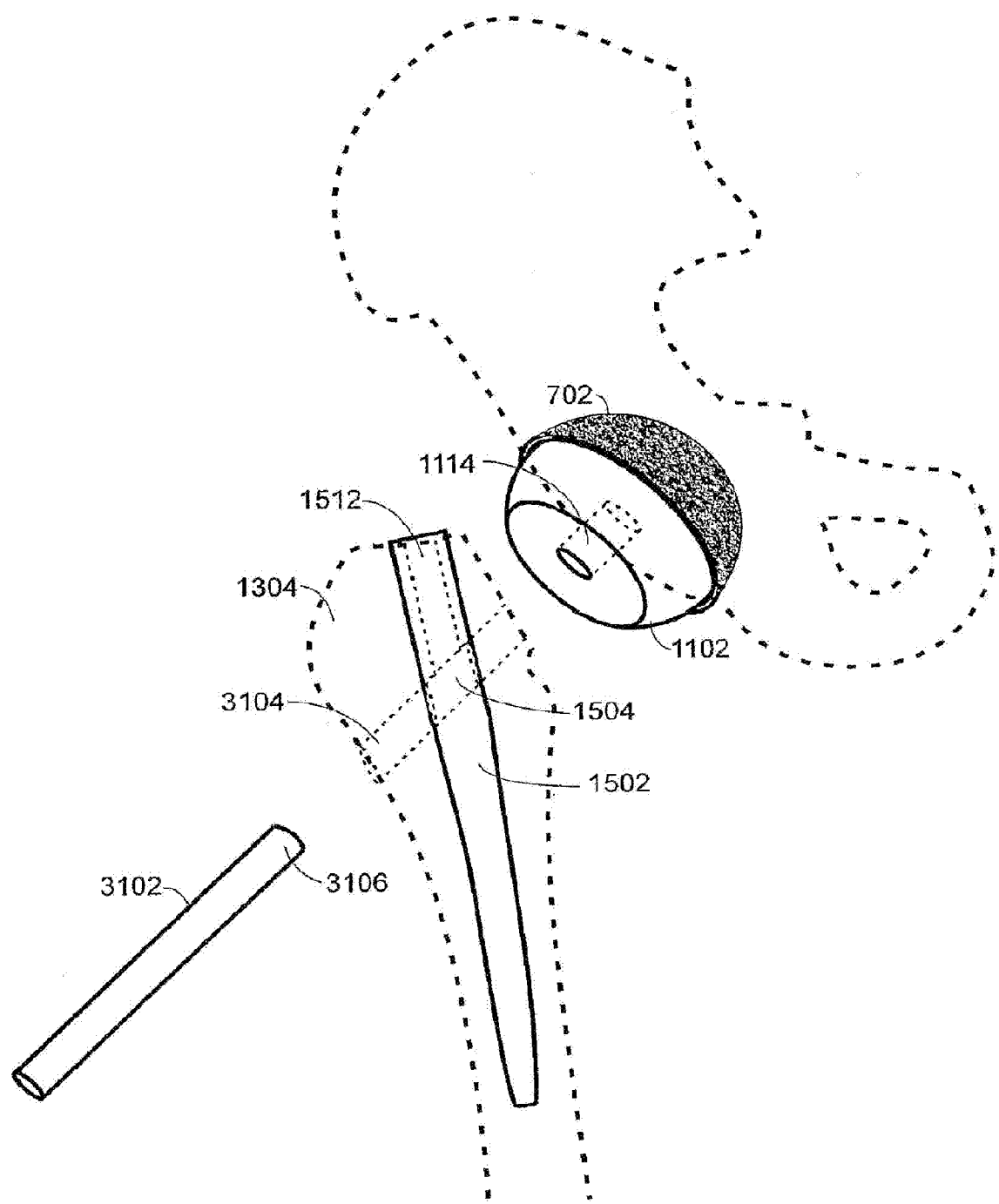
FIG. 31 illustrates a representation of a prosthetic acetabular cup, a prosthetic femoral head, an intramedullary rod positioned in a femur, and also illustrates a prosthetic femoral neck positioned for insertion within the neck bore of the intramedullary rod in accordance with an embodiment of the present invention.

The neck-sizing shaft may then be removed and a prosthetic femoral neck of proper length may be selected. FIG. 31 illustrates a representation of a prosthetic acetabular cup 812, a prosthetic femoral head 1102, an intramedullary rod 1502 positioned in a femur, and also illustrates a prosthetic femoral neck 3102 positioned for insertion within a neck insertion bore 3104 that includes the neck bore 1504 of the intramedullary rod 1502 in accordance with an embodiment of the present invention. The slightly tapered head-engaging end 3106 of the selected prosthetic femoral neck 3102 is then inserted into the neck-insertion bore 3104 and positioned through the femur 3104 and the neck bore 1504 of the intramedullary rod 1502 such that the head-engaging end 3106 of the prosthetic femoral neck 3102 engages the neck bore 1114 in the prosthetic femoral head 1102. The prosthetic femoral neck 3102 may be impacted into position in the neck bore 1114 of the prosthetic femoral head 1102 by one or more sharp taps delivered using an appropriate driving tool to the non-engaging end of the prosthetic femoral neck 3102. The prosthetic femoral neck 3102 may then be securely fixed relative to the intramedullary rod 1502 by tightening a fixation screw 2902 through the fixation bore 1512 of the intramedullary rod 1502 to firmly hold the shaft of the prosthetic femoral neck 3102 in place within the neck bore 1504 of the intramedullary rod 1502.

FIG. 32A illustrates a representation of a prosthetic acetabular cup, a prosthetic femoral head and neck, and an intramedullary rod installed in a femur, and also illustrates a representation of a fixation screw 2902 to fix the position of the prosthetic femoral neck 3102 within the neck bore of the intramedullary rod in accordance with an embodiment of the present invention. FIG. 32B illustrates a representation of a fixation screw fixing 2902 the position of the prosthetic femoral neck 3102 within the neck bore of the intramedullary rod.

It will also be appreciated, as exemplified by embodiments described above, that ridges or grooves may be formed into the shaft of the prosthetic femoral neck 3102 to engage opposing ridges or grooves formed in the neck bore 1504 of the intramedullary rod 1502 and/or ridges or grooves formed in a support sleeve 1802 (see, e.g., FIGS. 20A,B,C and 21A,B and 27E,F,G,H,I), and it will be appreciated that engaging force may provided by the fixation screw 2902 forcing the ridges or grooves in the prosthetic femoral neck 3102 against the opposing ridges or grooves.

With the prosthetic femoral neck 3102 advantageously fixed in position, the surgical access incisions may then be closed in accordance with known technique.

Figure 33:
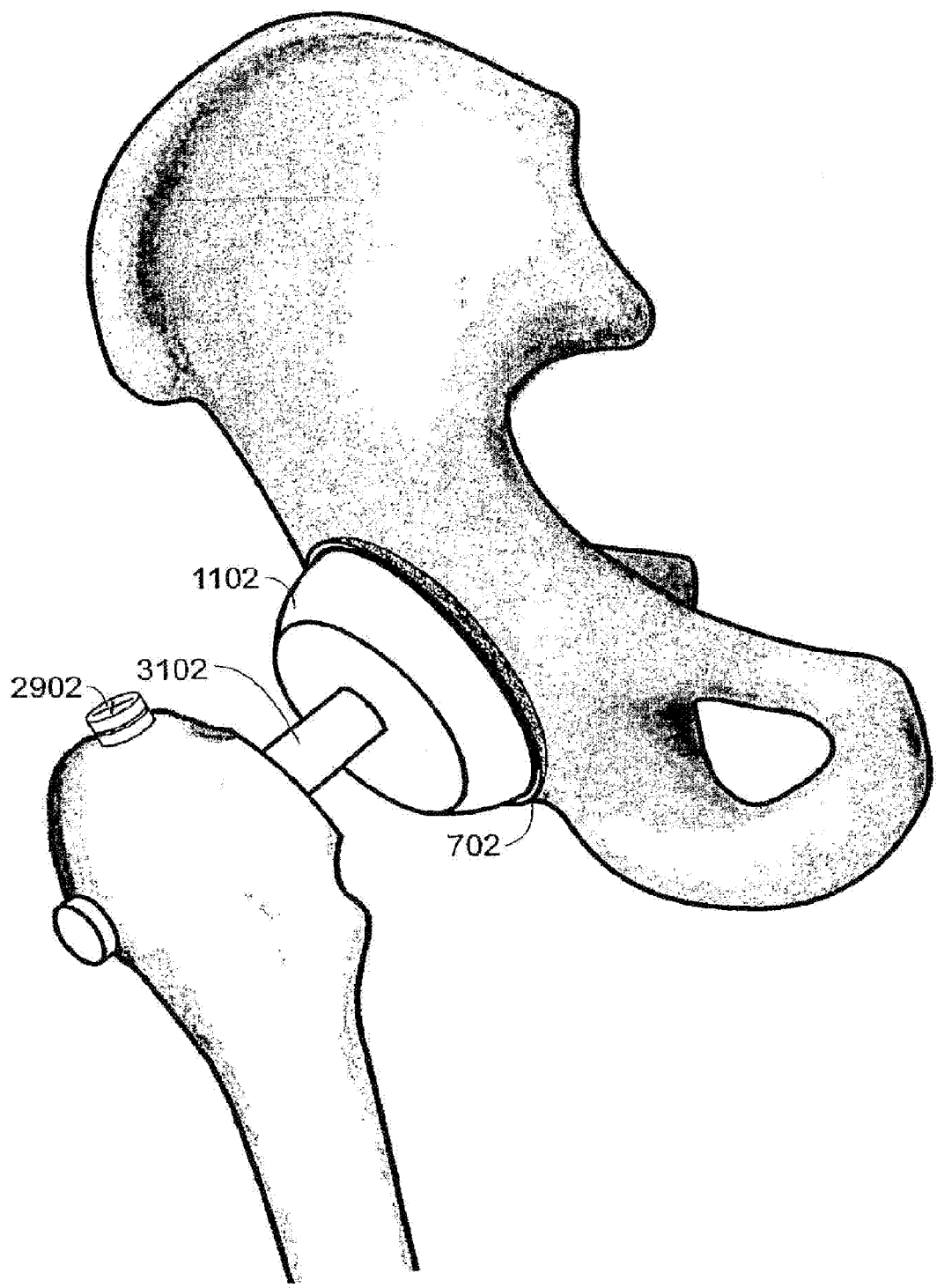
FIG. 33 illustrates a representation of a three-dimensional view of a prosthetic acetabular cup, a prosthetic femoral head and neck, and an intramedullary rod installed in a femur with a fixation screw fixing the position of the prosthetic femoral neck in accordance with an embodiment of the present invention.

FIG. 33 illustrates a representation of a three-dimensional view of a prosthetic acetabular cup 812, a prosthetic femoral head 1102 and neck 3102, and an intramedullary rod installed in a femur with a fixation screw 2902 fixing the position of the prosthetic femoral neck 3102 in accordance with an embodiment of the present invention. With the prosthetic femoral neck 3102 fixedly joined to the prosthetic femoral head 1102, and with the prosthetic femoral neck 3102 fixed with respect to the intramedullary rod, the femur is advantageously positioned in approximately normal rotational capacity with respect to the acetabulum. It will be appreciated that normal rotational capacity, i.e., the degree of comfortable rotational movement under various day-to-day stress loads that was available to a patient prior to injury or deterioration of the hip joint, differs from patient to patient, based, for example, on age, anatomy and lifestyle, and it will also be appreciated that a rotational capacity facilitated by the various embodiments of the present invention may usefully approximate a normal rotational capacity even though a resulting degree of movement may be different than normal rotational capacity.

Figure 34:
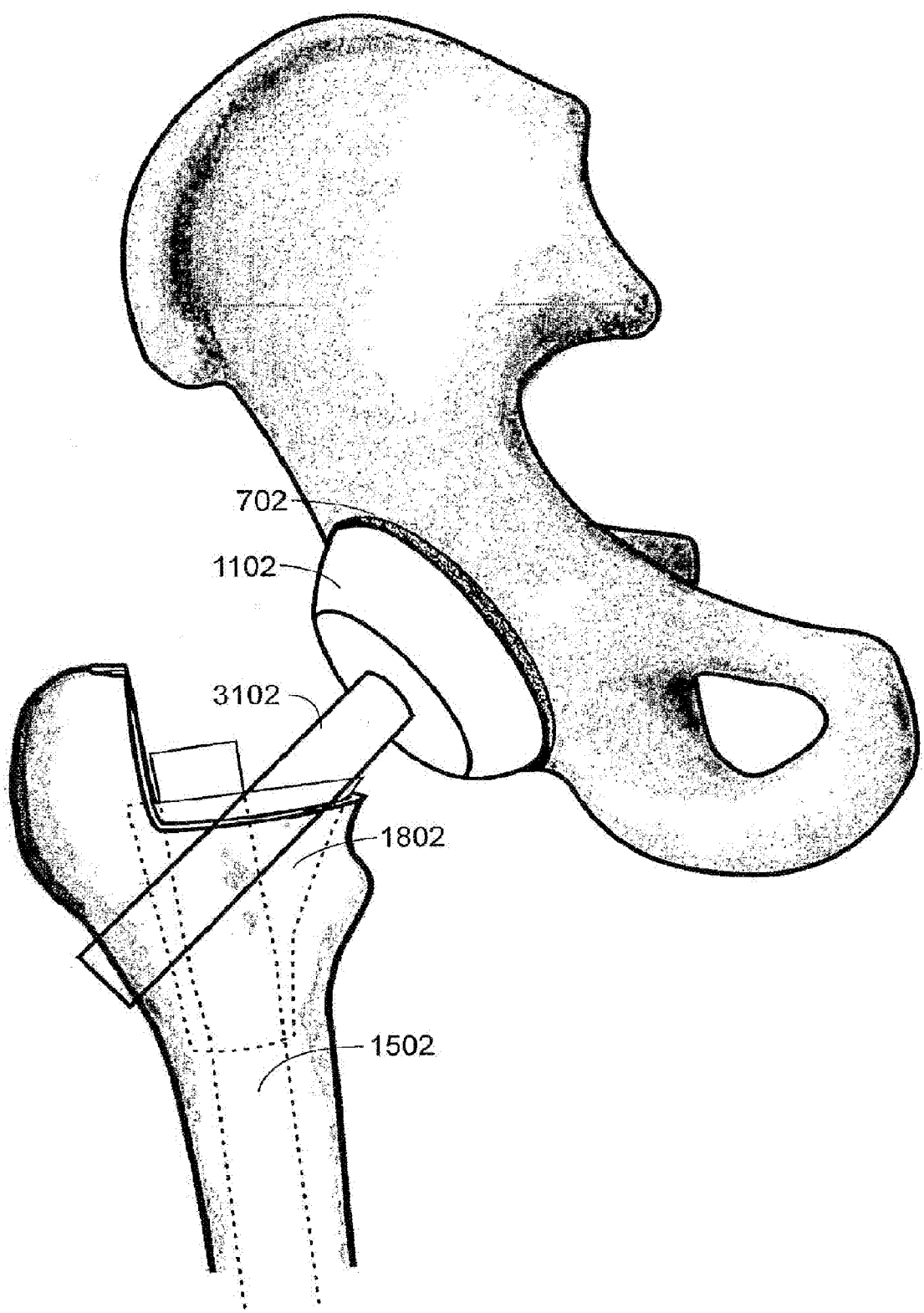
FIG. 34 illustrates a representation of a prosthetic acetabular cup, a prosthetic femoral head and neck, and an intramedullary rod installed in a support sleeve in the proximal femur in accordance with an embodiment of the present invention.
Figure 35A:
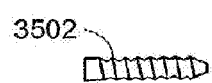
FIG. 35A illustrates a representation of a fixation screw for fixing the prosthetic femoral neck in relation to the support sleeve and intramedullary rod in accordance with an embodiment of the present invention.
Figure 35B:
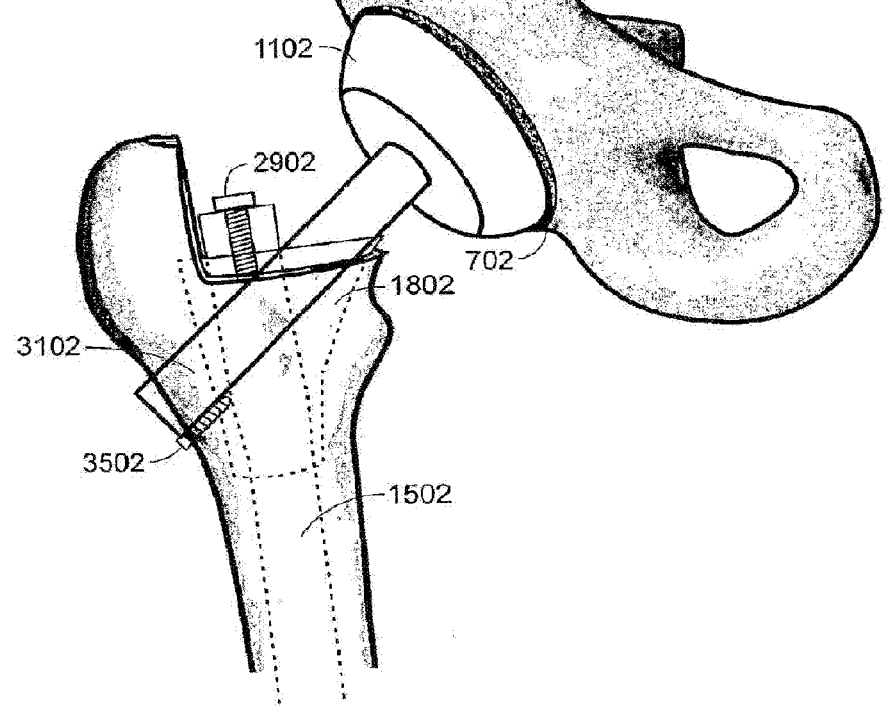
FIG. 35B illustrates a representation of a prosthetic acetabular cup, a prosthetic femoral head and neck, and an intramedullary rod installed in a support sleeve in the proximal femur and fixation screws to fix the prosthetic femoral neck in relation to the support sleeve and intramedullary rod in accordance with an embodiment of the present invention.

As described above, the present invention contemplates various embodiments of intramedullary rods, and also the optional use of a support sleeve (e.g., 1802). FIG. 34 illustrates a representation of a prosthetic acetabular cup 812, a prosthetic femoral head 1102 and neck 3102, and an intramedullary rod 1502 positioned in a support sleeve 1802 in the proximal femur in accordance with an embodiment of the present invention. It will be appreciated that the prosthetic femoral neck may receive additional fixation force relative to the intramedullary rod with the addition of a second fixation screw. FIG. 35A illustrates a representation of a prosthetic femoral neck fixation screw 3502, and FIG. 35B illustrates a representation of a prosthetic acetabular cup 812, a prosthetic femoral head 1102 and neck 3102, and an intramedullary rod 1502 positioned in a support sleeve 1802 in the proximal femur, and fixation screws 2902, 3502 to fix the prosthetic femoral neck 3102 relative to the intramedullary rod 1502 in accordance with an embodiment of the present invention. In one embodiment, a prosthetic femoral neck fixation screw 3502 may be inserted between the prosthetic femoral neck 3102 and the femur and threaded inward to wedge into a space between the prosthetic femoral neck 3102 and floor 1814 of the neck slot 1812. It will be appreciated that the wedging force created by such threading of the prosthetic femoral neck fixation screw 3502 advantageously fixes the prosthetic femoral neck 3102 in relation to the intramedullary rod 1502.

Figure 36:
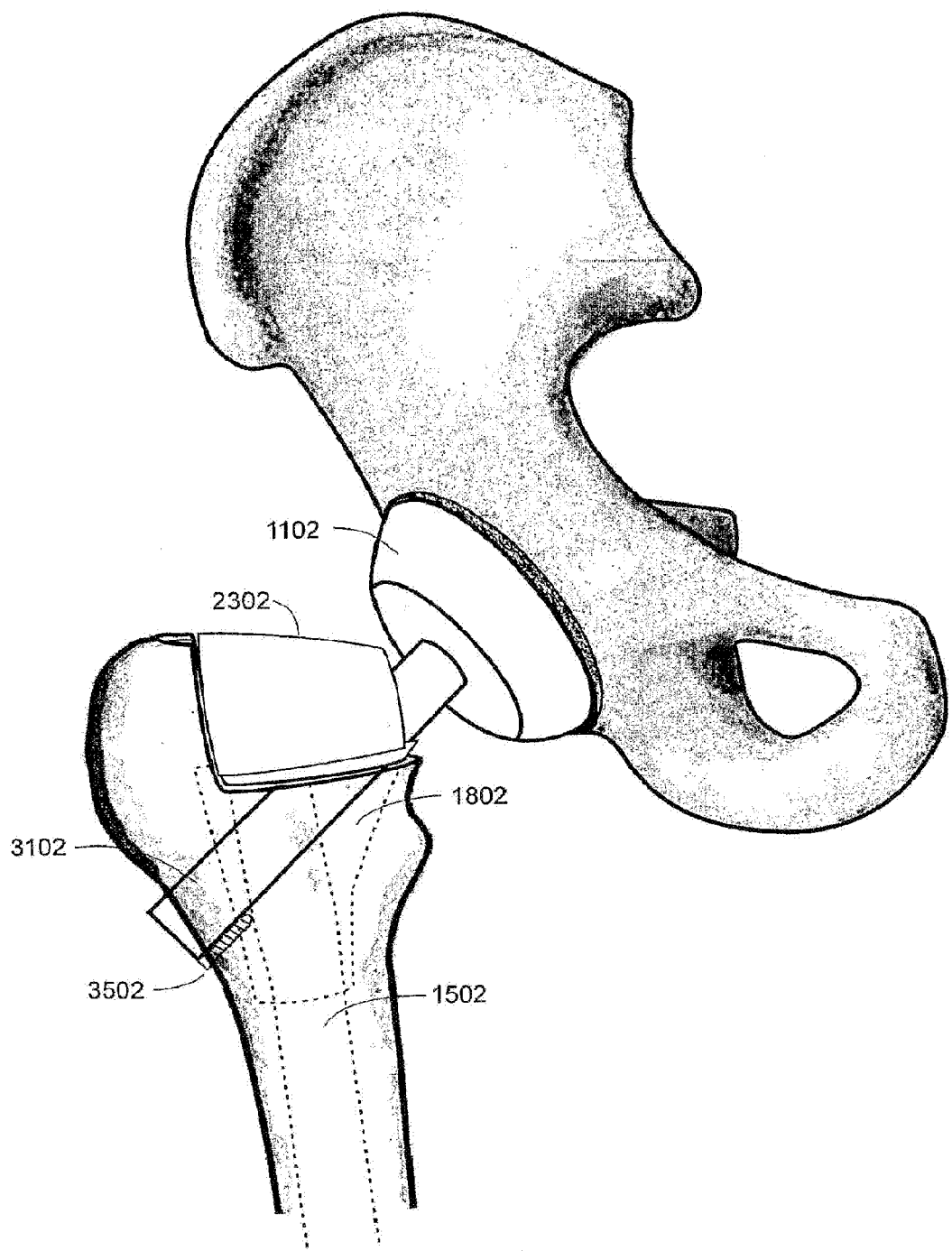
FIG. 36 illustrates a representation of a prosthetic acetabular cup, a prosthetic femoral head and neck, and an intramedullary rod installed in a support sleeve in the proximal femur with prosthetic femoral neck fixation screws and a cover in accordance with an embodiment of the present invention.

Embodiments of the present invention further contemplate that a portion of the prosthetic femoral neck may optionally be covered using a support sleeve cover that may advantageously provide support for the tissues about the hip joint. FIG. 36 illustrates a representation of a prosthetic acetabular cup, a prosthetic femoral head 1102 and neck 3102, and an intramedullary rod 1502 positioned in a support sleeve 1802 in the proximal femur with prosthetic femoral neck fixation screws and a support sleeve cover 2302 in accordance with an embodiment of the present invention.

Embodiments of the present invention further contemplate variations in the order that surgical steps are carried out. For example, in one such embodiment of the present invention, the proximal femur is prepared for insertion of an intramedullary rod prior to resection of the femoral neck and head. In this embodiment (and in other embodiments), an anterior or posterior incision may be used for surgical access the proximal femur. It will be appreciated, for example, that the posterior incision described in U.S. Pat. No. 6,991,656 may be used. With access to the proximal femur gained through appropriate incision, the proximal femur may be prepared as described above, e.g., in FIG. 14 and the associated text. Among other options, one of the support sleeves described above may be used, and if so, then the steps to prepare the proximal femur for a support sleeve may be performed as described above, including as in FIGS. 23A and 23B and associated text. If a support sleeve is to be used, it may then be positioned, and an intramedullary rod may then be inserted. If no support sleeve will be used, then the intramedullary rod may be inserted into the femur, e.g. as described in connection with FIG. 17A and the associated text. At this point, the alignment tool, e.g. as described in connection with FIG. 29B, may be joined via fixation bolt to the intramedullary rod, and a bore for a prosthetic femoral neck may then be created by introducing a neck bore drill bit through a guide block of the alignment tool. It will be appreciated that, in this embodiment, with the femoral neck and femoral head still in place, imaging may be used to advantageously confirm optimum path for the bore, which may be advanced into the femoral neck and head. Once the bore for the prosthetic femoral neck is created, attention is then turned to resection of the femoral neck and head, which may be performed in accordance with the steps described above, e.g., in connection with FIGS. 3A, 3B and 3C. Next, the acetabulum is prepared to receive the prosthetic acetabular cup. Advantageously, reaming of the acetabulum may be performed by fitting a reamer head into position through the surgical access to the proximal femur, and a reamer shaft may be advanced either through the created bore for the prosthetic femoral neck or through a stab incision lateral to a mid-portion of Smith-Peterson approach. It will be readily appreciated that a tissue-protecting guide sheath may be used to protect tissues from injury that may be caused by the rotating reamer shaft. It will be appreciated that the reamer shaft, once advanced to meet the reamer head, may be affixed to the reamer head and reaming may be performed with minimal insult to the soft tissue envelope about the hip joint. Once reaming of the acetabulum is complete, substantially as described above, e.g. in connection with FIG. 4B, the reamer head is detached from the reamer shaft and the reamer head and shaft are removed from the surgical space. A prosthetic acetabular cup is then positioned for impacting within the prepared acetabulum. Impacting may likewise be performed by advancing an impactor tool either through the bore created for the prosthetic femoral neck or through a stab incision. Again, a tissue-protecting guide sheath may be used. If desired, a conical sleeve with rounded end (e.g., FIG. 9A, item 912) may be positioned through the surgical access to the proximal femur whereupon the engaging threaded end of the impactor tool may be advanced through the conical sleeve. The impactor may then be threaded into the impaction bore of the prosthetic acetabular cup, and impacting may be performed as described above, e.g. in accordance with FIGS. 9A and 9B and the associated text. With the prosthetic acetabular cup impacted into place, one or more fixation screws may optionally be used to further secure the prosthetic acetabular cup to the acetabulum (e.g. FIGS. 8A, 8B, 8C and 8D and associated text). Attention may then be turned to positioning the prosthetic femoral head within the prosthetic acetabular cup, which may be carried out as described above in connection with FIGS. 11 and 12 and the associated text. As also described above (see FIG. 31 and associated text), the prosthetic femoral neck may then be advanced through the bore created for same and impacted to engage the prosthetic femoral head. Fixation screws may then be positioned and tightened to fix the location of the prosthetic femoral neck relative to the intramedullary rod (see, e.g., FIGS. 32A, 32B, 35A and 35B and associated text). If a support sleeve is used, then a support sleeve cover optionally may also be used. This is merely one of many alternative variations in the order of steps that may be performed in accordance with the method of the present invention.

In various embodiments, a prosthetic acetabular cup may be used in conjunction with a hip replacement. In some embodiments, a total hip arthroplasty includes an artificial cup. In some embodiments, a hemiarthroplasty does not include an artificial cup. In various embodiments, an acetabular cup may include one, two, three or more materials that attaché to each other. In various embodiments, an acetabular cup can include any material, metal, alloy, plastic, polymer, polyethylene, ceramic, coating, and/or surface. In one embodiment, combinations and/or transitions in materials can be used for abrasion and/or friction resistance with other components or tissue. In one embodiment, the acetabular cup can comprise a zirconium alloy metal substrate that transitions in to a ceramic zirconium oxide surface. In one embodiment, a material can be oxidized, such as a titanium oxide. In one embodiment, oxinium may be used as a material.

Figure 40:
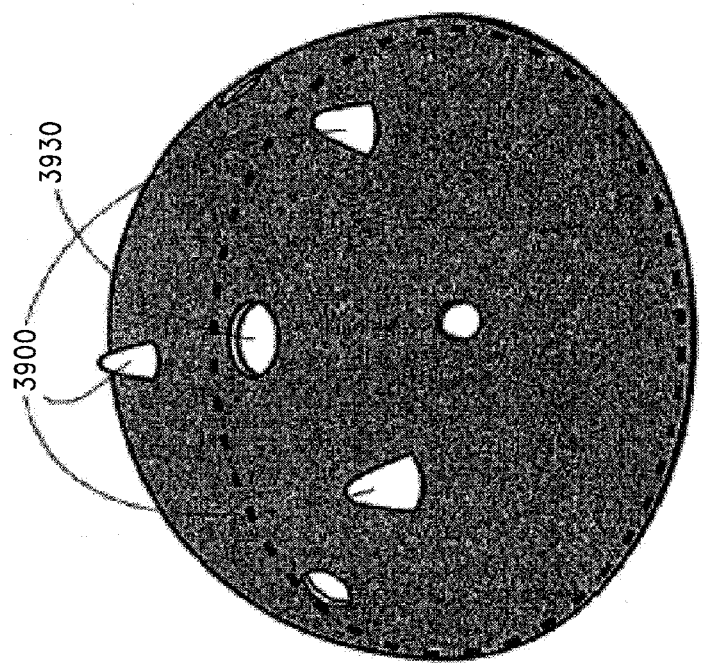
FIG. 40 is a representation of a prosthetic acetabular cup having a plurality of anchoring protrusions in accordance with an embodiment.
Figure 39A:
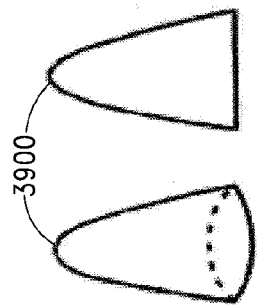
FIG. 39A is a representation of a three-dimensional perspective and cross-sectional view of an anchoring protrusion for an outer surface of a prosthetic acetabular cup in accordance with an embodiment.
Figure 39B:
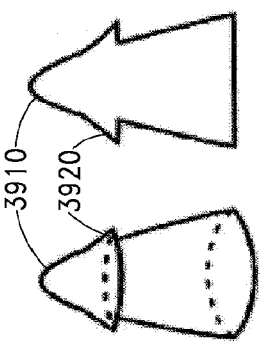
FIG. 39B is a representation of a three-dimensional perspective and cross-sectional view of an anchoring protrusion for an outer surface of a prosthetic acetabular cup in accordance with another embodiment.
Figure 37:
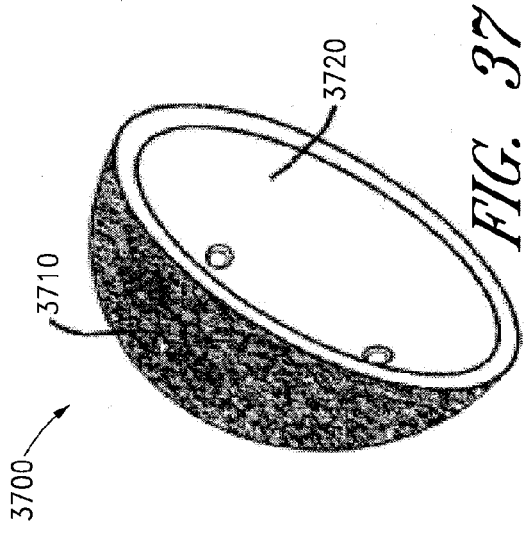
FIG. 37 is a perspective view of a prosthetic acetabular cup, according to an embodiment of the present invention.
Figure 38:
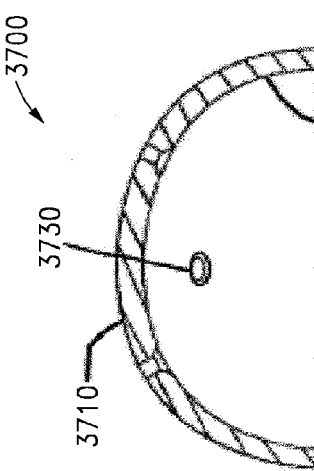
FIG. 38 is a cross-sectional side view of the prosthetic acetabular cup shown in FIG. 37.

FIGS. 37 and 38 illustrate an embodiment of a monoblock acetabular cup 3700, in accordance with an embodiment disclosed herein. The term "monoblock" can generally refer to a single-piece, monolithic, or unitary structure of the acetabular cup 3700. For example, a monoblock cup can comprise a generally rounded body defining a inner concave surface and an outer convex surface. The inner concave surface and the outer convex surface can be separated by a thickness. In some embodiments, the thickness of the cup can be generally constant or can vary in accordance with structures or other features of the cup. Further, the term "monoblock" can also refer to the ability to use the cup as the only support or engagement structure that is anchored to the acetabulum and used to support or engage with a prosthetic femoral head in order to form a prosthetic hip system or joint. Thus, in contrast to a two-part cup, which includes an outer cup that is anchored to the acetabulum and a separate inner cup that is inserted into the outer cup, a "monoblock" cup can comprise a single or monolithic part that both anchors to the acetabulum and supports the femoral head. In some embodiments, the cup 3700 can comprise an outer contact surface 3710, an inner contact surface 3720, and a plurality of mounting apertures 3730. Alternatively, the cup 3700 can comprise a plurality of anchoring protrusions. Various embodiments of anchoring protrusions are shown in FIGS. 39A, 39B and 40. The outer contact surface 3710 can be configured to mate against the acetabulum of the patient when implanted, as referenced herein. Further, the inner contact surface 3720 can be comprised to contact against a prosthetic femoral head.

Embodiments of the monoblock acetabular cup 3700 can provide various advantages over prior art acetabular cups. For example, some embodiments of the monoblock cup disclosed herein can allow the prosthetic femoral head size to be maximized relative to the prosthetic joint, thus reducing dislocations and improving joint wear. Further, some embodiments can provide reduced deformation and deflection of the cup during implantation and use. Thus, in embodiments using a metal material, the ion production can be minimized in order to achieve superior health benefits for the patient. According to some embodiments, the acetabular cup 3700 can advantageously provide superior rigidity while maximizing the internal size of the cup in order to prevent and/or minimize dislocation of a prosthetic femoral head from the cup 3700. Thus, the monoblock configuration can advantageously enable the thickness of the cup to be optimized to prevent and/or minimize deformation to an acceptable degree. However, because the monoblock cup may not require an inner cup (unlike traditional two-part cups that have an inner cup, which decreases the inner diameter or size of the cup), the monoblock cup 3700 can be configured with a maximized internal size or diameter, thereby allowing for improved engagement between the prosthetic femoral head and the cup to reduce and/or prevent dislocation. In some embodiments, the acetabular cup 3700 can have an outside diameter and a prosthetic femoral head can define an outer diameter. For example, the outside diameter of the cup 3700 can be between at least about 30 mm and/or less than or equal to about 75 mm. In some embodiments, the outside of the cup can be between at least about 50 mm and/or less than or equal to about 65 mm. Further, in some embodiments, the outside diameter of the cup 3700 can be about 58 mm. Further, some embodiments can be configured such that the acetabular cup defines a thickness within a range of about at least 2 mm and/or less than or equal to about 10 mm. In some embodiments, the thickness can be within a range of about at least 3 mm and/or less than or equal to about 8 mm. For example, in some embodiments, the acetabular cup can comprise a metal material, which can allow the cup to be sized with a thickness within the range of at least about 2 mm and/or less than or equal to about 7 mm. Some embodiments of a metal cup can have a thickness within the range of at least about 2.5 mm and/or less than or equal to about 5 mm. Further, in some embodiments, the cup can have a thickness with a range of at least about 3.5 mm and/or less than or equal to 4.5 mm. For example, some embodiments can comprise a cobalt cromium metal having a thickness of about 3.5 mm. Further, some embodiments can comprise a cobalt cromium metal having a thickness of about 2.5 mm. Further, in some embodiments, the acetabular cup can comprise a plastic material. For example, the material of the cup can comprise polyethylene, PEEK or other like material. Thus, in some embodiments, the cup can be sized with a thickness within a range of at least about 4 mm and/or less than or equal to about 9 mm. Some embodiments can be sized with a thickness within a range of at least about 6 mm and/or less than or equal to about 9 mm. Further, in some embodiments, the cup can have a thickness with a range of at least about 7 mm and/or less than or equal to 8 mm. For example, some embodiments can comprise a polyethylene (PE) plastic having a thickness of about 8 mm. Thus, in various embodiments, the cup 3700 can be used along with an appropriately matched prosthetic femoral head having a relatively large outside diameter, such as, for example, 52 mm. It will be appreciated that smaller or larger respective diameters of the cup and the femoral head, such as, for example, 30-75 mm, or even larger or smaller can be used, depending upon various factors such as patient anatomy. Nor are the embodiments disclosed herein limited by any particular material for the prosthetic femoral head or the acetabular cup, which may preferably be made from cobalt chromium, but could also be made from titanium, tantalum, surgical grade stainless steel, ceramic, alumina ceramic or other materials of suitable strength and acceptance properties. In some embodiments, the outer contact surface 3710 can be formed from titanium and may also be machined or grit-blasted to have a mesh-like, porous or roughened outer surface. The outer surface of the acetabular cup can also be machined to engage the surgically prepared bone of the acetabulum. In some embodiments, the outer surface of the prosthetic acetabular cup can be machined to have a mesh-like and/or porous surface or grit-blasted or Titanium plasma sprayed to have a roughened surface (e.g., for press-fit anchoring) to grip the surgically prepared bone surface of the acetabulum to prevent displacement and slippage during the cup insertion process and, as time passes after the procedure, to permit and receive bone growth into recesses in the outer surface of the prosthetic acetabular cup to prevent slippage and displacement as the patient makes use of the prosthetic hip joint.

In another embodiment of the invention, the prosthetic acetabular cup may include one or more protrusions or fins formed on its outer surface to further engage the acetabular bone and prevent slippage and/or rotation of the cup relative to the acetabulum. For example, FIG. 39A illustrates a representation of a three-dimensional perspective and cross-sectional view of an anchoring protrusion 3900 for an outer surface of a prosthetic acetabular cup in accordance with one embodiment of the present invention. FIG. 39B illustrates a representation of a three-dimensional perspective and cross-sectional view of an anchoring protrusion 3910 for an outer surface of a prosthetic acetabular cup in accordance with another embodiment of the present invention. In this embodiment, each rounded conical protrusion 3910 may include a circumferential indentation 3920 to form a lateral lip approximately mid-way up the side of the conical structure. The indentation and lip advantageously engage new bone growth to resist displacement and assist fixation of the prosthetic acetabular cup over time. The protrusions may take the form of one or more spikes, small posts and/or ridges with or without barb-like or lip structures suitably shaped for penetrating and/or engaging the acetabular bone.

FIG. 40 illustrates a representation of an outer surface of a prosthetic acetabular cup 3700 having a plurality of anchoring protrusions 3900 in accordance with an embodiment of the present invention. The prosthetic acetabular cup 3700 may also include a threaded impaction bore 3930 located at or near its near-hemispherical center. During impacting of the acetabular cup, the threaded impaction bore 3930 engages a threaded head of an impactor tool to hold the acetabular cup in place during impacting to help ensure secure seating. The embodiment of the prosthetic acetabular cup shown in FIG. 40 includes three approximately rounded conical protrusions 3900 located on the outer surface of the acetabular cup approximately equidistant from each other and each approximately equidistant from the rim of the cup and the impaction bore 3930. It will be appreciated that alternative placements of the protrusions or fins 3900 may be used. Each protrusion may have a slightly rounded and/or dulled tip.

FIG. 41 illustrates a representation of a prosthetic acetabular cup 3700 in preparation for impacting in a reamed acetabulum 4100 in accordance with an embodiment of the present invention. An outer surface of the prosthetic acetabular cup 3700 may have a porous surface to engage bone growth from the reamed surface of the acetabulum 4100. Additional fixation may be derived from protrusions along the outer surface of the prosthetic acetabular cup 3700, as described above with respect to FIGS. 39A-40, and/or from fixation screws inserted through mounting apertures. As discussed above, embodiments of the monoblock acetabular cup can be configured to optimize the thickness of the cup while maximizing the internal size of the cup to prevent and/or minimize deformation, complications, and dislocations. Thus, in addition to achieving proper fixation and sizing to address concerns of stability and dislocation, some embodiments can also provide a monoblock acetabular cup having a desired rigidity. For example, some embodiments of the cup can be configured to undergo only an acceptable amount of deformation when installed into the socket of the pelvis. The cup can exhibit an allowable degree of deformation such that when installed, the inner contact surface of the acetabular cup maintains a desired shape that can mate well with the shape of the prosthetic femoral head. In this manner, the cup can be configured to more effectively prevent and/or withstand the occurrence of debris, metallosis, hoop stress, and other complications. Deformation of the cup can be influenced by the cup's internal and external structural geometry and the material of which the cup is made. In general, for embodiments having a substantially constant shell thickness, the rigidity of the cup may be a factor of material type and shell thickness. However, it is also contemplated that other structural components can be incorporated into the cup, such as reinforcing members or reinforcing structures, whether such features be of the same material or a different material than other portions of the cup. Some embodiments can be formed by using a single material that is formed into a desired final shape, and some embodiment can be formed by overmolding, casting, comolding, bonding, or otherwise joining a first structure or material with a second material or structure to create a monoblock acetabular cup having desirable structural properties. Accordingly, some embodiments may define a spherical inner contact surface and exhibit little or no deformation from that shape. Accordingly, the cup can be installed and used without deviating from a desired geometry that allows a prosthetic femoral head to properly mate with the cup without creating undesired friction or pressure points along the inner contact surface that could lead to some of the complications noted herein. Thus, in some embodiments, the cup can provide reduced metal ion production during use. For example, in the prior art, the use of a joint prosthesis that required metal-on-metal contact can result in the generation of metal particles and metal ions. Such use often resulted in an increased metal ion count in the patient's blood and urine. Elevated ion levels can put the patient at risk for various illnesses and complications, including carcinogenesis, delayed-type hypersensitivity, and organ toxicity. If the joint prosthesis worked reasonably well, the ion levels would gradually decrease as the contact surfaces became worn in. However, some embodiments disclosed herein advantageously provide a joint prosthesis that can exhibit minimal ion production due to the minimized distortion or deformation of the prosthesis during implantation and use. In some embodiments, a monoblock cup of a hip prosthesis can be configured to not only provide sufficient thickness or geometric stability to mitigate against deflection, but also can provide maximized interior volume and/or area in order to mitigate against dislocations. Thus, according to some embodiments, the monoblock acetabular cup can advantageously define a thickness that is greater than the traditional thicknesses of an inner cup of a two-piece acetabular cup and/or provide structural geometries that enhance the rigidity of the cup. For example, as noted above, some embodiments can be configured such that the acetabular cup defines a thickness within a range of about at least 2 mm and/or less than or equal to about 10 mm. In some embodiments, the thickness can be within a range of about at least 3 mm and/or less than or equal to about 8 mm. Depending on the type of material(s) used and/or the structural features of the cup, the thickness of the cup can also vary. Thus, the structural strength and rigidity of the monoblock acetabular cup can exceed that of the traditional inner cup of a two-part cup, thus providing superior properties and tending to avoid the complications associated with deformation, such as debris creation, metallosis, hoop stresses, fracture, and other forms of failure and adverse reactions.

Some embodiments also provide for improved techniques for seating the monoblock acetabular cup against the acetabulum. FIGS. 41-42 generally illustrate aspects of the implantation process. Some embodiments disclosed herein reflect the realization that during implantation of prior acetabular cups, whether two-part or monoblock, it was difficult to ensure that the cup had been properly seated against the acetabulum. As such, revisions and repositioning of the cup would be required. Accordingly, some embodiments of the acetabular monoblock cup 3700 disclosed herein can be configured such that the mounting apertures 3730 allow the surgeon to inspect (e.g., visually) and confirm that the cup has been properly seated in the acetabulum of the patient. Some embodiments can provide a plurality of mounting apertures that allows the seating of the cup to be inspected from several points along the interface of the cup and the acetabulum. In some embodiments, the inspection can be performed visually.

For example, referring to FIGS. 42, 43A and 43B, an embodiment of an implantation process is described. First, an impactor tool can be used that may include an apparatus indicative of an abduction angle. FIG. 42 illustrates a representation of an impactor tool having apparatus 1002 indicative of an abduction angle in accordance with an embodiment of the present invention. A guide bar assembly 1004 rotatably fixed to a cylindrical sleeve 1006 fit over the shaft of the impactor tool advantageously assists in measuring and/or confirming the angle of abduction, which may desirably be approximately 45 degrees. With the acetabulum prepared, the prosthetic acetabular cup 3700 may be seated into place, for example, by impaction. FIG. 43A illustrates a representation of a cross-sectional side view of a prosthetic acetabular cup 3700 in position for impacting in accordance with an embodiment. FIG. 43A illustrates the presence of a gap or space 78 between the cup 3700 and the acetabulum 4100. A threaded portion of a shaft of the impactor tool may be threaded into the impaction bore of the prosthetic acetabular cup 3700 to hold the cup in relation to the impactor tool while it is impacted into the prepared acetabulum 4100. The impactor can be configured with a conical sleeve having a convex engaging surface formed to engage an inner surface of the prosthetic acetabular cup 3700. The engaging surface may be fitted around the threaded end of the shaft of the impactor tool to advantageously spread the force of the impaction across additional area of the inner surface of the prosthetic acetabular cup 3700. Advantageously, the conical sleeve may be made from any surgically acceptable material that will not scratch, score or damage the inner surface of the prosthetic acetabular cup 3700 during impaction. A few taps on the end of the impactor tool opposite the threaded portion may impact the prosthetic acetabular cup 3700 firmly into the acetabulum 4100. FIG. 43B illustrates a representation of a cutaway view of the prosthetic acetabular cup 3700 after being impacted into an acetabulum 4100 such that no impermissible gap or space is present between the cup and the acetabulum, in accordance with an embodiment. In still another embodiment, the acetabular cup, as described above but optionally without the placement fixation hole and optionally with anchoring protrusions or fins, is pre-operatively fitted (for example, previously machined to optimal tolerance gap, e.g. 100 micron) with the prosthetic femoral head. Advantageously, the pre-operatively assembled prosthetic acetabular cup and prosthetic femoral head—which may advantageously be sterilely packaged together—may be impacted into the prepared acetabulum as a single unit. As will be appreciated, an impacting insertion device may fit into a Morse taper of the prosthetic femoral head and also connect to or engage the rim of the prosthetic acetabular cup for rotation control. Once the prosthetic acetabular cup is impacted into and properly seated in the acetabulum, and preferably after proper orientation of the prosthetic acetabular cup has been confirmed, the impactor tool may be removed by unscrewing it from the threaded impaction bore in the prosthetic acetabular cup. FIGS. 43A-B illustrate positioning of the cup 3700 relative to the acetabulum 4100. Once the cup 3700 has been placed into a socket of the acetabulum 4100, the surgeon can inspect the placement of the cup relative to the acetabulum by identifying whether a gap or space of unacceptable dimension is present between the cup and the acetabulum. FIG. 43A illustrates a situation in which the surgeon would be able to detect that the cup is not properly seated against the acetabulum. While it is contemplated that a gap or space may be a localized occurrence, the presence of multiple gaps or spaces or a given pattern of gaps or spaces can indicate that the cup is not properly seated in the acetabulum. For example, a detectable (whether visually or otherwise) gap or space at more than one of the mounting apertures 3730 can serve as an indication that the cup is not properly seated. The cup may also not be properly seated if a gap or space is present at three or more mounting apertures 3730. Further, the surgeon can adjudge that the cup is improperly seated if the presence of a gap or space is detected at a select pattern of mounting apertures 3730. If inspection reveals that an unacceptable gap or space is present along the interface of the cup and the acetabulum, the surgeon may reposition the cup as desired until a proper position is achieved. Methods of implanting an acetabular cup can be provided that comprise these and other aspects. In addition to providing superior rigidity for avoiding the complications of traditional two-part cups, embodiments disclosed herein provide advantages over traditional monoblock cups. For example, some embodiments disclosed herein reflect the realization that superior results can be obtained if the cup is configured to provide sufficient rigidity and reduced friction and wear at the interface of the prosthetic femoral head and the inner contact surface. Some embodiments provide a uniquely configured inner contact surface that is substantially continuous while providing a plurality of mounting apertures for securing the monoblock acetabular cup to the acetabulum. Accordingly, in some embodiments, the surface configuration can thereby prevent and/or mitigate some of the complications such as debris formation, metallosis, hoop stress, and other complications.

Referring to FIGS. 44A-C, the inner contact surface 3720 of the acetabular cup 3700 can be machined and/or polished to have a smooth inner surface. Further, the outer surface of the prosthetic femoral head may be highly polished for reduced friction. Press-fit and other prosthetic acetabular cups known in the art may be used without departing from aspects of the present invention. Such press-fit cups include designs offered by numerous manufacturers, including Depuy, Zimmer and Wright Medical. For example, in an embodiment, the acetabular cup of approximately 40 to 70 mm near-hemispherical diameter may be made from cobalt chromium, and may be hemispherically shaped and polished in the interior of the cup to minimize friction in a metal-on-metal engagement of the outer hemispherical surface of the prosthetic femoral head, which may be made from the same material, and also precisely shaped for fit and polished to minimize friction. In another embodiment, the inner surface of the prosthetic acetabular cup may comprise less than a full hemisphere, and may extend through an angle ranging from approximately 150 degrees to approximately 179.9 degrees about a radial center. It is contemplated that, following the surgical procedure, bodily fluid may collect between the outer surface of the prosthetic femoral head and the inner surface of the prosthetic acetabular cup and may further reduce friction between the surfaces and also reduce wear upon the surfaces. Further, with the prosthetic acetabular cup 3700 impacted into place, one or more fixation screws 4400 may be threaded through a given mounting aperture 3730 and into the bone of the acetabulum 4100. Preferably the mounting aperture 3730 is oriented approximately toward the iliac crest where acetabular bone is sufficiently thick to receive the fixation screw 4400, which may be approximately 7-14 mm long. It will be appreciated that the prosthetic acetabular cup 3700 may have additional mounting apertures 3730 oriented toward thick bony areas of the acetabulum, and that additional fixation screws tightened through these mounting apertures 3730 may provide for additional fixation of the prosthetic acetabular cup 3700. The mounting apertures 3730 can be configured and spaced such that friction between the inner contact surface of the cup and the prosthetic femoral head is minimized. In some embodiments, the mounting apertures 3730 can be spaced apart from each other on the inner contact surface of the cup. The mounting apertures 3730 can be generally circular in shape. In some embodiments, the mounting apertures 3730 can be larger than a head of a screw disposed therein due to the presence of a bevel for the mounting aperture. As illustrated in FIGS. 44A-C, the mounting apertures 3730 can define a counterbore or bevel 3732 into which the head of the screw 4400 can be recessed. The bevel 3732 can define a depth with the range of at least about ⅛ mm and/or less than or equal to at least about ¾ mm. In some embodiments, the bevel 3732 can define a depth with the range of at least about ¼ mm and/or less than or equal to at least about ⅝ mm. Further, the bevel 3732 in some embodiments can be about ½ mm in depth. Additionally, in some embodiments, the bevel 3732 of the mounting aperture 3730 can define a transition surface 134 to a wall 130 of a prosthetic acetabular cup 3700. The transition surface 134 can be rounded, thereby eliminating a corner that could cause wear and friction between the head and the cup 3700. In some embodiments, the transition surface can define an increasing arc of curvature approaching the wall. In some embodiments, the overall surface area of the inner contact surface of the cup can be reduced by between about 4% and/or less than or equal to at least about 18% due to the presence of the mounting apertures 3730. Further, the overall surface area of the inner contact surface of the cup can be reduced by between about 6% and/or less than or equal to at least about 14% due to the presence of the mounting apertures 3730. Furthermore, the overall surface area of the inner contact surface of the cup can be reduced by between about 7% and/or less than or equal to at least about 12% due to the presence of the mounting apertures 3730. For example, in one embodiment with a cup having an inner contact surface with a diameter of approximately 1.2 inches and a surface area of approximately 2.26 square inches, the total surface area lost due to the presence of mounting apertures can be between about 0.05 square inches and/or less than at least about 0.45 square inches. In an embodiment having four mounting apertures, the total surface area lost can be approximately 0.20 square inches, and the percentage of reduction of surface area can be about 8.8%. In an embodiment having five mounting apertures, the total surface area lost can be approximately 0.25 square inches, and the percentage of reduction of surface area can be about 11%. In some embodiments, the prosthetic acetabular cup 3700 includes one or more placement mounting apertures 3730, which may have beveled edges. FIG. 44A illustrates a representation of a cross-sectional view of the wall 130 of a prosthetic acetabular cup 3700 in relationship to an acetabulum 4100, with a fixation screw 4400 positioned to be fitted into a placement mounting aperture 3730 in the wall to fix the prosthetic acetabular cup to the acetabulum 4100 in accordance with an embodiment. FIG. 44B illustrates a representation of an inner surface 3720 of a prosthetic acetabular cup 3700 with a fixation screw 4400 positioned to be fitted into a placement mounting aperture 3730 extending through the wall of the prosthetic acetabular cup 3700 to receive the fixation screw 4400 and thereby fix the prosthetic acetabular cup 3700 to an acetabulum. In a preferred embodiment, the prosthetic acetabular cup 3700 includes a placement mounting aperture 3730 at a point approximately midway between the rim of the prosthetic acetabular cup 3700 and the hemispherical center. FIG. 44C illustrates a representation of a cross-sectional view of the wall of a prosthetic acetabular cup 3700 in relationship to the acetabulum 4100 with the fixation screw 4400 fitted through the placement mounting apertures 3730 in the wall and fixing the prosthetic acetabular cup to the acetabulum 4100. In one embodiment, the diameter of the placement mounting aperture 3730 is slightly larger at the inner surface and slightly smaller further along the mounting apertures 3730 toward the outer surface of the prosthetic acetabular cup so that the mounting apertures 3730 are slightly tapered for at least a portion of its length, and a head of the fixation screw 4400 may be likewise tapered so that, when threaded into bone through the placement mounting aperture 3730 and tightened, the head of the fixation screw 4400 is fully recessed into the tapered region of the placement mounting aperture 3730 and thus advantageously creates no friction or wear by any engagement of the outer surface of the prosthetic femoral head. In order to facilitate this objective, in some embodiments, the mounting apertures 3730 can define the bevel 3732 into which the head of the screw 4400 can be recessed. Further, in some embodiments, the bevel 3732 can define a transition surface 134 to the wall 130. The transition surface 134 can be rounded, thereby eliminating a corner that could cause wear and friction between the head 4700 and the cup 3700. In some embodiments, the transition surface 134 can define an increasing arc of curvature approaching the wall. Accordingly, to further assure seating fixation of the prosthetic acetabular cup 3700 in the acetabulum, a fixation screw 4400 or similarly suitable anchoring device is fit through the placement mounting aperture 3730 to affix the prosthetic acetabular cup 3700 into the reamed acetabulum 4100. Such use of the placement mounting aperture 3730 advantageously supports the impacting step by further avoiding slippage of the prosthetic acetabular cup 3700 and reducing any consequent need for repeated trials of acetabular cup placement or further surgical procedures to properly fit, secure and seat the prosthetic acetabular cup 3700. In some embodiments, the fixation screw 4400 can include a central bore creating an open path approximately along its longitudinal center from head to tip. FIG. 9 illustrates a representation of a fixation screw 4400 having a central bore 140 in accordance with an embodiment of the present invention. It is contemplated that the central bore 140 in the fixation screw 4400 advantageously permits fluid to enter from the bone and through the central bore 140 into the space between the outer surface of the prosthetic femoral head and the inner surface of the prosthetic acetabular cup 3700 and thereby further minimizes friction and wear resulting from the movement of those two surfaces relative to each other.

FIGS. 46-47 illustrate an embodiment of a prosthetic femoral head in exploded view with a prosthetic acetabular cup 3700. FIG. 46 illustrates a representation of a prosthetic femoral head in position for placement in relation to a seated prosthetic acetabular cup 3700 fixed by a fixation screw or by protrusions in accordance with an embodiment. In some embodiments, the prosthetic femoral head 4700 at a cup-engaging surface or end 152 comprises a partial sphere having a curvature machined to precisely fit the inner surface of the prosthetic acetabular cup 3700. The partial sphere of the prosthetic femoral head 4700 may extend, in various embodiments from approximately 160 degrees to approximately 340 degrees, and thus may comprise any range from somewhat less than a hemisphere to nearly a full sphere. In some embodiments, to place the prosthetic femoral head into the acetabular cup, the partial sphere of the prosthetic femoral head is placed against the exposed rim of the hemispherical inner surface of the prosthetic acetabular cup 3700. As will be appreciated, one or more light taps using a firm rubber-headed impacting tool may then seat the prosthetic femoral head properly into the prosthetic acetabular cup 3700.

FIG. 47 illustrates a representation of a prosthetic femoral head 4700 positioned in a prosthetic acetabular cup 3700 in accordance with an embodiment of the present invention. FIG. 47 is a cross-sectional side view of the prosthetic femoral head 4700 and the monoblock acetabular cup 3700. FIG.

47 illustrates that in some embodiments, the prosthetic femoral head 4700 mates well with the cup 3700 such that undesired friction and pressure points are avoided. Accordingly, in some embodiments, the inner contact surface 3720 of the cup 3700 and the cup-engaging surface 152 of the prosthetic femoral head 4700 provides a smooth engagement with maximized benefits. As noted above, the presence of the mounting apertures 3730 can reduce the overall surface area of the inner contact surface 3720 of the cup 3700, which can reduce frictional resistance with a prosthetic femoral head 4700. Further, because the cup 3700 is a monoblock cup, the thickness of the cup 3700 can be minimized while preserving rigidity of the cup 3700. Thus, the size of the prosthetic femoral head 4700 can be maximized, thereby improving the engagement between the cup 3700 and the head 4700 to minimize dislocations. Furthermore, the presence of the mounting apertures 3730 will not tend to adversely impact the interaction between the surfaces. For example, some embodiments can provide a transition surface that mitigates any friction or point loading between the head 4700 and the cup 3700.

In accordance with some embodiments, surgical methods are provided for accessing a femoral and acetabulum region of a patient, preparing the femoral neck, preparing the acetabulum, preparing the intramedullary space, and placing the components of a hip replacement apparatus, such as an intramedullary rod or stem, a support sleeve, a femoral neck, a femoral head, and/or an acetabular cup. Methods and devices are disclosed and taught in Applicant's U.S. patent application Ser. No. 12/518,081, filed on Jun. 5, 2009 titled Method and Apparatus for Total Hip Replacement, and U.S. application Ser. No. 13/049,619, filed Mar. 16, 2011, titled Methods And Systems For Total Hip Replacement, and in the publications titled, "Minimally Invasive Calcar Miller Surgical Technique," S-ROM Modular Hip System, and titled, "The Anterior Approach for Total Hip Arthroplasty: Background and Operative Technique," and also titled, "Surgical Technique," Pinnacle Acetabular Cup System, the entireties of the contents of each which are incorporated herein by reference.

Figure 48A:
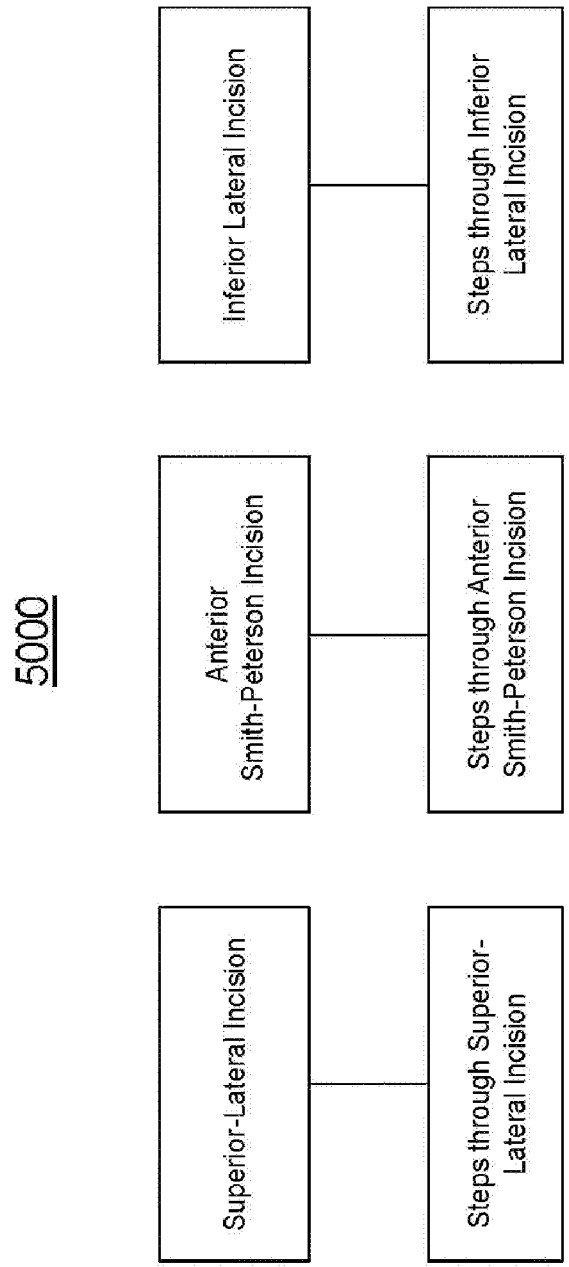
FIGS. 48A-48B are schematic flow diagrams of steps, in various embodiments, in methods of performing a minimally invasive, hip arthroplasty procedure with a prosthetic hip system.
Figure 48B:
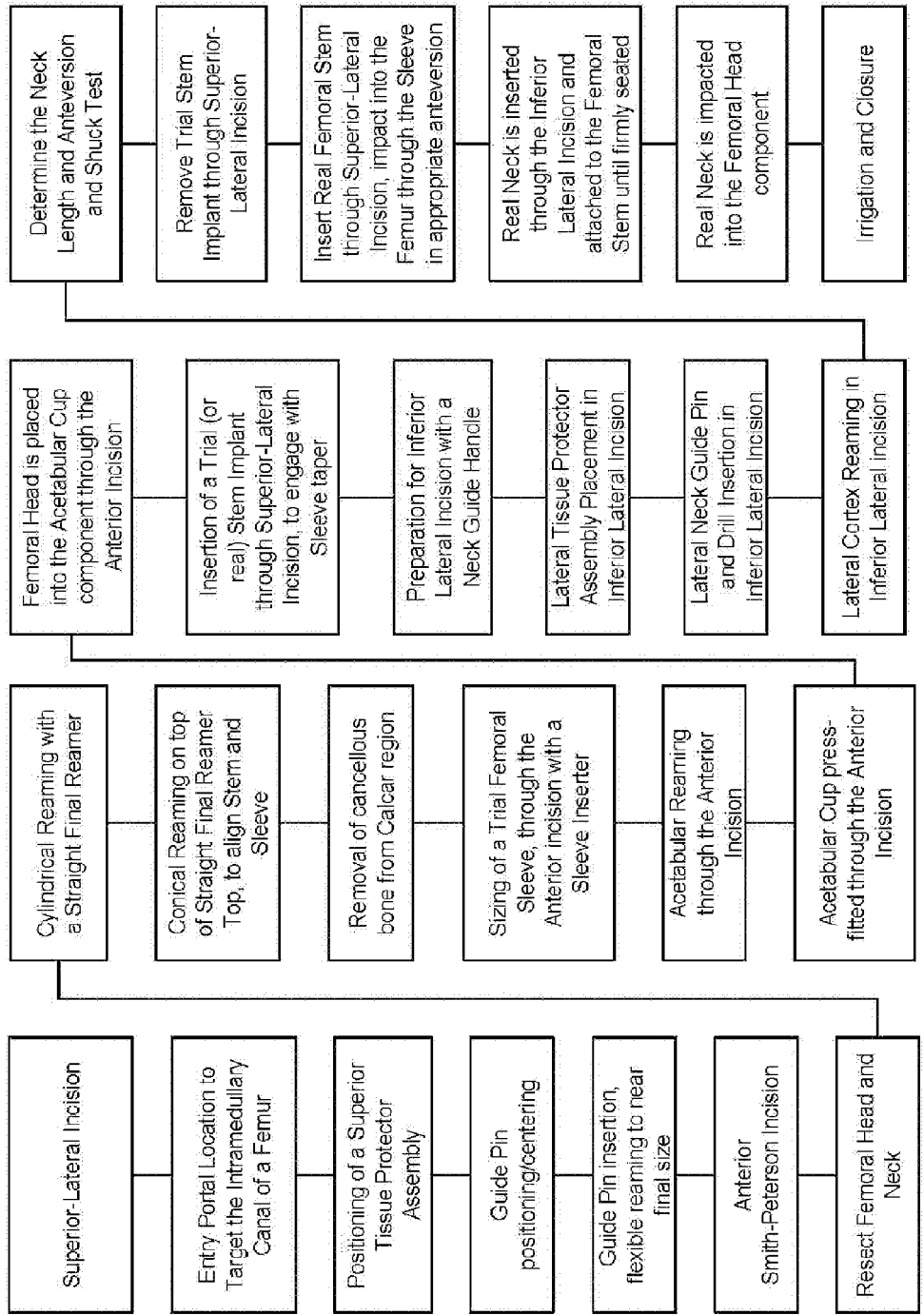

FIGS. 48A-48B illustrate steps, in various embodiments, in methods of performing a minimally invasive, hip arthroplasty procedure 5000. In various embodiments, the procedure 5000 can involve any combination of any of the steps, in various sequences, with various embodiments of a prosthetic hip system 5100.

In various embodiments, a prosthetic hip system 5100 may comprise none, some, all, part of or any embodiment of a part, component, and/or feature of any implant described herein. In one embodiment, a prosthetic hip system 5100 is modular with any combination of parts, components, and/or features of various sizes, dimensions, and/or functions of any of the embodiments described herein. In one embodiment, a prosthetic hip system 5100 comprises a femoral stem implant component 5110, a femoral neck implant component 5200, and a femoral head implant component 5300. In one embodiment, a prosthetic hip system 5100 comprises a sleeve implant component 5400. In various embodiments, the stem 5110 can have some, all, part of or any embodiment of a part, component, and/or feature of any embodiment of an intramedullary rod. In various embodiments, the neck 5200 can have some, all, part of or any embodiment of a part, component, and/or feature of any embodiment of a neck. In various embodiments, the head 5300 can have some, all, part of or any embodiment of a part, component, and/or feature of any embodiment of a head, including but not limited to head 1102. In various embodiments, the sleeve 5400 can have some, all, part of or any embodiment of a part, component, and/or feature of any embodiment of a sleeve, including but not limited to sleeve 1802.

In various embodiments, as illustrated at FIG. 48B, a sequence of a hip arthroplasty procedure 5000 can include all or any subset of the following steps, in various orders:

1) Superior-Lateral Incision
2) Entry Portal Location to Target the Intramedullary Canal of a Femur
3) Positioning of a Superior Tissue Protector Assembly
4) Guide Pin positioning/centering
5) Guide Pin insertion, reaming to near final size
6) Anterior Incision, a portion of a Smith-Peterson Incision
7) Resect Femoral Head and Neck
8) Cylindrical Reaming with a Straight Final Reamer (final size), roughly 0.5 mm larger than Stem size
9) Conical Reaming on top of Straight Final Reamer Top, to align Stem and Sleeve
10) Removal of cancellous bone from Calcar region of the Femur (burr or curette)
11) Sizing of a Trial Femoral Sleeve, through the Anterior incision with a Sleeve Inserter
12) Acetabular Reaming through the Anterior Incision
13) Acetabular Cup is press-fit through the Anterior Incision
14) Femoral Head is placed into the Acetabular Cup component through the Anterior Incision
15) Insertion of a Trial (or real) Stem Implant through Superior-Lateral Incision, to engage with Sleeve taper (Stem is attached to Neck Guide Handle)
16) Preparation for Inferior Lateral Incision
17) Lateral Tissue Protector Assembly Placement in Inferior Lateral Incision
18) Lateral Neck Guide Pin and Drill Insertion in Inferior Lateral Incision
19) Lateral Cortex Reaming in Inferior Lateral incision
20) Determine the Neck Length and Anteversion according to Surgeon's preferences and Shuck Test for stability assessment.
21) Remove Trial Stem Implant (if real stem was not yet inserted) through Superior-Lateral Incision
22) Insert Real Femoral Stem through Superior-Lateral Incision, impact into the Femur through the Sleeve in appropriate anteversion
23) Real Neck Component is inserted through the Inferior Lateral Incision and attached to the Femoral Stem until firmly seated
24) The Real Neck is impacted into the Femoral Head component
25) Irrigation and Closure In various embodiments, a minimally invasive, hip arthroplasty procedure 5000 is configured for implantation of the component parts of a hip system 5100 by reducing the amount of hyperextension and/or dislocation of the proximal femur, which damages tissues in the patient. In various embodiments, a minimally invasive, hip arthroplasty procedure 5000 involves a three-incision surgical technique for implantation of a prosthetic hip system 5100. In one embodiment, the exposure is achieved by three small incisions: (1) a superior-lateral incision 5010, (2) an inferior lateral incision 5020, and (3) an anterior Smith-Peterson approach 5030 (Hoppenfeld and deBoer, Surgical Exposures in Orthopaedics—The Anatomic Approach, 1984). In various embodiments of a hip arthroplasty procedure 5000, the sequence of incisions can be in any order. In one embodiment, the superior-lateral incision 5010 is configured for the insertion of a femoral stem implant component 5110. In one embodiment, the inferior lateral incision 5020 is configured for the insertion of a femoral neck implant component 5200. In one embodiment, an incision 5030 with a portion of an anterior Smith-Peterson approach is configured for femoral neck resection, acetabular reaming and acetabular cup 702 insertion, placement of the femoral head implant component 5300 and/or the insertion of a sleeve implant component 5400. In one embodiment, the anterior Smith-Peterson approach incision 5030 is located along a line that is approximately parallel to the length of the femur 104 and positioned approximately over the femoral head 106, with the distal (toward the patient's foot) extent of the line extending approximately to a point lateral to the lesser trochanter 108. This approach provides safe access to the hip joint by exploiting the internervous plane between the sartorius and the tensor fasciae latae and avoiding the femoral and superior gluteal nerves. This internervous plane can be developed by known methods. The incision may advantageously be extended in either direction as needed.

In one embodiment, a THA procedure 5000 places a patient in a supine position with the legs and the hip prepared and draped free in a sterile manner. A fluoroscopy unit can be set up as it would be for an intertrochanteric hip fracture fixation with an intramedullary device.

In various embodiments, various steps of a THA procedure 5000 may be performed through the superior lateral incision 5010. In various embodiments, various steps of a THA procedure 5000 may be performed through the superior lateral incision 5010 can include a proximal, distal and/or conical femoral reaming and/or an insertion of a femoral component stem 5110 or trial stem 5120 into the femur 104.

Figure 49:
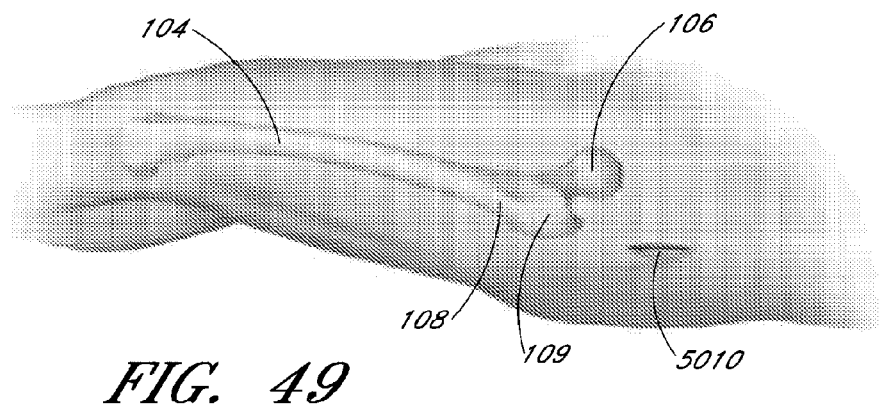
FIG. 49 is a schematic side view of a hip arthroplasty procedure using a prosthetic hip system with a superior lateral incision according to an embodiment of the present invention.

FIG. 49 illustrates an embodiment of a superior lateral incision 5010 with a length of approximately 2.5 cm that is made roughly 3-4 cm above the greater trochanter 109 tip. In various embodiments, the superior lateral incision 5010 can be roughly 1, 1.25, 1.5, 1.75, 2, 2.25, 2.5, 2.75, 3, 3.25, 3.5, 3.75 or 4 cm, and/or in the range of 1-4 cm, 2-3 cm, and/or 2.25-2.75 cm long. In one embodiment, the superior lateral incision 5010 can be performed by identifying the greater trochanter, making a 2.5 cm incision that is approximately 3 to 4 cm proximal to the tip of the greater trochanter. In one embodiment, the superior lateral incision 5010 can be angled posteriorly at its proximal end. In one embodiment, the superior lateral incision 5010 can be carried through the fascia of hip abductors as far posterior as possible.

Figure 50:
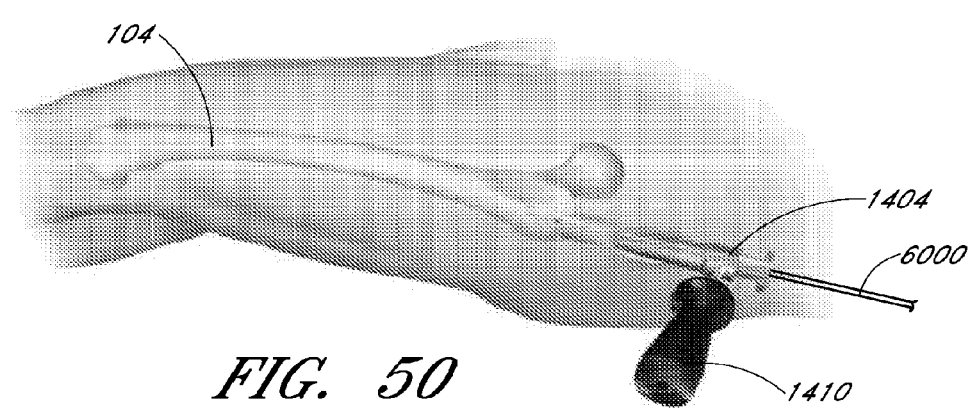
FIG. 50 is a schematic side view of a hip arthroplasty procedure using a prosthetic hip system with an entry portal location to target the intramedullary canal with a tissue protecting guide according to an embodiment of the present invention.

FIG. 50 illustrates an embodiment of a step for placement of an entry portal location to target the intramedullary canal of a femur 104 with a tissue protecting guide 1404. In one embodiment, a tissue protecting guide 1404 has a handle 1010. In one embodiment, a tissue protecting guide 1404 is a superior tissue protector assembly. In one embodiment, a tissue protecting guide 1404 includes docking features or docking pins to align the guide 1404 with other tooling or equipment. In one embodiment, a tissue protecting guide 1404 has no docking features or docking pins.

Figure 51:
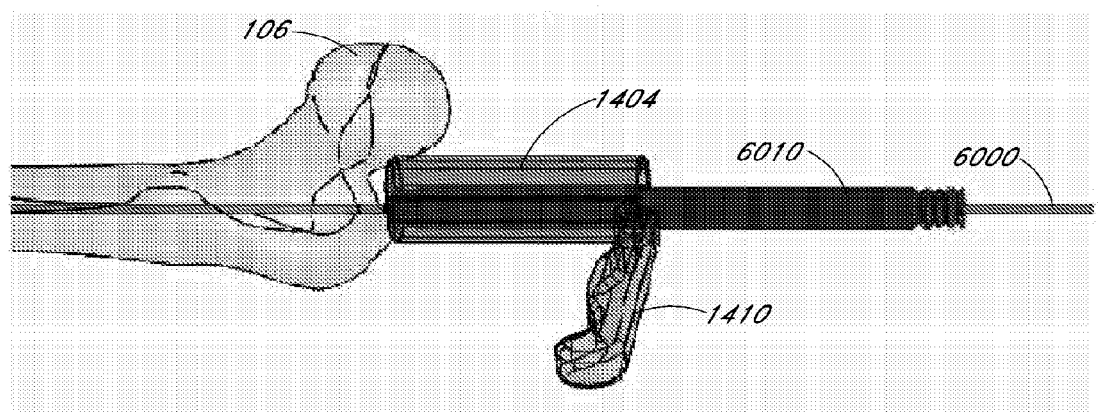
FIG. 51 is a schematic side view of a hip arthroplasty procedure using a prosthetic hip system with a guide pin with a guide pin centering sleeve according to an embodiment of the present invention.
Figure 52:
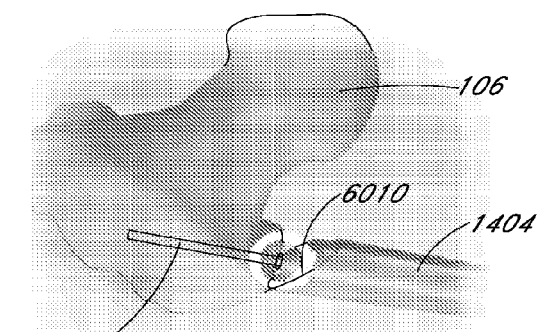
FIG. 52 is a schematic side view of a hip arthroplasty procedure using a prosthetic hip system with a guide pin with a guide pin centering sleeve according to an embodiment of the present invention.

FIG. 51 illustrates an embodiment of a step for placement of a guide pin 6000 through the superior lateral incision 5010. In one embodiment, a guide pin 6000 is a guide wire. In one embodiment, a guide pin centering sleeve 6010 is configured to position a guide pin 6000 such that it rests on the apex of the greater trochanter 109. In one embodiment, a guide pin centering sleeve 6010 is a guide pin stiffener. In one embodiment, as shown in FIG. 52, a 3.2 mm guide pin 6000 is inserted through the guide pin centering sleeve 6010 into the greater trochanter 109 toward the center of the femoral intramedullary canal.

Figure 53:
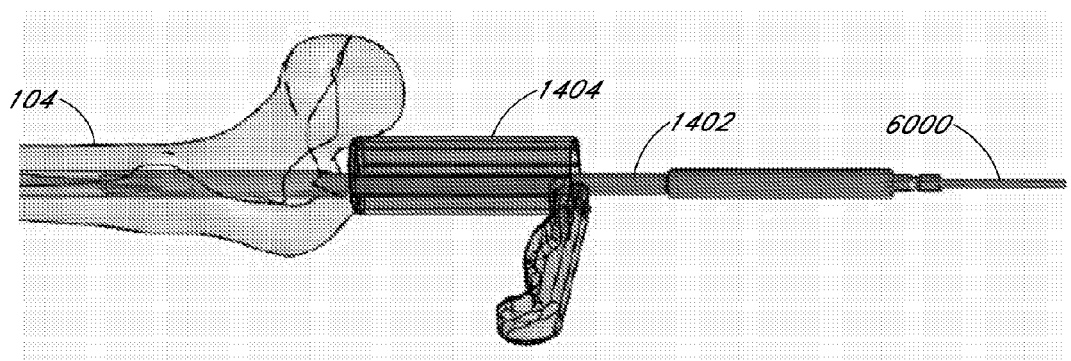
FIG. 53 is a schematic side view of a hip arthroplasty procedure using a prosthetic hip system with a reaming tool according to an embodiment of the present invention.
Figure 54:
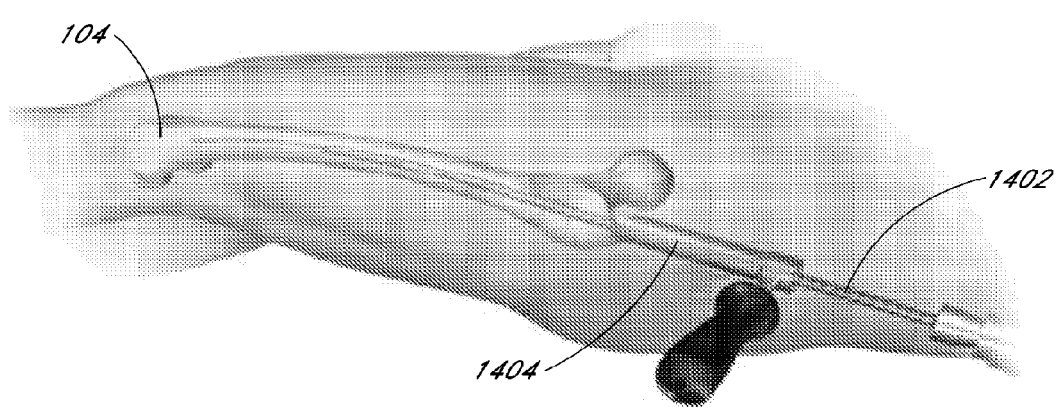
FIG. 54 is a schematic side view of the reaming tool according to FIG. 53.
Figure 55:
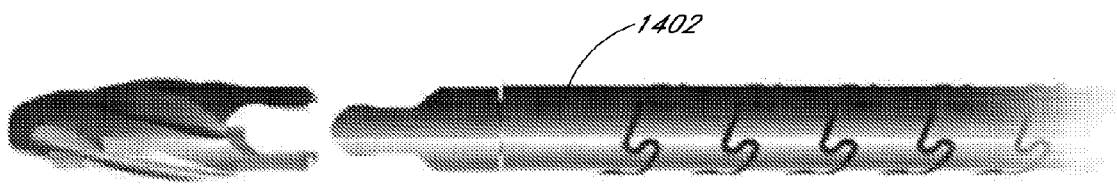
FIG. 55 is a schematic side view of a reaming tool according to an embodiment of the present invention.

FIGS. 53-54 illustrate embodiments of a step for placement of a femoral reaming tool 1402 configured for proximal femur reaming and intramedullary canal preparation for distal femoral fit. In one embodiment, a guide pin 6000 is positioned in the greater trochanter 109 toward the center of the femoral intramedullary canal. In one embodiment, the guide pin 6000 is a 3.2 mm guide pin. In one embodiment, the guide pin 6000 is an atraumatic tip, or ball tip guide rod. In one embodiment, a femoral reaming tool 1402 includes a lumen through which the guide pin 6000 guides the reamer 1402 in to bone. In one embodiment, a femoral reaming tool 1402 is inserted in the tissue protecting guide 1404. In one embodiment, the femoral reaming tool 1402 reams until the proximal femur is prepared to accept the proximal portion of a femoral stem implant 5110 or a trial stem 5120. In one embodiment, the femoral reaming tool 1402 includes an indicator for showing reamer position in bone. In one embodiment, the reaming depth is sufficient when the indicator on the reamer 1402 is level with the top of the tissue protector. In one embodiment, the depth of the reaming can be checked on an AP x-ray to ensure that the widest part of the reamer has reached the level of the lesser trochanter and has sufficiently opened the canal. If not satisfied with depth, continue reaming and confirm depth with x-ray. In various embodiments, the length of a prosthetic stem or trial stem can be in the range of 4-10 inches, 5-9 inches, 6-8 inches, 7 inches, 7.1, 7.3, 7.5, 7.7, 7.9, 8.1, or any length therein. Proceed to sequentially ream over the guide pin 6000 through the tissue protecting guide 1404 using the one or more reamers 1402 contained in a set or kit. In various embodiments, the femoral reaming tool 1402 can be cylindrical, straight, curved, conical, or another shape. In one embodiment, as shown in FIG. 55, the femoral reaming tool 1402 can have modular cutting heads and and/or a flexible shaft. In one embodiment, cylindrical reaming with a straight femoral reaming tool 1402 can be incrementally advanced or increased in size to roughly 0.5 mm larger than the stem 5110 or trial stem 5120 size. In one embodiment, a 9.0 mm End Cutting Reamer Head sequentially reams to roughly ½ mm over the selected distal femoral stem 5110 diameter. Conical reaming accommodates the sleeve 5400. In one embodiment, conical reaming can be performed to align the stem 5110 or trial stem 5120 with a sleeve 5400.

Figure 56:
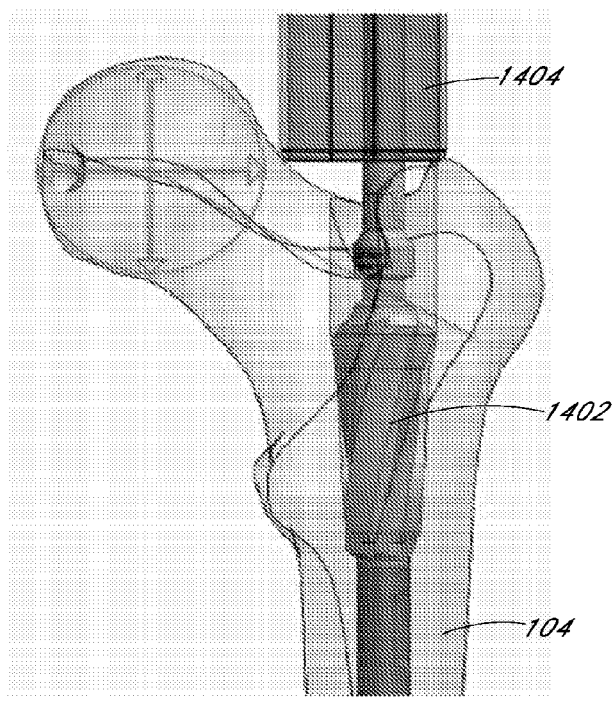
FIG. 56 is a schematic front view of a hip arthroplasty procedure using a prosthetic hip system with a conical reamer according to an embodiment of the present invention.
Figure 57:
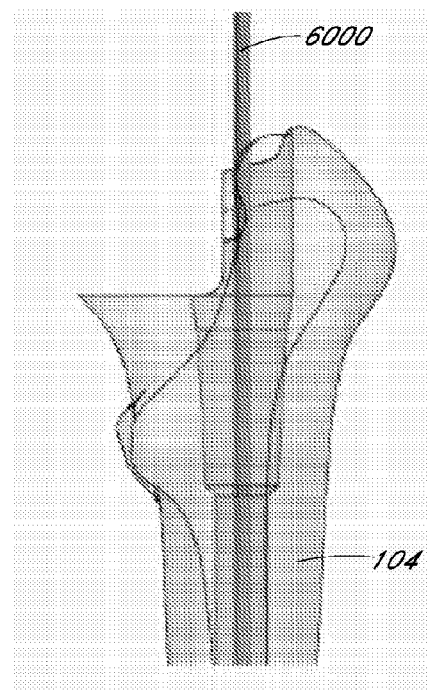
FIG. 57 is a schematic front view of a hip arthroplasty procedure using a prosthetic hip system with a guide pin with the femoral head removed according to an embodiment of the present invention.

In various embodiments, as shown in FIGS. 56-57, the femoral head 106 and/or the femoral neck 306 can be resected and/or removed prior to, during, or after reaming of the greater trochanter 109 toward the center of the femoral intramedullary canal through the superior lateral incision 5010. In one embodiment, the femoral head 106 and/or the femoral neck 306 can be resected and/or removed through a superior lateral incision 5010. In one embodiment, the femoral head 106 and/or the femoral neck 306 can be resected and/or removed through an anterior Smith-Peterson approach 5030. In one embodiment, a 5 to 6 cm anterior Smith-Peterson approach incision 5030 is centered over the femoral neck. In various embodiments, the anterior Smith-Peterson approach incision 5030 can be roughly 3, 3.5, 4, 4.5, 5, 5.25, 5.5, 5.75, 6, 6.5, 7 cm, and/or in the range of 3-7 cm, 4-6, 5-6, and/or 5.25-5.75 cm long. In one embodiment, an oscillating drill is used to resect bone. In one embodiment, a saw is used to resect bone. In one embodiment, guide pin 6000 is left in place in the greater trochanter 109 to provide a mechanical stop for a saw during neck resection. In one embodiment, a ring curette is used to excavate the calcar portion of the femur. In one embodiment, a burr is used to excavate the calcar portion of the femur.

In various embodiments, various steps of a THA procedure 5000 may be performed through the anterior Smith-Peterson approach 5030. In some embodiments, acetabular reaming is performed through the anterior Smith-Peterson approach 5030 incision. In some embodiments, an acetabular cup 702 is press-fit in to a prepared acetabular reaming site on the pelvis through the anterior Smith-Peterson approach 5030 incision. In some embodiments, a polymer component is snapped or attached into an acetabular cup 702. In some embodiments, the femoral head implant 5300 is placed into the acetabular cup 702 component through the through the anterior Smith-Peterson approach 5030 incision. In one embodiment, the acetabulum is prepared by sequential reaming and the acetabular cup 702 is press-fit at 20° of anteversion and 45° of abduction. In one embodiment, the femoral head component 5300 is placed into the acetabular cup 702 to "float loose" awaiting the neck 5200 insertion.

Figure 58:
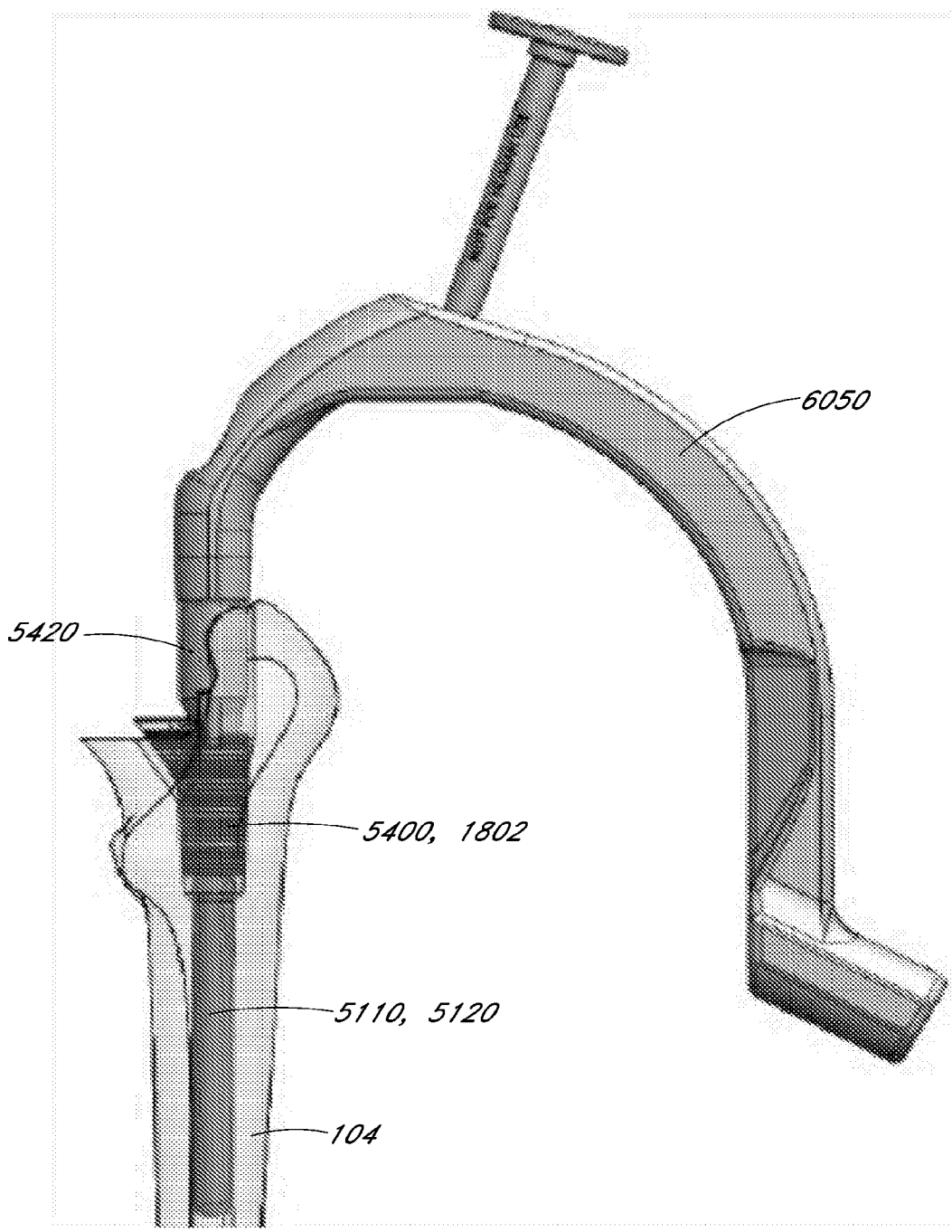
FIG. 58 is a schematic front view of a hip arthroplasty procedure using a prosthetic hip system with an implant insertion and drill guide according to an embodiment of the present invention.

FIG. 58 illustrates an embodiment of a step for sizing and placement of a trial femoral sleeve 5410, through the anterior incision 5030 with a sleeve inserter 5420. In one embodiment, the sleeve inserter 5420 is attached to an implant insertion and drill guide 6050. The sizing and placement of a trail sleeve 5410 can be performed before, during, or after the insertion of a trial stem 5120 or a real stem implant 5110 through the superior-lateral incision 5010, to engage with a sleeve 5400 or trial sleeve 5420.

Figure 59:
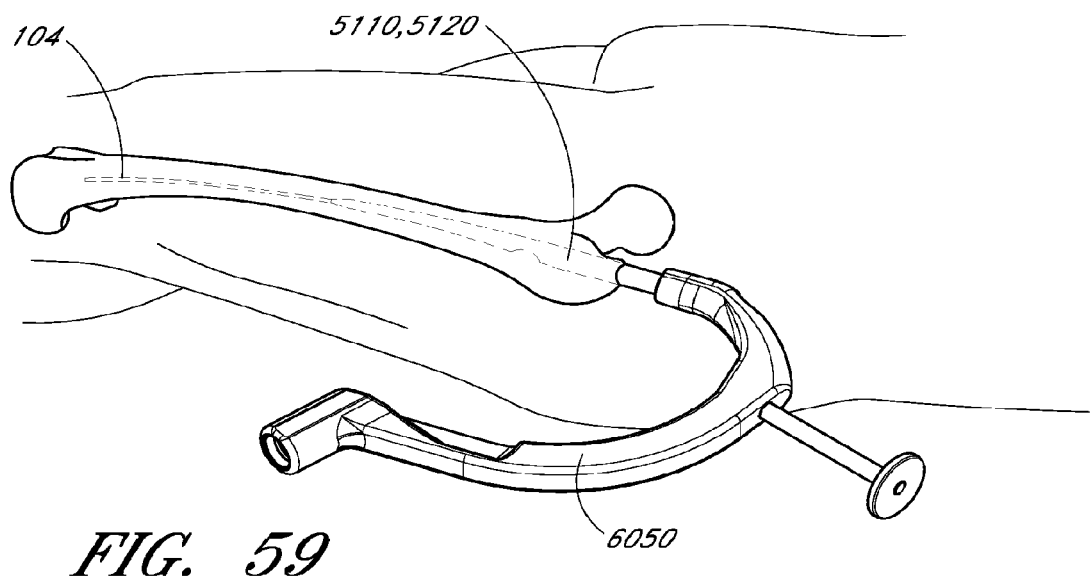
FIG. 59 is a schematic side view of a hip arthroplasty procedure using a prosthetic hip system with an implant insertion and drill guide according to an embodiment of the present invention.
Figure 60:
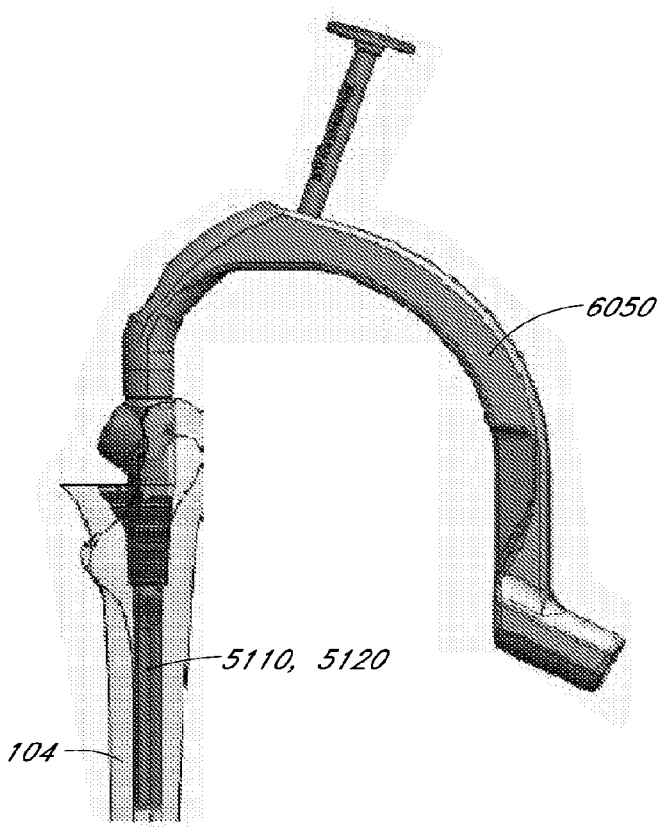
FIG. 60 is a schematic front view of a hip arthroplasty procedure using a prosthetic hip system with an implant insertion and drill guide according to an embodiment of the present invention.

FIGS. 59 and 60 illustrate steps in which embodiments of a trial stem 5120 or stem implant 5110 are attached to an implant insertion and drill guide 6050. The position of the insertion and drill guide 6050 is based on the neck anteversion angle desired (e.g., such as 15° to 20° below horizontal). FIG. 59 illustrates an embodiment of a step for use of a femoral stem insertion and drill guide assembly 6050 to place a trial stem 5120. In one embodiment, the trial femoral stem 5120 has a 1 mm smaller distal diameter then the real stem implant 5110. In one embodiment, the trial femoral stem 5120 is attached to the insertion and drill guide assembly 6050. The insertion and drill guide assembly 6050 is positioned based on the neck anteversion angle desired (15° to 20° below horizontal). In one embodiment, a guide bolt is inserted into the insertion and drill guide assembly 6050, and a guide bolt wrench and/or T-handle to secure the guide bolt to the trial femoral stem 5120. In one embodiment, to help ensure the accuracy of the insertion and drill guide assembly 6050, it is helpful to tighten the guide bolt with a tissue protector and a neck reamer in place. In one embodiment, a stem implant 5110 or trail stem 5120 is rotated 20 degrees and inserted through a sleeve 5400 or trial sleeve 5410.

In various embodiments, various steps of a THA procedure 5000 may be performed through the inferior lateral incision 5020. In various embodiments, aspects of sizing and/or placement or implantation of a femoral neck implant component 5200 are performed through the inferior lateral incision 5020. In one embodiment, a roughly 1.5 cm long inferior-lateral incision 5020 is made. In one embodiment, a roughly 2 cm long inferior-lateral incision 5020 is made. In various embodiments, the inferior-lateral incision 5020 can be roughly 1, 1.25, 1.5, 1.75, 2, 2.25, 2.5 cm, and/or in the range of 0.5-3 cm, 1-2 cm, and/or 1.25-1.75 cm long. In various embodiments, the incision can be made prior, during, or after placement of a guide and/or positioning tool.

Figure 61:
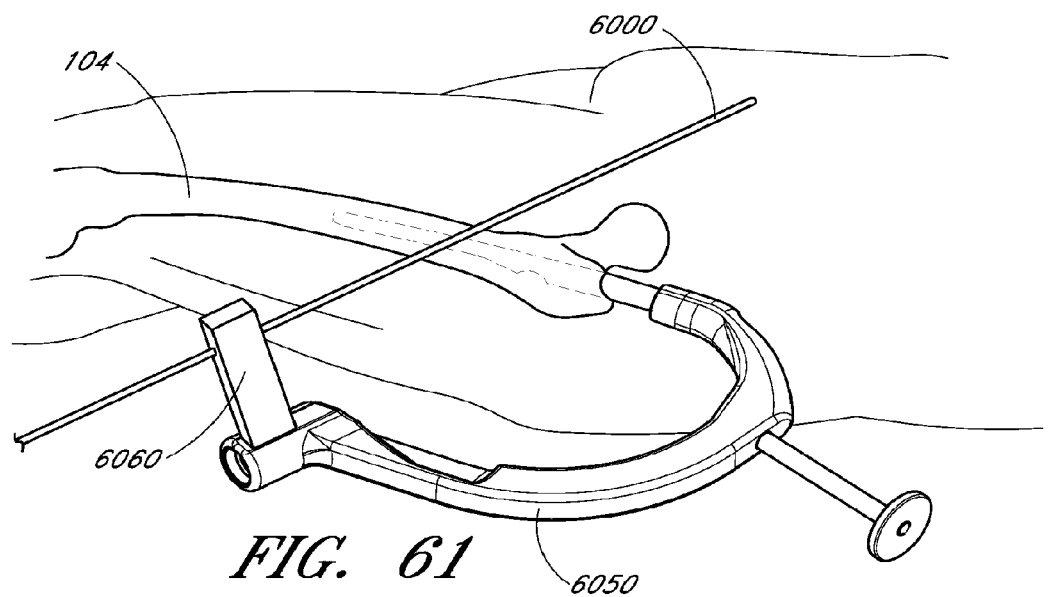

FIG. 61 illustrates an embodiment of a step for placement of a femoral neck orientation guide 6060 to help determine the proper AP position and orientation of the femoral neck component 5200 with respect to the femoral neck and femoral head. In one embodiment, a femoral neck orientation guide 6060 is attached to the implant insertion and drill guide 6050. A guide pin 6000 can be inserted through the femoral neck orientation guide 6060 to provide a visual orientation line anterior to the patient's soft tissue. In one embodiment, the guide pin 6000 is a 3.2 mm guide wire. A visualization device, such as a C-Arm, and the implant insertion and drill guide 6050 are positioned so that the guide pin 6000 and the center of the femoral neck component hole in the femoral stem component 5110 are in line with the beam from the visualization device. In one embodiment, the implant insertion and drill guide 6050 are positioned so that the guide pin 6000 and the center of the femoral neck component hole in the trial femoral stem component 5120 are in line with the beam from the visualization device. The trial stem 5120 or real stem 5110 are properly placed in the AP plane when the guide pin 6000 is seen on the visualization device (C-Arm, x-ray, etc.) to be parallel to the original position of the femoral neck and center in the femoral head 106 prior to resection.

Figure 62:
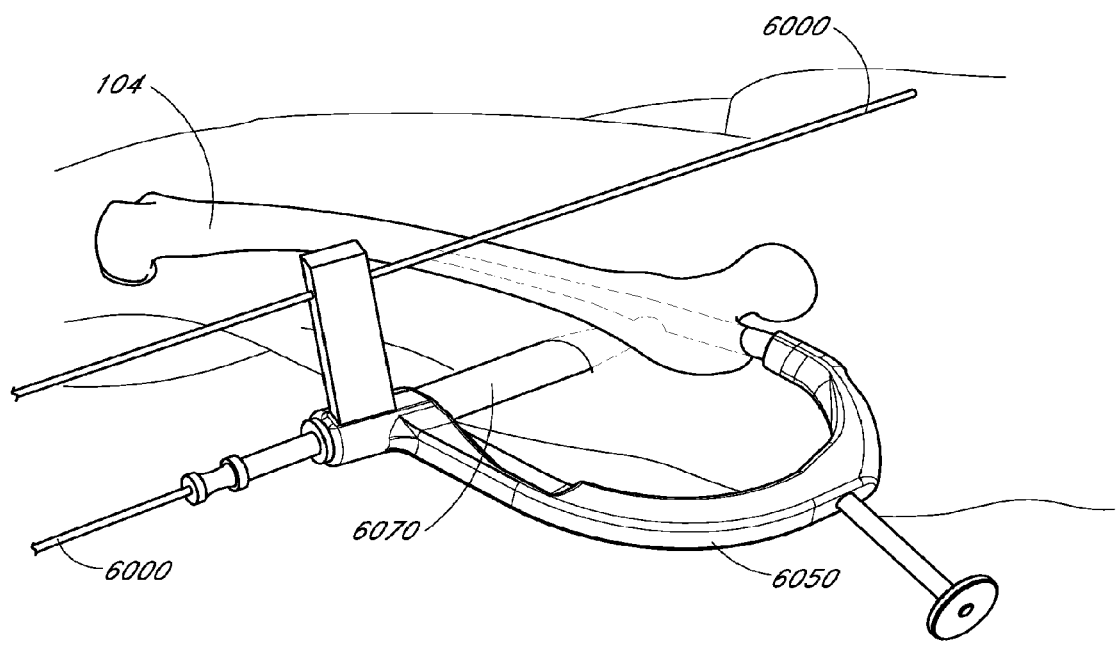

FIG. 62 illustrates an embodiment of a step for placement of a lateral tissue protector assembly 6070 on an implant insertion and drill guide assembly 6050. In one embodiment, the lateral tissue protector assembly 6070 is a telescoping reamer sleeve. In one embodiment, the inferior-lateral incision 5020 is made once the lateral tissue protector assembly 6070 and implant insertion and drill guide assembly 6050 are positioned for proper alignment to a femoral neck component hole in the stem implant 5110 or trial stem 5120. In one embodiment, the inferior-lateral incision 5020 is made in the skin and tensor fascia and the lateral tissue protector assembly 6070 is pushed to bone. Maintaining the desired anteversion with the implant insertion and drill guide assembly 6050, a femoral neck guide pin 6000 is inserted through the inferior-lateral incision 5020 inside the lateral tissue protector assembly 6070, through the lateral femoral cortex and directed toward the original position of the middle of the femoral neck and head 106. Final positioning of the femoral neck guide pin 6000 can be performed and/or confirmed with the C-Arm in the AP plane. In one embodiment, the femoral neck guide pin 6000 tip reaches the center of femoral head position. In an embodiment, the guide pin 6000 is inserted until the tip reaches the optimal center of femoral head 106 original position. In an embodiment, the guide pin 6000 is inserted until the tip reaches the distance of a femoral head 106 radius from the tip of the guide pin 6000 to the acetabulum 316.

Figure 63:
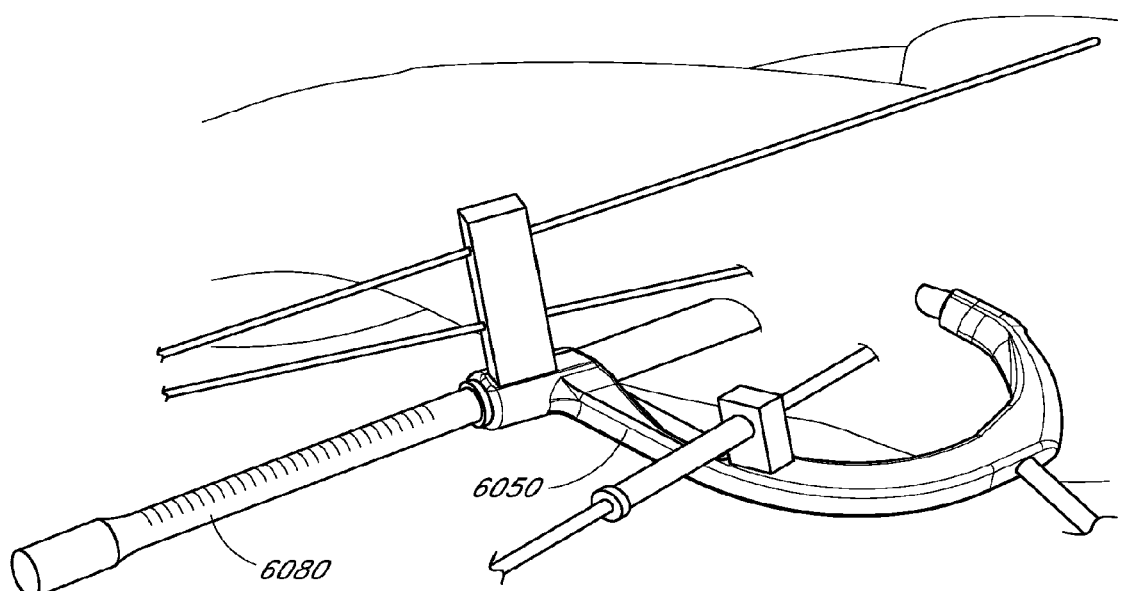

FIG. 63 illustrates an embodiment of an optional femoral neck length gauge 6080 configured for measuring the neck length before the guide pin 6000 is overreamed or overinserted. The femoral neck length gauge 6080 is inserted into the lateral tissue protector assembly 6070 until it abuts the end of the lateral tissue protector assembly 6070. The femoral neck length gauge 6080 measurements are taken by lining up the end of the guide pin 6000 with the calibration markings on the femoral neck length gauge 6080.

Figure 64:
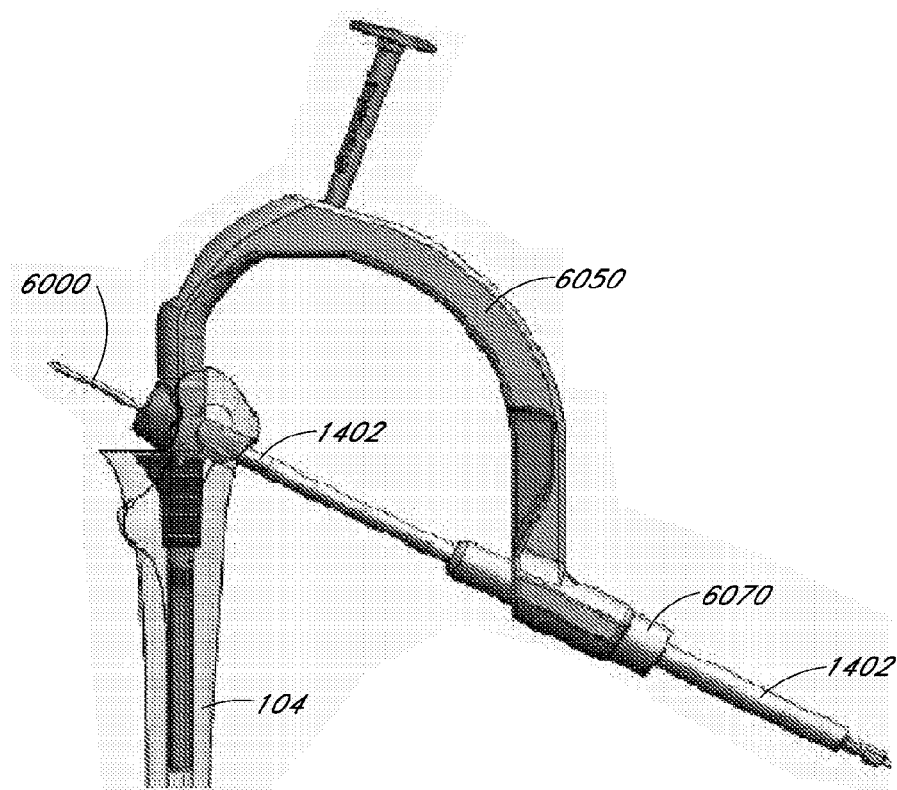

FIG. 64 illustrates an embodiment of a step for lateral cortex reaming. In various embodiments, lateral cortex reaming may be extended through the femoral neck prior to resection, or can take place after the femoral head and/or neck are resected and/or removed. In one embodiment, a reamer 1402 is selected with an appropriate length as indicated on the femoral neck length gauge 6080. In one embodiment, the reamer 1402 is advanced over the guide pin 6000. In one embodiment, the reaming is visualized with x-ray to confirm that the guide pin 6000 is not being forced forward. In one embodiment, the reamer 1402 is advanced until a positive stop on the reamer abuts the lateral tissue protector assembly 6070. In one embodiment, differences in shaft and hole diameters or dimensions prevent the reamer 1402 cutter head from contacting or damaging the stem implant 5110 or trial stem 5120.

In various embodiments, the prosthetic femoral neck implant component 5200 can be selected based on neck measurement, anteversion, visualization, surgeon preference, and/or a Shuck test for stability assessment. A Shuck test can be performed on the neck implant component 5200 by pulling the neck implant 5200 along its longitudinal axis for distraction only to determine how much play or movement is present. In one embodiment, if 2-3 mm of play is acceptable. In one embodiment, more than 3 mm of play can indicate a danger of dislocation and a longer neck implant 5200 is selected.

If a trial stem 5120 is present, the trial stem 5120 is removed from the femur through the superior-lateral incision 5010 prior to final placement of the neck implant 5200.

In one embodiment, the final size real stem 5110 is impacted through a self-broaching sleeve (pre-templated and inserted through the anterior incision). The neck implant 5200 is inserted through the inferior lateral incision 5020 and lateral femoral cortex into a hole and/or interface in the femoral stem implant 5110. In various embodiments, the stem implant 5110 and neck implant 5200 are attached with one, two, or more interfaces, threads, locks, pins, locking screws, top locking screws, seals, adhesives, glues, cement, temperature differentials, cold welding, interference fits, tapers, Morse tapers, impacting, tapping, hammering, and/or other attachment mechanisms. In one embodiment, the neck implant 5200 positioning is tested by a comparison of the positions of the knees after leg length is determined to be equal (left and right legs) with a Galeazzi test.

Figure 65:
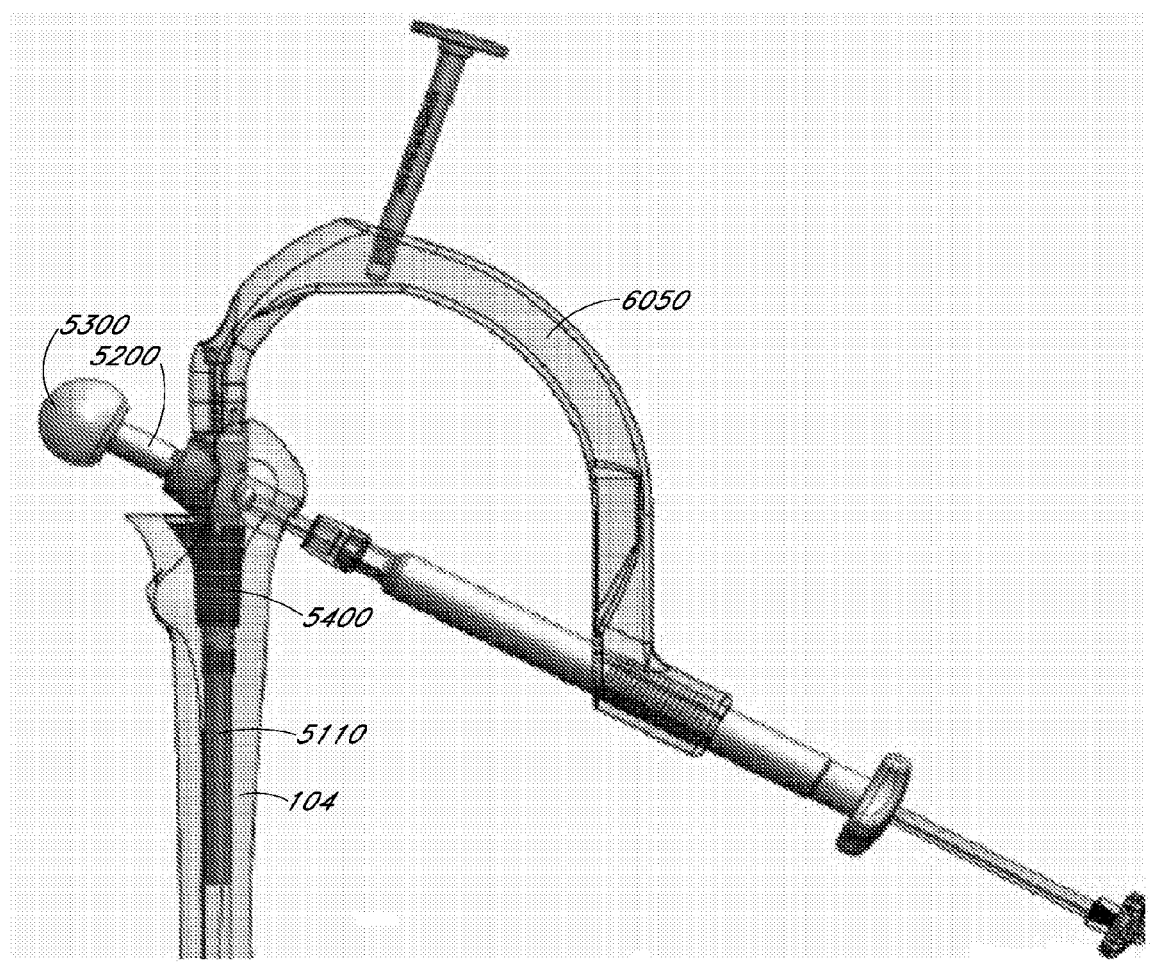
Figure 66:
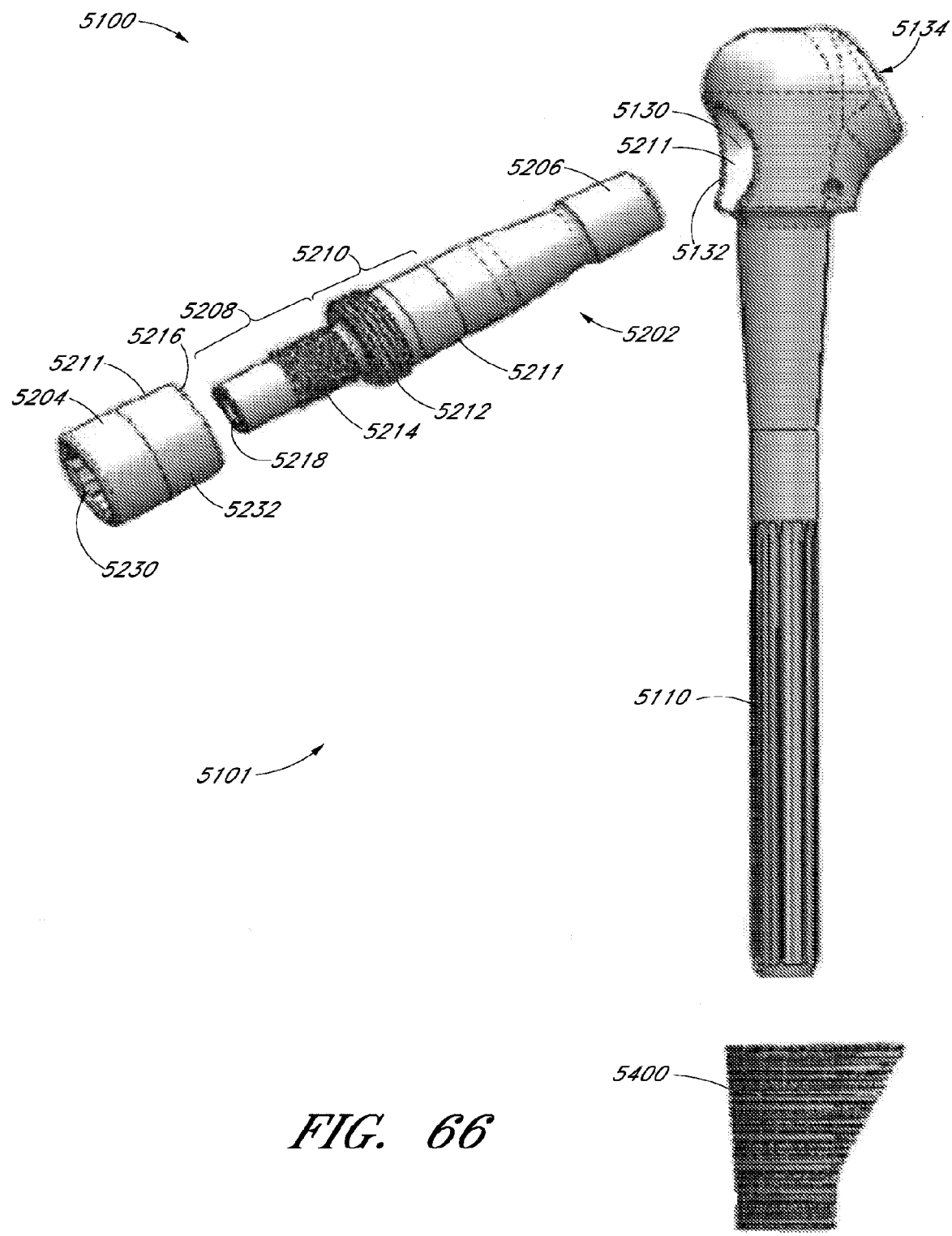
Figures 67, 68:
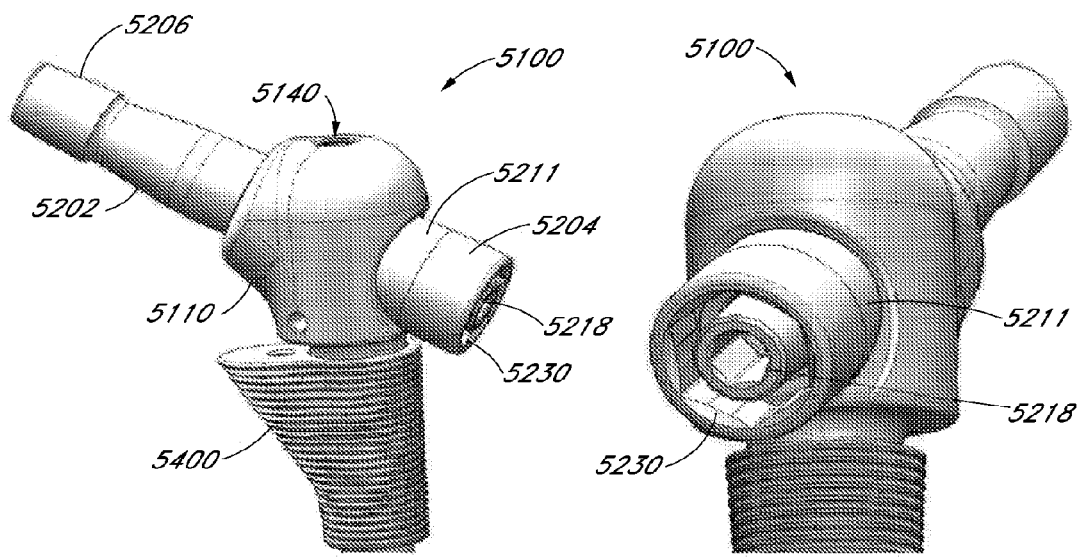

FIG. 65 illustrates an embodiment of a step for attaching the components of the prosthetic hip system 5100, with the neck implant 5200 inserted in to the head implant 5300. In various embodiments, the prosthetic hip system 5100 may have one, two, three, or more components, parts, portions, features, or sub-components that are attachable that include one, two, or more interfaces, threads, locks, pins, locking screws, top locking screws, seals, adhesives, glues, cement, temperature differentials, cold welding, interference fits, tapers, Morse tapers, impacting, tapping, hammering, and/or other attachment mechanisms. According to some embodiments, methods and systems for providing stable and secure interconnection of components are provided. Some embodiments can utilize structural interconnections that create press or interference fits between interlocking components. Some embodiments can utilize rotational or translational couplings that involve the use of torque or other force to engage the components. In various embodiments, any components can be joined or attached in any way—for example, the stem 5110 can be attached to the sleeve 5400, the neck 5200 can be attached to the stem 5110, the neck 5200 can be attached to the sleeve 5400, the neck 5200 can be attached to the head 5300, or any components, parts, portions, features, or sub-components thereof Further, some embodiments can utilize joining techniques that can enhance the interconnection of the components, such as by the use of temperature differential through heating or cooling the components to enhance a press, taper and/or interference fit. In various embodiments, components can be manufactured from the same or different materials in order to achieve desired characteristics and temperature-dimensional responsiveness. In some embodiments, at least a portion of one or more of interconnecting components can be cooled, such as by a nitrogen bath, to cause interconnecting aspects of the component to be reduced in size or dimension prior to being coupled with the other component. For example, once cooled, the interconnection aspects can be coupled to achieve a maximum press or interference fit in a cooling stage. Thereafter, as the component warms and expands, the engagement provided by the press or interference fits can be enhanced as dimensions of the interconnecting aspects of the components increase, thereby enhancing the interference and contact between the interconnecting aspects of the components.

In one embodiment, a temperature differential 7000 can be applied to one or more components to expand or shrink a component material or part, such that upon equalization of temperature an interference fit, cold-weld, or other attachment holds or supplements the connection between the components. A living human body has a body temperature of roughly 37 degrees Celsius. Various compositions or materials are available in the operating room to cool components. For example, a ratio of 1:2.5 of $CaCl_2.6H_2O$/ice is roughly −10 degrees Celsius, a ratio of 1:3 of NaCl/ice is roughly −20 degrees Celsius, carbon tetrachloride/$CO_2$ is roughly −23 degrees Celsius, acetonitrile/$CO_2$ is roughly −42 degrees Celsius, a ratio of 1:0.8 $CaCl_2.6H_2O$/ice is roughly −40 degrees Celsius, Acetone/$CO_2$ is roughly −78 degrees Celsius, Methanol/$N_2$ is roughly −98 degrees Celsius, and liquid nitrogen (Liquid $N_2$) is roughly −196 degrees Celsius. In one embodiment, a freezer or refrigerating unit is used to cool a component.

In one embodiment, a temperature differential 7000 includes cooling a component of the prosthetic hip system 5100 and/or tooling associated with the prosthetic hip system 5100. Once the cooled component is implanted in vivo, the body temperature of the patient warms the cooled component, resulting in some material expansion to improve a connection between components. In various embodiments, cooling through a temperature differential 7000 can benefits that include less-traumatic hammering, less damage, automatically locking features, improved connection through a cold weld, reduction in component material flaking or debris, reduction in dispersal of flaking or debris, minimal damage to tissue, materials such as metals tend to equalize in temperature through thermal conduction before tissue is damaged. In one embodiment, cooling of one or more parts or components through a temperature differential 7000 can cause condensation or the formation of moisture from the surrounding air, which can act as a lubricant to aid the insertion or implantation process.

In one embodiment, the femoral stem implant 5110 can be cooled prior to installation into the bore of the support sleeve 5400 in order to create material shrinkage of the stem 5110. Thus, the size of the stem 5110 can be reduced such that upon installation, the stem 5110 can heat up and expand to create an interference fit with the bore by virtue of the expanding size of the stem within the bore. In one embodiment, the femoral neck implant 5200 can be cooled prior to installation into the bore of the stem 5110 in order to create material shrinkage of the neck implant 5200. Thus, the size of the neck implant 5200 can be reduced such that upon installation, the neck implant 5200 can heat up and expand to create an interference fit with the bore by virtue of the expanding size of the neck within the bore. In one embodiment, the femoral neck implant 5200 can be cooled prior to installation into the bore of the head implant 5300 in order to create material shrinkage of the neck implant 5200. Thus, the size of the neck implant 5200 can be reduced such that upon installation, the neck implant 5200 can heat up and expand to create an interference fit with the bore by virtue of the expanding size of the neck within the bore. In various embodiments, additional parts or sub-components in the prosthetic hip system 5100 can have temperature differentials 7000 applied to improve the connection between parts or sub-components. Combinations of cooling with one, two or more tapers, threads, or other features are contemplated. Some embodiments can provide advantages that are superior to some traditional interfaces that may be driven together by impact or force in order to create in a fit sufficiently permanent to operatively support load-bearing movement about the prosthetic hip without slippage. Although such interface joining techniques can provide a tight fit, such structures and methods of use involve a high degree of force and can be undesirable for providing a careful, yet secure installation procedure. In contrast, embodiments disclosed herein provide exceptional engagement and fit. Further, some embodiments provide superior engagement using a unique cooling process to achieve maximum interference between mated surfaces and features of the components of the system.

In one embodiment, the hip arthroplasty procedure 5000 includes irrigation and closure upon completion of the implantation of the prosthetic hip system 5100. Various embodiments of a hip arthroplasty procedure 5000 can include any or all of the steps, in any order.

In accordance with various embodiments, a prosthetic hip system 5100 is provided for a minimally invasive, hip arthroplasty procedure. In various embodiments, any or all parts or components of the prosthetic hip system 5100 can be made of various materials, including but not limited to cobalt chromium, titanium, tantalum, surgical grade stainless steel, ceramic, alumina ceramic or other materials of suitable strength and acceptance properties.

Referring to FIGS. 66-69, FIGS. 81-95, and FIGS. 96-103, various embodiments of a prosthetic hip system 5100 include at least a dual-taper lock prosthetic hip system 5101. In one embodiment, the dual-taper lock prosthetic hip system 5101 comprises a femoral stem implant component 5110, a femoral neck implant component 5200, and a sleeve implant component 5400. In one embodiment, a prosthetic hip system 5100 comprises a femoral head implant component 5300 (not illustrated in FIGS. 66-69). In various embodiments, each component is configured for insertion through one or more minimally-invasive incisions in patient to reduce the damage to tissue and speed the recovery in a hip replacement. In some embodiments, the stem implant 5110 can be monolithically formed with an intramedullary rod portion. However, in another embodiment, the stem implant 5110 may be formed separately from and subsequently coupled to an intramedullary rod. In some embodiments, the stem implant 5110 is configured to taper and define ridges to facilitate engagement and fit into the intramedullary canal of the femur. Further, the stem implant 5110 can comprise ridges and other structures for engaging the femur and promoting osseointegration, rotational registration, engagement, and other advantageous features. In one embodiment, as illustrated in FIGS. 82, 84 and 85, the femoral stem implant component 5110 includes a slot 5152 to provide additional flexibility in the rod portion of the stem implant along the intramedullary canal. In one embodiment, as illustrated in FIGS. 96-99, the stem implant 5100 includes an orientation marking 5150 to indicate the relative position of the stem implant 5100 with respect to another component, such as a sleeve 5400.

In one embodiment, the stem implant 5110 comprises an interface 5140 configured for temporary attachment to an implant insertion and drill guide assembly 6050. In one embodiment, the interface 5140 includes one or more features, recesses, locks, keys, or other aspects for aligning or positioning the stem implant 5110 in a particular orientation. In one embodiment, the interface 5140 is a thread for releasable positioning and deployment or retrieval of the stem implant 5110 with respect to the implant insertion and drill guide assembly 6050. In one embodiment, the interface 5140 is a cam.

In one embodiment, the stem implant 5110 comprises a neck implant bore 5130 extending between a proximal bore end 5132 and a distal bore end 5134. In various embodiments, the neck implant bore 5130 is any shaped interface. In one embodiment, the neck implant bore 5130 is round. In various embodiments, the neck implant bore 5130 is a femoral neck bore 1504, lateral neck bore 1504, or any other embodiment of a neck interface. The neck implant bore 5130 is configured to receive the neck implant 5200. The neck implant bore 5130 can comprise one or more registration structures to rotationally secure the neck implant 5200. The registration structures can comprise one or more protrusions and/or recesses extending along an outer surface of the neck implant 5200 and/or the neck implant bore 5130. In one embodiment, the neck implant bore 5130 includes one or more threads. In one embodiment, the neck implant bore 5130 includes one, two, or more tapered surfaces 5211. In one embodiment, the proximal bore end 5132 includes one, two, or more tapered surfaces 5211. In one embodiment, the tapered surface 5211 is a Morse taper. In one embodiment, the neck implant bore 5130 includes one, two, or more tapered surfaces 5211. In one embodiment, the distal bore end 5134 includes one, two, or more tapered surfaces 5211. In one embodiment, the tapered surface 5211 is a Morse taper. In various embodiments, the taper 5211 is configured to seal the interface between system parts to prevent the escape of debris or flaking from components that may rub against each other in use. In various embodiments, the taper 5211 is configured to provide an adjustable interface to account for differences in tolerances in dimensions between parts or components.

In one embodiment, the neck implant 5200 includes a distal neck portion 5202, and a proximal cap portion 5204. The distal neck portion 5202 can comprise features such as related to the proximal femoral neck devices described in various embodiments herein.

In one embodiment, the distal neck portion 5202 includes a head engaging end 5206, a cap securing end 5208, and a bore engaging portion 5210. In one embodiment, the distal neck portion 5202 includes a distal neck engaging portion 5218 configured for a tool to engage the distal neck portion 5202 for implantation or removal. In one embodiment, the distal neck engaging portion 5218 is at a proximal end of the distal neck portion 5202. In one embodiment, the distal neck engaging portion 5218 includes features for rotatable engagement. In various embodiments, the distal neck engaging portion 5218 can apply 0-100, 10-80, 20-70, 30-60, 33, 45, and/or 55 ft-lb of torque to the distal neck portion 5202. In one embodiment, the head engaging end 5206 includes a Morse taper for engaging the prosthetic femoral head 5300. For example, some embodiments, head engagement may be achieved by providing a very slightly and narrowingly tapered cylindrical section at the head engaging end 5206. The prosthetic femoral head 5300 can also comprise a corresponding Morse taper for engaging with the head engaging end 5206 of the distal neck portion 5202.

Figure 69:
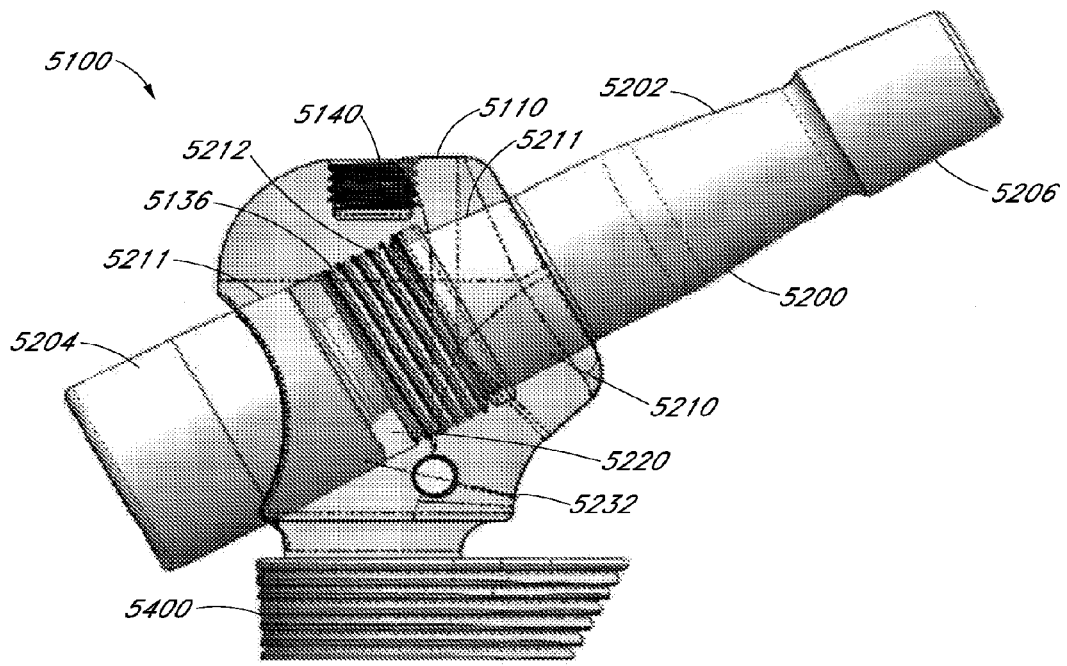

As shown in FIG. 69, in which the femoral stem implant component 5110 is shown in hidden lines, and in FIGS. 89-95 and in FIGS. 100-103, in various embodiments, the bore engaging portion 5210 can comprise one or more tapered surfaces 5211. In some embodiments, the taper 5211 can be a Morse taper. In various embodiments, the taper 5211 can be in the range of 0-10 degrees, 1-9 degrees, 2-8 degrees, 4-7 degrees, 5-6 degrees. Further, a distal section of the neck implant bore 5130 near the distal bore end 5134 can also include a corresponding taper 5211 for engagement with the bore engaging portion 5210 of the distal neck portion 5202 of the femoral neck implant component 5200. In various embodiments, one, two or more tapers 5211 of the bore engaging portion 5210 can extend along between about 0.1-3, 0.5-2, 1-1.5 cm and/or less than or equal to about 3 cm of the distal neck portion 5202 of the femoral neck implant component 5200. In various embodiments, one, two or more tapers 5211 of the bore engaging portion 5210 can extend along about 2 cm of the distal neck portion 5202 of the femoral neck implant component 5200. In various embodiments, the diameter of the bore engaging portion 5210 can be between at least about 10 mm and/or less than or equal to about 17 mm. In some embodiments, the diameter of the bore engaging portion 5210 can be between at least about 11 mm and/or less than or equal to about 15 mm. Further, the diameter of the distal section of the neck implant bore 5130 can be between at least about 10 mm and/or less than or equal to about 17 mm. In some embodiments, the diameter of the distal section of the neck implant bore 5130 can be between at least about 11 mm and/or less than or equal to about 15 mm. The diameter of the distal section of the neck implant bore 5130 and the diameter of the bore engaging portion 5210 can decrease very gradually as the bore extends toward the prosthetic femoral head 5300 to accommodate the Morse taper. In some embodiments, the diameters of the bore engaging portion 5210 and the distal section of the neck implant bore 5130 can define a generally identical taper and geometry. For example, the tapering of the bore engaging portion 5210 and the distal section of the neck implant bore 5130 can be linear or define an arcuate (either increasingly or decreasingly smaller diameter) taper 5211.

In some embodiments, the bore engaging portion 5210 of the distal neck portion 5202 includes an engagement means, such as a thread, protrusion, and/or recess that can engage with a portion of an interior surface of the neck implant bore 5130. In one embodiment, the bore engaging portion 5210 comprises a thread 5212 that can engage with an internal bore thread 5136 of the femoral stem implant component 5110. Thus, the distal neck portion 5202 can be inserted into the neck implant bore 5130 and rotated to engage the threads 5212, 5136. The rotational engagement can continue until the tapers 5211 of the bore engaging portion 5210 and the distal section of the neck implant bore 5130 of the femoral stem implant component 5110 are matched or mated against each other. In one embodiment, the connection between the components is further engaged through expansion and contraction of components exposed to a temperature differential 7000.

In one embodiment, the cap securing end 5208 of the distal neck portion 5202 includes a structure for engaging the proximal cap portion 5204. The proximal cap portion 5204 can include a corresponding engagement structure that facilitates engagement with the engagement structure of the proximal cap portion 5204. In one embodiment, the proximal cap portion 5204 has an external cap thread 5214. In one embodiment, the proximal cap portion 5204 has an internal cap thread 5216. In one embodiment, the engagement structures include corresponding inner and outer threads 5214, 5216. The threads 5214, 5216 can allow the proximal cap portion 5204 to be rotated onto the distal neck portion 5202 with some adjustability. For example, the threaded portions and any tapered portions of the neck implant bore 5130 can be configured to provide an adjustable zone 5220 in which the respective threads one the proximal cap portion 5204 and the distal neck portion 5202 can be adjusted as needed. Thus, when the proximal cap portion 5204 and the distal neck portion 5202 are tightened together, a small gap may be present in the adjustable zone 5220 in order to allow further tightening as necessary. In some embodiments, the aspects of the neck implant bore 5130 and the femoral neck implant component 5200 are configured such that a gap will be present in the adjustable zone 5220 when the proximal cap portion 5204 is fully tightened onto the distal neck portion 5202. In one embodiment, the proximal cap portion 5204 includes a proximal cap end engagement structure 5230 at its proximal end that facilitates engagement with a tool to install, remove, tighten, and/or loosen the proximal cap portion 5204. In one embodiment, the proximal cap end engagement structure 5230 includes features for rotatable engagement. In various embodiments, the proximal cap end engagement structure 5230 can apply 0-100, 10-80, 20-70, 30-60, 33, 45, and/or 55 ft-lb of torque to the proximal cap portion 5204.

In one embodiment, the proximal cap portion 5204 can comprise a cap bore engaging portion 5232. In some embodiments, the cap bore engaging portion 5232 can comprise a taper 5211. In one embodiment, the taper 5211 is a Morse taper. In various embodiments, the taper 5211 can be in the range of 0-10 degrees, 1-9 degrees, 2-8 degrees, 4-7 degrees, 5-6 degrees. In various embodiments, the taper of the cap bore engaging portion 5232 can extend along between about 0.1-20 mm and/or less than or equal to about 30 mm of the proximal cap portion 5204 of the femoral neck implant component 5200. In some embodiments, the taper 5211 of the cap bore engaging portion 5232 can extend along about 10-20 mm of the proximal cap portion 5204 of the femoral neck implant component 5200. In various embodiments, the diameter of the cap bore engaging portion 5232 can be between at least about 10 mm and/or less than or equal to about 20 mm. In some embodiments, the diameter of the cap bore engaging portion 5232 can be between at least about 11 mm and/or less than or equal to about 20 mm. Further, the diameter of a proximal section of the neck implant bore 5130 can be between at least about 10 mm and/or less than or equal to about 20 mm. In some embodiments, the diameter of the proximal section of the neck implant bore 5130 can be between at least about 11 mm and/or less than or equal to about 20 mm. The diameter of the proximal section of the neck implant bore 5130 and the diameter of the cap bore engaging portion 5232 can decrease very gradually as the bore extends toward the prosthetic femoral head to accommodate the Morse taper. In some embodiments, the diameters of the cap bore engaging portion 5232 and the proximal section of the neck implant bore 5130 can define a generally identical taper and geometry. For example, the tapering of the cap bore engaging portion 5232 and the proximal section of the neck implant bore 5130 can be linear or define an arcuate (either increasingly or decreasingly smaller diameter) taper. In some embodiments, the distal section of the neck implant bore 5130 can define a smaller diameter than the proximal section of the neck implant bore 5130. Further, the distal section and the proximal section of the neck implant bore 5130 can both define a linear taper or arcuate taper, as discussed above. According to some embodiments, the Morse tapers of the femoral neck implant component 5200 and the distal and proximal sections of the neck implant bore 5130 allow the femoral neck implant component 5200 to be securely engaged with the femoral stem implant component 5110. Further, in some embodiments, the threaded engagement enhances the connection between the femoral neck implant component 5200 and the neck implant bore 5130.

In one embodiment, the distal neck portion 5202 is exposed to a temperature differential 7000 to cool the distal neck portion 5202 to reduce at least one dimension of the distal neck portion 5202 through thermal contraction. In one embodiment, the distal neck portion 5202 the neck is cooled in a cooling medium, such as liquid nitrogen, prior to inserting the distal neck portion 5202 in the neck implant bore 5130 of the femoral stem implant component 5110. In one embodiment, the femoral stem implant component 5110 can receive the distal neck portion 5202 in a cooled, contracted state, at which time the distal neck portion 5202 will be shrunk to a reduced dimensional geometry. The distal neck portion 5202 can then be installed into the neck implant bore 5130 until an interference fit is obtained between the femoral neck implant component 5200 and the neck implant bore 5130. The interference fit can be achieved due to interaction of corresponding engagement structures, such as threads, Morse tapers, protrusions, recesses, and other such geometries and corresponding features. In such embodiments, the engagement between the neck and the support sleeve can provide superior strength and permanence. In some embodiments, a temperature differential 7000 can be used in conjunction with one, two, or more Morse tapers that are configured to interact between components to cause an interference fit and/or cold welding to achieve exceptional engagement as the cooled component(s) enlarge when exposed to the body temperature, warming and expanding components.

In one embodiment, the distal neck portion 5202 is threadably engaged with the neck implant bore 5130 until one or more Morse tapers of the bore engaging portion 5210 and the distal section of the neck implant bore 5130 match against each other. The Morse tapers of the bore engaging portion 5210 and the distal section of the neck implant bore 5130 can achieve exceptional engagement as the distal neck portion 5202 later warms from exposure to ambient or body temperatures and the bore engaging portion 5210 enlarges and expands against the distal section of the neck implant bore 5130.

In one embodiment, the method includes installing the proximal cap portion 5204 of the femoral neck implant component 5200 after the proximal cap portion 5204 has been cooled in a cooling medium. The proximal cap portion 5204 can be threadably engaged with the distal neck portion 5202 during installation. In some embodiments, the distal neck portion 5202 and proximal cap portion 5204 are installed in quick successive order in order to ensure that both portions 5202, 5204 are at a cool temperature when initially engaged with each other. Thus, as the distal neck portion 5202 and proximal cap portion 5204 warm from the cooled temperature, the engagement sections (e.g. threads, tapers, etc.) can expand against each other to create an interference fit that secures the distal neck portion 5202 and proximal cap portion 5204 together with a superior, strong bond.

In one embodiment, the Morse tapers of the bore engaging portion 5210 and the distal section of the neck implant bore 5130, the Morse tapers of the cap bore engaging portion 5232 and the proximal section of the neck implant bore 5130 can be matched against each other and urged together using the threaded engagement of the distal neck portion 5202 and proximal cap portion 5204 of the femoral neck implant component 5200. The Morse tapers of the cap bore engaging portion 5232 and the proximal section of the neck implant bore 5130 can achieve exceptional engagement as the proximal cap portion 5204 later warms and the cap bore engaging portion 5232 enlarges and expands against the proximal section of the neck implant bore 5130.

In various embodiments, one or more threads 5136, 5212, 5214, 5216 are sized with a pitch and dimensions configured to be rotatably threadable with respect to a corresponding thread at an ambient, body, and/or cooled temperature. In one embodiment, one or more threads 5136, 5212, 5214, 5216 are rotatable when cooled to a threshold temperature under a temperature differential 7000, and lock in place with an interference fit or cold welding when heated to ambient or body temperature. In various embodiments, monitoring of component temperature and/or dimensions may be involved in a hip arthroplasty procedure.

Figures 70, 71, 72:
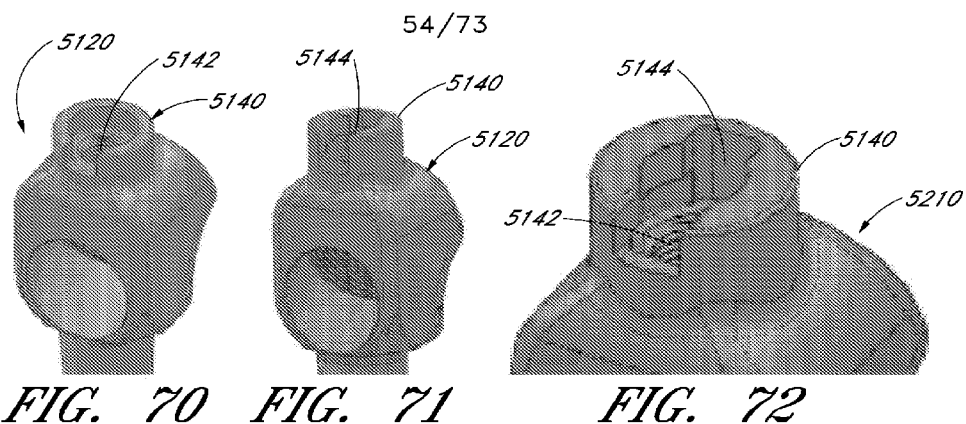

In accordance with various embodiments, a prosthetic hip system 5100 with one or more trial components is provided for a minimally invasive, THA procedure. Various trial components are used to check or confirm sizing and orientation, or can be used as guides for any of the steps of a THA procedure 5000. In various embodiments, trial implants or components can have any of the same or similar features and/or materials as a real implant or component. In various embodiments, real implants or components can have any of the same or similar features and/or materials as a trial implant or component. In various embodiments, a trial stem 5120 can be used as a broach or hammer to position or test a trial sleeve 5140 or a sleeve implant component 5400, and/or as a guide for preparing tissue for a neck implant 5200. In one embodiment, the trial stem 5120 includes an interface 5140 configured for temporary attachment to an implant insertion and drill guide assembly 6050. In one embodiment, as shown in FIG. 70, the interface 5140 includes one or more features, recesses, locks, keys, slots, channels, guides, walls, or other aspects for aligning or positioning the trial stem 5120 in a particular orientation. In one embodiment, as shown in FIG. 70, the interface 5140 is a thread 5142 for releasable positioning and deployment or retrieval of the trial stem 5120 with respect to the implant insertion and drill guide assembly 6050. In one embodiment, as shown in FIG. 71, the interface 5140 is a cam 5144 or a partial cam. In various embodiments, such as is shown in FIG. 72, the interface 5140 can include a combination of features, such as a thread 5142 and a cam 5144. In one embodiment, the implant insertion and drill guide assembly 6050 includes a stem interface control 6052 configured to control the connection to a stem implant 5110 or trial stem 5120. In one embodiment, a stem interface control 6052 includes a spring 6054 to facilitate pulling parts together and/or holding the control in a particular position. In various embodiments, the interface 5140 is the same for a stem implant 5100 and a trial stem 5120. In one embodiment, the interface 5140 is configured to minimize movement between the stem implant 5110 or trial stem 5120 and the implant insertion and drill guide assembly 6050. In various embodiments, as shown in FIGS. 73-74, a stem interface control 6052 can include a corresponding structure to the thread 5142 and/or the cam 5144. For example, in FIG. 75 the stem interface control 6052 includes a cam 5145 configured to operate with the interface 5140 cam 5144. In various embodiments, the interface 5140 provides stability for broaching. In various embodiments, the interface 5140 provides stability for broaching. In various embodiments, the interface 5140 is configured for a quick-connect or quick-disconnect through a partial turn, quarter-turn, and/or half turn. As shown in FIGS. 76-77, some embodiments of a trial stem 5120 include an undercut region 5122 along a portion of the stem that is sized to slide a slotted sleeve 5430. In one embodiment, a trial stem 5120 can be configured as a base for broaching with a quick connect to a broach or broach control, including optional mechanisms for deployment, retraction and/or extraction. FIG. 78 illustrates one embodiment of a trial stem 5120 with a slotted sleeve 5430. The slotted sleeve 5430 has a slot extending along a length to allow removal of the slotted sleeve 5430 at an undercut region 5122 by laterally removing the gap or slot in the slotted sleeve 5430 over the reduced dimension at the undercut region 5122. FIGS. 79 and 80 illustrate various embodiments of slotted sleeves 5430 with a feature 5432 for releasable holding mechanisms for positioning, guiding, releasing or grasping the sleeve. In various embodiments, the feature 5432 is a recess, hole, quick connect, key, pin, or mechanism interface that can interact with a tool, stem component 5110 or trial stem 5120.

Referring to FIGS. 104-115 and to FIGS. 116-121, various embodiments of a prosthetic hip system 5100 include a collet lock prosthetic hip system 5102. In addition to any of the embodiments of any of the components of a prosthetic hip system 5100, the collet lock prosthetic hip system 5102 includes at least one collet 5500. In some embodiments, the collet lock prosthetic hip system 5102 is a dual-taper lock prosthetic hip system 5101.

In one embodiment, the collet 5500 is configured allow for a slimmer stem component 5110 to pass through the abductor muscles with minimal damage. In one embodiment, the collet 5500 locks into position with the stem 5110 with at least one taper 5211. In one embodiment, the taper 5211 is a Morse taper. In one embodiment, the collet 5500 interfaces with a neck implant 5200 with threads. In one embodiment, the collet 5500 interfaces with a neck implant 5200 with one or more tapers 5211. In one embodiment, a collet 5500 includes both a thread and at least one taper 5211. In one embodiment, the press fit-taper combination is designed to isolate the threads from the bodily cavity on the medial end of the neck-to-stem interface. In one embodiment, the collet 5500 transfers the loads from the neck 5200 into the stem 5110. In one embodiment, the collet 5500 increases the functional diameter of the neck, which allows the neck design to be slimmer in order to reduce the profile needed minimize the lateral incision size, and to reduce damage to soft tissues upon implantation. In one embodiment, the collet 5500 taper(s) are configured to create an interference fit or a press fit for sealing the thread from the bodily environment between the neck and the collet. In one embodiment, the collet 5500 taper(s) take up the tolerance stack in the assembly to ensure a seal.

In one embodiment, the collet 5500 includes a collet bore 5510 through which a neck implant 5200 can be placed. In one embodiment, the collet 5500 includes a collet stem interface 5520 configured to contact and connect with a stem implant 5110. In one embodiment, the collet 5500 includes a boss surface 5520 that extends outside the stem bore. In one embodiment, the collet 5500 includes a collet bore thread 5540 corresponding to a neck thread 5212. In one embodiment, the collet 5500 includes a reverse Morse-type taper that is seated by being sucked into the stem 5110 as the neck 5200 is threaded into position. In one embodiment, the collet 5500 allows the stem to be slimmer to make insertion through the abductor muscles more minimally invasive. In one embodiment, the collet 5500 allows for the neck to be slimmer, by transferring the primary bending moment fulcrum medially. In one embodiment, the collet 5500 an anti-rotation feature is flat that is not normal to the axis of the collet taper, and is designed to improve manufacturability.

In one embodiment, as shown in FIGS. 104-115, the collet lock prosthetic hip system 5102 includes a neck implant 5200 with a distal neck portion 5202, and a proximal cap portion 5204. In one embodiment, the distal neck portion 5202 includes a thread 5212 configured to interface with a collet bore thread 5510 instead of a stem implant bore thread 5136.

In one embodiment, the collet 5500 is expandable, as shown in FIGS. 110 and 115. In one embodiment, the collet 5500 includes a collapsible section 5550 with a plurality of collet fingers on the proximal end of the collet 5500. In one embodiment, one or more collet fingers can include a snap fit configured to snap on or in to a corresponding feature on the neck implant 5200 and/or the stem implant 5110. In one embodiment, collet 5500 is configured to prevent a neck implant 5200 from spinning in a stem implant 5110. In one embodiment, the collet 5500 can have no threads.

As shown in FIGS. 116-117, in one embodiment, the collet 5500 is locked in place with a holding pin 5560. In one embodiment, the press fit pin 5560 is a capture/anti-rotation feature to prevent the neck implant 5200 from moving with respect to the stem implant 5110. In one embodiment, the collet 5500 internal bore diameter is threaded, and mating threads are also found on the neck component 5200. In one embodiment, as shown in FIGS. 118-121, the collet 5500, the collet includes a sharp angled portion along with axial cuts to allow the medial end of the sleeve to collapse onto the neck when the neck is installed. In one embodiment, the stem component 5110 bore includes a Morse-type tapered collet that is preinstalled into the of the stem using a press fit pin as a capture/anti-rotation feature. The internal diameter of the collet is threaded, and mating threads are also found on the neck component. Medial to the threads, the collet includes a sharp angled portion along with axial cuts to allow the medial end of the sleeve to collapse onto the neck when the neck is installed.

Referring to FIGS. 122-124, various embodiments of a prosthetic hip system 5100 include a screw-lock prosthetic hip system 5103, including a fixation screw 2902 that is tightened on to the neck implant 5200 to hold it in place with respect to the stem implant 5110. In one embodiment, the fixation screw 2902 is engaged through the interface 5140.

Referring to FIGS. 122-124, various embodiments of a prosthetic hip system 5100 include a split-stem prosthetic hip system 5104 with a split body stem 5160. In one embodiment, the split body stem 5160 simplifies the construction of a stem by using deflection of the proximal stem to pinch the neck 5200 in place. The split body stem 5160 includes an axial cut through the proximal portion of the stem, which allows the stem to splay apart to allow for insertion of the neck 5200. In one embodiment, the split body stem 5160 includes a corresponding split body stem cap 5162 to lock the axial cut in the construct together and to prevent motion of the neck implant 5200. In one embodiment, the neck implant 5200 is configured with flats, features, and/or locking features to assist in the locking of the neck 5200 in the stem 5110.

Numerous variations and modifications of the invention will become readily apparent to those skilled in the art. Accordingly, the invention may be embodied in other specific forms without departing from its spirit or essential characteristics. The embodiments presented herein are to be considered in all respects only as illustrative and not restrictive and the scope of the invention is, therefore, indicated by the appended claims rather than by the foregoing descriptions. Although embodiments of these inventions have been disclosed in the context of certain examples, it will be understood by those skilled in the art that the present inventions extend beyond the specifically disclosed embodiments to other alternative embodiments and/or uses of the inventions and obvious modifications and equivalents thereof. In addition, while several variations of the inventions have been shown and described in detail, other modifications, which are within the scope of these inventions, will be readily apparent to those of skill in the art based upon this disclosure. It is also contemplated that various combinations or sub-combinations of the specific features and aspects of the embodiments may be made and still fall within the scope of the inventions. It should be understood that various features and aspects of the disclosed embodiments can be combined with or substituted for one another in order to form varying modes of the disclosed inventions. Any of the embodiments of the devices, systems, assemblies, components, methods, and/or steps can be combined with other embodiments.

What is claimed is:

1. A modular prosthetic hip system for hip arthroplasty, comprising:
- a prosthetic femoral stem comprising a neck bore, the prosthetic femoral stem configured to be inserted in a femur such that at least a portion of a proximal end of the prosthetic femoral stem is positioned within a trochanteric region of the femur and a distal end of the prosthetic femoral stem is positioned in an intramedullary canal of the femur;
- a prosthetic femoral neck comprising:
  - a neck bore engaging portion configured for lateral advancement through the neck bore and for fixed attachment to the neck bore of the prosthetic femoral stem, the neck bore engaging portion comprising at least one tapered surface for fixedly attaching the prosthetic femoral neck to the prosthetic femoral stem with at least one interference fit;
  - a head engaging end; and
  - wherein the neck bore engaging portion further comprises a thread for engagement of the neck bore to the prosthetic femoral neck, the thread configured to lock the femoral neck in the femoral stem with the interference fit at the at least one tapered surface; and
- a prosthetic femoral head attachable to the head engaging end of the prosthetic femoral neck, the prosthetic femoral head configured to fit rotatably within an acetabulum.

2. The prosthetic hip system of claim 1, the femoral neck comprising: a distal neck portion; and a proximal cap portion, the distal neck portion comprising the head engaging end, a cap bore engaging portion, and a cap securing end, the cap bore engaging portion comprising a taper and a thread, the cap securing end comprising an external cap thread, the proximal cap portion comprising an internal cap thread for adjustable engagement with the external cap thread.

3. The prosthetic hip system of claim 2, the cap securing end comprising an a distal neck engaging portion configured for releasable connection to a distal neck portion driving tool, and the proximal cap portion comprising a proximal cap end engagement structure configured for releasable connection to a proximal cap portion driving tool.

4. The prosthetic hip system of claim 2, wherein the cap bore engaging portion is configured for engagement with the neck bore of the femoral stem, at least a portion of the cap bore engaging portion having a tapered surface.

5. The prosthetic hip system of claim 1, wherein the prosthetic femoral head is configured to fit rotatably within a prosthetic acetabular cup in the acetabulum.

6. The prosthetic hip system of claim 1, further comprising a sleeve configured for anchoring the stem to a bone.

7. The prosthetic hip system of claim 1, wherein the at least one tapered surface of the neck bore engaging portion is a Morse taper.

8. A modular prosthetic hip system for hip arthroplasty, comprising:
- a prosthetic femoral stem comprising a neck bore, the prosthetic femoral stem configured to be inserted in a femur such that at least a portion of a proximal end of the prosthetic femoral stem is positioned within a trochanteric region of the femur and a distal end of the prosthetic femoral stem is positioned in an intramedullary canal of the femur;
- a prosthetic femoral neck comprising:
  - a neck bore engaging portion configured for lateral advancement through the neck bore and for fixed attachment to the neck bore of the prosthetic femoral stem, the neck bore engaging portion comprising at least one tapered surface for fixedly attaching the prosthetic femoral neck to the prosthetic femoral stem with at least one interference fit;
  - a head engaging end,
  - a distal neck portion; and
  - a proximal cap portion, the distal neck portion comprising the head engaging end, a cap bore engaging portion, and a cap securing end, the cap bore engaging portion comprising a taper and a thread, the cap securing end comprising an external cap thread, the proximal cap portion comprising an internal cap thread for adjustable engagement with the external cap thread, the cap securing end comprising an a distal neck engaging portion configured for releasable connection to a distal neck portion driving tool, and the proximal cap portion comprising a proximal cap end engagement structure configured for releasable connection to a proximal cap portion driving tool;
- a prosthetic femoral head attachable to the head engaging end of the prosthetic femoral neck, the prosthetic femoral head configured to fit rotatably within an acetabulum.

9. The prosthetic hip system of claim 8, wherein the cap bore engaging portion is configured for engagement with the neck bore of the femoral stem, at least a portion of the cap bore engaging portion having a tapered surface.

10. The prosthetic hip system of claim 8, wherein the prosthetic femoral head is configured to fit rotatably within a prosthetic acetabular cup in the acetabulum.

11. The prosthetic hip system of claim 8, further comprising a sleeve configured for anchoring the stem to a bone.

12. The prosthetic hip system of claim 8, wherein the at least one tapered surface of the neck bore engaging portion is a Morse taper.

13. The prosthetic hip system of claim 8, wherein the taper of the cap bore engaging portion is a Morse taper.

14. A modular prosthetic hip system for hip arthroplasty, comprising:
- a prosthetic femoral stem comprising a neck bore extending entirely through the prosthetic femoral stem from a first side of the prosthetic femoral stem to a second side of the prosthetic femoral stem;
- a prosthetic femoral neck comprising a neck bore engaging portion configured for lateral advancement through the neck bore, the neck bore engaging portion comprising at least one tapered surface for fixedly attaching the prosthetic femoral neck to the prosthetic femoral stem with at least one interference fit, wherein the neck bore engaging portion further comprises a thread for engagement of the neck bore to the prosthetic femoral neck, the thread configured to lock the femoral neck in the femoral stem with an interference fit at the at least one tapered surface; and
- a prosthetic femoral head disposed at a distal neck portion of the prosthetic femoral neck, the prosthetic femoral head configured to fit rotatably within an acetabulum.

15. The prosthetic hip system of claim 14, the femoral neck comprising: a proximal cap portion, a cap bore engaging portion, and a cap securing end, the distal neck portion comprising a head engaging end, the prosthetic femoral head being attachable to the head engaging end, the cap bore engaging portion comprising a taper and a thread, the cap securing end comprising an external cap thread, the proximal cap portion comprising an internal cap thread for adjustable engagement with the external cap thread.

16. The prosthetic hip system of claim 15, the cap securing end comprising a distal neck engaging portion configured for releasable connection to a distal neck portion driving tool, and the proximal cap portion comprising a proximal cap end engagement structure configured for releasable connection to a proximal cap portion driving tool.

17. The prosthetic hip system of claim 15, wherein the cap bore engaging portion is configured for engagement with the neck bore of the femoral stem, at least a portion of the cap bore engaging portion having a tapered surface.

18. The prosthetic hip system of claim 14, wherein the prosthetic femoral head is configured to fit rotatably within a prosthetic acetabular cup in the acetabulum.

19. The prosthetic hip system of claim 14, further comprising a sleeve configured for anchoring the stem to a bone.

20. The prosthetic hip system of claim 14, wherein the at least one tapered surface of the neck bore engaging portion is a Morse taper.

21. The prosthetic hip system of claim 14, wherein the thread of the neck bore engaging portion comprises a largest cross-sectional dimension of the femoral neck.

\* \* \* \* \*